United States Patent [19]

Ashton et al.

[11] Patent Number: 5,411,980

[45] Date of Patent: May 2, 1995

[54] SUBSTITUTED TRIAZOLINONES, TRIAZOLINETHIONES, AND TRIAZOLINIMINES AS ANGIOTENSIN II ANTAGONISTS

[75] Inventors: Wallace T. Ashton, Clark; Linda L. Chang, Wayne; Malcolm MacCoss, Freehold; Prasun K. Chakravarty, Edison; William J. Greenlee, Teaneck; Arthur A. Patchett, Westfield; Kelly Flanagan, Edison, all of N.J.

[73] Assignee: Merck & Co., Inc., Rahway, N.J.

[21] Appl. No.: 994,228

[22] Filed: Dec. 21, 1992

Related U.S. Application Data

[63] Continuation-in-part of Ser. No. 899,868, Dec. 17, 1992, abandoned, and continuation-in-part of Ser. No. 812,891, Dec. 20, 1991, abandoned which is a continuation-in part of Ser. No. 725,720, Jul. 3, 1991, abandoned, which is a continuation-in-part of Ser. No. 504,507, Apr. 4, 1990, abandoned, which is a continuation-in-part of Ser. No. 386,328, Jul. 28, 1989, abandoned.

[51] Int. Cl.⁶ .................... A61K 31/41; C07D 249/12
[52] U.S. Cl. .................... 514/384; 548/263.2
[58] Field of Search .................... 548/263.2; 514/384

[56] References Cited

U.S. PATENT DOCUMENTS 5,015,651  5/1991  Carini et al. .................... 514/381

FOREIGN PATENT DOCUMENTS

| 323737 | 7/1989 | European Pat. Off. . |
| 323841 | 7/1989 | European Pat. Off. . |
| 409332 | 1/1991 | European Pat. Off. . |
| 412594 | 2/1991 | European Pat. Off. . |
| WO91/18888 | 12/1991 | WIPO . |

OTHER PUBLICATIONS

Burger, Medicinal Chemistry, 2d Edition (1960) pp. 565–571, 578–581 and 600–601.
Denkewalter et al., Progress in Drug Reserch 10, 510–512 (1966).

Primary Examiner—Patricia L. Morris
Attorney, Agent, or Firm—Valerie J. Camara; Mark R. Daniel; Joseph F. DiPrima

[57] ABSTRACT

There are disclosed new substituted triazolinone, triazolinethione, and triazolinimine compounds which are useful as angiotensin II antagonists. These compounds have the general formula:

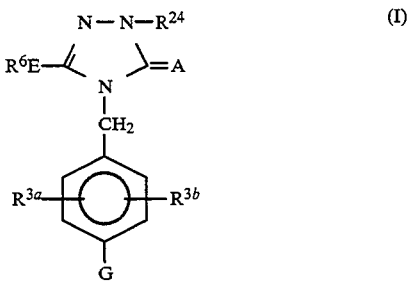

wherein G is $R^1$ or

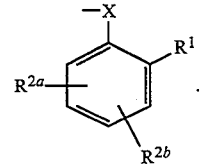

9 Claims, No Drawings

SUBSTITUTED TRIAZOLINONES, TRIAZOLINETHIONES, AND TRIAZOLINIMINES AS ANGIOTENSIN II ANTAGONISTS

INTRODUCTION OF THE INVENTION

This is a continuation-in-part of application Ser. No. 07/899,868, (abandoned), filed Dec. 17, 1992 and continuation-in-part of application Ser. No. 07/812,891, (abandoned), filed Dec. 20, 1991, abandoned, which is a continuation-in-part of application Ser. No. 07/725,720, (abandoned), filed Jul. 3, 1991, which is a continuation-in-part of Ser. No. 07/504,507, (abandoned), filed Apr. 4, 1990, which in turn is a continuation-in-part of application Ser. No. 07/386,328, filed Jul. 28, 1989, (abandoned).

This invention relates to novel substituted triazolinone, triazolinethione and triazolinimine compounds and derivatives thereof which are useful as angiotensin II antagonists in the treatment of elevated blood pressure and congestive heart failure. Thus, the substituted triazolinone, triazolinethione and triazolinimine compounds of the invention are useful as antihypertensives.

BACKGROUND OF THE INVENTION

Renin-angiotensin system (RAS) plays a central role in the regulation of normal blood pressure and seems to be critically involved in hypertension development and maintenance as well as congestive heart failure. Angiotensin II (A II) is an octapeptide hormone produced mainly in the blood during the cleavage of angiotensin I by angiotensin converting enzyme (ACE) localized on the endothelium of blood vessels of lung, kidney, and many other organs. It is the end product of the renin-angiotensin system (RAS) and is a powerful arterial vasoconstrictor that exerts its action by interacting with specific receptors present on cell membranes. One of the possible modes of controlling the RAS is angiotensin II receptor antagonism. Several peptide analogs of A II are known to inhibit the effect of this hormone by competitively blocking the receptors, but their experimental and clinical applications have been limited by the partial agonist activity and lack of oral absorption [M. Antonaccio. *Clin. Exp. Hypertens.* A4, 27–46 (1982); D. H. P. Streeten and G. H. Anderson, Jr.—*Handbook of Hypertension, Clinical Pharmacology of Antihypertensive Drugs*, ed. A. E. Doyle, Vol. 5, pp. 246–271, Elsevier Science Publisher, Amsterdam, The Netherlands, 1984].

Recently, several non-peptide compounds have been described as A II antagonists. Illustrative of such compounds are those disclosed in U.S. Pat. Nos. 4,207,324; 4,340,598; 4,576,958; 4,582,847; and 4,880,804; in European Patent Applications 028,834; 245,637; 253,310; and 291,969; and in articles by A. T. Chiu, et al. [*Eur. J. Pharm. Exp. Therap,* 157, 13–21 (1988)] and by P. C. Wong, et al. [*J. Pharm. Exp. Therap,* 247, 1–7(1988)]. All of the U.S. Patents, European Patent Applications 028,834 and 253,310 and the two articles disclose substituted imidazole compounds which are generally bonded through a lower alkyl bridge to a substituted phenyl. European Patent Application 245,637 discloses derivatives of 4,5,6,7-tetrahydro-2H-imidazo[4,5-c]pyridine-6-carboxylic acid and analogs thereof as antihypertensive agents, specifically $Ca^{2+}$ channel blockers.

DETAILED DESCRIPTION OF THE INVENTION

This invention relates to novel substituted triazole compounds and derivatives thereof which are useful as angiotensin II antagonists, as antihypertensives, in the treatment of congestive heart failure and in the treatment of elevated intraocular pressure. The compounds of this invention have the general formula (I):

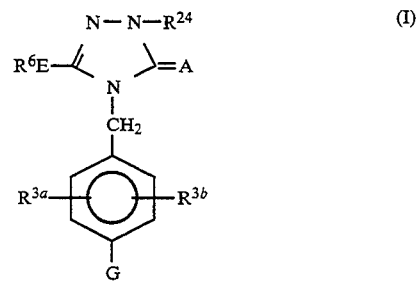

wherein G is $R^1$ or

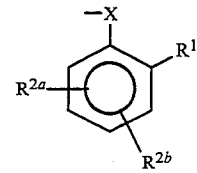

or a pharmaceutically acceptable salt thereof, wherein:
$R^1$ is
(a) $-CO_2R^4$,
(b) $-NHSO_2CF_3$,
(c) $-SO_2-NH-R^9$,
(d) $-SO_2NH$-heteroaryl,
(e) $-SO_2NHCOR^{23}$,
(f) $-CONHSO_2R^{23}$,
(g) $-NHSO_2NHCOR^{23}$,
(h)

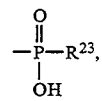

(i)

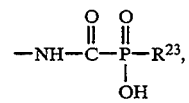

(j)

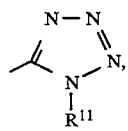

$R^{2a}$ and $R^{2b}$ are each independently:
(a) hydrogen,
(b) $-Cl$, $-Br$, $-I$, or $-F$,
(c) $-CF_3$, (d) $C_1$–$C_4$-alkyl $R^{3a}$ is
(a) —H,
(b) —Cl, —Br, —I, or —F, or
(c) $C_1$–$C_3$-alkyl;

$R^{3b}$ is
(a) —H,
(b) —Cl, —Br, —I, —F, $CF_3$, $CH_3$, $OCH_3$ or $NO_2$;

$R^4$ is H, $C_1$–$C_6$-alkyl, —$CH_2$-aryl or aryl;

E is a single bond, —S— or —O—;

$R^6$ is
(a) $C_1$–$C_6$-alkyl, $C_2$–$C_6$-alkenyl or $C_2$–$C_6$-alkynyl each of which is unsubstituted or substituted with one or more substituents selected from the group consisting of $C_3$–$C_7$-cycloalkyl, —O—$C_1$–$C_4$-alkyl, and —S—$C_1$–$C_4$-alkyl;
(b) mono-, di-, tri- or polyfluoro-$C_1$–$C_5$-alkyl;
(c) $C_3$–$C_7$-cycloalkyl unsubstituted or substituted with one or more substituents selected from the group consisting of $C_1$–$C_4$-alkyl, O—$C_1$–$C_4$-alkyl, S—$C_1$–$C_4$-alkyl, OH, perfluoro-$C_1$–$C_4$-alkyl, or Cl, Br, F, and I;
(d) $C_3$–$C_7$-cycloalkyl-$C_1$–$C_3$-alkyl wherein the cycloalkyl is unsubstituted or substituted as in (c) above;

A is =O, =S or =$NR^{21}$;

$R^{24}$ is
(a) H provided A is not $NR^{21}$,
(b) $C_1$–$C_{10}$-alkyl;
(c) substituted $C_1$–$C_{10}$-alkyl in which one or more substituent(s) is selected from
(1) I, Br, Cl, or F,
(2) hydroxy,
(3) $C_1$–$C_{10}$-alkoxy,
(4) $C_1$–$C_5$-alkoxycarbonyl,
(5) $C_1$–$C_4$-alkylcarbonyloxy,
(6) $C_3$–$C_8$-cycloalkyl,
(7) phenyl, naphthyl or biphenyl substituted with $V_1$, $V_2$, $V_3$, $V_4$ and $V_5$,
(8) $C_1$–$C_{10}$-alkyl-S(O)$_p$ in which p is 0 to 2,
(9) $C_3$–$C_8$-cycloalkyl-S(O)$_p$,
(10) phenyl-S(O)$_p$ substituted with $V_1$–$V_5$,
(11) oxo,
(12) carboxy,
(13) $NR^9R^9$,
(14) $C_1$–$C_5$-alkylaminocarbonyl,
(15) di($C_1$–$C_5$-alkyl)aminocarbonyl,
(16) cyano,
(17) —$OCONR^{21}R^{22}$,
(18) —$NR^{21}COR^{22}$,
(19) —$NR^{21}CO_2R^{22}$,
(20) —$NR^{21}CONR^{21}R^{22}$,
(21)

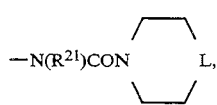

(22)

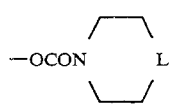

wherein L is a single bond, $CH_2$, O, $S(O)_p$ or $NR^9$,
(d) $C_2$–$C_{10}$-alkenyl,
(e) $C_2$–$C_{10}$-alkynyl,
(f) $C_3$–$C_8$-cycloalkyl,
(g) substituted $C_3$–$C_8$-cycloalkyl or substituted $C_3$–$C_8$-cycloalkyl-$C_1$–$C_4$-alkyl having one or more substituents selected from the group:
(1) Cl, Br, F, or I,
(2) hydroxy,
(3) $C_1$–$C_6$-alkyl,
(4) $C_1$–$C_6$-alkoxy,
(5) $C_1$–$C_4$-alkylcarbonyloxy,
(6) $C_1$–$C_5$-alkoxycarbonyl,
(7) carboxy,
(8) oxo,
(9) $C_1$–$C_5$-alkylaminocarbonyl,
(10) di($C_1$–$C_5$-alkyl)aminocarbonyl
(11) $C_1$–$C_4$-alkylcarbonyl;
(12) phenyl, naphthyl or biphenyl substituted with $V_1$, $V_2$, $V_3$, $V_4$ and $V_5$;
(13) —$NR^{21}COR^{22}$,
(14) —$NR^{21}CO_2R^{22}$,
(15) —$OCONR^{21}R^{22}$ and
(16) —CN
(h) phenyl, naphthyl, or biphenyl substituted with $V_1$, $V_2$, $V_3$, $V_4$ and $V_5$,
(i) phenyl-$(CH_2)_r$—$(Q)_c$—$(CH_2)_r$— in which the phenyl group is substituted with $V_1$, $V_2$, $V_3$, $V_4$ and $V_5$
(j) heterocycle-$(CH_2)_r$—$(Q)_c$—$(CH_2)_r$—, wherein the heterocycle is 5- or 6-membered containing one or two heteroatoms such as pyridine, furan, pyrrole, imidazole or thiazole and unsubstituted or substituted with $V_1$ and $V_2$;

$R^9$ is H, $C_1$–$C_5$-alkyl, aryl or —$CH_2$-aryl;

$R^{10}$ is H, $C_1$–$C_4$-alkyl, or $R^9$ and $R^{10}$ together can be —$(CH_2)_m$— where m is 3–6;

$R^{21}$ is
(a) H,
(b) phenyl unsubstituted or substituted with 1 or 2 substituents selected from the group consisting of Cl, Br, I, or F, —O—$C_1$–$C_4$-alkyl, $C_1$–$C_4$-alkyl, —$NO_2$, —$CF_3$;
(c) $C_1$–$C_6$-alkyl, $C_2$–$C_6$-alkenyl or $C_2$–$C_6$-alkynyl each of which is unsubstituted or substituted with one or more substituents selected from the group consisting of aryl, $C_3$–$C_7$-cycloalkyl, Cl, Br, I, F, —OH, —O—$C_1$–$C_4$-alkyl, and —S—$C_1$–$C_4$-alkyl;
(d) an unsubstituted, monosubstituted or disubstituted aromatic 5 or 6 membered ring comprising one or two heteroatoms selected from the group consisting of N, O, and S, and wherein the substituents are members selected from the group consisting of —OH, $C_1$–$C_4$-alkyl, $C_1$–$C_4$-alkyloxy, —$CF_3$, Cl, Br, I, and F; or
(e) $C_3$–$C_7$-cycloalkyl unsubstituted or substituted with one or more substituents selected from the group consisting of $C_1$–$C_4$-alkyl, —O—$C_1$–$C_4$-alkyl, —S—$C_1$–$C_4$-alkyl, perfluoro-$C_1$–$C_4$-alkyl, Cl, Br, F, and I;

$R^{22}$ is $R^{21}$, excluding H;

$R^{23}$ is
(a) aryl,
(b) heteroaryl, (c) $C_3$–$C_7$-cycloalkyl unsubstituted or substituted with one or more substituents selected from the group consisting of $C_1$–$C_4$-alkyl, —O—$C_1$–$C_4$-alkyl, $C_1$–$C_4$-alkyl-S(O)$_p$, —OH, =O, —COOR$^4$, —CONR$^9$R$^{10}$, perfluoro-$C_1$–$C_4$-alkyl, Cl, Br, F, I, $C_2$–$C_4$-alkenyl, aryl and aryl-$C_1$–$C_2$-alkyl;

(d) $C_1$–$C_9$-alkyl unsubstituted or substituted with aryl, heteroaryl, —OH, =O, $C_1$–$C_4$-alkyl, $C_2$–$C_4$-alkenyl, $C_2$–$C_4$-alkynyl —O($C_1$–$C_4$-alkyl), ($C_1$–$C_4$-alkyl)-S(O)$_p$, —CF$_3$, Cl, Br, F, I, —CN, —CO$_2$H, —CO$_2$—$C_1$–$C_4$-alkyl, —CONR$^9$R$^{10}$, —NH$_2$, —NH($C_1$–$C_4$-alkyl), —N($C_1$–$C_4$-alkyl)$_2$, N-(aryl)$_2$,

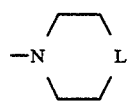

where L is a single bond, CH$_2$, O, S(O)$_p$, or NR$^9$,
(e) polyfluoro-$C_1$–$C_4$-alkyl;
(f) —NR$^{21}$R$^{21}$,
(g)

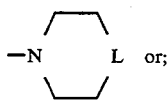 or;

(h) a saturated 5- to 7-membered ring linked through a carbon atom and containing one or two heteroatoms selected from oxygen, nitrogen, and sulfur such as piperazine, piperidine, tetrahydrofuran, thiazolidine, imidazolidine, oxazolidine, tetrahydrothiopene, dioxolane, dioxane, dithiolane, dithiane or the like and which may be substituted on carbon with $C_1$–$C_6$-alkyl, aryl, aryl-$C_1$–$C_2$-alkyl or oxo and on nitrogen, if present, with $C_1$–$C_4$-alkyl, $C_1$–$C_4$-alkyl-CO—;
(i) $C_7$–$C_{10}$ bi- or tricycloalkyl such as norbornan-2-yl, adamantan-1-yl or noradamantan-3-yl, either unsubstituted or substituted with $C_1$–$C_2$-alkyl or =O;

X is
(a) a single bond,
(b) —CO—,
(c) —NHCO—,
Q is —C(O)—, —S—, —O— or —NR$^4$;
c is 0 or 1;
r and t are 0 to 2;
$V_1$, $V_2$, $V_3$, $V_4$ and $V_5$ are each independently selected from:
(a) H,
(b) $C_1$–$C_5$-alkoxy,
(c) $C_1$–$C_5$-alkyl,
(d) hydroxy,
(e) —S(O)$_p$R$^{22}$,
(f) —CN,
(g) —NO$_2$,
(h) —NR$^{10}$R$^{21}$;
(i) $C_1$–$C_5$-alkyl-CONR$^{21}$R$^{22}$,
(j) —CONR$^{21}$R$^{22}$,
(k) —CO$_2$R$^9$,
(l) —(CH$_2$)$_r$COR$^{22}$,
(m) CF$_3$,
(n) I, Br, Cl, or F,
(o) hydroxy-$C_1$–$C_4$-alkyl-,
(p) carboxy-$C_1$–$C_4$-alkyl-,
(q) —1H-tetrazol-5-yl,
(r) —NH—SO$_2$R$^{22}$,
(s) aryl,
(t) $C_1$–$C_5$-alkyl-CO$_2$R$^9$,
(u) aryloxy,
(v) aryl-$C_1$–$C_3$-alkoxy,
(w) aryl-$C_1$–$C_3$-alkyl,
(x) carboxyphenyl,
(y) heteroaryl,
(z) 2-oxazolin-2-yl optionally bearing one or more $C_1$–$C_4$-alkyl substituents,
(aa) —(CH$_2$)$_r$OCOR$^{22}$,
(bb) —(CH$_2$)$_r$OCONR$^{21}$R$^{22}$,
(cc) —(CH$_2$)$_t$NR$^{21}$COR$^{22}$,
(dd) —(CH$_2$)$_t$NR$^{21}$CO$_2$R$^{22}$,
(ee) —(CH$_2$)$_t$NR$^{21}$CONR$^{21}$R$^{22}$,
(ff)

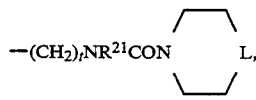

(gg)

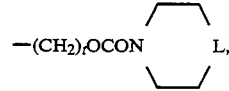

(hh)

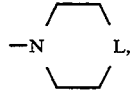

(ii)

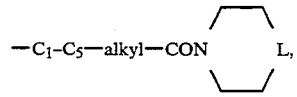

(jj)

wherein L is a single bond, O, S(O)$_p$ or NR$^9$,
(kk) —SO$_2$NR$^{21}$R$^{22}$ The terms "alkyl", "alkenyl", "alkynyl" and the like include both the straight chain and branched chain species of these generic terms wherein the number of carbon atoms in the species permit. Unless otherwise noted, the specific names for these generic terms shall mean the straight chain species. For example, the term "butyl" shall mean the normal butyl substituent, n-butyl. The term "halo" means Cl, Br, I or F.

The term "aryl", unless otherwise defined herein is meant to include phenyl, biphenyl or naphthyl unsubstituted or substituted with one, two or three substituents selected from the group consisting of —Cl, —Br, —I, —F, $C_1$-$C_6$-alkyl, $C_1$-$C_6$-alkoxy, $NO_2$, $CF_3$, $C_1$-$C_6$-alkyl-$S(O)_p$—, $CF_3SO_2$—, —OH, —$NR^9R^{10}$, —$CO_2H$, —$CO_2$—$C_1$-$C_4$-alkyl, —$CONR^9R^{10}$, —CN, —NHCOR$^9$, $OCF_3$, phenyl-$C_1$-$C_2$-alkyl, phenyl-$S(O)_p$, and phenyl-$C_1$-$C_2$-alkyl-$S(O)_p$.

The term "heteroaryl", unless otherwise defined herein is meant to be a 5- or 6-membered aromatic ring comprising from 1 to 3 heteroatoms selected from the group consisting of O, N and S such as thiazole, imidazole, oxazole, pyrazole, thiophene, furan, pyridine, pyrimidine, pyrazine, oxadiazole, thiadiazole, triazine or the like which can be fused to a benzo group and wherein the mono- or bicyclic system can be unsubstituted or substituted with one or two substituents selected from the group consisting of —OH, —SH, $C_1$-$C_6$-alkyl, $C_1$-$C_6$-alkoxy, $C_1$-$C_5$-alkylthio, —$CF_3$, Cl, Br, F, I, —$NO_2$, —$CO_2H$, aryl, —$CO_2$—$C_1$-$C_4$-alkyl, —$NH_2$, —CN, aryl-$C_1$-$C_2$-alkyl, arylthio, aryl-$C_1$-$C_2$-alkylthio, —NH($C_1$-$C_6$-alkyl) and —N($C_1$-$C_6$-alkyl)$_2$.

One embodiment of the compounds of Formula (I) are those compounds wherein:

$R^1$ is (a) —COOH,
(b)

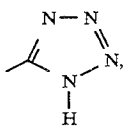

(c) —NH—$SO_2CF_3$,
(d) —CONH—$SO_2R^{23}$,
(e) —$SO_2NH$—$COR^{23}$, or
(f) —$SO_2NH$-heteroaryl;

$R^{2a}$ is H or F;
$R^{2b}$ is H, F, Cl, $CF_3$ or $C_1$-$C_4$-alkyl;
$R^{3a}$ is H, F or $C_1$-$C_3$-alkyl;
$R^{3b}$ is H, F, Cl;
E is a single bond, —O— or —S—;
$R^6$ is
(a) $C_1$-$C_6$-alkyl unsubstituted or substituted with a substituent selected from the group consisting of $CF_3$, —O—$CH_3$, —$OC_2H_5$, —S—$CH_3$, —S—$C_2H_5$, cyclopropyl, or $C_1$-$C_2$-alkylcyclopropyl;
(b) $C_2$-$C_6$-alkenyl or $C_2$-$C_6$-alkynyl;
(c) perfluoro-$C_1$-$C_4$-alkyl which is a member selected from the group consisting of $CF_3$—, $CF_3CF_2$—, $CF_3CF_2CF_2$—, or $CF_3CF_2CF_2CF_2$—;
(d) $C_3$-$C_7$-cycloalkyl unsubstituted or substituted with methyl, ethyl, $CF_3$ or $CF_3CF_2$;

A is =O, =S or =$NR^{21}$;
B is
(a) H provided A is not $NR^{21}$,
(b) $C_1$-$C_{10}$-alkyl,
(c) substituted $C_1$-$C_{10}$-alkyl in which one or two substituents are selected from:
(1) hydroxy,
(2) $C_1$-$C_5$-alkoxy,
(3) $C_1$-$C_5$-alkoxycarbonyl,
(4) $C_1$-$C_4$-alkylcarbonyloxy,
(5) $C_3$-$C_8$-cycloalkyl,
(6) phenyl, naphthyl or biphenyl substituted with $V_1$, $V_2$, $V_3$, $V_4$ and $V_5$,
(7) $C_1$-$C_5$-alkyl-$S(O)_p$
(8) phenyl-$S(O)_p$— substituted with $V_1$,
(9) oxo,
(10) carboxy,
(11) —CONH($C_1$-$C_5$-alkyl),
(12) —$NR^{21}COR^{22}$,
(13) —$NR^{21}CO_2R^{22}$,
(14) —$NR^{21}CONR^{21}R^{22}$,
(15) —$OCONR^{21}R^{22}$, or
(16) —CN;
(d) mono-, di-, tri-, or polyfluoro-$C_1$-$C_{10}$-alkyl,
(e) $C_2$-$C_{10}$-alkenyl,
(f) $C_2$-$C_{10}$-alkynyl,
(g) $C_3$-$C_8$-cycloalkyl,
(h) substituted $C_3$-$C_8$-cycloalkyl or substituted $C_3$-$C_8$-cycloalkyl-$C_1$-$C_4$-alkyl in which one or more substituent(s) is selected from:
(1) hydroxy,
(2) $C_1$-$C_5$-alkoxy,
(3) $C_1$-$C_5$-alkoxycarbonyl,
(4) $C_1$-$C_4$-alkylcarbonyloxy,
(5) $C_1$-$C_6$-alkyl,
(6) phenyl, naphthyl or biphenyl substituted with $V_1$, $V_2$, $V_3$, $V_4$, and $V_5$,
(7) oxo,
(8) carboxy,
(9) $C_1$-$C_5$-alkylaminocarbonyl,
(10) —$NR^{21}COR^{22}$,
(11) —$NR^{21}CO_2R^{22}$,
(12) —$OCONR^{21}R^{22}$ or
(13) —CN;
(i) phenyl, naphthyl or biphenyl substituted with $V_1$, $V_2$, $V_3$, $V_4$ and $V_5$,
(j) phenyl-$(CH_2)_r$—$(Q)_c$—$(CH_2)_r$— substituted with $V_1$, $V_2$, $V_3$, $V_4$ and $V_5$,
(k) heterocycle-$(CH_2)_r$—$(Q)_c$—$(CH_2)_r$—, wherein the heterocycle is 5- or 6-membered containing one or two heteroatoms selected from pyridine, furan, pyrrole, imidazole and thiazole and substituted with $V_1$ and $V_2$;

$V_1$, $V_2$, $V_3$, $V_4$ and $V_5$ are independently selected from:
(a) hydrogen,
(b) $C_1$-$C_5$-alkoxy,
(c) $C_1$-$C_5$-alkyl,
(d) hydroxy,
(e) $NR^{10}R^{21}$,
(f) $CO_2R^9$,
(g) trifluoromethyl;
(h) halogen;
(i) hydroxy-$C_1$-$C_4$-alkyl;
(j) -1H-tetrazol-5-yl,
(k) —NH—$SO_2R^{22}$;
(l) CN;
(m) $NO_2$;
(n) $C_1$-$C_5$-alkyl-$CO_2R^9$,
(o) aryl,
(p) aryl-$C_1$-$C_3$-alkyl,
(q) heteroaryl,
(r) $C_1$-$C_5$-alkyl-$CONR^{21}R^{22}$,
(s) —$CONR^{21}R^{22}$,
(t) 2-oxazolin-2-yl optionally bearing one or more $C_1$-$C_4$-alkyl substituents,
(u) —$S(O)_pR^{22}$,
(v) $(CH_2)_rOCOR^{22}$,
(w) $(CH_2)_rNR^{21}COR^{22}$,
(x) $(CH_2)_rNR^{21}CO_2R^{22}$, (y) $(CH_2)_tNR^{21}CONR^{21}R^{22}$,
(z) $(CH_2)_tOCONR^{21}R^{22}$,
(aa)

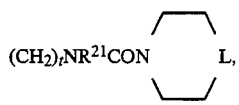

(ab)

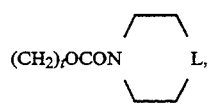

(ac)

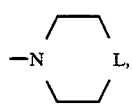

(ad)

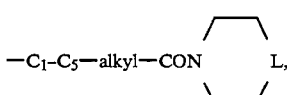

(ae)

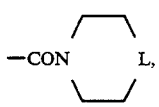

(af) aryl-$C_1$-$C_3$-alkoxy; or
(ag) $(CH_2)_tCOR^{22}$;
(ah) $SO_2NR^{21}R^{22}$ X is:
(a) a single bond;
(b) —C(O)—;
(c) —NHC(O)—.

In one class of this embodiment are those compounds of formula (I) wherein:
E is a single bond or —S—;
$R^6$ is
(a) $C_1$-$C_6$ alkyl unsubstituted or substituted with —F, —$CF_3$, cyclopropyl or $C_1$-$C_2$-alkylcyclopropyl; or
(b) cyclopropyl, unsubstituted or substituted with —$CH_3$, —$C_2H_5$, —$CF_3$, or —$CF_3CF_2$;
A is =O, =S or =$NR^{21}$;
$R^{24}$ is
(a) H provided A is not $NR^{21}$,
(b) $C_1$-$C_{10}$-alkyl,
(c) $C_3$-$C_8$-cycloalkyl,
(d) $C_3$-$C_8$-cycloalkyl-$C_1$-$C_4$-alkyl,
(e) substituted $C_1$-$C_{10}$-alkyl, $C_3$-$C_8$-cycloalkyl, or $C_3$-$C_8$-cycloalkyl-$C_1$-$C_4$-alkyl each of which can have one or two substituents selected from the group:
(1) hydroxy,
(2) $C_1$-$C_5$-alkoxy,
(3) $C_1$-$C_5$-alkoxycarbonyl,
(4) phenyl, naphthyl or biphenyl substituted with $V_1$, $V_2$, $V_3$, $V_4$, and $V_5$,
(5) carboxy,
(6) $C_1$-$C_5$-alkylaminocarbonyl,
(7) oxo,
(8) —$NR^{21}COR^{22}$,
(9) —$NR^{21}CO_2R^{22}$,
(10) —$OCONR^{21}R^{22}$, or
(11) —CN;
(f) mono-, di-, tri-, or polyfluoro-$C_1$-$C_{10}$-alkyl,
(g) phenyl, naphthyl or biphenyl substituted with $V_1$, $V_2$, $V_3$, $V_4$ and $V_5$,
(h) phenyl-$(CH_2)_r$—$(Q)_c$—$(CH_2)_r$— in which the phenyl is substituted with $V_1$, $V_2$, $V_3$, $V_4$ and $V_5$,
(i)

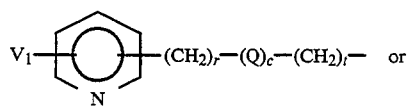 or (j)

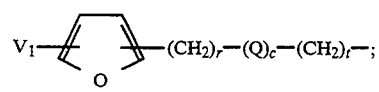;

$V_1$, $V_2$, $V_3$, $V_4$ and $V_5$ are selected from:
(a) hydrogen,
(b) $C_1$-$C_5$-alkyl,
(c) $C_1$-$C_5$-alkoxy,
(d) $CO_2R^9$,
(e) halogen,
(f) hydroxy-$C_1$-$C_4$-alkyl-,
(g) $C_1$-$C_5$-alkyl-$CO_2R^9$,
(h) $C_1$-$C_5$-alkyl-$CONR^9R^{10}$,
(i) $CONR^{21}R^{22}$,
(j) CN,
(k) $NO_2$,
(l) $CF_3$;
(m) aryl,
(n) heteroaryl,
(o) —NH—$SO_2R^{22}$,
(p) —$S(O)_pR^{22}$,
(q) $(CH_2)_tOCOR^{22}$,
(r) $(CH_2)_tNR^{21}COR^{22}$,
(s) $(CH_2)_tNR^{21}CO_2R^{22}$,
(t) $(CH_2)_tNR^{21}CONR^{21}R^{22}$,
(u) $(CH_2)_tOCONR^{21}R^{22}$,
(v)

(w)

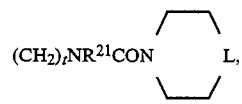

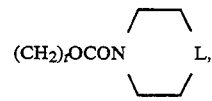

(x)

(y) 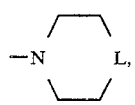

(z) 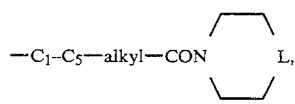

(aa) hydroxy,
(ab) NR$^{10}$R$^{21}$,
(ac) aryl-C$_1$-C$_3$-alkyl,
(ad) aryl-C$_1$-C$_3$-alkoxy, or
(ae) (CH$_2$)$_r$COR$^{22}$;
(af) —SO$_2$NR$^{21}$R$^{22}$ A subclass of the foregoing class of compounds is that wherein:

G is R$^{2a}$ 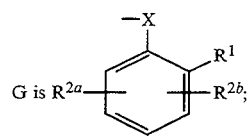

and
R$^1$ is:
(a) —CO$_2$H,
(b) 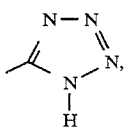

(c) —NHSO$_2$CF$_3$,
(d) —SO$_2$NHCOR$^{23}$,
(e) —SO$_2$NH-heteroaryl; and
X is a single bond.

Another sub-class is that comprising compounds wherein:
R$^1$ is

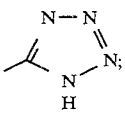

R$^{2a}$ and R$^{2b}$ are H;
R$^{3a}$ is H or F;
R$^{3b}$ is H;
R$^6$ is C$_3$-C$_5$-alkyl;
A is O;
R$^{24}$ is (a) C$_1$-C$_6$-alkyl,
(b) C$_3$-C$_8$-cycloalkyl,
(c) C$_3$-C$_8$-cycloalkyl-C$_1$-C$_4$-alkyl,
(d) substituted C$_1$-C$_6$-alkyl, C$_3$-C$_8$-cycloalkyl, or C$_3$-C$_8$-cycloalkyl-C$_1$-C$_4$-alkyl each of which can have one or two substituents selected from the group:
  (1) hydroxy,
  (2) C$_1$-C$_5$-alkoxy,
  (3) C$_1$-C$_5$-alkoxycarbonyl,
  (4) phenyl, naphthyl or biphenyl substituted with V$_1$ and V$_2$,
  (5) carboxy,
  (6) C$_1$-C$_5$-alkylaminocarbonyl,
  (7) oxo,
  (8) —CN
(e) mono-, di-, tri-, or polyfluoro-C$_1$-C$_6$-alkyl,
(f) phenyl substituted with V$_1$ and V$_2$;
E is a single bond;
V$_1$ and V$_2$ are selected from:
(a) hydrogen,
(b) C$_1$-C$_5$-alkyl,
(c) C$_1$-C$_5$-alkoxy,
(d) F, Cl, Br, or I,
(e) NO$_2$,
(f) CF$_3$,
(g) phenyl.

Exemplifying this subclass are the following compounds:
(1) 5-n-Butyl-4-(4-carboxybenzyl)-2,4-dihydro-2-[2-(trifluoromethyl)phenyl]-3H-1,2,4-triazol-3-one;
(2) 5-n-Butyl-4-(4-carboxybenzyl)-2,4-dihydro-2-phenethyl-3H-1,2,4-triazol-3-one;
(3) 5-n-Butyl-4-(2-chloro-4-carboxybenzyl)-2,4-dihydro-2-phenethyl-3H-1,2,4-triazol-3-one;
(4) 5-n-Butyl-2,4-dihydro-4-[4-(5-tetrazolyl)benzyl]-2-[2-(trifluoromethyl)phenyl]-3H-1,2,4-triazol-3-one;
(5) 4-[4-(N-Benzoylsulfamoyl)benzyl]-5-n-butyl-2-(2-chlorophenyl)-2,4-dihydro-3H-1,2,4-triazol-3-one;
(6) 4-[4-(N-Benzenesulfonyl)carbamoyl]benzyl]-5-n-butyl-2,4-dihydro-2-phenethyl-3H-1,2,4-triazol-3-one; and
(7) 2-Benzyl-5-n-butyl-2,4-dihydro-4-[4-(trifluoromethanesulfonamido)benzyl]-3H-1,2,4-triazol-3-one.

Another class of compounds within this embodiment has structural formula:

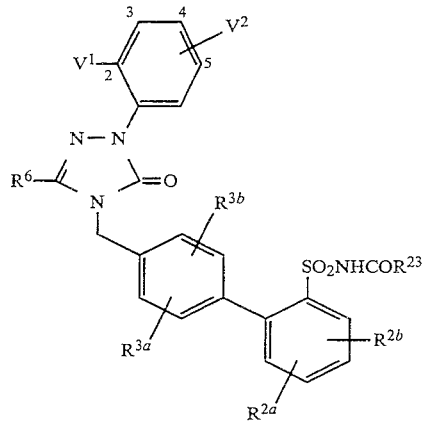

or a pharmaceutically acceptable salt thereof,
wherein V$^1$ is H, CF$_3$ or halogen;
V$^2$ is a group at the 3-, 4-, or 5-position selected from:

(a) H,
(b) —NO$_2$,
(c) —NR$^{10}$R$^{21}$,
(d)

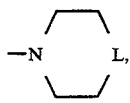

(e) —NR$^{21}$COR$^{22}$,
(f) —NR$^{21}$CO$_2$R$^{22}$,
(g) —NR$^{21}$CONR$^{21}$R$^{22}$,
(h)

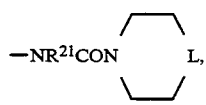

(i) —CONR$^{21}$R$^{22}$,
(j)

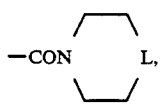

(k) —COR$^{22}$ and
(l) —S(O)$_p$R$^{22}$;
R$^{2a}$ is H, or F;
R$^{2b}$ is H, C$_1$–C$_4$-alkyl, F, Cl, Br, or I;
R$^{3a}$ is H, or F;
R$^{3b}$ is H, F, Cl, or CH$_3$;
R$^6$ is n-butyl or n-propyl;
R$^9$ is H, C$_1$–C$_5$-alkyl, aryl or —CH$_2$-aryl;
R$^{10}$ is H or C$_1$–C$_4$-alkyl;
R$^{21}$ is H or R$^{22}$ wherein
R$^{22}$ is:
 (a) C$_1$–C$_6$-alkyl, C$_2$–C$_6$-alkenyl, or C$_2$–C$_6$-alkynyl, each of which is unsubstituted or substituted with one or more substituents selected from the group consisting of aryl, heteroaryl, C$_3$–C$_6$-cycloalkyl, halo, —OH, —O—C$_1$–C$_4$-alkyl, —S—C$_1$–C$_4$-alkyl, —O-phenyl, or —S-phenyl;
 (b) C$_3$–C$_7$-cycloalkyl unsubstituted or substituted with one or more substituents selected from the group consisting of C$_1$–C$_4$-alkyl, halo or phenyl;
 (c) aryl;
 (d) heteroaryl;
R$^{23}$ is:
 (a) phenyl, unsubstituted or substituted with one or two substituents selected from Cl, —Br, —F, —I, —CH$_3$ and —CF$_3$, at least one of which occupies an ortho-position;
 (b) heteroaryl, such as furan-2-yl, thiophen-2-yl, benzo[b]furan-2-yl, benzo[b]thiophen-2-yl, furan-3-yl, thiophen-3-yl, or oxazol-5-yl, unsubstituted or substituted with one or two substituents selected from —Cl, —Br, —F, —I, —CH$_3$ and CF$_3$ wherein at least one of the substituents is located adjacent to the carbonyl substituent and/or to a ring heteroatom;
 (c) branched C$_3$–C$_6$-alkyl;
 (d) C$_3$–C$_7$-cycloalkyl, unsubstituted or substituted at the 1- and/or 2-position with one to three substituents selected from —Cl, —Br, —F, —I, —CH$_3$ and —CH$_2$CH$_3$;
 (e) C$_7$–C$_8$-bi- or tricycloalkyl;
 (f) saturated 5- or 6-membered heterocyclyl linked through a carbon atom and containing one or two heteroatoms selected from oxygen and sulfur such as tetrahydrofuryl, 1,3-dithiolan-2-yl, or 1,3-dithian-2-yl.

A subclass of this class of compounds is that wherein:
V$^1$ is H, CH$_3$, CF$_3$, Cl, Br, I or F;
V$^2$ is a group at the 3-, 4-, or 5-position selected from:
 (a) —NO$_2$,
 (b) —NR$^{10}$R$^{21}$,
 (c)

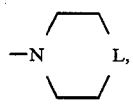

(d) —NR$^{21}$COR$^{22}$,
 (e) —NR$^{21}$CO$_2$R$^{22}$,
 (f) —NR$^{21}$CONR$^{21}$R$^{22}$,
 (g)

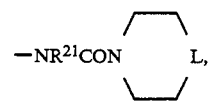

(h) —CONR$^{21}$R$^{22}$,
 (i)

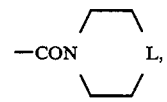

(j) —COR$^{22}$; or
 (k) —S(O)$_p$R$^{22}$.

Another subclass of compounds within this class comprises compounds of formula I wherein:
V$^1$ is CF$_3$, Cl, Br, I or F;
V$^2$ is a group at the 5-position selected from:
 (a) —NR$^{21}$COR$^{22}$,
 (b) —NR$^{21}$CO$_2$R$^{22}$,
 (c) —NR$^{21}$CONR$^{21}$R$^{22}$,
 (d)

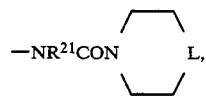

(e) —CONR$^{21}$R$^{22}$;
 (f)

(g) —COR$^{22}$; and
 (h) —S(O)$_p$R$^{22}$;
R$^{2a}$ is H or F;
R$^{2b}$ is H, F, or C$_1$–C$_4$-alkyl;

$R^{3a}$ is H;
$R^{3b}$ is H or F;
$R^{21}$ is H or $CH_3$;
$R^{22}$ is:
(a) $C_1$–$C_6$-alkyl, unsubstituted or substituted with one or more substituents selected from the group consisting of aryl, heteroaryl, $C_3$–$C_6$-cycloalkyl, —O—$C_1$–$C_4$-alkyl, —S—$C_1$–$C_4$-alkyl, —O-phenyl, or —S-phenyl;
(b) $C_3$–$C_7$-cycloalkyl unsubstituted or substituted with one or more substituents selected from the group consisting of $C_1$–$C_4$-alkyl or phenyl;
(c) aryl; or
(d) heteroaryl.

Another embodiment of the novel compounds of this invention is that wherein $V^1$ is $CF_3$; $V^2$, $R^{2a}$, $R^{2b}$ and $R^{3a}$ are H; $R^{3b}$ is H or F; and $R^6$ is n-butyl.

Abbreviations used in the schemes and examples are listed in Table 1.

TABLE 1

| Reagents | |
|---|---|
| NaOEt | sodium ethoxide |
| Et₃N | triethylamine |
| MeI | methyl iodide |
| RX (or R'X) | an alkylating agent, such as an alkyl or benzyl halide or p-toluenesulfonate |
| Ph₃P | triphenylphosphine |
| MeNH₂ | methylamine |
| t-BuLi | tert-butyllithium |
| NBS | N-bromosuccinimide |
| BzO₂ | benzoyl peroxide |
| TrCl | trityl chloride (triphenylmethyl choride) |
| ImH | imidazole |
| AIBN | 2,2'-azobis(isobutyronitrile) |
| DBU | 1,8-diazabicyclo[5.4.0]undec-7-ene |
| DMAP | 4-(dimethylamino)pyridine |
| CDI | 1,1'-carbonyldiimidazole |
| DCC | N,N'-dicyclohexylcarbodiimide |
| DIAD | diisopropyl azodicarboxylate |
| BOP reagent | benzotriazol-1-yloxytris(dimethylamino)phosphonium hexafluorophosphate |
| TFA | trifluoroacetic acid |
| Solvents | |
| EtOH | ethanol |
| DMF | dimethylformamide |
| AcOH | acetic acid |
| DMSO | dimethylsulfoxide |
| THF | tetrahydrofuran |
| EtOAc | ethyl acetate |
| hex | hexane |
| MEOH | methanol |
| Others | |
| Ar (or Ar') | aryl |
| Et | ethyl |
| Me | methyl |
| Het | heteroaryl |
| t-Bu (or Bu-t) | t-butyl |
| Bu | n-butyl |
| Im | imidazol-1-yl |
| FAB | fast atom bombardment |
| EI | electron impact |
| MS | mass spectrum |
| Ph | phenyl |
| aq. | aqueous |
| cat. | catalytic |
| eq. or equiv. | equivalent(s) |
| iPr | isopropyl |

DISCUSSION OF CHEMISTRY AND REACTION SCHEMES

The compounds of Formula I can be prepared by a variety of methods typified by those described below. General synthetic methods for 2,4,5-trisubstituted-2,4-dihydro-3H-1,2,4-triazol-3-ones and -triazole-3-thiones are discussed in books or review articles such as:

(1) C. Temple and J. A. Montgomery, "Triazoles: 1,2,4" (Vol. 37 of *The Chemistry of Heterocyclic Compounds*, A. Weissberger and E. C. Taylor, eds.), Wiley-Interscience, New York, 1981, pp. 365–442.

(2) J. B. Polya, *Comprehensive Heterocyclic Chemistry. The Structure, Reactions, Synthesis and Uses of Heterocyclic Compounds*, A. R. Katritzky and C. W. Rees, eds., Vol. 5, Pergamon Press, Oxford, 1984, pp. 733–790.

(3) J. H. Boyer, *Heterocyclic Compounds*, R. C. Elderfield, ed., Vol. 7, John Wiley & Sons, New York, 1961, pp. 384–461.

In general, the compounds of Formula I are constructed in such a way that $N^1$ and $N^2$ of the triazole ring are derived from hydrazine or a hydrazine derivative, while $N^4$ of the triazole and the 4-(arylmethyl) substituent are derived directly or indirectly from a suitably substituted benzylamine (or isocyanate or isothiocyanate) or from a benzyl halide (or methanesulfonate, p-toluenesulfonate, etc.).

Although the Reaction Schemes described below are reasonably general, it will be understood by those skilled in the art of organic synthesis that one or more functional groups present in a given compound of Formula I may render the molecule incompatible with a particular synthetic sequence. In such a case an alternative route, an altered order of steps, or a strategy of protection and deprotection may be employed. In all cases the particular reaction conditions (including reagents, solvent, temperature, and time) should be chosen so that they are consistent with the nature of the functionality present in the molecule.

The Reaction Schemes below have been generalized for simplicity. It is to be understood that the "ArCH₂" substituent present at $N^4$ of the triazole derivatives or in their precursors is any substituted arylmethyl moiety consistent with the definition of the $N^4$ substituent in Formula I or which may be transformed to such a grouping either before or after the assembly of the triazole ring system. Such transformations may involve protection and/or deprotection, formation of the "X" linkage between the two aromatic rings as shown in Formula I, or other modifications. It is also to be understood that in most of the Reaction Schemes, the "ArCH₂" (Ar=aryl) substituent may be replaced by the homologous "Ar(CH₂)₂" group as consistent with the definition of Formula I.

It is further to be understood that in the generalized schemes below, unless specified otherwise, the R, R' and R" groups represent functionalized or unfunctionalized alkyl, aryl, heteroaryl, aralkyl, and the like, while Ar' represents a functionalized or unfunctionalized aryl or heteroaryl group. The moiety, R'X, represents an alkylating agent in which R' is typically a functionalized or unfunctionalized alkyl or aralkyl group, while X is a leaving group such as chloro, bromo, iodo, methanesulfonate, or p-toluenesulfonate. In structures showing an "X" group double-bonded to a carbon atom (as in 22 and products derived therefrom), X is O or S.

REACTION SCHEME 1

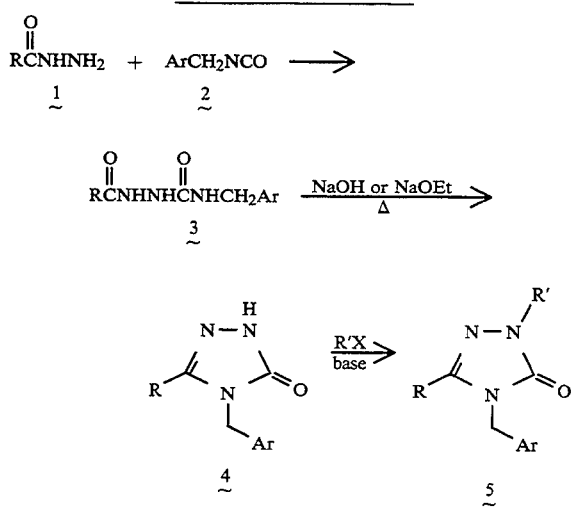

One of the most widely used routes to 2,4,5-trisubstituted-2,4-dihydro-3H-1,2,4-triazol-3-ones ("triazolinones") is shown in Reaction Scheme 1 in its adaptation for the synthesis of compounds of Formula I. Reaction of a carboxylic acid hydrazide 1 (readily obtained from the corresponding ester) with the appropriate arylmethyl isocyanate 2 gives the 1-acyl-4-(arylmethyl)-semicarbazide 3. The isocyanate 2 itself is obtainable by well-known methods from various sources, including the (arylmethyl)amine (by phosgene treatment), the arylmethyl halide (by treatment with cyanate anion), and the arylacetic acid or derivative (via Curtius rearrangement of the acyl azide). Upon heating in the presence of hydroxide or alkoxide, cyclization of 3 to the triazolinone 4 occurs. Finally, in the presence of a base (e.g., sodium hydride, sodium ethoxide, sodium hydroxide, or potassium carbonate), 4 is converted to the trisubstituted triazolinone 5 on treatment with a suitable alkylating agent R'X, where R' is alkyl, aralkyl, etc., and X is bromo, iodo, chloro, methanesulfonate, p-toluenesulfonate, and the like. Such reaction pathways have been described by D. L. Temple, Jr., and W. G. Lobeck, Jr., U.S. Pat. No. 4,487,773 (1984), R. E. Gammans, D. W. Smith, and J. P. Yevich, U.S. Pat. No. 4,613,600 (1986), and (in part) H. Gehlen and W. Schade, Liebigs Ann. Chem., 675, 180 (1964), G. Palazzo, U.S. Pat. No. 3,857,845 (1974), and K. H. Hauptmann and K. Zeile, British Patent 971,606 (1964). A modified approach to an intermediate of type 3 and its subsequent cyclization to a triazolinone analogous to 4 have been reported by H. Hrebabecky and J. Beranek, Collect, Czech. Chem. Commun., 50, 779 (1985).

REACTION SCHEME 2

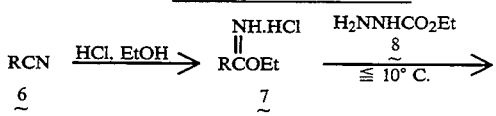

-continued
REACTION SCHEME 2

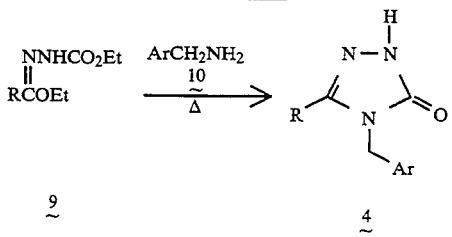

A highly useful alternative route to 4 is shown in Reaction Scheme 2. This approach has been described by M. Pesson, S. Dupin, and M. Antoine, Compt. Rend., 253, 285 (1961) and R. Un and A. Ikizler, Chim. Acta Turc., 3, 113 (1975). Addition of ethyl carbazate (8) to the imidate 7 (which is readily prepared from the corresponding nitrile 6) yields an adduct 9, which can be converted to the triazolinone 4 on heating with the (arylmethyl)amine 10 (typically at temperatures from 70°–150° C.). As in Reaction Scheme 1, 4 can be alkylated to give the trisubstituted triazolinone 5.

REACTION SCHEME 3

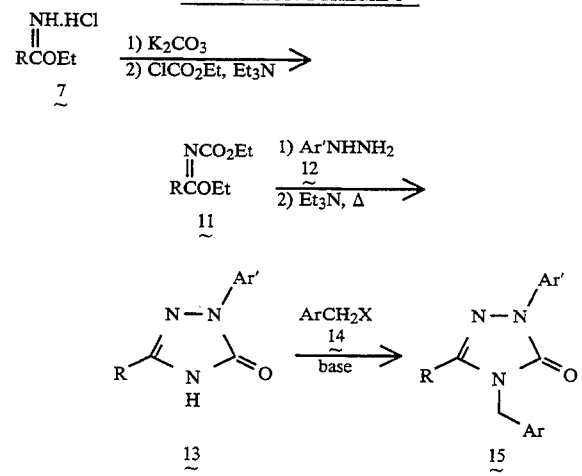

The procedures of Reaction Schemes 1 and 2 are not suitable for the introduction of most aryl or heteroaryl substituents at $N^2$. In contrast, the procedures of Reaction Schemes 3 to 6 are especially well suited for the synthesis of compounds of Formula I having aryl or heteroaryl substituents at $N^2$, since the triazolinone ring is constructed with the $N^2$-substituent in place, whereas the $N^4$-substituent is introduced subsequently by alkylation. Reaction Scheme 3 presents a route patterned after that reported by K. Yabutani, K. Taninaka, M. Kajioka, K. Takagi, H. Matsui, K. Sutoh, and M. Yamamoto, European Patent Application 220,952 (1987). The N-carbethoxy imidate 11 (obtained by reaction of 7 with ethyl chloroformate) is treated with an arylhydrazine 12 (or analog), typically at about 40°–50° C. Without isolation of the intermediate, further heating at elevated temperature (usually in the range of 90°–150° C.) in the presence of a tertiary amine such as triethylamine effects cyclization to the triazolinone 13. In the presence of a suitable base (e.g., sodium hydride, sodium alkoxide, sodium hydroxide) treatment of 13 with the appropriate ArCH₂X, where X=bromo, iodo, chloro, methanesulfonate, p-toluenesulfonate, and the like, yields the N[4]-alkylated product 15. A variant of the method using a thioimidate has been described by M. Kajioka, H. Kurono, K. Okawa, and M. Harada, U.S. Pat. No. 4,318,731 (1982).

REACTION SCHEME 4

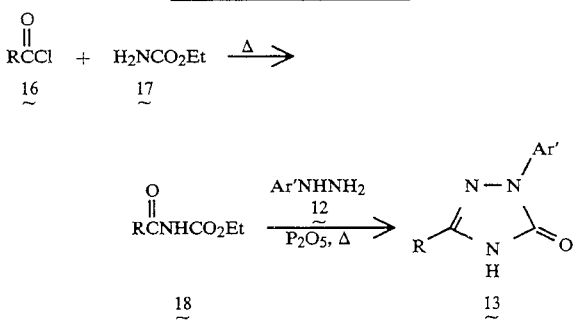

An alternative route to the N[2]-substituted triazolinone intermediate 13 is shown in Reaction Scheme 4. This chemistry has been described by T. N. Ghosh and M. V. Betrabet, *J. Indian Chem. Soc.*, 7, 899 (1930), S. Bellioni, *Ann. Chim. (Rome)*, 52, 187 (1962), G. Palazzo and G. Picconi, *Boll. Chim. Farm.*, 105, 217 (1966), and British Patent 1,021,070 (1966). An acid chloride 16 is heated with urethane (17) (typically at 80°–100° C.), to give the acylurethane 18. Reaction of 18 with an arylhydrazine 12 and phosphorus pentoxide (usually in toluene or xylene at reflux) gives 13, which can then be further alkylated on N[4] as in Reaction Scheme 3. A (thioacyl-)urethane modification of this pathway has been reported by D. L. Temple, Jr., and W. G. Lobeck, Jr., U.S. Pat. No. 4,487,773 (1984).

REACTION SCHEME 5

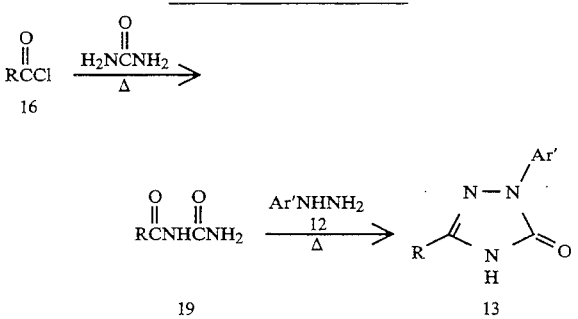

A variation of Reaction Scheme 4, shown in Reaction Scheme 5, has been described by P. Gold-Aubert, D. Melkonian, and L. Toribio, *Helv. Chim. Acta*, 47, 1188 (1964) and A. L. Langis, U.S. Pat. No. 3,499,000 (1970). The readily prepared acylurea 19 upon heating with an arylhydrazine 12 (at about 150°–200° C.) is converted to the triazolinone intermediate 13.

REACTION SCHEME 6

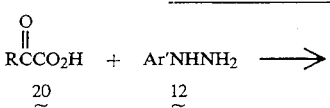

-continued
REACTION SCHEME 6

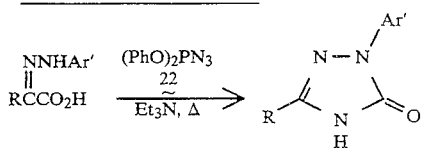

In a quite different approach (Reaction Scheme 6), L. Maravetz, U.S. Pat. No. 4,705,557 (1987) and G. Theodoridis, International Patent Application WO87/03782 (1987) disclose condensing an α-keto acid 20 with the arylhydrazine 12 to give derivatives such as 21, which can be converted to the triazolinone intermediate 13 by heating with diphenylphosphoryl azide and triethylamine (typically at 75°–115° C.). In the last step, an intermediate acyl azide loses nitrogen and undergoes the Curtius rearrangement to an isocyanate, which undergoes ring closure. As shown in Reaction Scheme 3, 13 can then be alkylated on N[4] to give the trisubstituted triazolinone 15.

REACTION SCHEME 6A

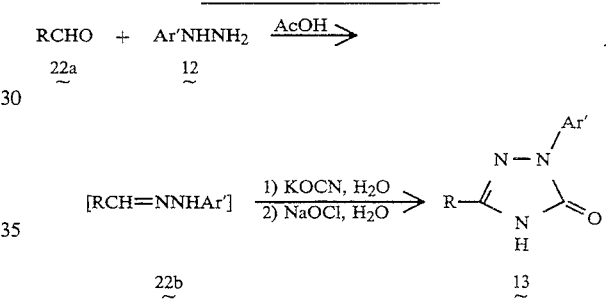

Still another route to N[2]-aryl triazolinone intermediates of structure 13 is illustrated in Reaction Scheme 6A. In this method [G. Theodoridis and J. W. Lyga, International Patent Application WO91/03470 (1991)], an aldehyde 22a is reacted with the arylhydrazine 12 in glacial acetic acid. The intermediate hydrazone 22b may either be isolated or treated directly in the same pot with aqueous potassium cyanate. The aryl triazolidinone thus formed is again frequently not isolated but rather treated directly with an aqueous sodium hypochlorite solution, resulting in oxidation to the triazolinone 13.

REACTION SCHEME 6B

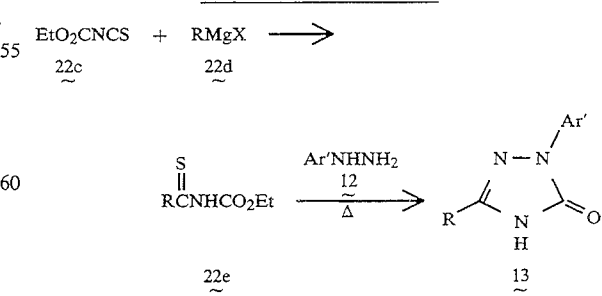

The triazolinone intermediate 13 can also be made according to reaction Scheme 6B [B. George and E. P. Papadopoulos, *J. Org. Chem.*, 41, 3233 (1976); R. E.

Manning, D. B. Reitz, and H.-C. Huang, PCT Patent Appl. WO 91/18888 (1991)]. Ethoxycarbonyl isothiocyanate (22c) is reacted with an alkylmagnesium halide 22d (typically in ether at about −50° C. to room temperature). The resulting N-(ethoxycarbonyl) thioamide 22e is heated with arylhydrazine 12 (for example, in ethanol or 2-methoxyethanol at reflux) to yield the triazolinone 13.

with the isocyanate or isothiocyanate 22 to yield the 1-acyl-2,4-disubstituted-semicarbazide or -thiosemicarbazide 29. Cyclization of 29 upon heating with hydroxide or alkoxide affords the triazolinone or triazolinethione 30. This chemistry has been described by H. Gehlen and W. Schade, *Liebigs Ann. Chem.*, 675, 180 (1964).

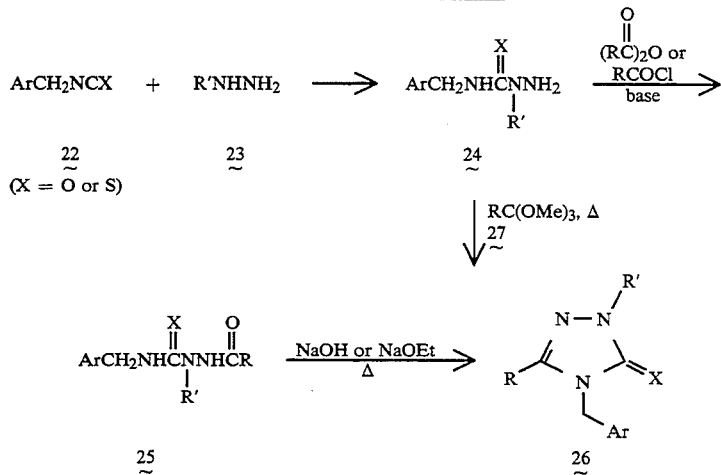

2,4,5-Trisubstituted-2,4-dihydro-3H-1,2,4-triazole-3-thiones ("triazolinethiones") cannot generally be prepared by routes analogous to those in Reaction Schemes 1 to 6 because of the propensity for alkylation to occur on sulfur rather than on the open ring nitrogen. It is thus preferable to have all of the substituents in place at the time of the ring closure to form the heterocycle. As shown in Reaction Scheme 7, for certain R' groups (e.g., R'=CH₃), reaction of the hydrazine derivative 23 with the appropriate isocyanate or isothiocyanate 22 yields the 2,4-disubstituted semicarbazide or thiosemicarbazide 24. Acylation of 24 gives 25, which can be cyclized upon heating with hydroxide or alkoxide to give the trisubstituted triazolinone or triazolinethione 26. This approach has been detailed by J. M. Kane and F. P. Miller, U.S. Pat. No. 4,775,688 (1988) and G. F. Duffin, J. D. Kendall, and H. R. J. Waddington, *J. Chem. Soc.*, 3799 (1959). Alternative methods of ring closure, such as heating 24 with the orthoester 27, can also be utilized.

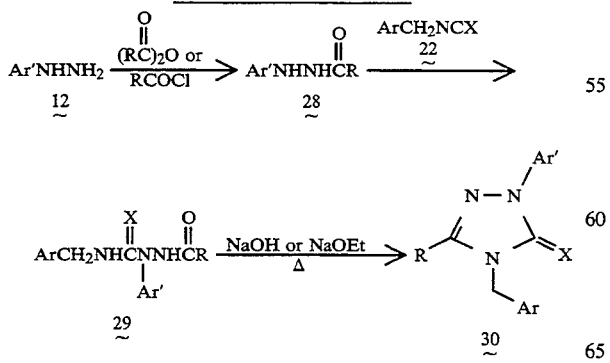

In Reaction Scheme 8, acylation of an aryl- or heteroaryl hydrazine gives 28, which can be reacted

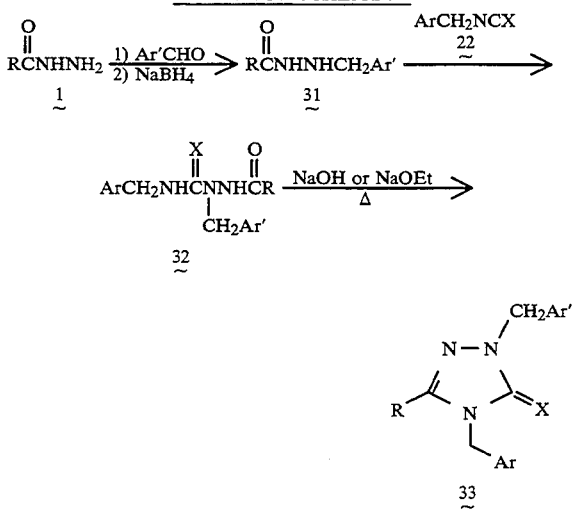

The method of F. Russo, M. Santagati, and G. Pappalardo [*Ann. Chim. (Rome)*, 62, 351 (1972)] (Reaction Scheme 9) is useful for the synthesis of trisubstituted triazolinones and triazolinethiones having benzylic substituents at N². Treatment of a hydrazide 1 with an aromatic or heteroaromatic aldehyde followed by reduction with sodium borohydride gives the substituted hydrazide 31. Reaction of 31 with the isocyanate or isothiocyanate 22 affords the semicarbazide or thiosemicarbazide derivative 32, which is cyclized to the triazolinone or triazolinethione 33 upon heating with hydroxide or alkoxide.

REACTION SCHEME 10

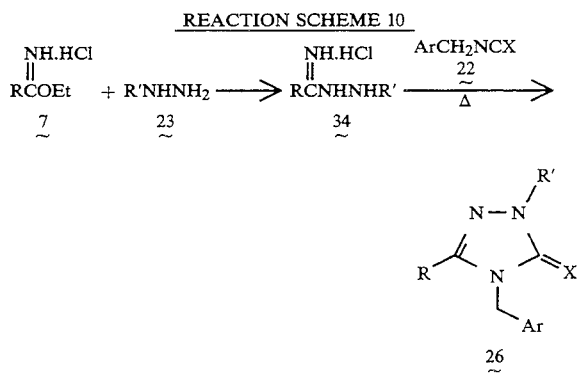

In another approach (Reaction Scheme 10), imidate 7 is treated with a substituted hydrazine 23 (especially an aryl or heteroaryl hydrazine) to give the amidrazone 34. Heating 34 with the isocyanate or isothiocyanate 22 gives the triazolinone or triazolinethione 26. Syntheses of this type have been reported by M. Santus, *Acta Pol. Pharm.*, 37, 293 (1980); T. Bany, *Rocz. Chem.*, 42, 247 (1968); and, T. Bany and M. Dobosz, *Ann. Univ. Mariae Curie-Sklodowska, Sect. AA,* 26/27, 23 (1971).

REACTION SCHEME 11

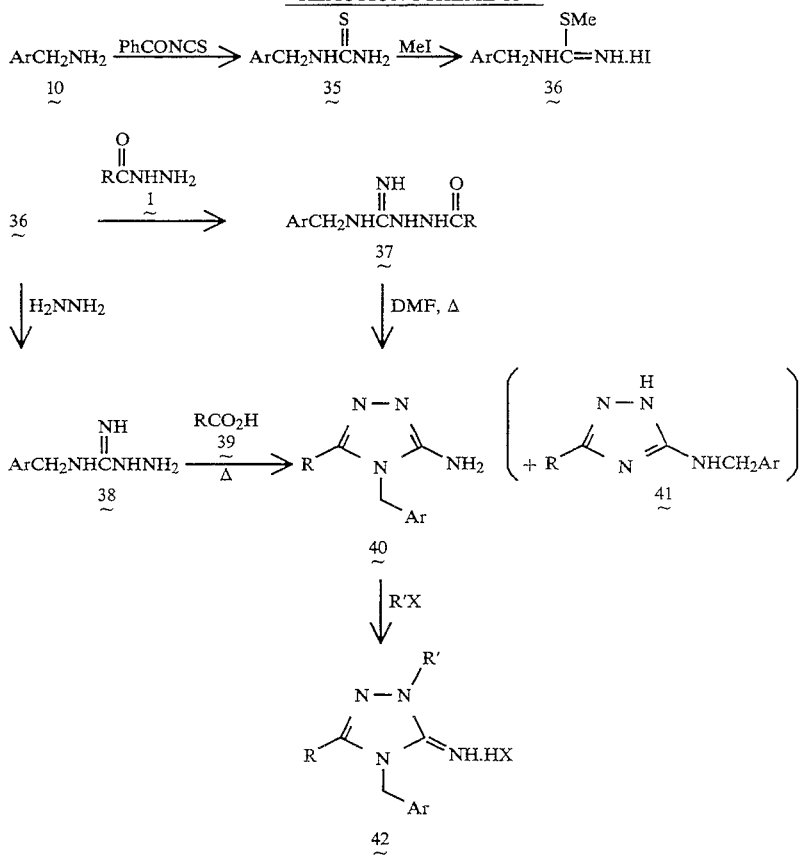

A route to 2,4,5-trisubstituted-2,4-dihydro-3H-1,2,4-triazol-3-imines ("triazolinimines") is outlined in Reaction Scheme 11. Reaction of the (arylmethyl)amine 10 with benzoyl isothiocyanate (or by other means) gives the substituted thiourea 35, which is methylated to prepare the isothiourea derivative 36. Compound 36 can be transformed to the acylaminoguanidine 37 by reacting with the hydrazide 1 or to the aminoguanidine 38 by reacting with hydrazine. Ring closure of 37 by heating in DMF or cyclization of 38 with carboxylic acid 39 at elevated temperature affords the aminotriazole 40, which can be separated from the isomer 41. Such pathways have been described by G. J. Durant, G. M. Smith, R. G. W. Spickett, and S. H. B. Wright, *J. Med. Chem.*, 9, 22 (1966) and E. Akerblom, *Acta Chem. Scand.*, 19, 1135 (1965). Finally, alkylation of 40 with the appropriate R'X (where X is a leaving group such as iodo, bromo, chloro, p-toluenesulfonate, or methanesulfonate) leads to the triazolinimine 42, which can be separated from any other isomers or by-products formed during the reaction. This method has been described by E. B. Akerblom and D. E. S. Campbell, *J. Med. Chem.*, 16, 312 (1973).

REACTION SCHEME 12

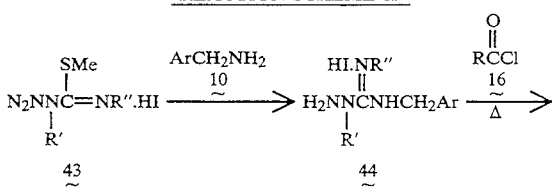

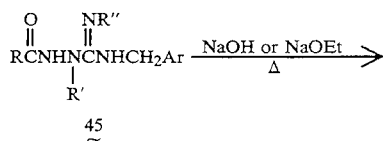

-continued
REACTION SCHEME 12

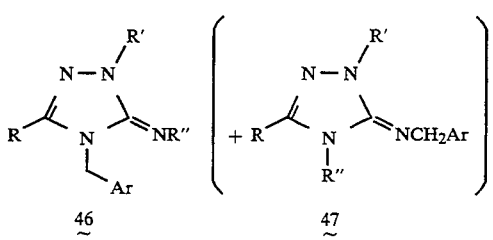

The route shown in Reaction Scheme 12 utilizes chemistry reported by E. Akerblom, *Acta Chem. Scand.*, 19., 1135 (1965). The substituted isothiourea 43 is treated with amine 10 to give the aminoguanidine derivative 44. Acylation of 44 with the acid chloride 16 provides the intermediate 45, which can be cyclized by heating with hydroxide or alkoxide. The desired triazolinimine 46 is separated from the isomeric product 47.

REACTION SCHEME 12A

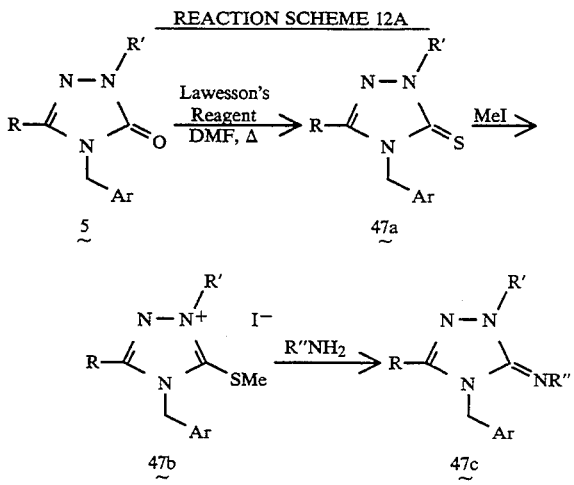

Reaction scheme 12A shows the conversion of triazolinone 5 to the triazolinethione 47a upon heating with Lawesson's Reagent [2,4-bis(4-methoxyphenyl)-1,3-dithia-2,4-phosphetane-2,4-disulfide] [S. O. Lawesson and B. S. Pedersen, Tetrahedron, 35, 2433 (1979)], preferably in a solvent such as DMF at reflux. Alkylation of 47a with methyl iodide (may be conducted with heating at about 50°–150° C. in a pressure vessel) yields the S-methyltriazolium iodide 47b [see S. D. Ziman, *J. Heterocycl. Chem.*, 17, 1319 (1980) for similiar reaction]. Alternatively, the alkylation can be run at lower temperature with a more reactive alkylating agent, such as trimethyloxonium tetrafluoroborate. Reaction of 47b with an excess of an amine (R"NH$_2$) furnishes the triazolinimine 47c. For volatile amines, this reaction may be carried out by heating 47b with the anhydrous amine in a pressure vessel. Optimally, the methylthio group of 47b may be converted to an even better leaving group by oxidation to the sulfoxide or sulfone with m-chloroperbenzoic acid prior to treatment with the amine, R"NH$_2$.

REACTION SCHEME 13

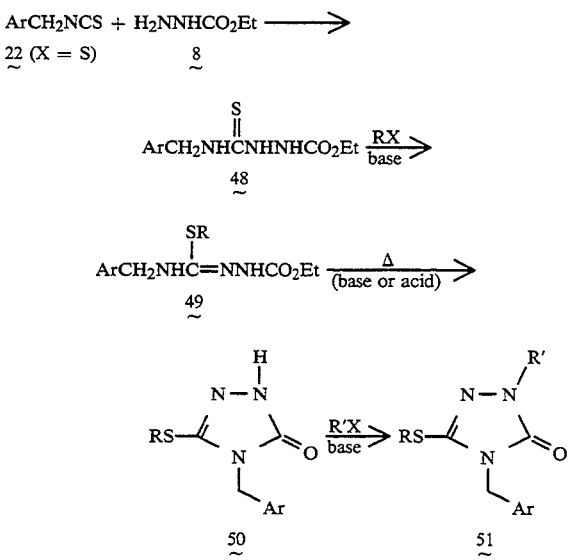

For the synthesis of compounds of formula (I) wherein E=—S—, Reaction Schemes 13 and 14 may be utilized. In Reaction Scheme 13, the isothiocyanate 22 is reacted with ethyl carbazate (8) to give the 1-(carbethoxy)thiosemicarbazide 48. By standard conditions, 48 is S-alkylated to yield 49, which can be cyclized to the triazolinone 50 by heating, optionally in the presence of base or acid [F. Kurzer and D. R. Hanks, *Chem. Ind. (London)*, 1143 (1966)]. Finally, alkylation of the triazolinone as in Reaction Scheme 1 provides the fully substituted product 51.

REACTION SCHEME 14

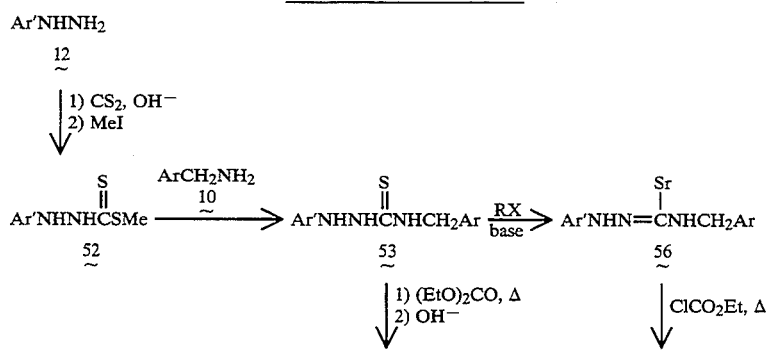

REACTION SCHEME 14

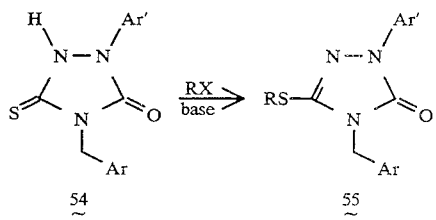

Following the chemistry of K. Sasse [*Liebigs Ann. Chem.*, 735, 158 (1970)](Reaction Scheme 14), an arylhydrazine 12 is treated with carbon disulfide in the presence of base followed by treatment with methyl iodide to give the dithiocarbamoyl derivative 52. Reaction of 52 with the (arylmethyl)amine 10 yields the 1,4-disubstituted thiosemicarbazide 53. Cyclization of 53 to 54 is accomplished in two steps by first heating with diethyl carbonate and then treating with hydroxide to induce ring closure. Further treatment of 54 with an alkyl halide gives the desired S-alkyl triazolinone 55. A modification allowing the synthesis of compounds analogous to 55 in which the "Ar" substituent is replaced by an alkyl (or aralkyl) group has also been described by Sasse (see reference above). In a variation [method of A. Dornow and H. Paucksch, *Chem. Ber.*, 99, 85 (1966)], 53 may be first S-alkylated to give 56, which can be cyclized to 55 upon heating with ethyl chloroformate.

REACTION SCHEME 15

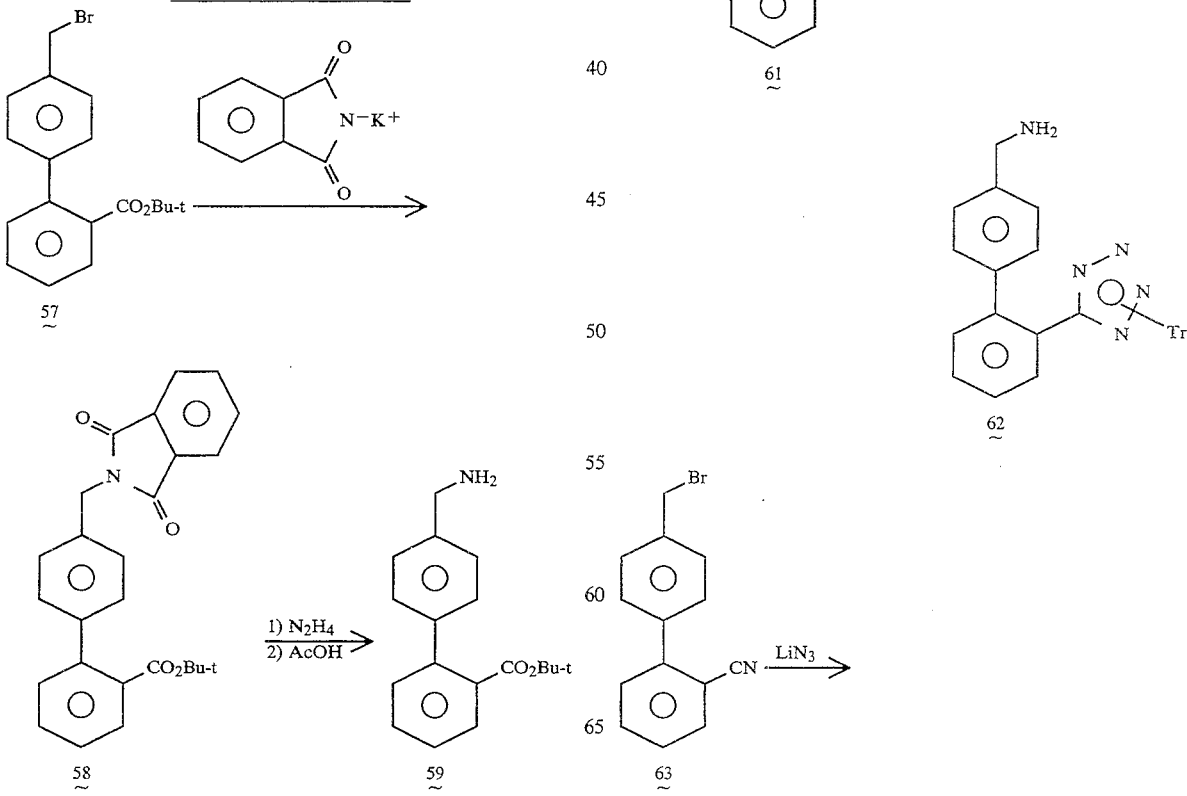

-continued
REACTION SCHEME 15

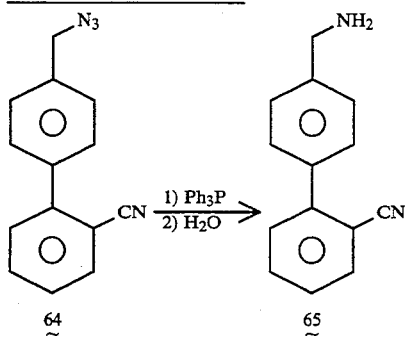

Reaction Scheme 15 shows routes to key intermediates used for incorporation of a (2'-carboxybiphenyl-4-yl)methyl or [2'-(5-tetrazolyl)biphenyl-4-yl]methyl substituent into a 2,4-dihydro-3H-1,2,4-triazol-3-one or -triazole-3-thione at the 4-position. One starting material, 4-bromomethyl-2'-(t-butoxycarbonyl)biphenyl (57), can be prepared as described in European Patent Application 253,310 (or as modified in U.S. application Ser. No. 351,508, filed 15 May 1989. Treatment of 57 with potassium phthalimide at room temperature in a suitable solvent such as N,N-dimethylformamide gives the phthalimido product 58, which is converted to the amine 59 by a standard hydrazinolysis procedure. Alternatively, using the methods described in European Patent Application 253,310, 57 may be treated with sodium azide in dimethylformamide, and the resulting azide intermediate may be reduced to the amine 59 by hydrogenation in the presence of palladium catalyst or by other methods known in the literature. After conversion of 57 or 59 to a triazolinone, triazolinethione, or triazolinimine by methods illustrated in the previous schemes, the t-butyl ester is readily deprotected by treatment with trifluoroacetic acid at room temperature.

Transformation of 5-[4'-(bromomethyl)biphenyl-2-yl]-N-trityltetrazole (60) (prepared as in European Patent Application 291,969 or as modified in U.S. application Ser. No. 351,508, filed 15 May 1989 to the azido intermediate 61 is accomplished by standard means such as treatment with lithium azide in dimethyl sulfoxide at room temperature. Reduction of 61 to the amine 62 proceeds readily using the conditions of M. Vaultier, N. Knouzi, and R. Carrie [*Tetrahedron Lett.*, 24, 763 (1983)] (triphenylphosphine in tetrahydrofuran followed by water). By use of the methods outlined in previous schemes, 60 or 62 can be converted to a triazolinone, triazolinethione, or triazolinimine. Removal of the trityl protecting group from the tetrazole is achieved by warming in aqueous acetic acid.

Alternatively, 4-bromomethyl-2'-cyanobiphenyl (63) (described in European Patent Application 253,310) can be converted to the azide intermediate 64 as disclosed in U.S. patent application Ser. No. filed (attorney docket No. 17960, submitted for filing Jul. 17, 1989). Reduction of 64 by the method described above for the synthesis of 62 gives the amine 65. After conversion of 63 or 65 to a triazolinone, triazolinethione, or triazolinimine by methods illustrated in the previous schemes, the cyano substituent may be converted to the desired 5-tetrazolyl group by reaction with trimethyltin azide at elevated temperature in a suitable solvent such as toluene or xylene according to methods described in European Patent Application 291,969. Final destannylation to the free tetrazole may be accomplished by treatment with silica gel as described in U.S. patent application Ser. No. 382,138, filed Jul. 19, 1989.

Although specific examples have been shown for the synthesis of compounds of formula (I) wherein X is a single bond, these methods are readily extended to the preparation of compounds of formula (I) having other X linkages allowed by the specifications. Depending on the nature of X, this linkage may be constructed either before or after assembly of the triazole ring. The construction of heterocyclic side chains analogous to the $N^4$ side chain of compounds of formula (I), in which variations of the X group are exemplified, has been disclosed in U.S. patent applications Ser. Nos. 351,508, filed May 15, 1989, 382,138, filed Jul. 19, 1989 and European Patent Application 253,310.

REACTION SCHEME 16

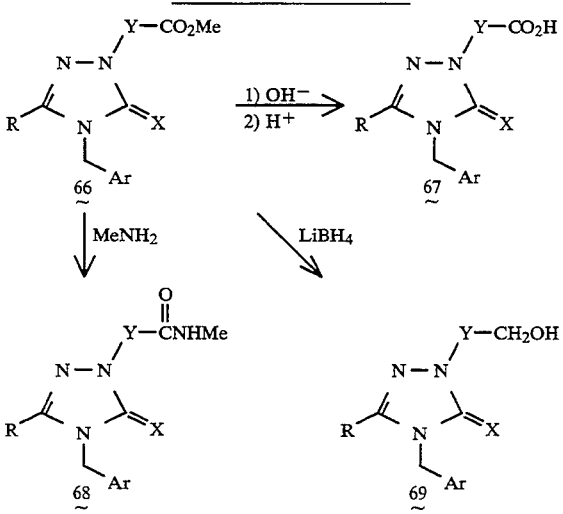

wherein:

Y represents an alkyl, aryl, heteroaryl, or aralkyl group bearing the designated substituent (i.e., carbomethoxy, carboxy, etc.)

Further transformations of substituent functional groups can be carried out after assembly of the triazole ring and either before or after full elaboration of the arylmethyl substituent at $N^4$. Typical examples are shown in Reaction Scheme 16. Thus the methyl ester of 66 can be saponified by treatment with aqueous sodium hydroxide (optionally in the presence of a cosolvent such as alcohol, tetrahydrofuran, or dioxane) at room temperature to give, after acidification, the acid 67. The N-methyl amide 68 is readily obtained by reaction of 66 with excess aqueous methylamine at room temperature in the presence of a cosolvent such as methanol. Reduction of the methyl ester 66 to the alcohol 69 can be accomplished by treatment with lithium borohydride in a solvent such as tetrahydrofuran. These examples are in no way exclusive of other functional group transformations which can be accomplished after formation of the triazolinone, triazolinethione, or triazolinimine system, and which will be apparent to anyone skilled in the art.

REACTION SCHEME 17

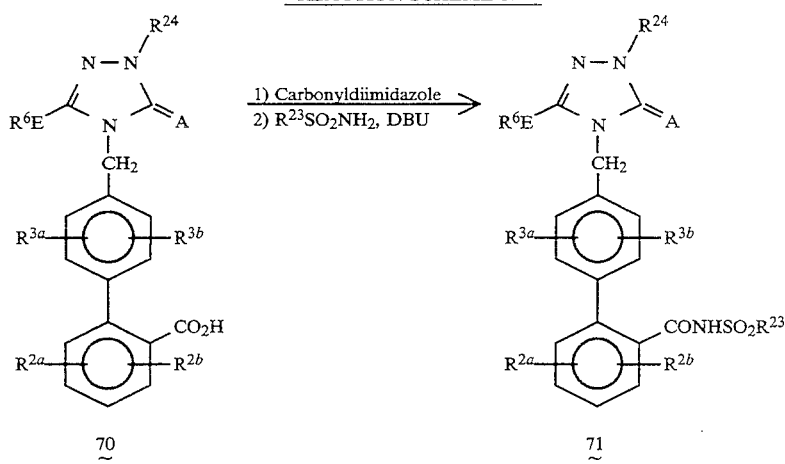

Alternative Methods:
- a) (i) $SOCl_2$, $\Delta$ (ii) $R^{23}SO_2NH^-M^+$ (where M is Na or Li)
- b) (i) $(COCl)_2/DMF, -20°$ C. (ii) $R^{23}SO_2NH^-M^+$
- c) (i) N-(N,N-Diphenylcarbamoyl)pyridinium chloride/aq. NaOH (ii) $R^{23}SO_2NH^-M^+$.

Compounds of formula (I) wherein $R^1$ is —CONHSO$_2R^{23}$ (where $R^{23}$ is substituted or unsubstituted alkyl, aryl, or heteroaryl) may be prepared from the corresponding carboxylic acid derivatives (70) as outlined in Reaction Scheme 17. The carboxylic acid 70, obtained as described in Reaction Scheme 15 and preceding schemes (followed by deprotection of the t-butyl ester with trifluoroacetic acid), can be converted into the corresponding acid chloride by treatment with thionyl chloride at reflux or, preferably, with oxalyl chloride and a catalytic amount of dimethylformamide at low temperature [A. W. Burgstahler, et al., *Synthesis*, 767 (1976)]. The acid chloride can then be treated with the alkali metal salt of $R^{23}SO_2NH_2$ to form the desired acylsulfonamide 71. Alternatively, 71 may be prepared from 70 using N,N-diphenylcarbamoyl anhydride intermediates [F. J. Brown, et al., European Patent Application EP 199,543; K. L. Shepard and W. Halczenko, *J. Heterocycl. Chem.*, 16, 321 (1979)]. Preferably, the carboxylic acid 70 is treated with carbonyldiimidazole to give an acyl-imidazole intermediate, which can then be treated with an appropriate aryl- or alkylsulfonamide in the presence of 1,8-diazabicyclo[5.4.0]undec-7-ene (DBU) to give the desired acylsulfonamide 71.

SCHEME 18

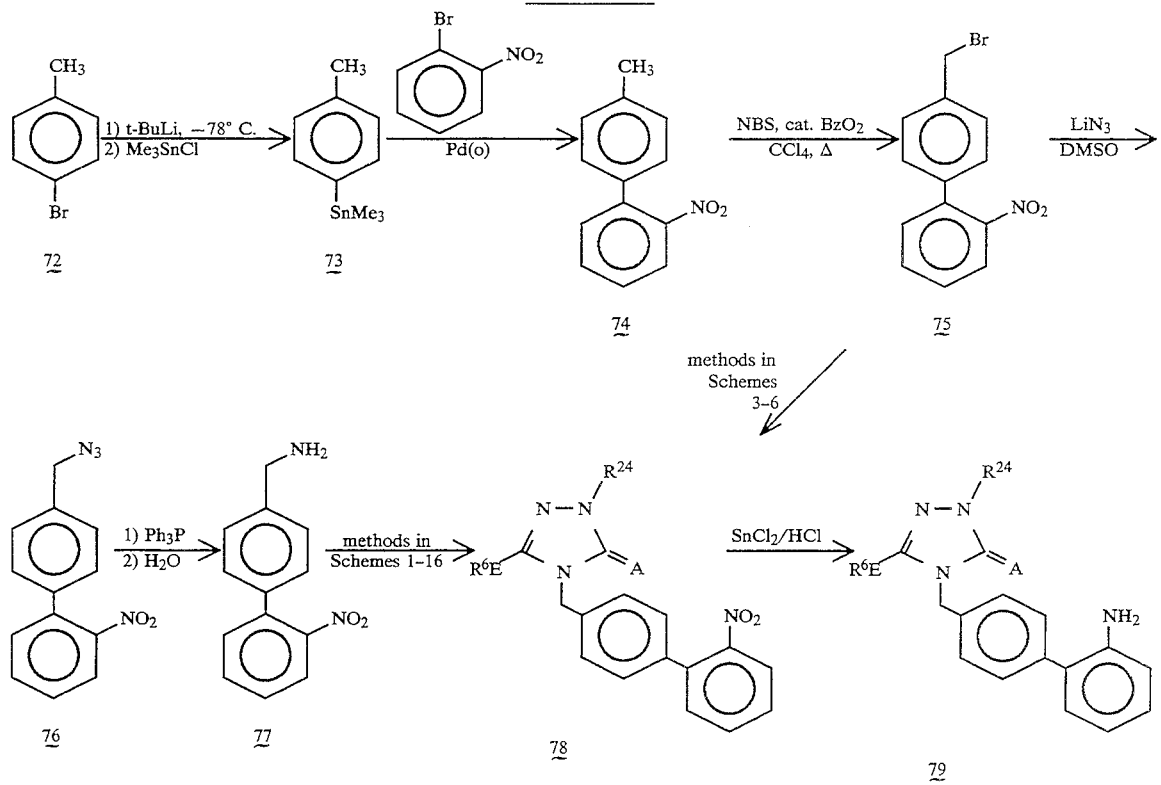

5,411,980
SCHEME 18 -continued
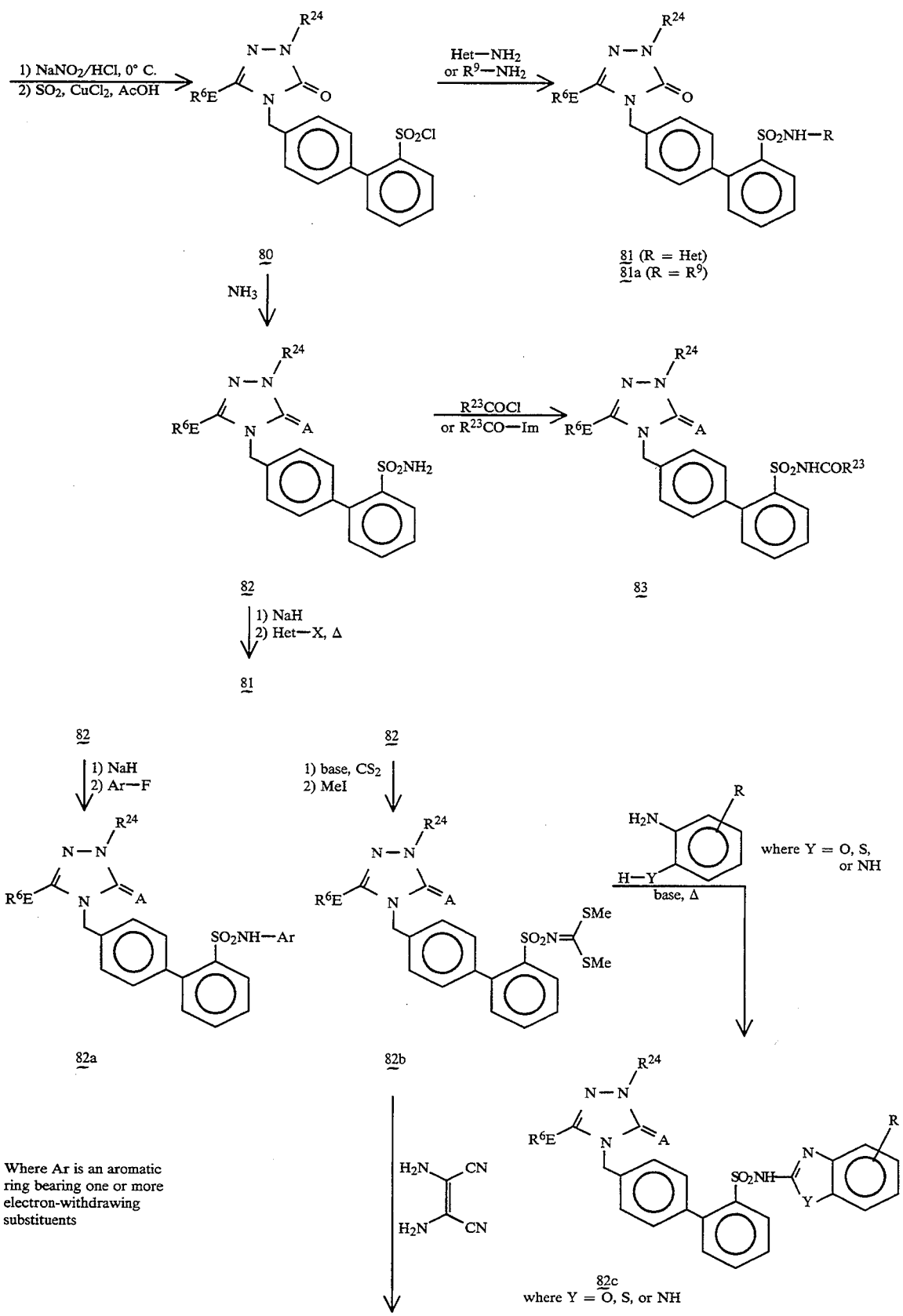
Where Ar is an aromatic ring bearing one or more electron-withdrawing substituents
82c where Y = O, S, or NH -continued
SCHEME 18

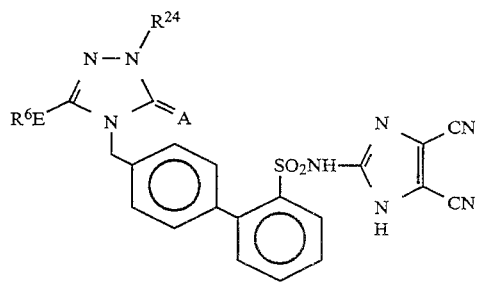

83d where
NBS = N-bromosuccinimide
Bz = benzoyl
Het = heteroaryl
Im = 1-imidazolyl.

The preparation of compounds of formula (I) wherein $R^1$ is —SO₂NH-heteroaryl, —SO₂NH-$R^9$ or —SO₂NHCOR²³ is outlined in Reaction Scheme 18. p-Bromotoluene (72) is converted to the trimethylstannane derivative 73 [S. M. Moerlein, *J. Organometal. Chem.*, 319, 29 (1987)], which may be coupled with o-bromonitrobenzene in the presence of (Ph₃P)₄Pd or (Ph₃P)₂PdCl₂ catalyst to give the biphenyl derivative 74. Such couplings have been described by J. K. Stille, *Pure Appl. Chem.*, 57, 1771 (1985); T. R. Bailey, *Tetrahedron Lett.*, 27, 4407 (1986); and D. A. Widdowson and Y-Z. Zhang, *Tetrahedron*, 42, 2111 (1986). Bromination of 74 with N-bromosuccinimide in the presence of catalytic benzoyl peroxide gives 75, which upon treatment with lithium azide in DMSO yields the azido derivative 76. Reduction of 76 to the amine 77 may be accomplished by treatment with triphenylphosphine followed by water. In an alternative route, the bromo group of 75 may be displaced by potassium phthalimide. Hydrazinolysis of the phthalimide derivative yields 77.

By the methods described in the previous schemes, the amine 77 can be converted to a variety of triazolinones, triazolinethiones, and triazolinimines of the general formula 78. Certain triazolinones, especially those in which B is aryl or heteroaryl, may be made directly from 75 by alkylation of a pre-formed triazolinone as in Reaction Schemes 3–6. Reduction of the nitro group of 78, preferably with stannous chloride/hydrochloric acid gives the amino derivative 79. Diazotization of the amine 79. and reaction of the diazonium salt with sulfur dioxide in the presence of cupric chloride affords the corresponding arylsulfonyl chloride 80 [see H. Meerwein, et al., *Chem. Ber.*, 90, 841 (1957); A. J. Prinsen and H. Cerfontain, *Rec. Trav. Chim.*, 84, 24 (1965); E. E. Gilbert, *Synthesis*, 3 (1969); and references cited therein]. Treatment of the sulfonyl chloride 80 with an appropriate heteroaryl amine provides the N-heteroaryl sulfonamide 81. Similar treatment with R⁹-NH₂ yields a substituted sulfonamide of structure 81a. Reaction of the sulfonyl chloride with ammonia yields the sulfonamide 82, which is then treated with an appropriate acylating agent (such as an acid chloride, a carbamoyl chloride, or an acyl-imidazole derivative) to give the acyl-sulfonamide product 83. The reaction is generally conducted in the presence of a base such as pyridine (may be used as solvent) or DBU (in a solvent such as THF). Alternatively, the sulfonamide 82 may be deprotonated with a strong base such as sodium hydride prior to the acylation. For the synthesis of 83 wherein $R^{23}$ is —NHR²¹, the carbamoylating reagent may be an isocyanate of the formula R²¹NCO.

N-Heteroarylsulfonamides of structure 81 may also be prepared from the sulfonamide 82 by deprotection with sodium hydride followed by heating with a compound of the type Het-X, where X is an appropriate leaving group such as Cl. Reactions of this type have been described by H. Bretschneider, J. Dehler, and W. Klotzer, *Monatsh. Chem.*, 95, 207 (1964). Similarly, a subclass of structure 81a wherein $R^9$ is an aryl group bearing one or more electron-withdrawing substituents may be prepared from 82. Thus, treatment of 82 with sodium hydride in DMF followed by reaction with an appropriate aryl fluoride (such as 4-fluoronitrobenzene), generally at 50°–150° C., yields the N-arylsulfonamide 82a Certain N-heterocyclylsulfonamides may also be obtained by use of the chemistry developed by Merchan [E. Melendez, F. L. Merchan, P. Merino, J. Orduna and R. Urchegui, *J. Heterocycl. Chem.*, 28, 653 (1991); F. L. Merchan, J. Garin, and T. Tejero, *Synthesis*, 984 (1982)]. By these methods, the sulfonamide 82 is deprotonated with sodium hydride in DMF and treated first with carbon disulfide at room temperature and then with methyl iodide at 0° C. to give the bis(methylthio)methylene derivative 82b. This intermediate can be reacted with an o-aminophenol, an o-aminothiophenol, or an o-phenylenediamine (typically in DMF at 100°–150° C. and optionally in the presence of a base) to give a benzoxazol-2-yl, benzothiazol-2-yl, or benzimidazol-2-yl derivative 82c. Similarly, heating 82b with diaminomaleonitrile (optionally in the presence of base) yields the 4,5-dicyanoimidazol-2-yl derivative 82d. In a variation of the procedure, 82b is first treated with a solution of chlorine in acetic acid at 15° C. to give a dichloromethylene derivative, which is similarly convertible to 82c and 82d but under somewhat milder conditions.

SCHEME 19

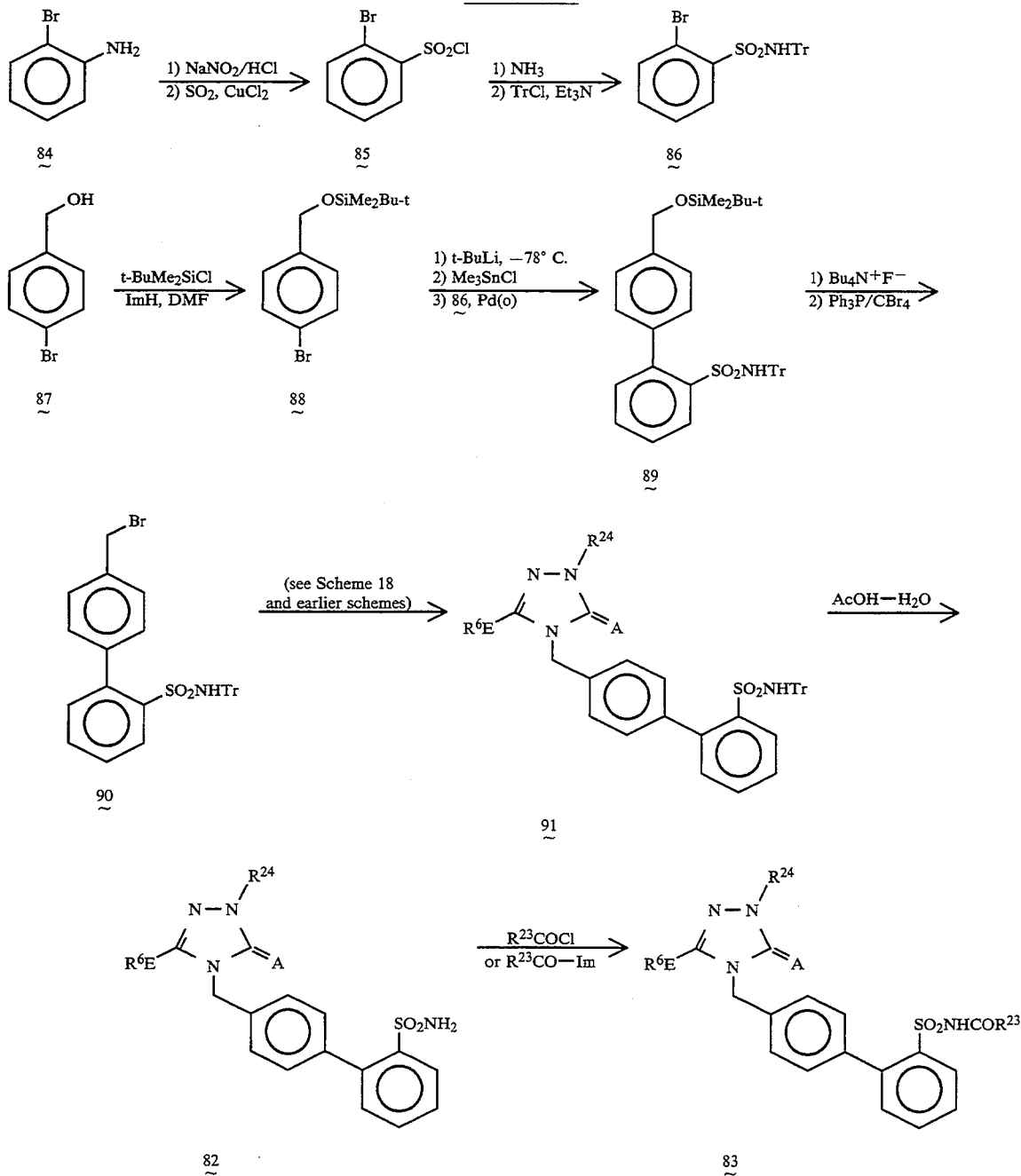

wherein:
Tr = trityl (i.e. triphenylmethyl)
Im = 1 - imidazolyl.

Reaction Scheme 19 shows an alternative sequence leading to 83 in which a protected sulfonamide is present at the time of the biaryl coupling. By the methods described above, o-bromoaniline (84) is converted to the corresponding sulfonyl chloride 85. Treatment of 85 with ammonia and then with trityl chloride in the presence of triethylamine yields the N-trityl sulfonamide 86. p-Bromobenzyl alcohol (87) is t-butyldimethylsilylated, and the resulting 88 is coupled with 86 under the conditions described above to give the biphenyl product 89. The silyl group is removed with tetrabutylammonium fluoride, and treatment of the alcohol with triphenylphosphine/carbon tetrabromide gives the bromo derivative 90. Using the methods of Scheme 18 and earlier schemes, 90 may be transformed into a variety of triazoles of the general formula 91. The trityl protecting group is removed with aqueous acetic acid to give the free sulfonamide 82 which is acylated to yield the target 83 as in Scheme 18.

SCHEME 20

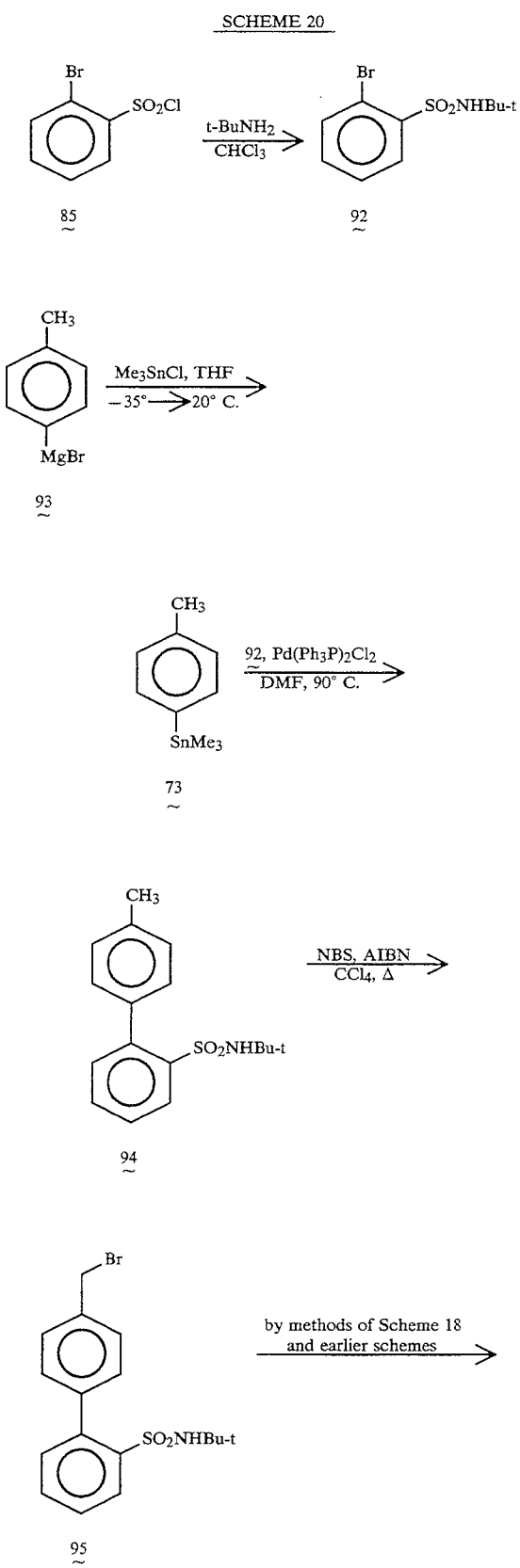

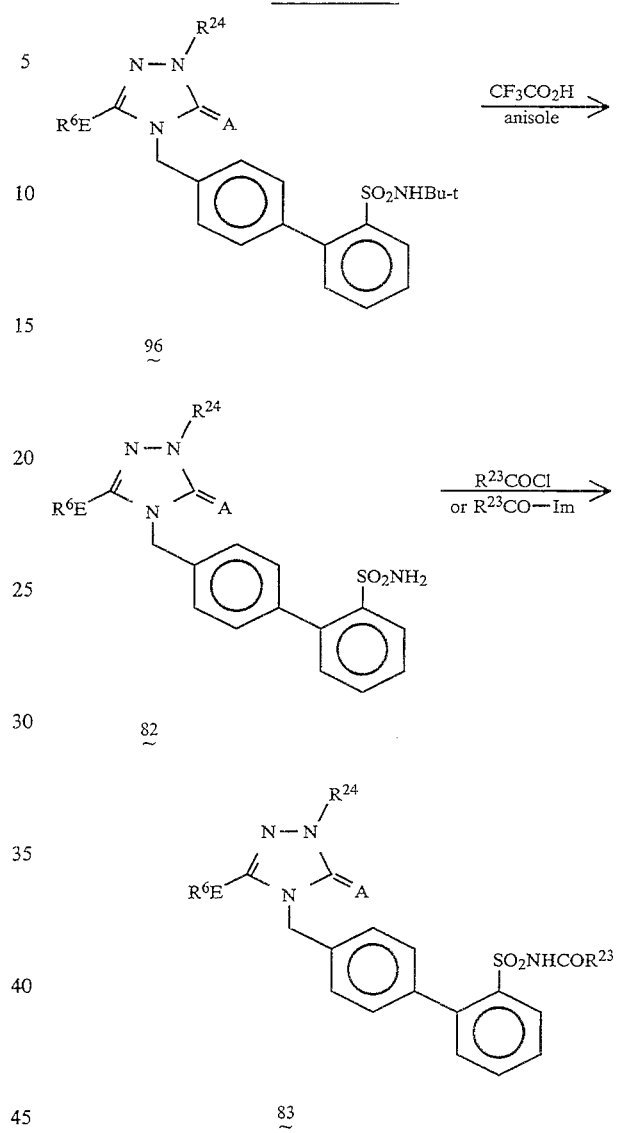

Still another route to target compounds of structure 83 is illustrated in Reaction Scheme 20. In a variation of Scheme 19, 2-bromobenzenesulfonyl chloride (85) is reacted with an excess of t-butylamine to yield the t-butylsulfonamide 92. The trimethylstannyl derivative 73 may be prepared as shown in Scheme 18 or may be conveniently prepared from p-tolylmagnesium bromide (93) by treatment with trimethyltin chloride at −35° C. to room temperature. Cross-coupling of 73 with 92 catalyzed by bis(triphenylphosphine)palladium(II) chloride in DMF at about 90° C. affords the biphenyl derivative 94. The bromomethyl species 95 is obtained by heating 94 with N-bromosuccinimide (NBS) in carbon tetrachloride in the presence of an initiator such as 2,2′-azobis(isobutyronitrile) (AIBN). The heterocycle 96 is elaborated by the methods of Scheme 18 and earlier schemes. The free sulfonamide 82 is obtained by deprotection of 96 with trifluoroacetic acid in the presence of anisole. Conversion of 82 to 83 is accomplished as in Scheme 19.

SCHEME 21

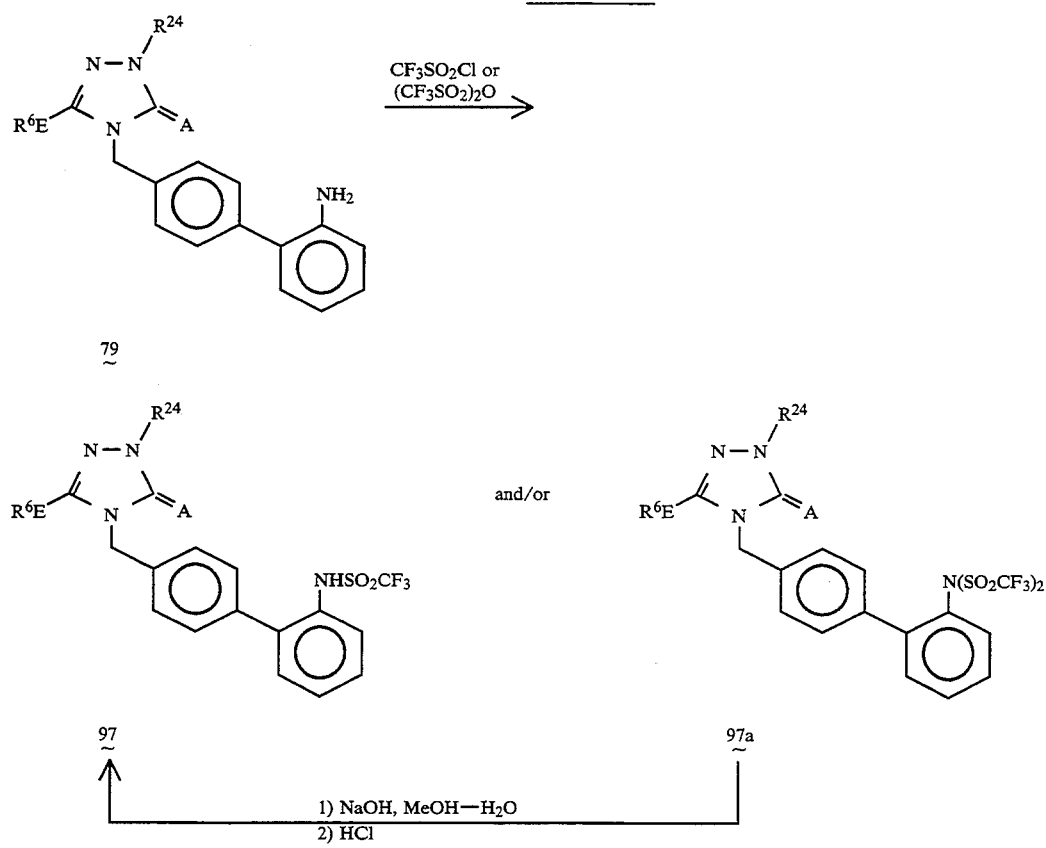

Reaction Scheme 21 demonstrates the synthesis of compounds of formula I in which $R^1$ is a trifluoromethanesulfonamido group. Treatment of the amino derivative 79 with either trifluoromethanesulfonyl chloride or trifluoromethanesulfonic anhydride gives, depending on the conditions, either the mono(trifluoromethanesulfonyl) derivative 97 or the bis(trifluoromethanesulfonyl) derivative 97a as the major or exclusive product. The sulfonylation may be carried out in pyridine or, alternatively, in methylene chloride in the presence of a base such as 2,6-di-t-butyl-4-methylpyridine. The disulfonylated product 97a is converted to the target compound 97 by warming with sodium hydroxide in aqueous methanol.

SCHEME 22

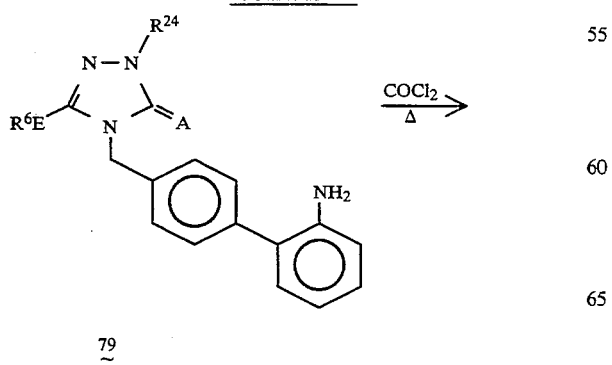

-continued
SCHEME 22

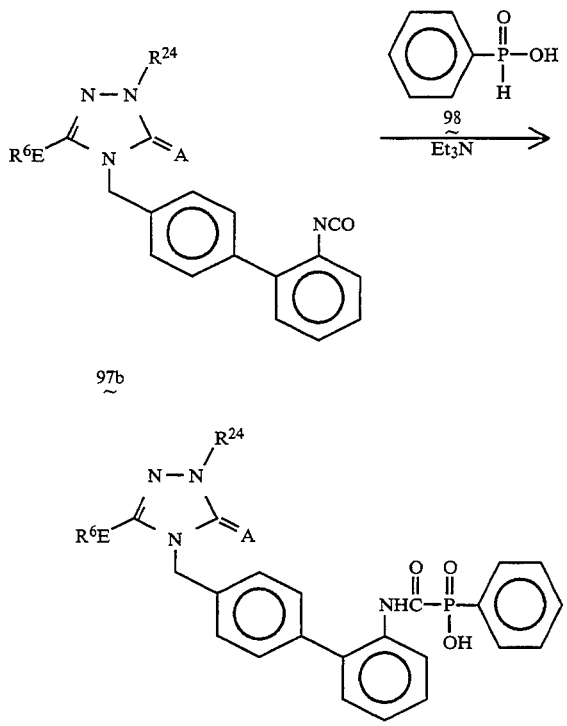

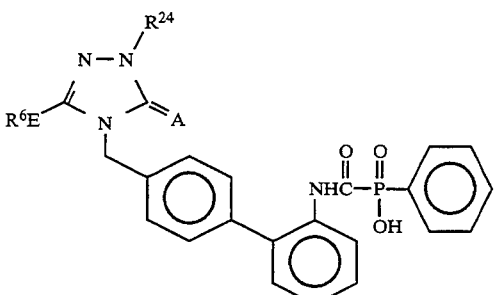

A route to compounds of formula I bearing a carbamoylphosphinic R¹ group is illustrated in Reaction Scheme 22. The amino intermediate 79 may be converted to the isocyanate 97b upon heating with phosgene in an inert solvent. Reaction of 97b with phenylphosphinic acid (98) in the presence of triethylamine, according to the method of Fox and Bailey [R. B. Fox and W. J. Bailey, *J. Org. Chem.*, 25, 1447 (1960)], gives the carbamoylphosphinic acid derivative 99. The method may be extended to the use of ring-substituted phenylphosphinic acids.

rivative 102 is obtained from 101 by standard NBS bromination conditions as described in previous schemes. Employing the methods of Reaction Scheme 18 and earlier schemes, 102 is converted to the triazolinone, triazolinethione, or triazolinimine 103. Next, 103 undergoes palladium-catalyzed cross-coupling with a monoethyl arene- or alkanephosphonite 104, using the conditions of Xu [Y. Xu, Z. Li, J. Xia, H. Guo, and Y. Huang, *Synthesis*, 377 (1983); Y. Xu, H. Wei, and J. Xia, *Liebigs Ann. Chem.*, 1139 (1988)], to give the disubstituted phosphinate ester 105. The phosphonite interme-

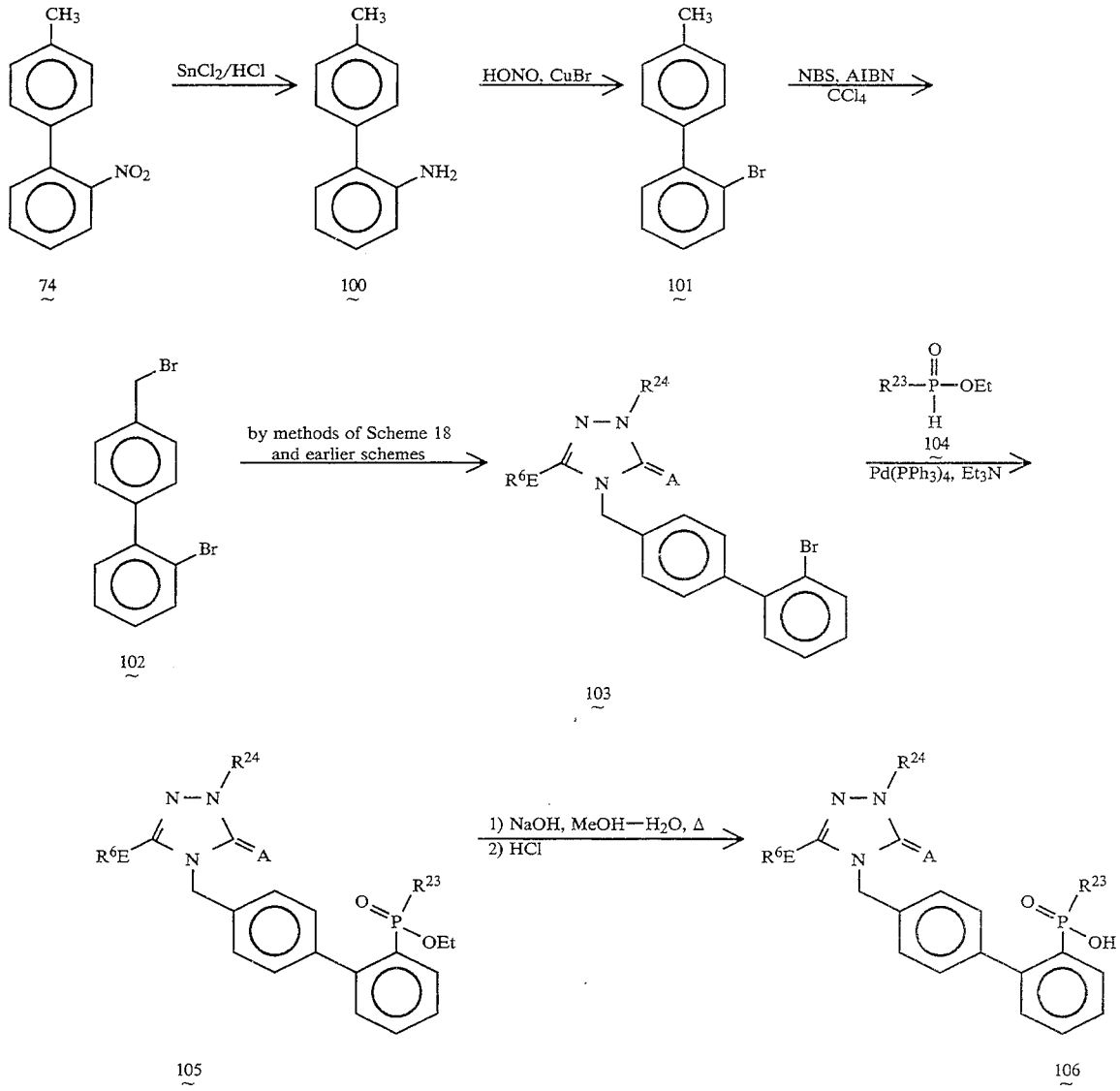

SCHEME 23

The incorporation of an aryl- or alkylphosphinoyl group at the R¹ position of compounds of formula I is shown in Reaction Scheme 23. The nitrobiphenyl intermediate 74 is readily reduced to the amine 100 using either stannous chloride reduction or catalytic hydrogenation. The amine 100 upon diazotization with nitrous acid and treatment with cuprous bromide yields the bromobiphenyl derivative 101. The bromomethyl dediate 104 may be obtained by reaction of a Grignard reagent R²³MgBr with diethyl chlorophosphite followed by partial hydrolysis [Y. Xu, H. Wei, and J. Xia, *Liebigs Ann. Chem.*, 1139 (1988)]. Finally, the phosphinate ester of 105 may be saponified by heating with sodium hydroxide in aqueous methanol [P. Tavs, *Chem. Ber.*, 103, 2428 (1970)].

SCHEME 24

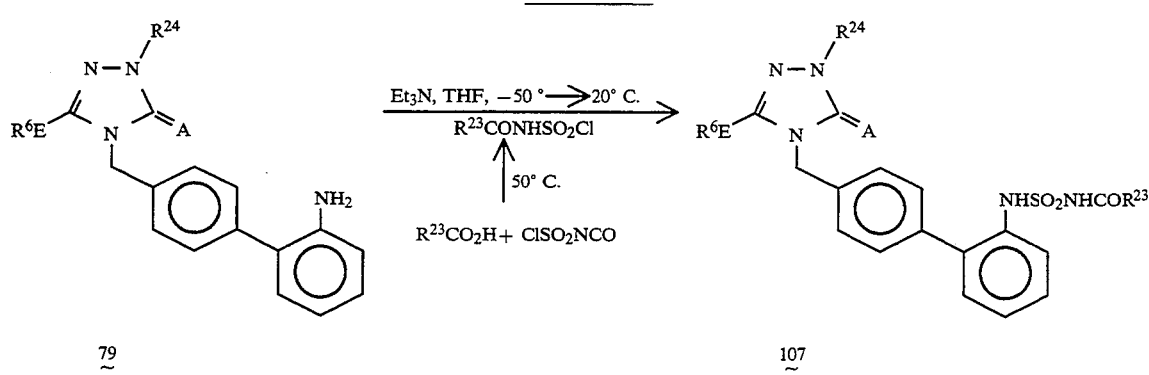

Compounds of formula I in which $R^1$ is an acylsulfamide group, $-NHSO_2NHCOR^{23}$, may be prepared as outlined in Scheme 24. The amine 79 is treated with an acylsulfamoyl chloride, $R^{23}CONHSO_2Cl$ (prepared by reacting the corresponding carboxylic acid with chlorosulfonyl isocyanate at 50° C.) in THF in the presence of triethylamine at −50° C. to room temperature, yielding the acylsulfamide 107.

SCHEME 25

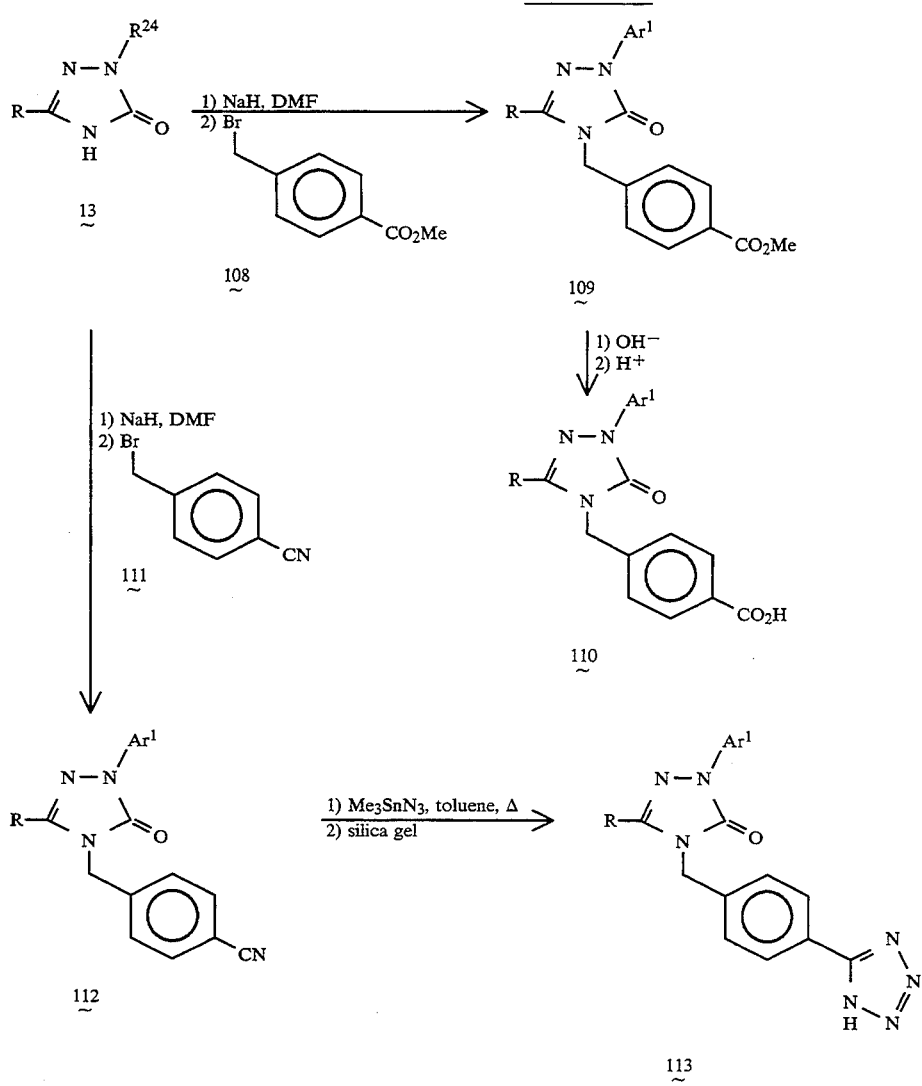

-continued
SCHEME 25

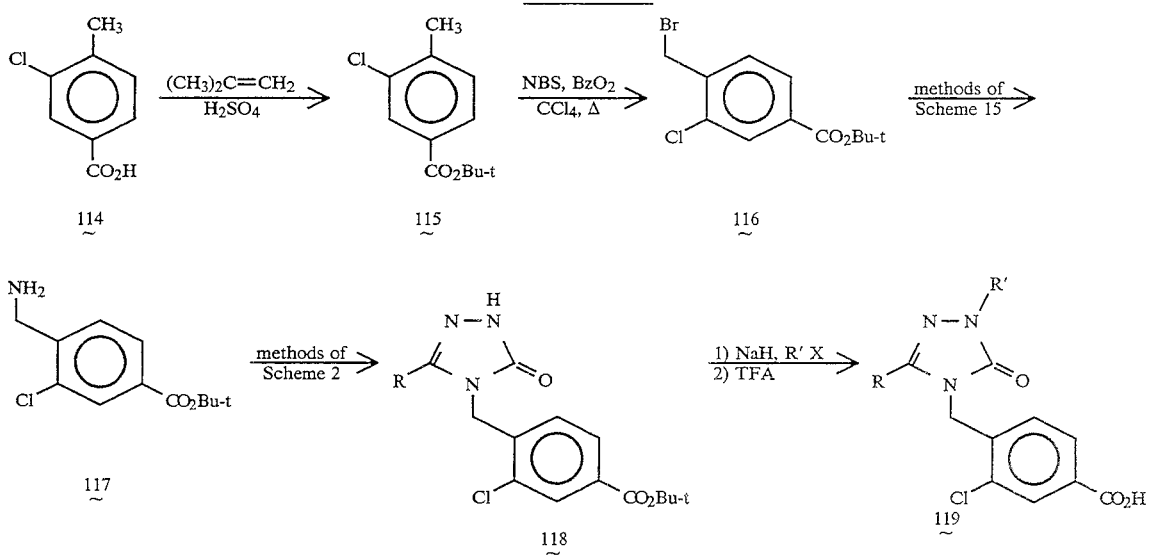

The synthesis of some compounds of formula (I) in which n is 0 (zero) and X is $R^1$ are shown in Reaction Scheme 25. The triazolinone 13 may be alkylated with methyl 4-(bromomethyl)benzoate (108) under conditions previously described to give 109, which is readily saponified to the free acid 110. Similarly, 13 is alkylated with 4-cyanobenzyl bromide (111) to yield 112, which is converted to the tetrazole 113 by reaction with trimethyltin azide according to previously described conditions. Treatment of 3-chloro-4-methylbenzoic acid (114) with isobutylene under pressure in the presence of sulfuric acid affords the t-butyl ester 115. α-Bromination of 115 with N-bromosuccinimide under standard conditions gives 116, which is converted to the amine 117 by the methods of Scheme 15. This is further transformed to the triazolinone 118 according to the methods of Scheme 2. Further alkylation with R′X (see Scheme 1) followed by deprotection with trifluoroacetic acid provides the free acid 119. The transformations described in Schemes 17–24 can be adapted to prepare a variety of other acidic substituents at the para-position of a benzyl group linked to $N^4$ of the triazolinone, triazolinethione, or triazolinimine.

-continued
REACTION SCHEME 26

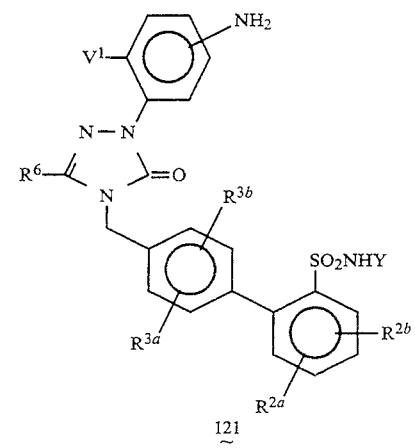

REACTION SCHEME 26

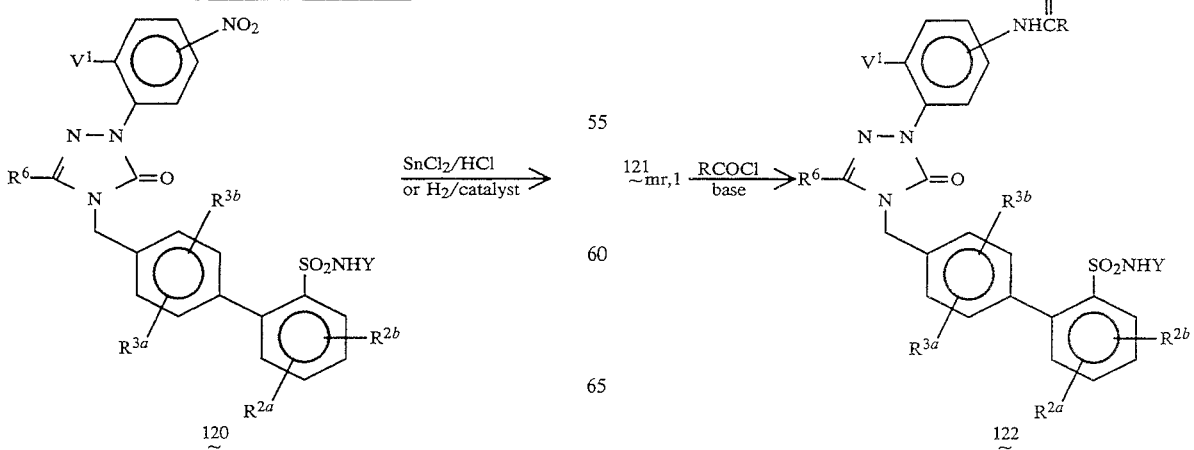

-continued
REACTION SCHEME 26

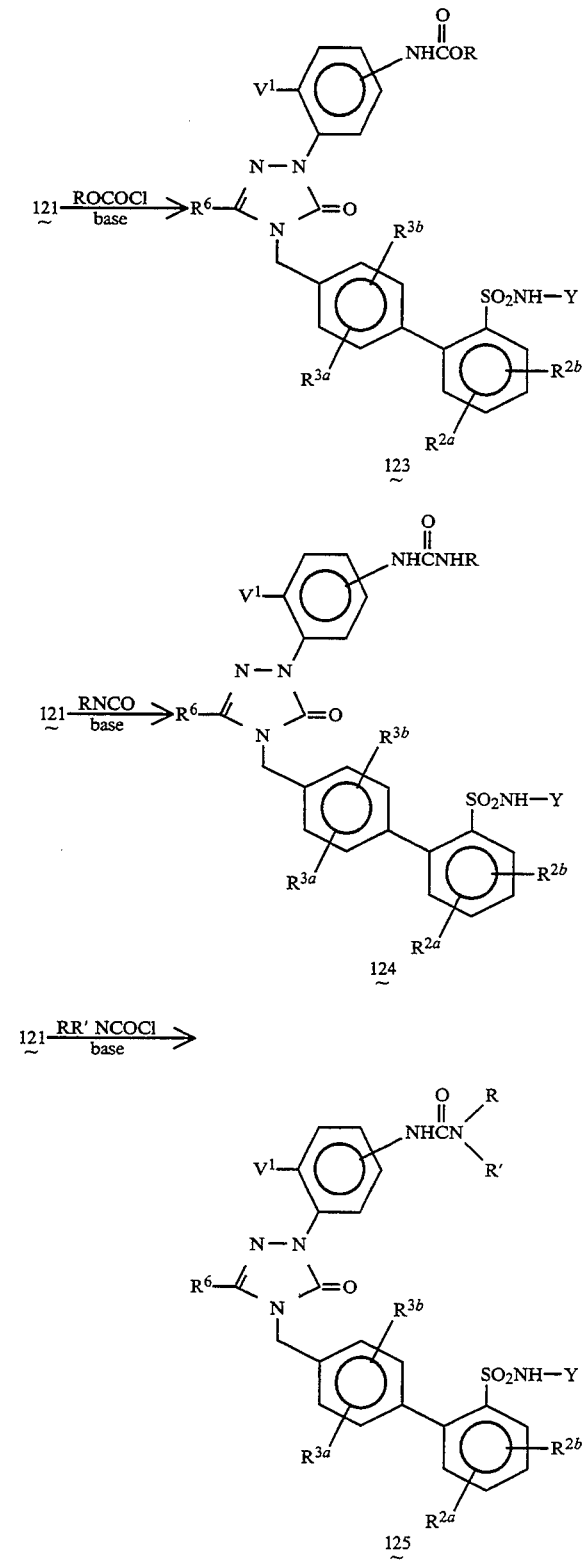

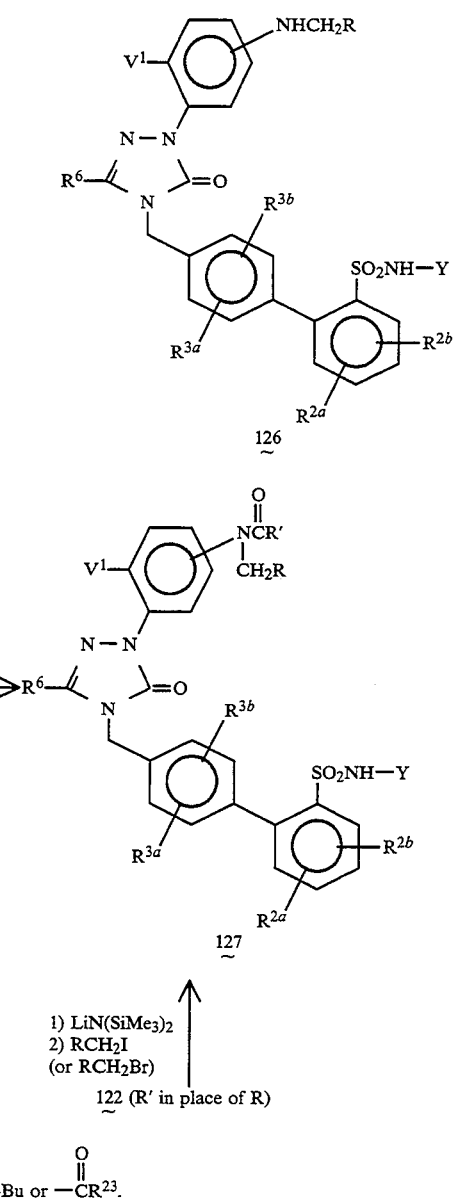

wherein Y is t-Bu or $-\overset{O}{\underset{\|}{C}}R^{23}$.

As shown in Reaction Scheme 26, intermediate 120, which contains a nitro substituent and is prepared according to the previous schemes, is reduced, as appropriate, with stannous chloride in the presence of concentrated hydrochloric acid or by catalytic hydrogenation to give the amino derivative 121. In the presence of a base such as sodium hydride, 121 can be reacted with an acid chloride to give the amide 122, with a chloroformate to give the carbamate 123, with an isocyanate to give the urea 124, or with a carbamoyl chloride to give a trisubstituted urea 125. Also, 121 can be converted to a substituted-amino derivative 126. For R=aryl, this may be accomplished conveniently by first heating 121 with the aldehyde in the presence of a catalytic amount of piperidine in a solvent such as isopropanol. The intermediate Schiff base is then reduced (optionally without isolation) by use of sodium borohydride in ethanol or sodium cyanoborohydride in methanol to provide 126.

For R=alkyl or aralkyl, the transformation may be accomplished by reacting 121 with the aldehyde in the presence of molecular sieves and sodium cyanoborohydride (present initially or added later), preferably at about 10°-40° C. Alternatively, for R=aryl, alkyl, hydrogen, etc., 121 may be deprotonated with a strong base such as lithium bis(trimethylsilyl)amide in a solvent such as DMF and then reacted with the appropriate alkyl or aralkyl iodide or bromide to afford 126. Subsequently, 126 can be acylated as described above to yield the tertiary amide 127, which may also be prepared by alkylation of 122 in the presence of a strong base such as lithium bis(trimethylsilyl)amide in a solvent such as DMF.

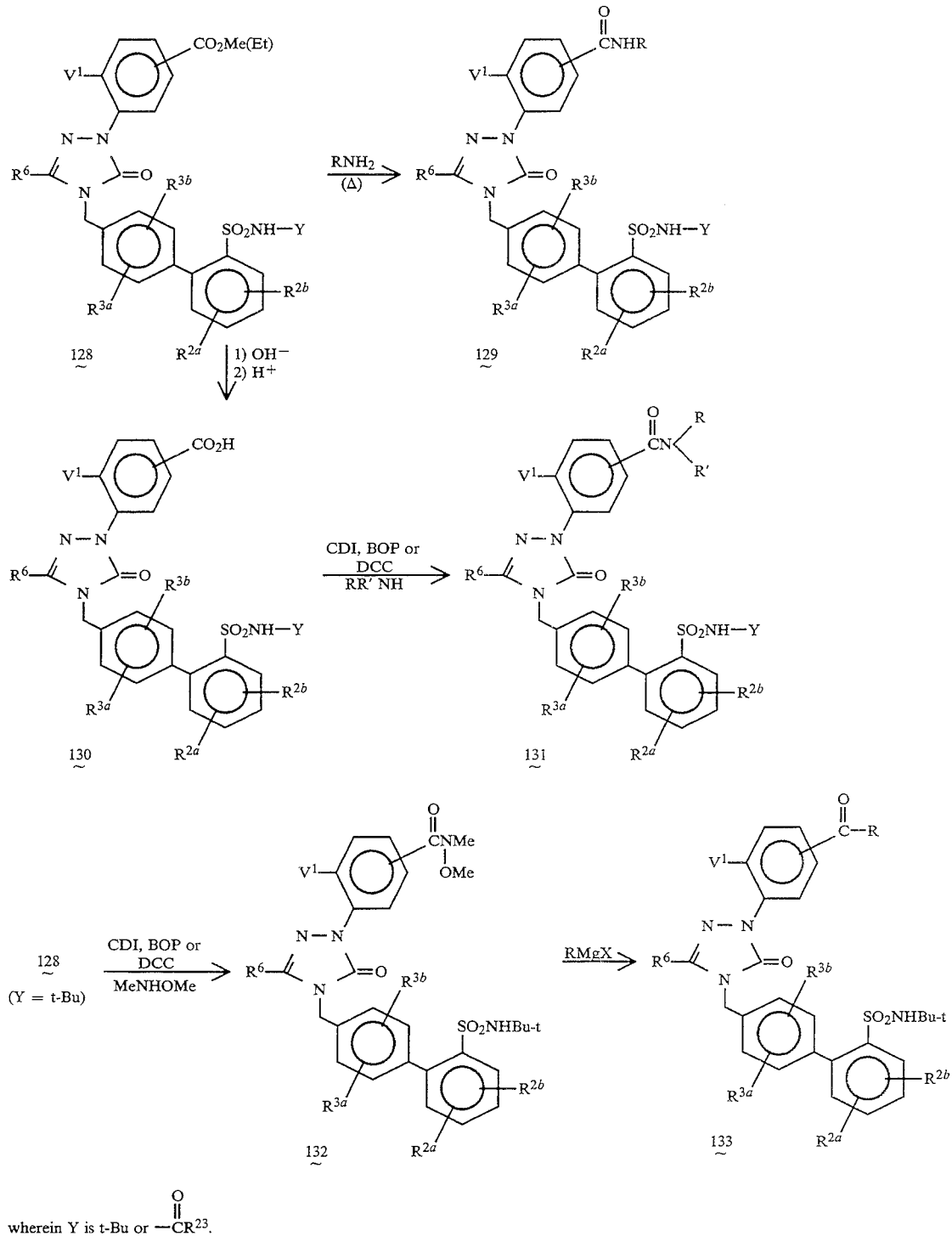

REACTION SCHEME 27

In Reaction Scheme 27, intermediate 128, which bears a methyl or ethyl ester substituent and is synthesized according to the previous reaction schemes, is treated with a neat amine, generally at about 20°-100°

C., to provide the amide 129. This method is particularly useful for primary amines. Compound 128 may also be saponified under standard conditions to the carboxylic acid 130. With use of a condensing agent such as 1,1'-carbonyldiimidazole, BOP reagent or N,N'-dicyclohexylcarbodiimide, 130 can be reacted with an amine to give the amide product 131. This method is suitable for secondary as well as primary amines. Similarly, 128 (at the t-butylsulfonamide intermediate stage) is converted to the N-methoxy-N-methylamide 132. Following the Weinreb method [S. Nahm and S. M. Weinreb, *Tetrahedron Lett.*, 22, 3815 (1981)], 132 can be reacted with a Grignard reagent to afford the ketone product 133.

By use of these methods and others analogous to those shown in Reaction Schemes 26 and 27, all of the $V^2$ substituents can be elaborated at the stage corresponding to the t-butylsulfonamide intermediate 96 or the acylsulfonamide 83. When the transformations are carried out at the t-butylsulfonamide stage, final conversion to the desired acylsulfonamide is accomplished as in Reaction Scheme 20.

The route shown in Scheme 28 is particularly useful for preparing compounds of Formula I in which the distal ring of the biphenylmethyl side chain bears a substituent (for example, alkyl) at the 5'-position in addition to the sulfamoyl moiety at the 2'-position. A 4-substituted benzenesulfonyl chloride 134 is converted to the N-t-butylsulfonamide 135 as in Scheme 20. Based on a literature method [M. J. Sharp, W. Cheng, and V. Snieckus, *Tetrahedron Lett.*, 28, 5093 (1987)], metalation ortho to the sulfonamide is achieved with n-butyllithium in THF at −40° to 0° C. Then treatment with triisopropyl borate followed by acidic work-up affords the boronic acid 136. This undergoes cross-coupling with 4-bromobenzyl alcohol (87) in the presence of tetrakis(triphenylphosphine)palladium(0) according to literature methods [M. J. Sharp, et al., op. cit.; N. Miyaura, T. Yanagi, and A. Suzuki, *Synth. Commun.*, 11, 513 (1981)] to give the biphenylmethyl alcohol 137. A triazolinone base 138, prepared as in the previous schemes, can be directly alkylated with 137 in the presence of diisopropyl azodicarboxylate (DIAD) in THF at −10° C. to room temperature, following the methods of Mitsunobu [O. Mitsunobu, *Synthesis*, 1 (1981)]. The product 139 can be further converted to compounds of formula I analogous to 83 by the methods of Schemes 20, 26 and 27.

SCHEME 28

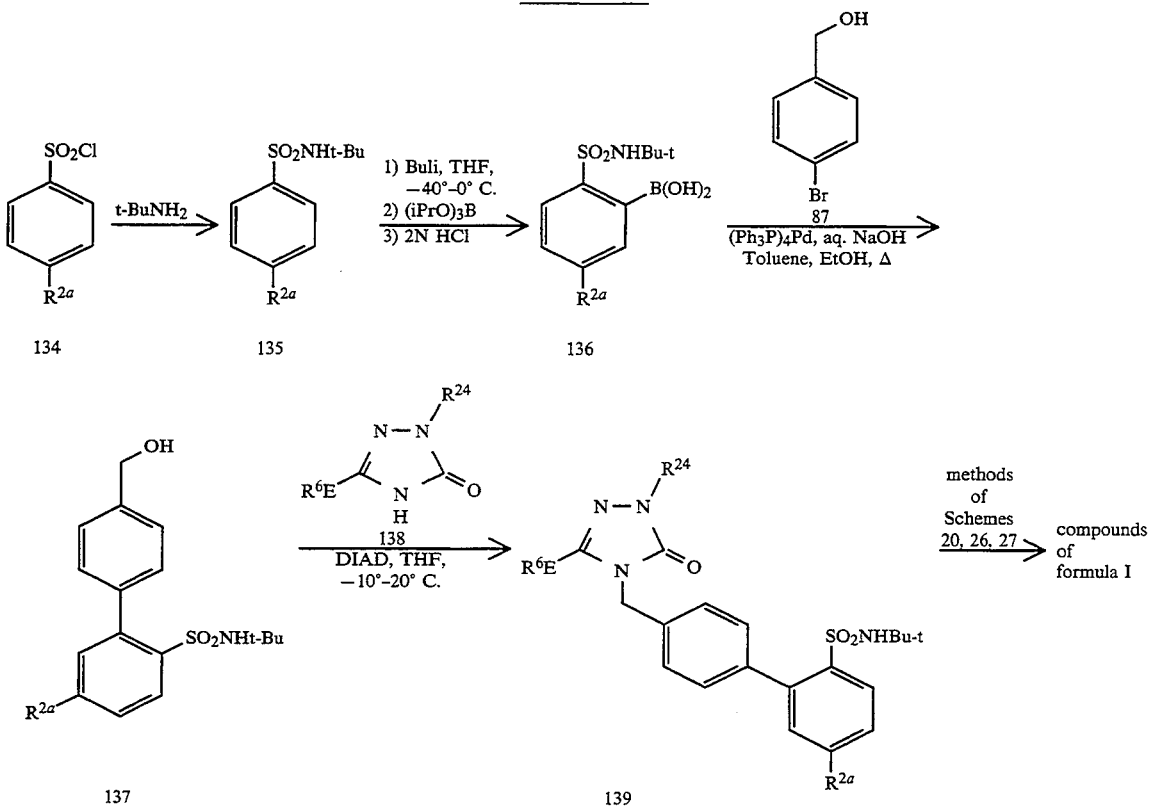

Scheme 29 illustrates a variation of Scheme 28 in which the coupling reaction to form the biphenyl side chain is carried out after alkylation of the triazolinone ring. This variation is especially useful for the introduction of one or two substituents ($R^{3a}$, $R^{3b}$) on the proximal ring of the biphenyl. The distal ring may be unsubstituted or substituted (for example, as shown in the scheme, $R^{2a}$ may be hydrogen or alkyl). The triazolinone 138 is deprotonated with a base such as sodium hydride in a solvent like DMF and treated with the 4-bromobenzyl bromide derivative 140 to yield the $N^4$-benzylated triazolinone 141. Useful examples of 140 include 4-bromo-2-fluorobenzyl bromide (commercially available) and 4-bromo-3-fluorobenzyl bromide (readily prepared by photochemical bromination of the commercially available 4-bromo-3-fluorotoluene). Palladium(0)-catalyzed coupling of 141 with the boronic acid 136 as in Scheme 28 gives triazolinone 142 bearing the substituted biphenyl side chain. This is elaborated to the desired compounds of formula I by the methods of Schemes 20, 26 and 27.

SCHEME 29

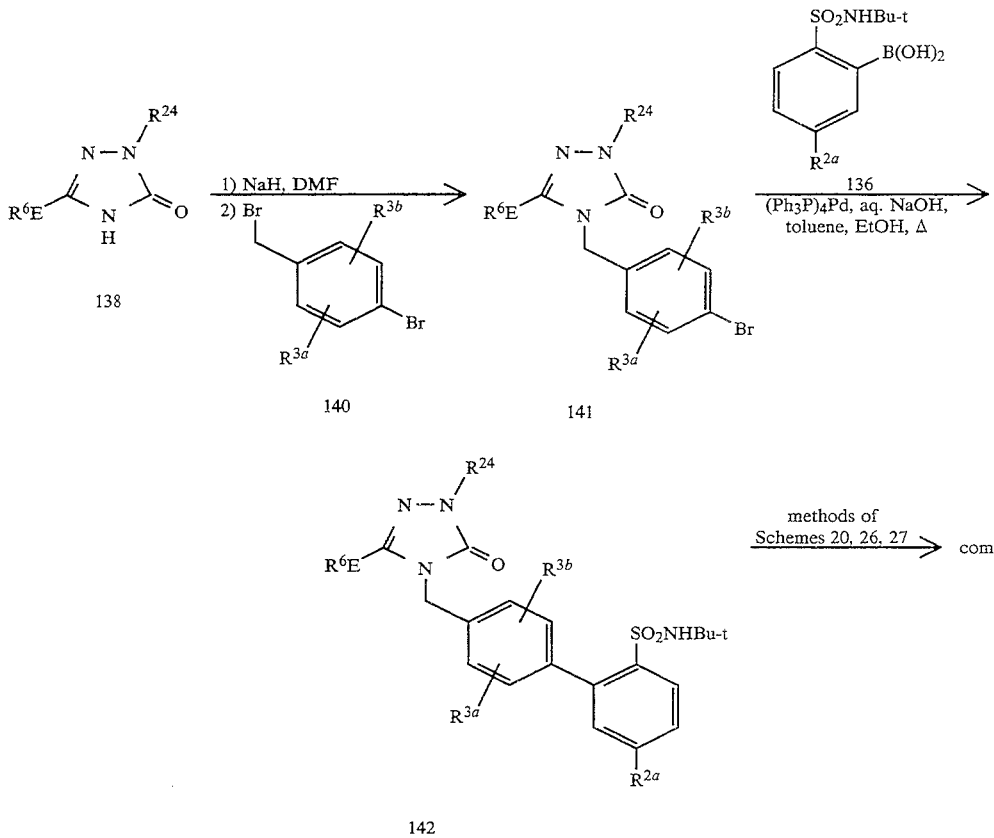

In a variation of Scheme 29, shown in Scheme 30, the 4-bromotoluene derivative 145 is coupled with 136 to give the 4-methylbiphenyl product 144. This is photochemically brominated, for example, with N-bromosuccinimide in the presence of an initiator such as AIBN or benzoyl peroxide, or with bromine, to give the bromomethyl derivative 145. Alkylation of the sodium salt of triazolinone 138 with 145 affords 142, which is processed further as in Scheme 29 to yield the desired compounds of formula I.

SCHEME 30

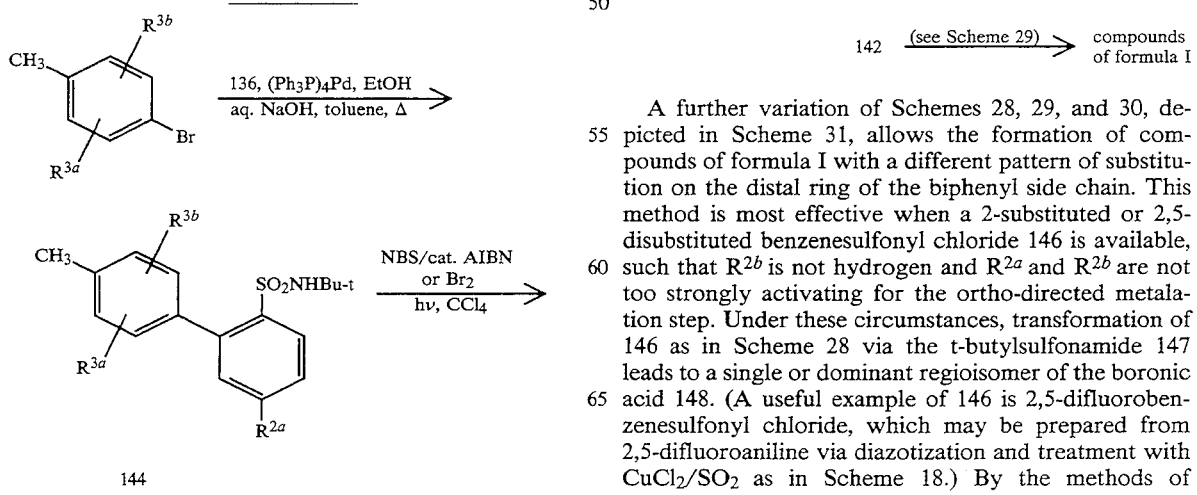

A further variation of Schemes 28, 29, and 30, depicted in Scheme 31, allows the formation of compounds of formula I with a different pattern of substitution on the distal ring of the biphenyl side chain. This method is most effective when a 2-substituted or 2,5-disubstituted benzenesulfonyl chloride 146 is available, such that $R^{2b}$ is not hydrogen and $R^{2a}$ and $R^{2b}$ are not too strongly activating for the ortho-directed metalation step. Under these circumstances, transformation of 146 as in Scheme 28 via the t-butylsulfonamide 147 leads to a single or dominant regioisomer of the boronic acid 148. (A useful example of 146 is 2,5-difluorobenzenesulfonyl chloride, which may be prepared from 2,5-difluoroaniline via diazotization and treatment with $CuCl_2/SO_2$ as in Scheme 18.) By the methods of Schemes 28–30, 148 is converted to the substituted biphenylmethyl triazolinone 149. Further transformation to the desired compounds of formula I is accomplished as previously described.

SCHEME 31

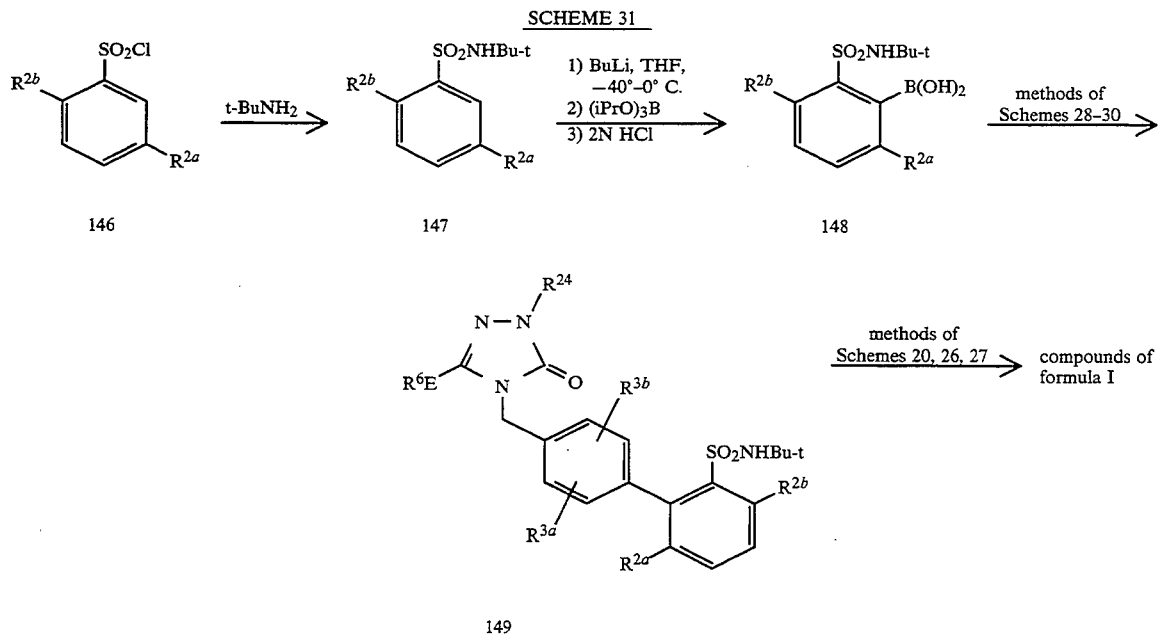

The synthesis of triazolinones having at $N^2$ a phenyl group substituted with trifluoromethyl at the 2-position and acylamino at the 5-position is presented in Scheme 32. Thus, 2-bromo-5-nitroaniline (150) is diazotized and reduced to the arylhydrazine 151. By the methods of Scheme 3, this is converted to the 2-bromo-5-nitrophenyl-substituted triazlinone 152. Based on literature conditions [D.-B. Su, J.-X. Duan, and Q.-Y. Chen, *Tetrahedron Lett.*, 32, 7689 (1991)], 152 is heated at about 120° C. with methyl chlorodifluoroacetate, cuprous iodide, potassium fluoride, and potassium bromide in DMF, resulting in displacement of bromo by trifluoromethyl to give 153. This transformation may be carried out at the N-t-butyl-biphenylsulfonamide stage corresponding to 142 or 149. Reduction of the nitro group in 153 with hydrogen in the presence of a catalyst like platinum oxide or with stannous chloride-hydrochloric acid affords the amine 154, which is acylated as in Scheme 26 to give the desired acylamino product 155.

SCHEME 32

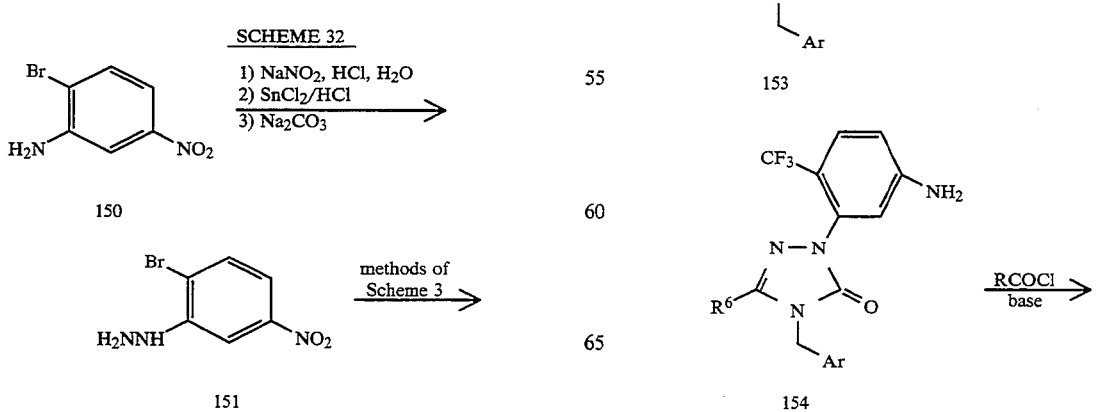

-continued
SCHEME 32

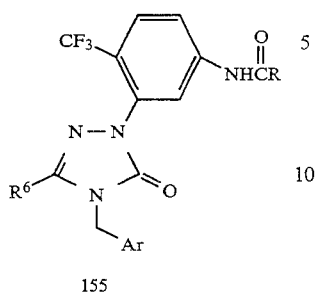

155

-continued
SCHEME 33

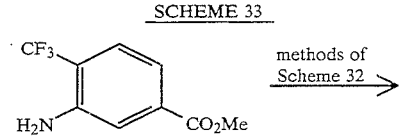

159

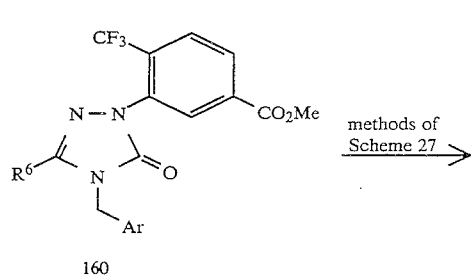

160

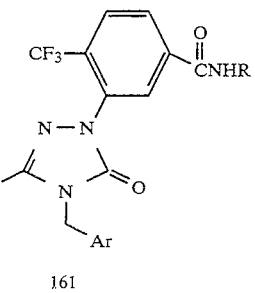

161 or

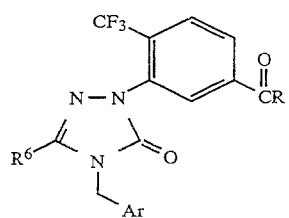

162

Scheme 33 illustrates the synthesis of triazolinones in which the $N^2$-phenyl moiety is substituted with a trifluoromethyl group at the 2-position and a substituted aminocarbonyl or ketone group at the 5-position. The commercially available compound 4-bromo-3-nitrotoluene (156) is converted to the trifluoromethyl analog 157 by the chemistry described in Scheme 32. The methyl group of 157 is oxidized to the carboxylic acid with potassium permanganate [H. T. Clarke and E. R. Taylor, Org. Syn., Coll. Vol., 2, 135 (1943)] or with tetrabutylammonium permanganate in pyridine [T. Sala and M. V. Sargent, J. Chem. Soc. Chem. Commun., 253 (1978)] or with the ruthenium tetroxide-sodium hypochlorite system [Y. Sasson, G. D. Zappi, and R. Neumann, J. Org. Chem., 51, 2880 (1986)] and then esterified to the methyl ester 158 under standard conditions by heating With methanol in the presence of concentrated sulfuric acid. Catalytic hydrogenation of 158 provides the amine 159, which is converted to the substituted triazolinone 160 by the methods of Scheme 32. Following the methods of Scheme 27, the methyl ester of 160 is transformed to the N-substituted aminocarbonyl group (as in 161) or the acyl group (as in 162).

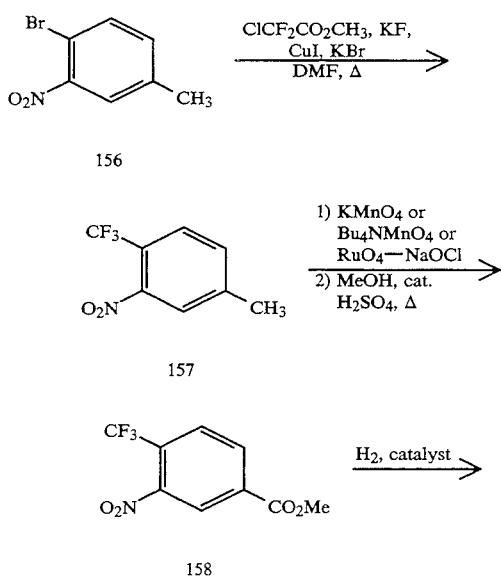

It will be appreciated by those skilled in the art that the protecting groups used in these syntheses will be chosen to be compatible with subsequent reaction conditions. Ultimately, they will be removed to generate the active compounds of formula (I). For example, $R^1$ as carboxyl is often protected as its t-butyl ester which in the last step is removed by treatment with trifluoroacetic acid. Aqueous acetic acid employed overnight is a preferred method to remove a trityl protecting group to liberate an $R^1$ tetrazole group.

The compounds of this invention form salts with various inorganic and organic acids and bases which are also within the scope of the invention. Such salts include ammonium salts, alkali metal salts like sodium and potassium salts, alkaline earth metal salts like the calcium and magnesium salts, salts with organic bases; e.g., dicyclohexylamine salts, N-methyl-D-glucamine salts, salts with amino acids like arginine, lysine, and the like. Also, salts with organic and inorganic acids may be prepared; e.g., HCl, HBr, $H_2SO_4$, $H_3PO_4$, methanesulfonic, toluensulfonic, maleic, fumaric, camphorsulfonic. The non-toxic, physiologically, acceptable salts are preferred, although other salts are also useful; e.g., in isolating or purifying the product.

The salts can be formed by conventional means such as by reacting the free acid or free base forms of the product with one or more equivalents of the appropriate base or acid in a solvent or medium in which the salt is insoluble, or in a solvent such as water which is then removed in vacuo or by freeze-drying or by exchanging the cations of an existing salt for another cation on a suitable ion exchange resin.

Angiotensin II (A II) is a powerful arterial vasoconstrictor, and it exerts its action by interacting with specific receptors present on cell membranes. The compounds described in the present invention act as competitive antagonists of A II at the receptors. In order to identify A II antagonists and determine their efficacy in vitro, the following two ligand-receptor binding assays were established.

Receptor binding assay using rabbit aortae membrane preparation:

Three frozen rabbit aortae (obtained from Pel-Freeze Biologicals) were suspended in 5 mM, Tris-0.25M Sucrose, pH 7.4 buffer (50 ml) homogenized, and then centrifuged. The mixture was filtered through a cheesecloth and the supernatant was centrifuged for 30 minutes at 20,000 rpm at 4° C. The pellet thus obtained was resuspended in 30 ml of 50 mM Tris-5 mM $MgCl_2$ buffer containing 0.2% Bovine Serum Albumin and 0.2 mg/ml Bacitracin and the suspension was used for 100 assay tubes. Samples tested for screening were done in duplicate. To the membrane preparation (0.25 ml) there was added $^{125}$I-Sar$^1$Ile$^8$-angiotensin II [obtained from New England Nuclear] (10 µl; 20,000 cpm) with or without the test sample and the mixture was incubated at 37° C. for 90 minutes. The mixture was then diluted with ice-cold 50 mM Tris-0.9% NaCl, pH 7.4 (4 ml) and filtered through a glass fiber filter (GF/B Whatman 2.4" diameter). The filter was soaked in scintillation cocktail (10 ml) and counted for radioactivity using Packard 2660 Tricarb liquid scintillation counter. The inhibitory concentration ($IC_{50}$) of potential A II antagonist which gives 50% displacement of the total specifically bound $^{125}$I-Sar$^1$Ile$^8$-angiotensin II was presented as a measure of the efficacy of such compounds as A II antagonists.

Receptor assay using rat brain membrane preparation

Membranes from rat brain (thalamus, hypothamus and midbrain) were prepared by homogenization in 50 mM Tris HCl (pH 7.4), and centrifuged at 50,000×g. The resulting pellets were washed twice in 100 mM NaCl, 5 mM $Na_2$.EDTA, 10 mM $Na_2HPO_4$ (pH 7.4) and 0.1 mM PMSF by resuspension and centrifugation. For binding assays, the pellets were resuspended in 160 volumes of binding assay buffer (100 mM NaCl, 10 mM $Na_2HPO_4$, 5 mM $Na_2$.EDTA, pH 7.4, 0.1 mM PMSF, 0.2 mg/ml soybean trypsin inhibitor, 0.018 mg/ml o-phenanthroline, 77 mg/ml dithiothreitol and 0.14 mg/ml bacitracin. For $^{125}$I.Ile$^8$-angiotensin II binding assays, 10 µl of solvent (for total binding), Sar$^1$,Ile$^8$-angiotensin II (1 µM) (for nonspecific binding) or test compounds (for displacement) and 10 µl of [$^{125}$I]Sar$^1$-,Ile$^8$-angiotensin II (23–46 pM) were added to duplicate tubes. The receptor membrane preparation (500 µl) was added to each tube to initiate the binding reaction. The reaction mixtures were incubated at 37° C. for 90 minutes. The reaction was then terminated by filtration under reduced pressure through glass-fiber GF/B filters and washed immediately 4 times with 4 ml of 5 mM ice-cold Tris HCl (pH 7.6) containing 0.15M NaCl. The radioactivity trapped on the filters was counted using a gamma counter.

Using the methodology described above, representative compounds of the invention were evaluated and all were found to exhibit an activity of at least $IC_{50}<50$ µM thereby demonstrating and confirming the utility of the compounds of the invention as effective A II antagonists.

The potential antihypertensive effects of the compounds described in the present invention may be evaluated using the methodology described below: Male Charles River Sprague-Dawley rats (300–375 gm) were anesthetized with methohexital (Brevital; 50 mg/kg i.p.) and the trachea was cannulated with PE 205 tubing. A stainless steel pithing rod (1.5 mm thick, 150 mm long) was inserted into the orbit of the right eye and down the spinal column. The rats were immediately placed on a Harvard Rodent Ventilator (rate—60 strokes per minute, volume—1.1 cc per 100 grams body weight). The right carotid artery was ligated, both left and right vagal nerves were cut, and the left carotid artery was cannulated with PE 50 tubing for drug administration, and body temperature was maintained at 37° C. by a thermostatically controlled heating pad which received input from a rectal temperature probe. Atropine (1 mg/kg i.v.) was then administered, and 15 minutes later propranolol (1 mg/kg i.v.). Thirty minutes later angiotensin II or other agonists were administered intravenously at 30-minute intervals and the increase in the diastolic blood pressure was recorded before and after drug or vehicle administration.

Using the methodology described above, representative compounds of the invention were evaluated and all were found to exhibit an activity of at least $IC_{50}<50$ µM thereby demonstrating and confirming the utility of the compounds of the invention as effective A II antagonists.

Thus, the compounds of the invention are useful in treating hypertension. They are also of value in the management of acute and chronic congestive heart failure and angina. These compounds are also expected to be useful in primary and secondary hyperaldosteronism, renal diseases such as diabetic nephropathy, glomerulonephritis, glomerular sclerosis, nephrotic syndrome, hypertensive nephrosclerosis, end stage renal disease, renal transplant therapy, renovascular hypertension, scleroderma, left ventricular dysfunction, systolic and diastolic dysfunction diabetic retinopathy, in the management of vascular disorders such as migraine or Raynaud's disease, as prophylaxis to minimize the atherosclerotic process, in neointimal hyperplasia following angioplasty or vascular injury and to retard the onset of type II diabetes. The application of the compounds of this invention for these and similar disorders will be apparent to those skilled in the art.

The compounds of this invention are also useful to treat elevated intraocular pressure and to enhance retinal blood flow and can be administered to patients in need of such treatment with typical pharmaceutical formulations such as tablets, capsules, injectables and the like as well as topical ocular formulations in the form of solutions, ointments, inserts, gels, and the like. Pharmaceutical formulations prepared to treat intraocular pressure would typically contain about 0.1% to 15% by weight, preferably 0.5% to 2% by weight, of a compound of this invention. For this use, the compounds of this invention may also be used in combination with other medications for the treatment of glaucoma including choline eaterase inhibitors such as physostigmine salicylate or demecarium bromide, parasympathomimetic agents, such as pilocarpine nitrate, β-adrenergic antagonists such as timolol maleate, adrenergic agonists such as epinephrine and carbonic anhydrase inhibitors such as MK-507.

In the management of hypertension and the clinical conditions noted above, the compounds of this invention may be utilized in compositions such as tablets, capsules or elixirs for oral administration, suppositories for rectal administration, sterile solutions or suspensions for parenteral or intramuscular administration, and the like. The compounds of this invention can be administered to patients (animals and human) in need of such treatment in dosages that will provide optimal pharmaceutical efficacy. Although the dose will vary from patient to patient depending upon the nature and severity of disease, the patient's weight, special diets then being followed by a patient, concurrent medication, and other factors which those skilled in the art will recognize, the dosage range will generally be about 1 to 1000 mg. per patient per day which can be administered in single or multiple doses. Perferably, the dosage range will be about 5.0 to 500 mg. per patient per day; more preferably about 5 to 300 mg. per patient per day.

The compounds of this invention can also be administered in combination with other antihypertensives and/or diuretics. For example, the compounds of this invention can be given in combination with diuretics such as hydrochlorothiazide, chlorothiazide, chlorthalidone, methyclothiazide, furosemide, ethacrynic acid, triamterene amiloride, atriopeptin and spironolactone; calcium channel blockers, such as diltiazem, felodipine, nifedipine, amlodipine, nimodipine, isradipine, nitrendipine and verapamil; β-adrenergic antagonists such as timolol, atenolol, metoprolol, propanolol, nadolol and pindolol; angiotensin converting enzyme inhibitors such as enalapril, lisinopril, captopril, ramipril, quinapril and zofenopril; renin inhibitors such as A-69729 and FK 906 and FK 744; α-adrenergic antagonists such as prazosin, doxazosin, and terazosin; sympatholytic agents such as methyldopa, clonidine and guanabenz, atriopeptidase inhibitors (alone or with ANP) such as UK-79300; serotonin antagonists such as ketanserin; A$_2$-adenosine receptor agonists such as CGS 22492C; potassium channel agonists such as pinacidil and cromakalim; and various other antihypertensive drugs including reserpine, minoxidil, guanethidine, hydralazine hydrochloride and sodium nitroprusside as well as combinations of the above-named drugs.

Combinations useful in the management of congestive heart failure include, in addition, compounds of this invention with cardiac stimulants such as dobutamine and xamoterol and phosphodiesterase inhibitors including amrinone and milrinone.

Typically, the individual daily dosages for these combinations can range from about one-fifth of the minimally recommended clinical dosages to the maximum recommended levels for the entities when they are given singly.

To illustrate these combinations, one of the angiotensin II antagonists of this invention effective clinically in the 5-500 milligrams per day range can be effectively combined at levels of the 1.0-500 milligrams per day range with the following compounds at the indicated per day dose range: hydrochlorothiazide (6-100 mg), chlorothiazide (125-500 mg), ethacrynic acid (5-200 mg), amiloride (5-20 mg), furosemide (5-80 mg), propanolol (10-480 mg), timolol maleate (1-20 mg), methyldopa (125-2000 mg), felodipine (1-20 mg), nifedipine (5-120 mg), nitrendipine (5-60 mg) and diltiazem (30-540 mg). In addition, triple drug combinations of hydrochlorothiazide (5-100 mg) plus amiloride (5-20 mg) plus an angiotensin II antagonist of this invention (1-500 mg) or hydrochlorothiazide (5-100 mg) plus timolol maleate (5-60) plus an angiotensin II antagonist of this invention (1-500 mg) or hydrochlorothiazide (5-200 mg) and nifedipine (5-60 mg) plus an angiotensin II antagonist of this invention (1-500 mg) are effective combinations to control blood pressure in hypertensive patients. Naturally, these dose ranges can be adjusted on a unit basis as necessary to permit divided daily dosage and, as noted above, the dose will vary depending on the nature and severity of the disease, weight of patient, special diets and other factors.

Typically, these combinations can be formulated into pharmaceutical compositions as discussed below.

About 1 to 100 mg. of compound or mixture of compounds of Formula I or a physiologically acceptable salt is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

Illustrative of the adjuvants which can be incorporated in tablets, capsules and the like are the following: a binder such as gum tragacanth, acacia, corn starch or gelatin; an excipient such as microcrystalline cellulose; a disintegrating agent such as corn starch, pregelatinized starch, alginic acid and the like; a lubricant such as magnesium stearate; a sweetening agent such as sucrose, lactose or saccharin; a flavoring agent such as peppermint, oil of wintergreen or cherry. When the dosage unitform is a capsule, it may contain, in addition to materials of the above type, a liquid carrier such as fatty oil. Various other materials may be present as coatings or to otherwise modify the physical form of the dosage unit. For instance, tablets may be coated with shellac, sugar or both. A syrup or elixir may contain the active compound, sucrose as a sweetening agent, methyl and propyl parabens as preservatives, a dye and a flavoring such as cherry or orange flavor.

Sterile compositions for injection can be formulated according to conventional pharmaceutical practice by dissolving or suspending the active substance in a vehicle such as water for injection, a naturally occuring vegetable oil like sesame oil, coconut oil, peanut oil, cottonseed oil, etc., or a synthetic fatty vehicle like ethyl oleate or the like. Buffers, preservatives, antioxidants and the like can be incorporated as required.

The following examples illustrate the preparation of the compounds of formula (I) and their incorporation into pharmaceutical compositions and as such are not to be considered as limiting the invention set forth in the claims appended hereto.

EXAMPLE 1

5-n-Butyl-4-[(2'-carboxybiphenyl-4-yl)methyl]-2,4-dihydro-3H-1,2,4-triazole-3-thione Step A: N-[[2'-(t-Butoxycarbonyl)biphenyl-4-yl]methyl]phthalimide A mixture of 2.99 g (8 mmole, based on 93% purity) of 4-bromomethyl-2'-(t-butoxycarbonyl)biphenyl (EP 253,310), 1.63 g (8.8 mmole) of potassium phthalimide, and 24 ml of dry dimethylformamide (DMF) was stirred at room temperature for 7 hours and then partitioned between 200 ml of ether and 250 ml of H$_2$O. The organic phase was washed with 4×250 ml of H$_2$O, then dried (MgSO$_4$), filtered, and concentrated. The residue was leached twice with hot ether (15–20 ml), which was decanted off after cooling. The remaining solid was collected on a filter, washed with petroleum ether, and dried to yield 2.08 g of colorless crystals, mp 108.5°–109°, homogeneous by TLC in 4:1 hexane-EtOAc. The residue from evaporation of the mother liquor was triturated with two portions of ether to give a second crop of colorless crystals: 0.58 g, mp 122°–123° (preliminary softening). Despite the difference in melting point, the second crop was identical to the first by NMR and TLC. The total yield was thus 2.66 g (82%).

Analysis (C$_{26}$H$_{23}$NO$_4$) Calcd: C, 75.53; H, 5.61; N, 3.39 Found: C, 75.25; H, 5.75; N, 3.18 300 MHz NMR (CDCl$_3$) δ1.17 (s, 9H), 4.90 (s, 2H), 7.2–7.9 (m, 12H).

Step B: 4-Aminomethyl-2'-(t-butoxycarbonyl)biphenyl

A mixture of 2.62 g (6.35 mmole) of N-[[2'-(t-butoxycarbonyl)biphenyl-4-yl]methyl]phthalimide, 1.21 ml (1.25 g, 25 mmole) of 100% hydrazine hydrate, and 35 ml of absolute ethanol was stirred at room temperature for 7.5 hours. During this time all of the solid gradually dissolved, followed by precipitation. Glacial acetic acid (3.7 ml) was added, and stirring was continued overnight. The white solid was then removed by filtration, and the filtrate was concentrated at room temperature. The residual oil was taken up in 100 ml of ether and washed with 2×50 ml of saturated aqueous Na$_2$CO$_3$ solution. Next, the product was extracted by shaking the ethereal solution with 50 ml of 0.5N HCl. The aqueous layer was separated and basified by addition of excess saturated Na$_2$CO$_3$. The product, which oiled out, was extracted with 100 ml of ether. The other phase was dried (Na$_2$SO$_4$), filtered, and concentrated at 30° C. to give 1.58 g (88%) of a very pale yellow, viscous oil, homogeneous by TLC in 95:5:0.5 CH$_2$Cl$_2$—MeOH-concd. NH$_4$OH.

Analysis (C$_{18}$H$_{21}$NO$_2$.0.25 H$_2$O) Calcd: C, 75.10; H, 7.53; N, 4.87 Found: C, 75.14; H, 7.39; N, 4.78

300 MHz NMR (CDCl$_3$) δ1.27 (s, 9H), 1.50 (br s, 2H), 3.92 (s, 2H), 7.2–7.8 (m, 8H).

Step C: Methyl N-[[2'-(t-Butoxycarbonyl)biphenyl-4-yl]methyl]dithiocarbamate

A solution of 1.415 g (5 mmole) of 4-aminomethyl-2'-(t-butoxycarbonyl)biphenyl and 751 μl (545 mg, 5.4 mmole) of triethylamine in 5 ml of methanol was stirred under N$_2$ at room temperature as a solution of 342 μl (434 mg, 5.7 mmole) of carbon disulfide in 2 ml of methanol was added dropwise over about 10 minutes. After 2.5 hours the solution was cooled in an ice-methanol bath, and a solution of 311 μl (710 mg, 5 mmole) of methyl iodide in 2 ml of methanol was added dropwise over about 10 minutes. The cooling bath was removed, and the solution was allowed to warm to room temperature. After 2 hours the solution was concentrated at 25° C. The residue was partitioned between 50 ml of ether plus 10 ml of CH$_2$Cl$_2$ and 50 ml of 0.2N HCl. The organic phase was washed with 25 ml of saturated NaCl solution (aqueous), dried over MgSO$_4$, filtered, and concentrated. Crystallization of the residual oil from ether yielded 1.57 g (84%) of nearly colorless crystals, mp 127.5°–128.5° C., satisfactory purity by TLC in 4:1 hexane-EtOAc; mass spectrum (FAB) m/e 374 (M+1)$^+$.

Analysis (C$_{20}$H$_{23}$NO$_2$S$_2$) Calcd: C, 64.31; H, 6.21; N, 3.75. Found: C, 64.54; H, 6.46; N, 3.82.

300 MHz NMR (CDCl$_3$) δ1.28 (s, 9H), 2.66 (s, 3H), 4.97 (d, J=5 Hz, 2H), 7.13 (br, m 1H), 7.2–7.8 (m, 8H).

Step D: 4-[[2'-(t-Butoxycarbonyl)biphenyl-4-yl]methyl]-3-thiosemicarbazide

A mixture of 1.53 g (4.1 mmole) of methyl N-[[2'-(t-butoxycarbonyl)biphenyl-4-yl]methyl]dithiocarbamate, 796 μl (820 mg, 16.4 mmole) of hydrazine hydrate, and 10 ml of absolute ethanol was stirred at reflux under N$_2$. After 2 hours the resulting solution was cooled and concentrated. The residual oil was chromatographed on a column of silica gel (elution with 99:1 and the 98:2 CH$_2$Cl$_2$) to give (after concentration and vacuum-drying) 1.15 g (79%) of a stiff, white foam, mp>45° C. (gradual); homogeneous by TLC in 19:1CH$_2$Cl$_2$—MeOH; mass spectrum (FAB) m/e 358 (M+1)$^+$.

Analysis (C$_{19}$H$_{23}$N$_3$O$_2$S.0.1 H$_2$O) Calcd: C, 63.51; H, 6.51; N, 11.70. Found: C, 63.41; H, 6.50; N, 11.54.

300 MHz NMR (CDCl$_3$) δ1.28 (s, 9H), 3.76 (br s, 2H), 4.90 (d, J=5 Hz, 2H), 7.2–7.8 (m, 9H).

Step E: 4-[[2'-(t-Butoxycarbonyl)biphenyl-4-yl]-5-n-butyl-2,4-dihydro-3H-1,2,4-triazole-3-thione A solution of 1.11 g (3.1 mmole) of 4-[[2'-(t-butoxycarbonyl)biphenyl-4-yl]methyl]-3-thiosemicarbazide and 792 μl (745 mg, 4.6 mmole) of trimethyl orthovalerate in 10 ml of 2-methoxyethanol was stirred at reflux under N$_2$ for 15 hours. The cooled solution was concentrated, and the residue was purified by column chromatography on silica gel (gradient elution with 0–1% methanol in CH$_2$Cl$_2$) to give a gum which could be crystallized by trituration with petroleum ether. The total yield was 828 mg (63%), mp 135°–137° C., homogeneous by TLC in 19:1 CH$_2$Cl$_2$—MeOH; mass spectrum (FAB) m/e 424 (M+1)$^+$.

Analysis (C$_{24}$H$_{29}$N$_3$O$_2$S) Calcd: C, 68.05; H, 6.90; N, 9.92. Found: C, 67.95; H, 6.65; N, 9.84.

300 MHz NMR (CDCl$_3$) δ0.87 (t, J=7 Hz, 3H), 1.22 (s, 9H), 1.32 (m, 2H), 1.62 (m, 2H), 2.48 (t, J=7 Hz, 2H), 5.27 (s, 2H), 7.2–7.5 (m, 7H), 7.74 (d, J=8 Hz, 1H)

Step F: 5-n-Butyl-4-[(2'-carboxybiphenyl-4-yl)methyl]-2,4-dihydro-3H-1,2,4-triazole-3-thione A solution of 51 mg (0.12 mmole) of 4-[[2'-(t-butoxycarbonyl)biphenyl-4-yl]methyl]-5-n-butyl-2,4-dihydro-3H-1,2,4-triazole-3-thione in 0.5 ml of anhydrous trifluoroacetic acid was stirred under N$_2$ at room temperature for 2 hours and then evaporated to dryness under a stream of N$_2$. The residue was dissolved in a small volume of methanol and evaporated onto 1 g of silica gel. This was layered on top of a column of silica gel (43×2.4 cm) packed in CH$_2$Cl$_2$. Gradient elution with 1–5% methanol in CH$_2$C$_{12}$ containing 0.1% acetic acid eluted two major products. Concentration of fractions containing the first (higher R$_f$) product gave a residue which solidified upon trituration with ether: 9.5 mg (21%) of white powder, mp 218°–219° C., homogeneous by TLC in 95:5:0.1 CH$_2$Cl$_2$—MeOH—AcOH; mass spectrum (FAB) m/e 368 (M+1)$^+$.

Analysis (C$_{20}$H$_{21}$N$_3$O$_2$S.0.5 H$_2$O) Calcd: C, 63.80; H, 5.89; N, 11.16. Found: C, 63.93; H, 5.86; N, 10.82. 300 MHz NMR (DMSO-d$_6$) δ0.79 (t, J=7.5 Hz, 3H), 1.25 (m, 2H), 1.46 (m, 2H), 2.53 (partially obsured t, J=8 Hz, 2H), 5.29 (s, 2H), 7.25–7.4 (m, 5H), 7.45 (t, J=8 Hz, 1H), 7.57 (t, J=8 Hz, 1H), 7.72 (d, J=8 Hz, 1H), 12.7 (v br s, 1H)

Concentration of fractions containing the second (lower R$_f$) product and work-up as above gave 21.9 mg of a white powder, mp 166.5°–168° C. dec., identified as 3-n-butyl-5-(t-butylthio)-4-[(2'-carboxybiphenyl-4-yl)methyl]-4H-1,2,4-triazole, a by-product arising from t-butyl migration.

EXAMPLE 2

5-n-Butyl-2,4-dihydro-4-[[2'-(5-tetrazolyl)biphenyl-4-yl]methyl]-3H-1,2,4-triazol-3-one Step A: Ethyl Valerate Carbethoxyhydrazone To a solution of 7.0 g (25.3 mmole) of ethyl valerimidate hydrochloride [prepared by method of A. J. Hill and I. Rabinowitz, *J. Am. Chem. Soc.*, 48, 734 (1926)] in 35 ml of dry ethanol stirred under $N_2$ at $-78°$ C. was added dropwise a solution of 24 g (23 mmole) of ethyl carbazate in 35 ml of dry ethanol. Precipitation occurred during the addition, which took 20 minutes and was accompanied by a rise in the internal temperature to $-50°$ C. The mixture was allowed to stand at 5° C. for 60 hours and then filtered. The filtrate was concentrated, and the residue was flash chromatographed on a silica gel column (elution with 98.5:1.5 $CH_2Cl_2$—MeOH), yielding 3.06 g (61%) of a clear oil, homogeneous by TLC in 97:3 $CH_2Cl_2$—MeOH; mass spectrum (FAB) m/e 217 $(M+1)^+$. NMR suggested a mixture of syn and anti isomers.

200 MHz NMR ($CDCl_3$) $\delta 0.91$ (t, J=7 Hz, 3H), 1.2–1.4 (m, 8H), 1.4–1.6 (m, 2H), 2.2–2.4 (m, 2H), 3.95–4.3 (m, 4H), 6.91, 8.11 (br s, 1H total).

Step B: 5-[4'-(Azidomethyl)biphenyl-2-yl]-N-trityltetrazole

To a stirred suspension of 11.15 g (20 mmole) of 5-[4'-(bromomethyl)biphenyl-2-yl]-N-trityltetrazole [P. E. Aldrich, M. E. Pierce, and J. J. V. Duncia, European Patent Application 291,969 (1988)]in 55 ml of dry DMSO was added 1.23 g (25 mmole) of freshly pulverized lithium azide, and the mixture was stirred at room temperature under $N_2$. Within a few minutes virtually all of the solid had dissolved, accompanied by a mild exotherm, and this was followed immediately by precipitation of product. After 4 hours the solid was collected on a filter and washed with some methanol, then with a relatively large volume of $H_2O$, and finally again with methanol. The solid was air-dried overnight and then dried further in a vacuum oven at 70° C. (<1 mm) to give 8.60 g (83%) of white crystals, mp 139°–140.5° C. dec., satisfactory purity by TLC (9:1 hexane-ethyl acetate) for use in the next step. From the combined filtrate and washes was recovered a less pure second crop (1.68 g of cream-colored crystals, mp 129°–132° C. dec.), which was also usable in the next step. Mass spectrum (FAB) m/e 243 (trityl cation); IR (Nujol) 2100 $cm^{-1}$.

300 MHz NMR ($CDCl_3$) $\delta 4.22$ (s, 2H), 6.90 (d, J=8 Hz, 6H), 7.04, 7.14 (d, J=8 Hz, each 2H), 7.2–7.55 (m, 12H), 7.96 (dd, J=8, 1 Hz, 1H).

Step C: 5-[4'-(Aminomethyl)biphenyl-2-yl]-N-trityltetrazole

A solution of 10.2 g (19.6 mmole) of 5-[4'-(azidomethyl)biphenyl-2-yl]-N-trityltetrazole in 39.4 ml of dry tetrahydrofuran (THF) was stirred under $N_2$ at room temperature as 5.16 g (19.7 mmole) of triphenylphosphine was added in small portions over a period of about 10 minutes. After 2 hours, by which time gas evolution had ceased, 532 µl (532 mg, 29.6 mmole) of $H_2O$ was added. After an additional 23 hours, the solution was concentrated in vacuo to give a pale golden gum. This material was chromatographed on a column of silica gel (50×8.5 cm) packed in $CH_2Cl_2$. The column was eluted with a gradient of 0–6% methanol in $CH_2Cl_2$. Concentration of the product fractions gave a foam which solidified upon trituration with ether. This material was collected on a filter, washed further with some ether, and dried in vacuo at 50° C. to give 5.65 g (58%) of white crystals, mp 134°–136° C. dec., satisfactory purity by TLC in 95:5:0.5 $CH_2Cl_2$—MeOH-concd. $NH_4OH$; mass spectrum (FAB) m/e 243 (trityl cation), 494 $(M+1)^+$.

Analysis ($C_{33}H_{27}N_5 \cdot 0.5\ H_2O$) Calcd: C, 78.86; H, 5.61; N, 13.94. Found: C, 78.76; H, 5.70; N, 13.89.

300 MHz NMR ($CDCl_3$) $\delta 1.44$ (br s, 2H, overlapping $H_2O$ peak), 3.75 (s, 2H), 6.88 (d, J=8 Hz, 6H), 7.03, 7.09 (d, J=8 Hz, each 2H), 7.2–7.5 (m, 12H), 7.95 (dd, J=8, 1 Hz, 1H).

Step D: 5-n-Butyl-2,4-dihydro-4-[[2'-(N-trityltetrazol-5-yl)biphenyl-4-yl]methyl]-3H-1,2,4-triazol-3-one A mixture of 1.20 g (2.43 mmole) of 5-[4'-(aminomethyl)biphenyl-2-yl]-N-trityltetrazole, 683 mg (3.16 mmole) of ethyl valerimidate carbethoxyhydrazone, and 5 ml of ethanol was stirred under $N_2$ in an oil bath at 80° C. All of the solid dissolved within 15 minutes, and precipitation began after about 2 hours. After 3.5 hours the mixture was cooled and concentrated. The residue was re-concentrated from $CH_2Cl_2$ and then flash chromatographed on a column containing 400 cc of silica gel. Gradient elution with 1–5% methanol in $CH_2Cl_2$ afforded 628 mg (42%) of a white powder, mp 176.5°–177.5° C., homogeneous by TLC in 9:1 $CH_2Cl_2$—MeOH; mass spectrum (FAB) m/e 618 $(M+1)^+$.

300 MHz NMR ($CDCl_3$) $\delta 0.83$ (t, J=7 Hz, 3H), 1.26 (m, 2H), 1.51 (m, 2H), 2.27 (t, J=7.5 Hz, 2H), 4.69 (s, 2H), 6.90 (d, J=7.5 Hz, 6H), 6.99, 7.13 (d, J=8 Hz, each 2H), 7.2–7.5 (m, 12H), 7.91 (dd, J=8, 1.5 Hz, 1H), 9.03 (s, 1H).

Step E: 5-n-Butyl-2,4-dihydro-4-[[2'-(5-tetrazolyl)-biphenyl-4-yl]methyl]-3H-1,2,4-triazol-3-one A mixture of 34 mg (0.055 mmole) of 3-n-butyl-2,4-dihydro-4-[[2'-(N-trityltetrazol-5-yl)biphenyl-4-yl]methyl]-3H-1,2,4-triazol-3-one, 0.9 ml of glacial acetic acid, and 0.4 ml of $H_2O$ was stirred overnight at 55° C. The cooled, filtered solution was concentrated in vacuo, and the residue was re-concentrated from toluene. The resulting residue was triturated with ether, which (after centrifugation) was removed by decantation. This procedure was repeated 4× until TLC indicated no remaining trityl alcohol. The product residue was concentrated from methanol-chloroform, then from $CH_2Cl_2$, and finally from toluene to give 18 mg (86%) of white powder, mp 215°–216° C., homogeneous by TLC in 90:10:0.1 $CH_2Cl_2$—MeOH—AcOH; mass spectrum (FAB) m/e 376 $(M+1)^+$.

Analysis ($C_{20}H_{21}N_7 \cdot 0.4\ H_2O$) Calcd: C, 62.78; H, 5.74; N, 25.62. Found: C, 62.96; H, 5.65; N, 25.24.

300 MHz NMR ($CDCl_3$) $\delta 0.86$ (t, J=7.5 Hz, 3H), 1.33 (m, 2H), 1.59 (m, 2H), 2.44 (t, J=7.5 Hz, 2H), 4.78 (s, 2H), 7.10 (m, 4H), 7.4–7.6 (m, 3H), 7.88 (d, J=8 Hz, 1H).

EXAMPLE 3

2-Benzyl-5-n-butyl-2,4-dihydro-4-[[2'-(5-tetrazolyl)-biphenyl-4-yl]methyl]-3H-1,2,4-triazol-3-one Step A: 2-Benzyl-5-n-butyl-2,4-dihydro-4-[[2'-(N-trityltetrazol-5-yl)biphenyl-4-yl]methyl]-3H-1,2,4-triazol-3-one A mixture of 33 mg (0.053 mmole) of 5-n-butyl-2,4-dihydro-4-[[2'-(N-trityltetrazol-5-yl)biphenyl-4-yl]methyl]-3H-1,2,4-triazol-3-one (from Example 2, Step D), 8.1 mg (0.169 mmole) of sodium hydride (50% in oil), and 130 μl of dry DMF was stirred under $N_2$ at room temperature for 2 hours. Next, 30 μl (43 mg, 0.252 mmole) of benzyl bromide was added, and stirring at room temperature was continued for an additional 1.5 hours, during which time the mixture decolorized. The mixture was quenched by careful addition of 0.8 ml of $H_2O$ and then shaken with 1.5 ml of ethyl acetate. The aqueous fraction was extracted further with 2×3 ml of ethyl acetate. The combined ethyl acetate fractions were washed with 2×2 ml of $H_2O$ and then with saturated aqueous NaCl. The organic phase was dried over $Na_2SO_4$, filtered, and concentrated. Flash chromatography of the residue on a column of 40 cc of silica gel (elution with 0.6% methanol in $CH_2Cl_2$) gave 32.5 mg (85%) of a white powder, homogeneous by TLC in 99:1 $CH_2Cl_2$—MeOH, mass spectrum (FAB) m/e 708 $(M+1)^+$.

Analysis ($C_{46}H_{41}N_7O.0.2$ $CH_2Cl_2$) Calcd: C, 76.55; H, 5.98; N, 13.53. Found: C, 76.91; H, 5.67; N, 13.07.

300 MHz NMR ($CDCl_3$) δ0.80 (t, J=7 Hz, 3H), 1.23 (m, 2H), 1.46 (m, 2H), 2.24 (t, J=7.5 Hz, 2H), 4.69, 4.97 (s, each 2H), 6.90 (d, J=7 Hz, 6H), 6.98, 7.08 (d, J=8 Hz, each 2H), 7.2–7.9 (m, 17H), 7.91 (dd, J=8, 1.5 Hz, 1H).

Step B: 2-Benzyl-5-n-butyl-2,4-dihydro-4-[[2'-(5-tetrazolyl)biphenyl-4-yl]methyl]-3H-1,2,4-triazol-3-one To a solution of 27.5 mg (0.0389 mmole) of 2-benzyl-5-n-butyl-2,4-dihydro-4-[[2'-(N-trityltetrazol-5-yl)biphenyl-4-yl]-3H-1,2,4-triazol-3-one in 0.9 ml of glacial acetic acid was added dropwise 0.4 ml of $H_2O$. The mixture was heated to 55° C. for 4 hours and then allowed to stand at room temperature for 3 days. The solvent was removed in vacuo, and the residue was re-concentrated from toluene. Purification by flash chromatography on a column containing 30 cc of silica gel (gradient elution with 5–20% methanol in $CH_2Cl_2$) and subsequent concentration from toluene gave 17 mg (86%) of white, foamy solid, mp>111.5° C. (gradual), homogeneous by TLC in 9:1 $CH_2Cl_2$—MeOH and 90:10:0.1 $CH_2Cl_2$—MeOH—AcOH; mass spectrum (FAB) m/e 466 $(M+1)^+$.

Analysis [$C_{27}H_{27}N_7O.0.75$ $H_2O.0.3$ $C_7H_8$ (toluene)] Calcd: C, 68.98; H, 6.14; N, 19.35. Found: C, 69.25; H, 6.12; N, 19.15.

300 MHz NMR ($CDCl_3$) δ0.86 (t, J=7.5 Hz, 3H), 1.33 (m, 2H), 1.57 (m, 2H), 2.42 (t, J=8 Hz, 2H), 4.79, 4.90 (s, each 2H), 7.16 (apparent s, 4H), 7.2–7.6 (m, 8H), 8.05 (d, J=8Hz, 1H).

EXAMPLE 4

5-n-Butyl-2,4-dihydro-2-phenyl-4-[[2'-(5-tetrazolyl)-biphenyl-4-yl]methyl-3H-1,2,4-triazol-3-one Step A: Ethyl Valerimidate (Free Base)

A 12.7 g (76.7 mmole) sample of ethyl valerimidate hydrochloride [prepared from valeronitrile, ethanol, and hydrogen chloride gas as described by A. J. Hill and I. Rabinowitz, J. Am. Chem. Soc., 48, 734 (1926)] was dissolved in 33% (w/w) potassium carbonate solution (made by dissolving 15 g of $K_2CO_3$ in 30 ml of $H_2O$) and immediately extracted with ether (3×40 ml). The combined ether layers were dried over $Na_2SO_4$, filtered, and concentrated in vacuo to give 7.09 g (72%) of the product as a clear oil, which was used directly in the next step.

300 MHz NMR ($CDCl_3$) δ0.88 (t, J=7 Hz, 3H), 1.24 (t, H=7 Hz, 3H), 1.31 (m, 2H), 1.50 (m, 2H), 2.19 (t, J=7.5 Hz, 2H), 4.06 (q, J=7 Hz, 2H), 6.84 (br s, 1H).

Step B: Ethyl N-Carbethoxyvalerimidate

A solution of 6.5 g (50.3 mmole) of ethyl valerimidate (free base) in 90 ml of dry $CH_2Cl_2$ was treated with 7.71 ml (5.60 g, 55.3 mole) of triethylamine. The resulting solution was stirred under $N_2$ at −10° C. in an ice-salt bath as a solution of 4.81 ml (5.46 g, 50.3 mole) of ethyl chloroformate in 10 ml of $CH_2Cl_2$ was added dropwise over 25 minutes. Upon completion of the addition, the cooling bath was removed, and the mixture was stirred at room temperature for 2 hours. Next, the solvent was removed by evaporation in vacuo. The residue was taken up in hexane and filtered to remove triethylamine hydrochloride. Concentration of the filtrate yielded 7.08 g (70%) of the product as a yellow oil, suitable for use in the next step without further purification. NMR indicated a mixture of syn and anti isomers. TLC (98:2 $CH_2Cl_2$—MeOH) showed a close pair of spots, $R_f$0.48, 0.52; mass spectrum (EI) m/e 201 (M+).

200 MHz NMR ($CDCl_3$) δ0.86 (distorted t, J=7.5 Hz, 3H), 2.15–2.35 (m, 8H), 2.4–2.65 (m, 2H), 2.19, 2.35 (t, J=7.5 Hz, 2H total ), 4.0–4.2 (m, 4H).

Step C: 5-n-Butyl-2,4-dihydro-2-phenyl-3H-1,2,4-triazol-3-one

To a solution of 197 μl (216 mg, 2.0 mmole) of phenylhydrazine in 3 ml of toluene was added 442 mg (2.2 mmole) of ethyl N-carbethoxyvalerimidate, and the mixture was heated at 45°–50° C. for 1.5 hours. At this time 307 μl (223 mg, 2.2 mmole) of triethylamine was added, and the bath temperature was raised to 95° C. After being maintained at this temperature overnight, the dark red solution was cooled and concentrated in vacuo. Flash chromatography of the residue on silica gel (elution with 0.5% methanol in $CH_2Cl_2$) gave 252 mg (58%) of the product as an off-white solid, mp 107.5°–109° C., homogeneous by TLC in 19:1 $CH_2Cl_2$—MeOH; mass spectrum (FAB) m/e 218 $(M+1)^+$.

Analysis [$C_{12}H_{15}N_3O.0.1$ $H_2O.0.1$ $C_7H_8$ (toluene)] Calcd: C, 66.82; H, 7.06; N, 18.41. Found: C, 66.59; H, 6.89; N, 18.02.

200 MHz NMR ($CDCl_3$) δ0.96 (t, J=7 Hz, 3H), 1.44 (m, 2H), 1.74 (m, 2H), 2.64 (t, J=7.5 Hz, 2H), 7.24 (d, J=8 Hz, 1H), 7.44 (t, J=8 Hz, 2H), 7.95 (d, J=8 Hz, 2H), 11.8 (br s, 1H).

Step D: 5-n-Butyl-2,4-dihydro-2-phenyl-4-[[2'-(N-trityltetrazol-5-yl)biphenyl-4-yl]methyl]-3H-1,2,4-triazol-3-one A mixture of 100 mg (0.461 mmole) of 5-n-butyl-2,4-dihydro-2-phenyl-3H-1,2,4-triazol-3-one, 18.5 mg (0.461 mmole) of sodium hydride (60% in oil), and 0.5 ml of dry DMF was stirred under $N_2$ at 40°–50° C. for 20 minutes. After $H_2$ evolution was complete, the mixture was cooled to 35° C., and a solution of 257 mg (0.461 mmole) of 5-[4'-(bromomethyl)biphenyl-2-yl]-N-trityltetrazole (see Example 2, Step B) in 1.0 ml of DMF was added. The resulting mixture was stirred at 35° C. for 2.5 hours and then concentrated in vacuo. The residue was treated with 10 ml of $H_2O$, and the product was extracted by shaking with 3×12 ml of ethyl acetate. The combined organic fractions were washed with $H_2O$ and then with saturated NaCl. The organic phase was dried over $Na_2SO_4$, filtered, and concentrated. Flash chromatography of the residue on silica gel (gradual elution with 20–40% ethyl acetate in hexane) gave 238 mg (74%) of the product as a foam, mp>69.5° C. (gradual), homogeneous by TLC in 99:1 CH$_2$Cl$_2$—MeOH; mass spectrum (FAB) m/e 694 (M+1)$^+$. Eluted after the product was 22 mg of unreacted 5-n-butyl-2,4-dihydro-2-phenyl-3H-1,2,4- triazol-3-one. Based on recovered starting material, the product yield was 96%.

200 MHz NMR (CDCl$_3$) δ0.88 (t, J=7 Hz, 3H), 1.33 (m, 2H), 1.61 (m, 2H), 2.40 (t, J=7.5 Hz, 2H), 4.80 (s, 2H), 6.93 (d, J=7.5 Hz, 6H), 7.06, 7.12 (d, J=8 Hz, each 2H), 7.2–7.5 (m, 15H), 7.94 (d, J=8 Hz, 1H), 8.04 (d, J=8 Hz, 2H).

Step E: 5-n-Butyl-2,4-dihydro-2-phenyl-4-[[2'-(5-tetrazolyl)biphenyl-4-yl]methyl-3H-1,2,4-triazol-3-one A mixture of 70 mg (0.101 mmole) of 5-n-butyl-2,4-dihydro-2-phenyl-4-[[2'-(N-trityltetrazol-5-yl)biphenyl-4-yl]methyl]-3H-1,2,4-triazol-3-one, 1.6 ml of glacial acetic acid, and 1.0 ml of H$_2$O was stirred at room temperature for 3.5 days. After removal of solvents by evaporation in vacuo, the residue was leached with hexane and a small volume of ether and then flash chromatographed on silica gel (gradient elution with 5–10% methanol in CH$_2$Cl$_2$) to give 29 mg (61%) of an off-white solid, mp 187°–188° C., homogeneous by TLC in 9:1 CH$_2$Cl$_2$—MeOH; mass spectrum m/e 452 (M+1)$^+$.

Analysis (C$_{26}$H$_{25}$N$_7$O.1.1 H$_2$O) Calcd: C, 66.33; H, 5.82; N, 20.82. Found: C, 66.45; H, 5.43; N, 20.42.

300 MHz NMR (DMSO-d$_6$) δ0.84 (t, J=7.5 Hz, 3H), 1.32 (m, 2H), 1.54 (m, 2H), 2.53 (partially obscured t, J=7.5 Hz, 2H), 4.93 (s, 2H), 7.10, 7.23 (d, J=8 Hz, each 2H), 7.4–7.7 (m, 8H), 7.93 (d, J=8 Hz, 1H).

EXAMPLE 5

5-n-Butyl-2-(2-chlorophenyl)-2,4-dihydro-4-[[2'-(5-tetrazolyl)biphenyl-4-yl]methyl]-3H-1,2,4-triazol-3-one Step A: 5-n-Butyl-2-(2-chlorophenyl)-2,4-dihydro-3H-1,2,4-triazol-3-one By the procedure of Example 4, Step C, o-chlorophenylhydrazine (generated from the hydrochloride by partitioning between ether and 1N Na$_2$CO$_3$) was reacted with N-carbethoxyvalerimidate. After work-up, the residue was purified by flash chromatography on silica gel (gradient elution with 0.6–2% methanol in CH$_2$Cl$_2$) to give a 51% yield of the product as an off-white solid, mp 103°–104° C., homogeneous by TLC in 19:1 CH$_2$Cl$_2$—MeOH; mass spectrum (FAB) m/e 252 (M+1)$^+$.

Analysis (C$_{12}$H$_{14}$ClN$_3$O) Calcd: C, 57.26; H, 5.61; N, 16.69. Found: C, 57.31; H, 5.69; N, 16.58.

200 MHz NMR (CDCl$_3$) δ0.92 (t, J=7 Hz, 3H), 1.38 (m, 2H), 1.68 (m, 2H), 2.57 (t, J=7.5 Hz, 2H), 7.3–7.55 (m, 4H), 12.04 (br s, 1H).

Step B: 5-n-Butyl-2-(2-chlorophenyl)-2,4-dihydro-4-[[2'-(N-trityltetrazol-5-yl)biphenyl-4-yl]-methyl]-3H-1,2,4-triazol-3-one The alkylation of 5-n-butyl-2-(2-chlorophenyl)-2,4-dihydro-3H-1,2,4-triazol-3-one with 5-[4'-(bromomethyl)biphenyl-2-yl]-N-trityltetrazole (see Example 2, Step B) was carried out as described in Example 4, Step D, except that a 5% excess of sodium hydride and an 8% excess of the bromo compound were used. After work-up, flash chromatography using a relatively large volume of silica gel (150 cc for 0.5 mmole; gradient elution with 20–40% ethyl acetate in hexane) provided a 69% yield of the product as a glassy solid, mp>69° C. (gradual), homogeneous by TLC in 99:1 CH$_2$Cl$_2$—MeOH; mass spectrum (FAB) m/e 728 (M+1)$^+$.

300 MHz NMR (CDCl$_3$) δ0.83 (t, J=7 Hz, 3H), 1.28 (m, 2H), 1.56 (m, 2H), 2.35 (t, J=7.5 Hz, 2H), 4.78 (s, 2H), 6.90 (d, J=7.5 Hz, 6H), 7.06, 7.12 (d, J=8 Hz, each 2H), 7.2–7.55 (m, 16H), 7.93 (d, J=8 Hz)

Step C: 5-n-Butyl-2-(2-chlorophenyl)-2,4-dihydro-4-[[2'-(5-tetrazolyl)biphenyl-4-yl]methyl]-3H-1,2,4-triazol-3-one Deprotection of 5-n-butyl-2-(2-chlorophenyl)-2,4-dihydro-4-[[2'-(N-trityltetrazol-5-yl)biphenyl-4-yl]methyl]-3H-1,2,4-triazol-3-one in 80% acetic acid (aqueous) was accomplished by the procedure of Example 4, Step E, except that the mixture was kept at 65° C. overnight. After concentrating the mixture and azeotroping 3× with toluene, the residue was flash chromatographed on silica gel (40 g for 0.18 mmole; gradient elution with 5–10% methanol in CH$_2$Cl$_2$). Upon final concentration in vacuo from toluene, a 66% yield of the product was obtained as a glassy solid, mp>87° C. (gradual), homogeneous by TLC in 90:10:0.1 CH$_2$Cl$_2$—MeOH—AcOH; mass spectrum (FAB) m/e 486 (M+1)$^+$.

Analysis [C$_{26}$H$_{24}$ClN$_7$O.0.75 H$_2$O.0.33 C$_7$H$_8$ (toluene)] Calcd: C, 64.18; H, 5.35; N, 18.49. Found: C, 64.07; H, 5.18; N, 18.31.

300 MHz NMR (CDCl$_3$) δ0.87 (t, J=7.5 Hz, 3H), 1.37 (m, 2H), 1.63 (m, 2H), 2.49 (t, J=7.5 Hz, 2H), 4.86 (s, 2H), 7.1–7.6 (m, 11H), 7.97 (dd, J=7.5 Hz, 1H)

EXAMPLE 6

5-n-Butyl-2-[2-(carbomethoxy)benzyl]-2,4-dihydro-4-[[2'-(5-tetrazolyl)biphenyl-4-yl]methyl]-3H-1,2,4-triazol-3-one Step A: 5-n-Butyl-2-[2-(carbomethoxy)benzyl]-2,4-dihydro-4-[[2'-(N-trityltetrazol-5-yl)biphenyl-4-yl]methyl]-3H-1,2,4-triazol-3-one By the procedure of Example 3, Step A, 5-n-butyl-2,4-dihydro-4-[[2'-(N-trityltetrazol-5-yl)biphenyl-4-yl]methyl]-3H-1,2,4-triazol-3-one (from Example 2, Step D) was alkylated with methyl 2-(bromomethyl)-benzoate [R. M. Scrowston and D. C. Shaw, J. Chem. Soc. Perkin Trans. I, 749 (1976)] to give a 72% yield of the titled compound as a foam, homogeneous by TLC in 98:2 CH$_2$Cl$_2$—MeOH; mass spectrum (FAB) m/e 766 (M+1)$^+$.

Analysis (C$_{48}$H$_{43}$N$_7$O$_3$.0.8 H$_2$O) Calcd: C, 73.88; H, 5.77; N, 12.56 Found: C, 73.99; H, 5.51; N, 12.38

300 MHz NMR (CDCl$_3$) δ0.82 (t, J=7.5 Hz, 3H), 1.26 (m, 2H), 1.50 (m, 2H), 2.30 (t, J=7.5 Hz, 2H), 3.91 (s, 3H), 4.74 (s, 2H), 5.47 (s, 2H), 6.91 (d, J=7 Hz, 6H), 7.0–7.5 (m, 19H), 7.93, 7.99 (d, J=8 Hz, each 1H).

Step B: 5-n-Butyl-2-[2-(carbomethoxy)benzyl]-2,4-dihydro-4-[[2'-(5-tetrazolyl)biphenyl-4-yl]-methyl]-3H-1,2,4-triazol-3-one Detritylation of 5-n-butyl-2-[2-(carbomethoxy)benzyl]-2,4-dihydro-4-[[2'-(N-trityltetrazol-5-yl)biphenyl-4-yl]methyl]-3H-1,2,4-triazol-3-one was carried out according to the procedure of Example 3, Step B, except that the mixture was stirred initially at 35°–40° C. and then overnight at room temperature. Purification by flash chromatography on silica gel (gradient elution with 5–10% methanol in CH$_2$Cl$_2$) afforded a 95% yield of the titled compound as a white powder, mp 79°–80° C., homogeneous by TLC in 9:1 CH$_2$Cl$_2$—MeOH and 90:10:0.1 CH$_2$Cl$_2$—MeOH—AcOH; mass spectrum (FAB) m/e 524 (M+1)$^+$.

Analysis (C₂₉H₂₉N₇O₃.1.25 H₂O) Calcd: C, 63.78; H, 5.81; N, 17.95 Found: C, 64.03; H, 5.60; N, 17.66

300 MHz NMR (CDCl₃) δ0.86 (t, J=7.5 Hz, 3H), 1.33 (m, 2H), 1.58 (m, 2H), 2.44 (t, J=7.5 Hz, 2H), 3.88 (s, 3H), 4.84 (s, 2H), 5.39 (s, 2H), 7.05 (d, J=8 Hz, 1H), 7.15–7.6 (m, 9H), 7.95, 8.07 (d, J=8 Hz, each 1H).

EXAMPLE 7

5-n-Butyl-2-(2-carboxybenzyl)-2,4-dihydro-4-[[2′-(5-tetrazolyl)biphenyl-4-yl]methyl]-3H-1,2,4-triazol-3-one To a solution of 20 mg (0.038 mmole) of 5-n-butyl-2-[2-(carbomethoxy)benzyl]-2,4-dihydro-4-[[2′-(5-tetrazolyl)biphenyl-4-yl]methyl]-3H-1,2,4-triazol- 3-one (from Example 6) in 200 μl of dry THF was added all at once 84 μl (0.084 mmole) of 1N sodium hydroxide in methanol. The mixture was stirred overnight at room temperature and then evaporated to dryness. The residual solid was dissolved in 1.5 ml of methanol and treated with 90 μl of 1N HCl in methanol (final pH 2). The solvent was evaporated, and the residue was leached with CHCl₃. After removal of insoluble solid (NaCl) by filtration through glass wool, the filtrate was concentrated in vacuo and then re-concentrated from toluene. The residue was dried overnight in the presence of P₂O₅ to give 20 mg (95%) of the titled compound as a stiff, white foam, mp>106° C. (gradual), homogeneous by TLC in 90:10:0.1 CH₂Cl₂—MeOH—AcOH; mass spectrum (FAB) m/e 510 (M+1)⁺.

Analysis [C₂₈H₂₇N₇O₃.2H₂O.0.1C₇H₈ (toluene)] Calcd: C, 62.14; H, 5.77; N, 17.67 Found: C, 62.54; H, 5.68; N, 17.42

300 MHz NMR (CDCl₃) δ0.84 (t, J=7.5 Hz, 3H), 1.30 (m, 2H), 1.55 (m, 2H), 2.43 (t, J=7.5 Hz, 2H), 4.77 (s, 2H), 5.27 (s, 2H), 7.10 (m, 4H), 7.2–7.6 (m, 6H), 7.92, 7.96 (d, J=8 Hz, each 1H).

EXAMPLE 8

5-n-Butyl-2,4-dihydro-2-[2-(hydroxymethyl)phenyl]-4-[[2′-(5-tetrazolyl)biphenyl-4-yl]methyl]-3H-1,2,4-triazol-3-one and
2-[2-(Acetoxymethyl)phenyl]-5-n-butyl-2,4-dihydro-4-[[2′-(5-tetrazolyl)biphenyl-4-yl]-methyl]-3H-1,2,4-triazol-3-one.

Step A: 5-n-Butyl-2-[2-(carbomethoxy)phenyl]-2,4-dihydro-3H-1,2,4-triazol-3-one

By the procedure of Example 4, Step C, o-(carbomethoxy)phenylhydrazine [generated from the hydrochloride which was prepared according to H. Stroh and G. Westphal, Chem. Ber. 96, 184 (1963), by partitioning between ether and 5% aqueous sodium bicarbonate] was reacted with ethyl N-carbethoxyvalerimidate (Example 4, Step B). After work-up, the residue was purified by flash chromatography on silica gel (gradient elution with 0.6–2% methanol in CH₂Cl₂) to give a 51% yield of the product as a pale yellow oil, homogeneous by TLC (19:1 CH₂Cl₂—MeOH), mass spectrum (FAB) m/e 276 (M+1)⁺.

200 MHz ¹HNMR (CDCl₃) δ0.93 (t, J=7.2 Hz, 3H), 1.35 (m, 2H), 1.68 (m, 2H) 2.56 (t, J=7.8 Hz, 2H), 3.83 (s, 3H), 7.40 (m, 1H), 7.61 (d, J=3.7 Hz, 2H) 7.90 (d, J=7.8 Hz, 1H), 12.03 (s, 1H).

Step B: 5-n-Butyl-2-[2-(carbomethoxy)phenyl]-2,4-dihydro-4-[[2′-(N-trityltetrazol-5-yl)biphenyl-4-yl]methyl]-3H-1,2,4-triazol-3-one The alkylation of 5-n-butyl-2-[2-(carbomethoxy)phenyl]-2,4-dihydro-3H-1,2,4-triazol-3-one with 5-[4′-(bromomethyl)biphenyl-2-yl]-N-trityltetrazole (see Example 2, Step B) was carried out as described in Example 4, Step D, except that a 20% excess of sodium hydride and a 5% excess of the bromo compound were used, and the anion was generated during 2.5 hours at room temperature. After work-up, flash chromatography on silica gel (eluting with 0.6% methanol in CH₂Cl₂) provided a 65% yield of the product as a white foam, homogeneous by TLC in 99:1 CH₂Cl₂—MeOH; mass spectrum (FAB) m/e 752 (M+1)⁺.

300 MHz ¹HNMR (CDCl₃) δ0.84 (t, J=7.3 Hz, 3H), 1.30 (m, 2H), 1.60 (m, 2H), 2.35 (t, J=7.9 Hz, 2H), 3.76 (s, 3H), 4.75 (s, 3H), 6.90 (m, 4H), 7.10 (m, 6H), 7.35 (m, 15H), 7.85 (m, 2H).

Step C: 5-n-Butyl-2,4-dihydro-2-[2-(hydroxymethyl)phenyl]-4-[[2′-(N-trityltetrazol-5-yl)-biphenyl-4-yl]methyl]-3H-1,2,4-triazol-3-one To a vigorously stirred solution of 59 mg (0.079 mmole) of 5-N-butyl-2-[2-(carbomethoxy)phenyl]-2,4-dihydro-4-[[(2′-N-trityltetrazol-5-yl)biphenyl-4-yl]methyl]-3H-1,2,4-triazol-3-one in 1.0 mL dry CH₂Cl₂ at −25° C. was added dropwise 314 μL (0.314 mmole) of 1M diisobutylaluminum hydride in CH₂Cl₂. After stirring between −20° and −10° C. for 75 minutes, the mixture was cooled to −50° C., treated with 0.75 mL methanol and warmed up to room temperature. Subsequently, the mixture was treated with 1.5 mL of 2.5% NaOH, and extracted with 4 mL CH₂Cl₂ 3 times. The combined organic layers were washed with 5 mL H₂O twice followed by 5 mL brine, and dried over anhydrous Na₂S)₄. The residue obtained after evaporation of solvents was flash chromatographed over silica gel (eluting with 0.8% methanol in CH₂Cl₂) to yield 40 mg (70%) of a white foam, homogeneous by TLC in 98:2 CH₂Cl₂—MeOH, mass spectrum (FAB) m/e 724 (M+1)⁺.

300 MHz ¹HNMR (CDCl₃) δ0.85 (t, J=7.3 Hz, 3H), 1.30 (m, 2H), 1.53 (m, 2H), 2.39 (t, J=8.0 Hz, 2H), 4.49 (d, J–6.1 Hz, 2H), 4.79 (s, 2H), 6.90 (m, 7H), 7.10 (m, 5H), 7.40 (m, 14H), 7.92 (m, 1H).

Step D: 5-n-Butyl-2.4-dihydro-2-[2-(hydroxymethyl)-phenyl]-4-[[(2′-(5-tetrazolyl)biphenyl-4-yl]methyl]-3H-1,2,4-triazol-3-one (A) and 2-[2-(Acetoxymethyl)-phenyl]-5-n-butyl-2,4-dihydro-4-[[2′-(5-tetrazoly)biphenyl-4-yl]-methyl]-3H-1,2,4,-triazol-3-one (B)

A mixture of 35 mg (0.0484 mmole) of 5-n-butyl-2,4-dihydro-2-[2-(hydroxymethyl)phenyl]-4-[[2′-(N-trityltetrazol-5-yl)biphenyl-4-yl]methyl]-3H-1,2,4-triazol-3-one, 0.5 mL of glacial acetic acid, and 0.25 mL of H₂O was stirred at 60° C. overnight, TLC in 90:10 CH₂Cl₂—MeOH showed two products at R_f<0.25. After cooling to room temperature, solvents were evaporated and the residue flash chromatographed over silica gel (gradient elution with 4–10% methanol in CH₂Cl₂) to give 7 mg of product B (the acetate) as an oil and 12 mg of product A (the hydroxy compound) as a clear oil. Each compound was homogeneous by TLC in 90:10 CH₂Cl₂—MeOH, mass spectrum (FAB) for A m/e 482 (M+1)⁺ and for B m/e 524(M+1)⁺.

A: 300 MHz ¹HNMR (CDCl₃) δ0.88 (t, J=7.3 Hz, 3H), 1.37 (m, 2H), 1.64 (m, 2H), 2.51 (t, J=7.5 Hz, 2H), 4.39 (s, 2H), 4.81 (s, 2H), 7.30 (m, 11H), 7.93 (m, 1H).

B: 300 MHz ¹HNMR (CDCl₃) δ0.90 (t, J=7.2 Hz, 3H), 1.39 (m, 2H), 1.65 (m, 2H), 1.99 (s, 3H), 2.52 (t, J=8.1 Hz, 2H), 4.83 (s, 2H), 5.02 (s, 2H), 7.40 (m, 11H), 7.95 (m, 1H)

EXAMPLE 9

5-n-Butyl-2,4-dihydro-2-[4-methylbenzyl]-4-[[2'-(5-tetrazolyl)biphenyl-4-yl]methyl]-3H-1,2,4,-triazol-3-one Step A: 4-Azidomethyl-2'-cyanobiphenyl A mixture of 1.97 g (725 mole) of 4-bromomethyl-2'-cyanobiphenyl (EP 253,310), 445 mg (9.1 mmole) of lithium azide and 5 ml of dry DMSO was stirred at room temperature under nitrogen for one hour and then partitioned between 100 ml of ether and 100 ml of $H_2O$. The organic phase was washed with $3 \times 100$ ml of $H_2O$, then dried ($MgSO_4$), filtered, and concentrated in vacuo to give a residual oil which solidified on standing. This solid was triturated with petroleum ether, collected on a filter, washed with petroleum ether and dried overnight to yield 1.15 g (61%) of the title compound as white crystals, mp 69°–70° C.; mass spectrum (EI) m/e 234 ($M^+$). TLC in 4:1 hexane-EtOAc showed only minor impurities and the material was of sufficient purity to use in the next step.

300 MHz NMR ($CDCl_3$) δ4.41 (s, 2H), 7.4–7.7 (m, 7H), 7.75 (d, J=8 Hz, 1H).

Step B: [(2'-Cyanobiphenyl-4-yl)methyl]amine

A solution of 5.85 g (25 mmole) of 4-azidomethyl-2'-cyanobiphenyl (from Step A) in 50 ml of dry tetrahydrofuran was treated portionwise with 6.55 g (25 mmole) of triphenylphospine over 3–4 minutes. The solution was stirred at ambient temperature under $N_2$, and gas evolution proceeded at a moderate rate. A mild exotherm occurred, and the solution was cooled in a water bath as necessary. After 2 hours, by which time gas evolution had ceased, 675 μl (37.5 mmole) of $H_2O$ was added, and stirring was continued at room temperature under $N_2$. After 22 hours, the solution was concentrated in vacuo, and the residual oil was chromatographed on a column of silica gel (gradient elution with 2–10% methanol in $CH_2Cl_2$). The residue from evaporation of the pooled product fractions was partitioned between ether-$CH_2Cl_2$ and saturated $Na_2CO_3$ (aqueous). The organic phase was dried ($Na_2SO_4$), filtered, and concentrated in vacuo to yield 4.64 g (89%) of air-sensitive, nearly white crystals, mp 54°–55° C., homogeneous by TLC in 9:1 $CH_2Cl_2$—MeOH; mass spectrum (FAB) m/e 209$(M+1)^+$.

Analysis ($C_{14}H_{12}N_2$) Calcd: C, 80.74; H, 5.81; N, 13.45 Found: C, 80.53; H, 5.89; N, 13.12

300 MHz NMR($CDCl_3$) δ1.50 (br s, 2H), 3.92 (s, 2H), 7.35–7.65 (m, 7H), 7.75 (d, J=8 Hz, 1H)

Step C: 5-n-Butyl-4-[(2'-cyanobiphenyl-4-yl)methyl]-2,4-dihydro-3H-1,2,4-triazol-3-one A mixture of 400 mg (1.923 mmole) of [(2'-cyanobiphenyl-4-yl)methyl]amine, 457 mg (2.12 mmole) of ethyl valerimidate carbethoxyhydrazone (from Example 2, Step A), and 7 mL of ethanol was stirred under $N_2$ in an oil bath at 50° C. for 3 hours and then at 80° C. for 2 days. The mixture was cooled and concentrated. The residue, re-concentrated from toluene, was flash chromatographed over silica gel (gradient elution with 1.5–5% methanol in $CH_2Cl_2$) to give 591 mg (93%) of desired product, homogeneous in TLC (90:10 $CH_2Cl_2$—MeOH); mass spectrum (FAB) m/e 333 $(M+1)^+$.

300 MHz $^1$HNMR($CDCl_3$) δ0.85 (t, J=7.2 Hz, 3H), 1.35 (m, 2H), 1.60 (m, 2H), 2.42 (t, J=7.2 Hz, 2H), 4.87 (s, 3H), 7.35 (d, J=7 Hz, 2H), 7.50 (m, 4H), 7.62 (d, J=8.5 Hz, 1H), 7.75 (d, J=8.5 Hz, 1H), 9.13 (br s, 1H).

Step D: 5-n-Butyl-4-[(2'-cyanobiphenyl-4-yl)methyl]-2,4-dihydro-2-(4-methylbenzyl)-3H-1,2,4-triazol-3-one The alkylation of 5-n-butyl-4-[(2'-cyanobiphenyl-4-yl)methyl]-2,4-dihydro-3H-1,2,4-triazol-3-one with 4-methylbenzyl bromide was carried out as described in Example 3, Step A, except that no excess sodium hydride was used. After work-up, flash chromatography of the crude product on silica gel (eluting with 0.6% methanol in $CH_2Cl_2$) provided a 76% yield of the title compound as a clear oil, homogeneous by TLC (98:2 $CH_2Cl_2$—MeOH), mass spectrum (FAB) m/e 437 $(M+1)^+$.

300 MHz $^1$HNMR ($CDCl_3$) δ0.84 (t, J=7.3 Hz, 3H), 1.40 (m, 2H), 1.52 (m, 2H), 2.31 (s, 3H), 2.38 (m, 2H), 4.87 (s, 2H), 4.93 (s, 2H), 7.12 (d, J=7.8 Hz, 2H), 7.26 (d, J=8.5 Hz, 2H), 7.33 (d, J=8.2 Hz, 2H), 7.50 (m, 4H), 7.62 (m, 1H), 7.74 (m, 1H).

Step E: 5-n-Butyl-2,4-dihydro-2-(4-methylbenzyl)-4-[[2'-(5-tetrazolyl)biphenyl-4-yl]methyl]-3H-1,2,4-triazol-3-one A mixture of 56 mg (0.128 mmole) 5-n-butyl-4-[(2'-cyanobiphenyl-4-yl) methyl]-2,4-dihydro-2-(4-methylbenzyl)-3H-1,2,4-triazol-3-one, 2.0 mL dry toluene, and 134 mg (0.65 mmole) trimethyltin azide was stirred and heated at 60° under $N_2$ for 10 minutes, and then at 110° for 3 days. After cooling to room temperature, toluene was removed under reduced pressure and the residue was taken up in 1.5 mL methanol. The solution was treated with 0.75 g 230–400 mesh silica gel and stirred for 45 min. Upon removal of the methanol, the resulting powder was made into a slurry in $CH_2Cl_2$ and applied on a silica gel column, gradient eluted wih 4–10% methanol in $CH_2Cl_2$ to give 19 mg (13%) of a clear oil, homogeneous on TLC (90:10 $CH_2Cl_2$—MeOH), mass spectrum m/e 480 $(M+1)^+$.

300 MHz $^1$HNMR ($CDCl_3$) δ0.81 (t, J=7.2 Hz, 3H), 1.27 (m, 2H), 1.50 (m, 2H), 2.27 (s, 3H), 2.35 (m, 2H), 4.68 (s, 2H), 4.79 (s, 2H), 7.02 (m, 6H), 7.45 (m, 4H), 7.86 (d, J=7.6 Hz, 1H), 8.03 (d, J=7.6 Hz, 1H).

Additional 2,5-disubstituted -2,4-dihydro-4-[[2'-(5-tetrazolyl)biphenyl-4-yl]methyl-3H-1,2,4-triazol-3-ones prepared by the methods described in the foregoing Examples are tabulated below.

TABLE II

[Structure: triazolone core with R and R¹ substituents, N-CH2-biphenyl-tetrazole]

| | R | R¹ | mp | formula | | Analysis C | H | N |
|---|---|---|---|---|---|---|---|---|
| (1) | n-Bu | s-Bu | 79.81° C. | $C_{24}H_{29}N_7O \cdot 0.5H_2O \cdot 0.25CHCl_3$ | calcd. | 61.92 | 6.48 | 20.84 |
| | | | | | found: | 61.92 | 6.39 | 20.63 |
| (2) | n-Bu | 3-Cl-C₆H₄— | 89–90° C. | $C_{26}H_{24}ClN_7O \cdot 0.1CHCl_3$ | calcd. | 62.96 | 4.88 | 19.69 |
| | | | | | found: | 63.12 | 4.61 | 19.50 |
| (3) | n-Bu | 4-Cl-C₆H₄— | 94–95° C. | $C_{26}H_{24}ClN_7O \cdot 0.15CHCl_3$ | calcd. | 62.33 | 4.83 | 19.46 |
| | | | | | found: | 62.33 | 4.85 | 19.36 |
| (4) | n-Bu | —CH(CO₂CH₃)(C₆H₅) | >87.5° C. (gradual) | $C_{29}H_{29}N_7O_3 \cdot 1H_2O \cdot 0.1C_7H_8$ (toluene) | calcd. | 64.76 | 5.82 | 17.80 |
| | | | | | found: | 65.03 | 5.71 | 17.59 |
| (5) | n-Bu | —CH₂—(3-CH₃-C₆H₄) | 72–73.5° C. | $C_{28}H_{29}N_7O \cdot 1/6C_7H_8 \cdot 1/5CHCl_3$ (toluene) | calcd. | 67.99 | 5.93 | 18.90 |
| | | | | | found: | 68.03 | 6.07 | 18.59 |
| (6) | n-Bu | —CH₂—(2-CH₃-C₆H₄) | 192–193.5° C. | $C_{28}H_{29}N_7O \cdot 1/5C_7H_8 \cdot 1/8CHCl_3$ (toluene) | calcd. | 68.93 | 6.02 | 19.06 |
| | | | | | found: | 69.13 | 5.60 | 18.84 |
| (7) | n-Bu | —CH(CH₃)(C₆H₅) | 162.5–164° C. | $C_{28}H_{29}N_7O \cdot 0.1CHCl_3$ | calcd. | 68.67 | 5.97 | 19.95 |
| | | | | | found: | 69.04 | 5.74 | 19.65 |
| (11) | n-Bu | 2,4-Cl₂-C₆H₃— | >102° C. | $C_{26}H_{23}Cl_2N_7O \cdot 1/3H_2O$ | calcd. | 59.32 | 4.53 | 18.63 |
| | | | | | found: | 59.41 | 4.38 | 18.45 |
| (12) | n-Bu | 2-F-C₆H₄— | >86° C. (gradual) | $C_{26}H_{24}FN_7O \cdot 0.4H_2O$ | calcd. | 65.53 | 5.24 | 20.58 |
| | | | | | found: | 65.70 | 5.29 | 20.44 |

TABLE II-continued

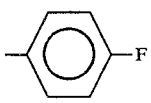

| R | R¹ | mp | formula | | Analysis C | H | N |
|---|---|---|---|---|---|---|---|
| (13) n-Bu | 4-F-phenyl | >87° C. (gradual) | $C_{26}H_{24}FN_7O \cdot 0.4H_2O$ | calcd. found: | 65.53 65.72 | 5.24 5.19 | 20.58 20.56 |
| (14) n-Bu | pentafluorophenyl | 89–91° C. | $C_{26}H_{20}F_5N_7O$ | calcd. found: | 57.67 57.39 | 3.72 3.83 | 18.11 17.81 |
| (15) n-Bu | 2-Br-phenyl | >98° C. (gradual) | $C_{26}H_{24}BrN_7O \cdot 0.05CH_2Cl_2$ | calcd. found: | 58.52 58.35 | 4.54 4.61 | 18.34 18.05 |
| (16) n-Bu | 2-CH₃-phenyl | 152–154.5° C. (toluene) | $C_{27}H_{27}N_7O \cdot 1/4C_7H_6 \cdot 1/2H_2O$ | calcd. found: | 69.40 69.54 | 6.08 5.97 | 19.70 19.62 |
| (17) n-Bu | 4-CH₂CH₃-phenyl | >87° C. (gradual) | $C_{28}H_{29}N_7O \cdot 0.1H_2O$ | calcd. found: | 69.86 69.70 | 6.11 5.94 | 20.36 20.13 |
| (18) n-Bu | 2-NO₂-phenyl | >92° C. (gradual) | $C_{26}H_{24}N_8O_3 \cdot 0.7H_2O$ | calcd. found: | 61.34 61.65 | 5.03 4.92 | 22.01 21.81 |
| (19) n-Bu | 4-NO₂-phenyl | >96° C. (gradual) | $C_{26}H_{24}N_8O_3 \cdot 1/8CH_2Cl_2$ | calcd. found: | 61.87 61.98 | 4.82 4.95 | 22.09 21.74 |
| (20) n-Bu | 2-OCH₃-phenyl | >100° C. (gradual) | $C_{27}H_{27}N_7O_2 \cdot 1.4H_2O$ | calcd. found: | 63.99 64.21 | 5.92 5.95 | 19.35 19.14 |
| (21) n-Bu | 4-OCH₃-phenyl | >78° C. (gradual) | $C_{27}H_{27}N_7O_2 \cdot 0.1C_7H_8 \cdot 0.6H_2O$ (toluene) | calcd. found: | 66.33 66.59 | 5.83 5.95 | 19.55 19.18 |

TABLE II-continued

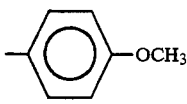

| | R | R¹ | mp | formula | | Analysis C | H | N |
|---|---|---|---|---|---|---|---|---|
| (22) | n-Bu | 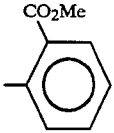 -OCH₃ | >84° C. (gradual) | $C_{27}H_{27}N_7O_2 \cdot 0.25CH_2Cl_2$ | calcd. found: | 65.09 65.36 | 5.51 5.25 | 19.49 19.09 |
| (23) | n-Bu | CO₂Me 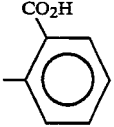 | >84° C. (gradual) | $C_{28}H_{27}N_7O_3 \cdot 0.4CH_2Cl_2$ | calcd. found: | 62.76 62.97 | 5.15 5.33 | 18.04 17.86 |
| (24) | n-Bu | CO₂H 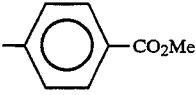 | 117–120° C. (toluene) | $C_{27}H_{25}N_7O_3 \cdot 0.2C_7H_6 1.5H_2O$ | calcd. found: | 63.05 63.29 | 5.51 5.76 | 18.12 18.03 |
| (25) | n-Bu | 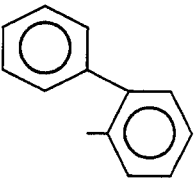 -CO₂Me | >94° C. (gradual) | $C_{28}H_{27}N_7O_3 \cdot 1/2H_2O$ | calcd. found: | 64.85 65.01 | 5.44 5.45 | 18.90 18.51 |
| (26) | n-Bu | 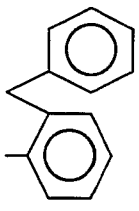 | >94° C. (gradual) | $C_{32}H_{29}N_7O \cdot 0.7CH_2Cl_2$ | calcd. found: | 66.90 67.09 | 5.22 5.30 | 16.70 16.76 |
| (27) | n-Bu | 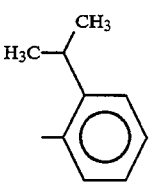 | >84° C. (gradual) | $C_{33}H_{31}N_7O \cdot 4H_2O$ | calcd. found: | 64.58 64.94 | 5.09 5.45 | 15.98 15.73 |
| (28) | n-Bu | CH₃ H₃C— | >85° C. (gradual) | $C_{29}H_{31}N_7O \cdot 0.1C_7H_8 \cdot 0.2CH_2Cl_2$ (toluene) | calcd. found: | 69.09 69.47 | 6.24 6.47 | 18.86 18.58 |

TABLE II-continued

[Structure: A 1,2,4-triazol-3-one ring bearing R at the 5-position, R¹ on N-2, and an N-4 CH₂ group attached to a biphenyl system where the 2'-position of the distal phenyl bears a 1H-tetrazol-5-yl group.]

| | R | R¹ | mp | formula | | Analysis C | H | N |
|---|---|---|---|---|---|---|---|---|
| (29) | n-Bu | 2-methyl-N,N-dimethylaniline (CH₃, N(CH₃)₂ on phenyl) | 179–181° C. | C₂₈H₃₀N₈O.1/4C₇H₆.1/2H₂O (toluene) | calcd. found: | 67.85 68.07 | 6.31 6.23 | 21.28 21.06 |
| (30) | n-Bu | 2-NO₂, 4-OCH₃ phenyl | >95° C. (gradual) | C₂₇H₂₆N₈O₄.0.7H₂O.0.4CH₂Cl₂ | calcd. found: | 57.42 57.80 | 4.96 4.61 | 19.55 19.17 |
| (31) | n-Pr | 2-chlorophenyl | >94° C. (gradual) | C₂₅H₂₂ClN₇O.0.8H₂O | calc'd: found: | 61.74 61.97 | 4.89 4.93 | 20.16 19.88 |
| (32) | n-Pr | 2-nitrophenyl | >92° C. (gradual) | C₂₅H₂₂N₈O₃.H₂O.0.2CH₂Cl₂ | calc'd: found: | 58.49 58.55 | 4.75 4.53 | 21.65 21.44 |
| (33) | n-C₅H₁₁ | 2-nitrophenyl | >76° C. (gradual) | C₂₇H₂₆N₈O₃.0.3CH₂Cl₂.0.1C₇H₈ (Toluene) | calc'd: found: | 62.16 61.84 | 5.10 4.93 | 20.71 20.57 |
| (34) | n-Bu | 2-pyridyl | >117° C. (gradual) | C₂₅H₂₄N₈O.5/8CH₂Cl₂ | calc'd: found: | 60.87 61.20 | 5.03 5.17 | 22.16 21.81 |
| (35) | n-Bu | —CH₂C₆F₅ | >79° C. (gradual) | C₂₇H₂₂F₅N₇O.0.4CH₂Cl₂.0.15C₇H₆ (toluene) | calc'd: found: | 56.64 56.94 | 4.01 3.67 | 16.25 16.10 |
| (36) | n-Bu | —CH₂-(3-CO₂Me-phenyl) | >74° C. (gradual) | C₂₉H₂₉N₇O₃.0.25CHCl₃ | calc'd: found: | 63.48 63.54 | 5.33 5.42 | 17.72 17.46 |
| (37) | n-Bu | —CH₂-(tetrahydrothiopyranyl) | 180–181° C. | C₂₇H₃₃N₇O.0.2H₂O | calc'd: found: | 68.24 68.23 | 7.08 7.01 | 20.63 20.52 |
| (38) | n-Bu | —CH₃ | 202–203° C. | C₂₁H₂₃N₇O | calc'd: found: | 64.76 64.57 | 5.95 5.97 | 25.18 25.16 |
| (39) | n-Bu | —CH₂CH₃ | 197–198° C. | C₂₂H₂₅N₇O.0.2H₂O | calc'd: found: | 64.91 65.03 | 6.29 5.94 | 24.09 23.92 |
| (40) | n-Bu | —CH₂CH₂CH₃ | 155–155.5° C. | C₂₃H₂₇N₇O.0.2H₂O | calc'd found: | 65.59 65.53 | 6.56 6.51 | 23.21 23.00 |

TABLE II-continued

[Structure: triazolone with R and R¹ substituents, N-benzyl linked to biphenyl-tetrazole]

| | R | R¹ | mp | formula | | Analysis C | H | N |
|---|---|---|---|---|---|---|---|---|
| (41) | n-Bu | —CH(CH$_3$)$_2$ | 187–188° C. | C$_{23}$H$_{27}$N$_7$O.0.75H$_2$O | calc'd: | 64.09 | 6.66 | 22.75 |
| | | | | | found: | 64.34 | 6.40 | 22.42 |
| (42) | n-Bu | —(CH$_2$)$_3$CH$_3$ | 175–177° C. | C$_{24}$H$_{29}$N$_7$O.0.3H$_2$O.0.1CH$_2$Cl$_2$ | calc'd: | 64.98 | 6.74 | 22.01 |
| | | | | | found: | 65.35 | 6.94 | 21.59 |
| (43) | n-Bu | —CH$_2$CH(CH$_3$)$_2$ | >80° C. (gradual) | C$_{24}$H$_{29}$N$_7$O.0.6H$_2$O | calc'd: | 65.18 | 6.86 | 22.17 |
| | | | | | found: | 65.21 | 6.85 | 21.92 |
| (44) | n-Bu | cyclopentyl | 226–227° C. | C$_{25}$H$_{29}$N$_7$O.0.4H$_2$O | calc'd: | 66.61 | 6.66 | 21.75 |
| | | | | | found: | 66.76 | 6.63 | 21.50 |
| (45) | n-Bu | —CH$_2$CO$_2$Me | >100° C. (gradual) | C$_{23}$H$_{25}$N$_7$O$_3$.0.75H$_2$O.0.1C$_4$H$_{10}$ | calc'd: | 60.00 | 5.92 | 20.93 |
| | | | | | found: | 60.41 | 5.86 | 20.61 |
| (46) | n-bu | —CH$_2$CF$_3$ | 66–70° C. | C$_{22}$H$_{22}$F$_3$N$_7$O.0.3C$_7$H$_8$.H$_2$O (toluene) | calc'd: | 57.54 | 5.29 | 19.49 |
| | | | | | found: | 57.56 | 5.13 | 19.16 |
| (47) | n-Pentyl | 2-chlorophenyl | 87–91° C. | C$_{27}$H$_{26}$ClN$_7$O.0.4H$_2$O | calc'd: | 63.94 | 5.32 | 19.33 |
| | | | | | found: | 64.09 | 5.27 | 18.93 |
| (48) | n-Bu | 2-(trifluoromethyl)phenyl | 88–90° C. | C$_{27}$H$_{24}$F$_3$N$_7$O.0.1CH$_2$Cl$_2$0.1H$_2$O | calc'd: | 61.44 | 4.64 | 18.51 |
| | | | | | found: | 61.83 | 4.79 | 18.15 |
| (49) | n-Bu | —(CH$_2$)$_2$C$_6$H$_3$ | 71–73° C. | C$_{28}$H$_{29}$N$_7$O.0.5H$_2$O | calc'd: | 68.83 | 6.19 | 20.07 |
| | | | | | found: | 68.84 | 6.05 | 19.68 |
| (50) | n-Bu | —CH(CH$_3$)CO$_2$Me | 69–71° C. | C$_{24}$H$_{27}$N$_7$O$_3$.0.6H$_2$O | calc'd: | 61.03 | 6.02 | 20.76 |
| | | | | | found: | 61.47 | 5.92 | 20.39 |
| (51) | n-Bu | —CH(CH$_3$)CO$_2$H | 105–109° C. | C$_{23}$H$_{25}$N$_7$O$_3$ | | | | |
| (52) | n-Bu | 4-(CO$_2$Me)phenyl-ethyl | 81–84° C. | C$_{29}$H$_{29}$N$_7$O$_3$.0.15CH$_2$Cl$_2$ | calc'd: | 65.76 | 5.51 | 18.28 |
| | | | | | found: | 65.58 | 5.56 | 17.89 |
| (53) | n-Bu | 2-hydroxycyclopentyl | >115° C. (gradual) | C$_{25}$H$_{29}$N$_7$O.0.4CH$_2$Cl$_2$ | calc'd: | 61.82 | 6.08 | 19.87 |
| | | | | | found: | 61.64 | 5.99 | 19.77 |
| (54) | n-Bu | —CH$_2$C(CH$_3$)$_3$ | 88–90° C. | C$_{25}$H$_{31}$N$_7$O.2/3H$_2$O | calc'd: | 65.62 | 7.12 | 21.43 |
| | | | | | found: | 65.80 | 6.89 | 21.13 |
| (55) | n-Bu | -t-Bu | >86° C. (gradual) | C$_{24}$H$_{29}$N$_7$O.0.7H$_2$O | calc'd: | 64.90 | 6.90 | 22.08 |
| | | | | | found: | 65.14 | 6.62 | 21.75 |
| (56) | n-Bu | —(CH$_2$)$_3$C$_6$H$_5$ | 63–65° C. | C$_{29}$H$_{31}$N$_7$O.0.6H$_2$O | calc'd: | 69.05 | 6.43 | 19.44 |
| | | | | | found: | 69.26 | 6.14 | 19.13 |
| (57) | n-Bu | —CH$_2$-naphthyl | 98–100° C. | C$_{31}$H$_{29}$N$_7$O.0.7H$_2$O.0.15CH$_2$Cl$_2$ | calc'd: | 69.16 | 5.72 | 18.12 |
| | | | | | found: | 69.54 | 5.33 | 17.80 |

TABLE II-continued

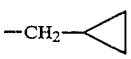

| | R | R¹ | mp | formula | Analysis C | H | N |
|---|---|---|---|---|---|---|---|
| (58) | n-Bu | —CH(CH₃)CH₂OH | 114–116° C. | $C_{23}H_{27}N_7O_2 \cdot H_2O \cdot 0.15CH_2Cl_2$ | calc'd: 59.89<br>found: 59.80 | 6.36<br>6.04 | 21.12<br>21.09 |
| (59) | n-Bu | —CH₂—△ | >70° C. (gradual) | $C_{24}H_{27}N_7O \cdot 0.8H_2O \cdot 0.1C_7H_8$ (toluene) | calc'd: 65.47<br>found: 65.44 | 6.53<br>6.16 | 21.64<br>21.23 |
| (60) | 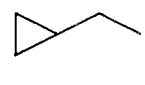 | —(CH₂)₂C₆H₅ | 82–84° C. | $C_{29}H_{31}N_7O$ | calc'd: 70.60<br>found: 70.59 | 6.30<br>6.17 | 19.90<br>19.63 |
| (61) | △⟍ | —(CH₂)₂C₆H₅ | 164–166° C. | $C_{28}H_{27}N_7O \cdot 0.25CH_3OH \cdot 0.15CH_2Cl_2$ | calc'd: 68.45<br>found: 68.64 | 5.73<br>5.37 | 19.67<br>19.32 |
| (62) | △⟍ |  | 114–116° C. | $C_{26}H_{22}ClN_7O \cdot 0.25CH_2Cl_2$ | calc'd: 62.41<br>found: 62.79 | 4.49<br>4.22 | 19.41<br>19.28 |

EXAMPLE 10

2-[3-(N-Benzyloxycarbonyl-N-methylamino)propyl]-5-n-butyl-2,4-dihydro-4-[[2'-(5-tetrazolyl)biphenyl-4-yl]methyl]-3H-triazol-3-one Step A: N-Benzyloxycarbonyl-3-bromopropylamine To a stirred suspension of 3-bromopropylamine hydrobromide (2 g, 9.14 mM) in 40 mL dry THF was added, via hypodermic syringe, benzyl chloroformate (1.64 g, 9.60 mM) at room temperature. After cooling to 0° C., diisopropylethylamine (1.6 mL, 9.20 mM) was added dropwise via syringe and the reaction mixture was allowed to stir at 0° C. for 1 hour. The crude reaction mixture was filtered over a pad of Celite and solvents were evaporated. The residue was flash chromatographed on silica gel, eluting with 10–20–30% EtOAc/hexane to afford 1.56 g desired product as a liquid, homogeneous by TLC in 80:20 hexane-EtOAc;

¹H-NMR (200 MHz, CDCl₃, ppm) δ2.06 (m, 2H), 3.37 (m, 4H), 4.92 (br, 1H), 5.10 (s, 2H), 7.34 (s, 5H). Mass spectrum (FAB) m/e 273 (M+1)⁺.

Step B: N-Benzyloxycarbonyl-N-methyl-3-bromopropylamine

N-Benzyloxycarbonyl-3-bromopropylamine (from Step A; 1.0 g, 3.68 mM) was dissolved in dry THF (4 mL) and methyl iodide (522 mg, 3.68 mM) was added. After cooling to 0° C., potassium t-butoxide (3.68 mL of a 1M solution in THF) was added dropwise to the reaction mixture. The crude reaction mixture was filtered over a pad of Celite and washed through with ether. The combined filtrate and washings were concentrated under reduced pressure. The residue was flash chromatographed over 125 mL silica gel, eluting with 8:1 hexane-EtOAc, to give 890 mg pale yellow liquid, homogeneous on TLC in 80:20 hexane-EtOAc;

¹H-NMR (300 MHz, CDCl₃, ppm) δ2.06 (m, 2H), 2.94 (s, 3H), 3.38 (m, 4H), 5.11 (s, 2H), 7.34 (m, 5H). Mass spectrum (FAB) m/e 288 (M+1)⁺.

Step C: 2-[3-(N-Benzyloxycarbonyl-N-methylamino)-propyl]-5-n-butyl-2,4-dihydro-4-[[2'-(N-trityltetrazol-5-yl)biphenyl-4-yl]methyl]-3H-triazol-3-one A mixture of 100 mg (0.162 mM) of 5-n-butyl-2,4-dihydro-4-[[2'-(N-trityltetrazol-5-yl)biphenyl-4-yl]methyl]-3H-1,2,4-triazol-3-one (Example 2, Step D), 13 mg (0.324 mM) of sodium hydride (50% oil dispersion), and 350 μL of dry DMF was stirred under N₂ at room temperature for 2.5 hours. Next, 185 mg (0.648 mM) of N-benzyloxycarbonyl-N-methyl-3-bromopropylamine (from Step B) was added, and stirring was continued at room temperature overnight. The reaction was quenched by addition of 4 mL water and shaken with 5 mL of ethyl acetate. The aqueous portion was further extracted with 2×5 mL of ethyl acetate. The combined ethyl acetate layers were washed with water (2×10 mL) and brine (1×10 mL), and then dried over anhydrous sodium sulfate, filtered, and concentrated. The residue was flash chromatographed over silica gel using 0.5–10% MeOH—CH₂Cl₂, to give 15 mg (86%) of a gum, homogeneous by TLC in 98:2 CH₂Cl₂—MeOH.

¹HNMR (300 MHz, CDCl₃, ppm) δ0.82 (t, J=7.3 Hz, 3H), 1.24 (m, 2H), 1.48 (m, 2H), 2.00 (m, 2H), 2.25 (m, 2H), 2.92 (s, 3H), 3.35 (m, 2H), 3.79 (m, 2H), 4.67 (m, 2H), 5.10 (s, 2H), 6.95–7.12 (m, 10H), 7.18–7.40 (m, 15H), 7.40–7.52 (m, 2H), 7.88–7.94 (m, 1H). Mass spectrum (FAB) m/e 823 (M+1)⁺.

Step D: 2-[3-(N-Benzyloxycarbonyl-N-methylamino)-propyl]-5-n-butyl-2,4-dihydro-4-[[2'-(5-tetrazolyl)-biphenyl-4-yl]methyl]-3H-triazol-3-one A mixture of 70 mg (0.085 mM) of 2-[3-(N-benzylcarbonyl-N-methylamino)propyl]-5-n-butyl-2,4-dihydro-4-[[2'-(N-trityltetrazol-5-yl)biphenyl-4-yl]methyl]-3H-triazol-3-one, and 0.7 mL of glacial acetic acid was warmed up to 65° C., with constant stirring. Subsequently water (0.7 mL) was added dropwise and heating was continued at 65° C. for 5 hours. After cooling to room temperature, volatiles were evaporated, and the residue was coevaporated with 2×3 mL dry toluene. Flash chromatography of the residue over 15 mL of silica gel (eluting with 2–5–10% MeOH—$CH_2Cl_2$) gave 16 mg (33%) of a white solid, homogeneous by TLC in 90:10 $CH_2Cl_2$—MeOH. Mass spectrum (FAB) m/e 581 $(M+1)^+$.

Analysis ($C_{32}H_{36}N_8O_3 \cdot H_2O$) Calc'd=C, 64.20; H, 6.06; N, 18.72 Found=C, 64.16; H, 5.85; N, 18.53

$^1$HNMR (400 MHz, $CDCl_3$, ppm) δ0.84 (t, J=7.2 Hz, 3H), 1.29 (m, 2H), 1.51 (m, 2H), 1.92 (t, J=6.7 Hz, 2H), 2.35 (m, 2H), 2.81 (s, 1.5H), 2.86 (s, 1.5H), 3.26 (m, 2H), 3.70 (m, 2H), 4.64 (s, 1H), 4.67 (s, 1H), 4.99 (s, 1H), 5.03 (s, 1H), 7.03 (s, 5H), 7.25 (m, 4H), 7.32–7.58 (m, 3H), 7.81 (d, J=7.9 Hz, 1H).

EXAMPLE 11

2-[3-(N-Benzyl-N-benzyloxycarbonylamino)propyl]-5-n-butyl-2,4-dihydro-4-[[2'-(5-tetrazolyl)biphenyl-4-yl]methyl]-3H-triazol-3-one Step A: N-Benzyl-N-benzyloxycarbonyl-3-bromopropylamine N-Benzyloxycarbonyl-3-bromopropylamine (Example 10, Step A; 131 mg, 0.482 mM) was dissolved in dry THF (1 mL) and benzyl bromide (82.4 mg, 0.482 mM) was added. After cooling to 0° C. potassium t-butoxide (482 μL of a 1.0M solution in THF) was added dropwise, and stirring was continued at 0° C. for 30 minutes and at room temperature for 1 hour after completion of addition. The crude reaction mixture was filtered and concentrated and the residue was flash chromatographed over 15 mL silica gel, eluting with 8:1 hexane-EtOAc, to give 105 mg of a colorless oil, homogeneous by TLC: 80:20 hexane-EtOAc.

$^1$HNMR (400 MHz, $CDCl_3$, ppm) δ2.03 (m, 2H), 3.33 (m, 4H), 4.50 (s, 2H), 5.17 (m, 2H), 7.15–7.42 (m, 10H) Mass Spectrum (FAB) m/e 363 $(M+1)^+$.

Step B: 2-[3-(N-Benzyl-N-benzyloxycarbonylamino)-propyl]-5-n-butyl-2,4-dihydro-4-[[2'-(N-trityltetrazol-5-yl)biphenyl-4-yl]methyl]-3H-triazol-3-one A mixture of 100 mg (0.162 mM) 5-n-butyl-2,4-dihydro-4-[[2'-(N-trityltetrazol-5-yl)-biphenyl-4-yl]methyl]-3H-1,2,4-triazol-3-one (Example 2, Step D), 7.8 mg (0.194 mM) of sodium hydride (50% oil dispersion), and 400 μL of dry DMF was stirred under $N_2$ at room temperature for 2 hours before 100 mg (0.276 mM) of N-benzyl-N-benzyloxycarbonyl-3-bromopropylamine (from Step A) was added. After stirring at room temperature for 24 hours, 4 mL of $H_2O$ was added and the resulting mixture was extracted with ethyl acetate (3×6 mL). The ethyl acetate layers were combined and washed with 2×10 mL water and 1×10 mL brine, and dried over anhydrous sodium sulfate. The residue obtained after filtration and concentration was flash chromatographed over 25 mL $SiO_2$ (eluted with 0.5–1.0% MeOH/$CH_2Cl_2$) to give 133 mg (92%) of a foam, homogeneous on TLC (2% MeOH/$CH_2Cl_2$).

$^1$HNMR (400 MHz, $CDCl_3$, ppm) δ0.82 (t, J=7.3 Hz, 3H), 1.24 (m, 2H), 1.45 (m, 2H), 1.98 (m, 2H), 2.23 (m, 2H), 3.34 (m, 2H), 3.79 (m, 2H), 4.52 (s, 2H), 4.65 (m, 2H), 5.16 (m, 2H), 6.85–7.18 (m, 12H), 7.18–7.40 (m, 18H), 7.40–7.52 (m, 2H), 7.88–7.92 (m, 1H), Mass Spectrum (FAB) m/e 899 $(M+1)^+$.

Step C: 2-[3-(N-Benzyl-N-benzyloxycarbonylamino)-propyl]-5-n-butyl-2,4-dihydro-4-[[2'-5-tetrazolyl)biphenyl-4-yl]methyl]-3H-triazol-3-one A mixture of 112 mg (1.25 mM) of 2-[3-(N-benzyl-N-benzyloxycarbonylamino)propyl]-5-n-butyl-2,4-dihydro-4-[[2'-(N-trityltetrazol-5-yl)biphenyl-4-yl]methyl]-3H-triazol-3-one (from Step B) and 1.2 mL of glacial acetic acid was warmed to 65° C. and 1.2 mL water was added dropwise, with constant stirring. After 5 hours at 60° C., the reaction mixture was cooled to room temperature; the volatiles were evaporated. The residue, after coevaporation with 2×3 mL dry toluene, was flash chromatographed over 15 mL $SiO_2$ (eluting with 2–5–10% MeOH/$CH_2Cl$) to give 51 mg of white solid, homogeneous by TLC (10% MeOH/$CH_2Cl_2$).

$^1$HNMR (300 MHz, $CDCl_3$, ppm) δ0.88 (t, J=7.3 Hz, 3H), 1.34 (m, 2H), 1.57 (m, 2H), 1.95 (m, 2H), 2.41 (m, 2H), 3.26 (m, 2H), 3.72 (m, 2H), 4.48 (s, 2H), 4.74 (s, 2H), 5.03 (s, 2H), 5.14 (s, 2H), 7.05–7.43 (m, 15H), 7.43–7.62 (m, 2H), 8.00 (m, 1H). Mass Spectrum (FAB) m/e 657 $(M+1)^+$.

Analysis ($C_{38}H_{40}N_8O_3 \cdot 0.5H_2O \cdot 0.15CH_2Cl_2$) Calc'd: C, 67.53; H, 6.13; N, 16.51 Found: C, 67.50; H, 5.81; N, 16.17

EXAMPLE 12

4-[[2'-(N-Benzoylsulfamoyl)biphenyl-4-yl)methyl]-5-n-butyl-2,4-dihydro-2-isopropyl-3H-1,2,4-triazol-3-one Step A: 2-Bromo-N-(tert-butyl)benzenesulfonamide To a stirred solution of 2-bromobenzenesulfonyl chloride (Lancaster Synthesis) (2.21 g, 8.65 mmol) in chloroform (40 ml) under nitrogen at room temperature was added tert-butylamine (Aldrich) (2.30 ml, 21.9 mmol). The orange solution was stirred at room temperature for 12 hours, then the mixture evaporated to dryness. Flash chromatography (silica gel, 15% ethyl acetate-hexane) afforded the title compound (2.12 g, 84%) as a white solid; $^1$H NMR (300 MHz, $CDCl_3$) δ8.18 (d, J=8.5 Hz, 1H), 7.73 (d, J=8.5 Hz, 1H), 7.50–7.35 (m, 2H), 5.11 (s, 1H), 1.20 (s, 9H).

Step B: p-Tolyltrimethyltin p-Tolylmagnesium bromide solution (Aldrich) (1.0M solution in diethyl ether) (53 ml, 0.0530 mol) was added dropwise to trimethyltin chloride (6.92 g, 0.0347 mol) in tetrahydrofuran (50 ml) under nitrogen at −10° C. The suspension was allowed to warm slowly to room temperature over 3 hours; then saturated ammonium chloride solution (10 ml) was added, followed by sufficient water to dissolve the precipitate. The solution was extracted three times with diethyl ether-hexane (1:1). The combined organic phase was washed with brine, dried (magnesium sulfate) and the solvents removed in vacuo. Vacuum distillation of the residue afforded a colorless liquid (bp 39°–40° C., 0.1 mm Hg) which was further purified by flash chromatography (silica gel, hexane) to give p-tolyltrimethyltin (7.30 g, 82%) as a colorless liquid; $^1$H NMR (300 MHz, $CDCl_3$) δ7.40 (d, J=7.7 Hz, 2H), 7.19 (d, J=7.7 Hz, 2H), 2.34 (s, 3H), 0.30 (s, 9H).

Step C: 2'-(N-t-Butylsulfamoyl)-4-methylbiphenyl

2-Bromo-N-(tert-butyl)benzenesulfonamide (from Step A) (1.00 g, 3.92 mmol), p-tolyltrimethyltin (from Step B) (1.95 g, 6.67 mmol), bis(triphenylphosphine)palladium(II) chloride (Aldrich) (165 mg, 0.235 mmol) and dimethylformamide (25 ml) were heated with stirring under nitrogen at 90° C. for 5 hours. The black suspension was cooled to room temperature, then filtered through a pad of Celite which was washed with tetrahydrofuran. The colorless filtrate was evaporated to dryness then chromatographed (silica gel, 10% ethyl acetate-hexane) to give the title compound (0.88 g, 74%) as a white solid; $^1$H NMR (300 MHz, CDCl$_3$) $\delta$8.16 (d, J=7.9 Hz, 1H), 7.60–7.37 (m, 4H), 7.36–7.24 (m, 3H), 3.57 (s, 1H), 2.42 (s, 3H), 0.99 (s, 9H).

Step D: [2'-(N-t-Butylsulfamoyl)biphenyl-4-yl]methyl bromide

N-Bromosuccinimide (387 mg, 2.17 mmol), $\alpha,\alpha'$-azobis(isobutyronitrile) (catalytic), 2'-(N-t-butylsulfamoyl)-4-methylbiphenyl (from Step C) (550 mg, 1.81 mmol) and carbon tetrachloride (50 ml) were heated with stirring at reflux for 3 hours. After cooling to room temperature the mixture was filtered and the filtrate evaporated to dryness. Flash chromatography (silica gel, initially 10 and then 20% ethyl acetate-hexane) afforded the title compound [699 mg, 77% pure (the remainder of the material was the corresponding dibromo derivative)] as a white solid; $^1$H NMR (300 MHz, CDCl$_3$) $\delta$8.17 (dd, J=7.5, 1.6 Hz, 1H), 7.68–7.45 (m, 6H), 7.31 (dd, J=7.5, 1.6 Hz, 1H), 4.55 (s, 2H), 3.52 (s, 1H), 1.00 (s, 9H).

Step E: [2'-(N-t-Butylsulfamoyl)biphenyl-4-yl]methyl azide

Reaction of [2'-(N-t-butylsulfamoyl)biphenyl-4-yl]methyl bromide (from Step D) with lithium azide was carried out according to the procedure of Example 9, Step A. The crude product was purified by flash chromatography on silica gel (elution with 10% EtOAc in hexane) to give a 74% yield of the title compound as a white solid; satisfactory purity (by TLC in 9:1 hexane-EtOAc) for use in the next step.

300 MHz NMR CDCl$_3$) $\delta$0.98 (s, 9H), 3.53 (s, 1H), 4.41 (s, 2H), 7.31 (d, 1H), 7.36–7.65 (m, 6H), 8.19 (d, 1B).

Step F: [[2'-(N-t-Butylsulfamoyl)biphenyl-4-yl]methyl]amine

Reaction of [2'-(N-t-butylsulfamoyl)biphenyl-4-yl]methyl azide (from Step E) according to the procedure of Example 9, Step B, afforded a 69% yield of the title compound; satisfactory purity by TLC in 9:1 CH$_2$Cl$_2$—MeOH.

400 MHz NMR CDCl$_3$) $\delta$0.99 (s, 9H), 1.68 (s, 2H), 3.61 (s, 1H), 3.92 (s, 2H), 7.29 (d, 1H), 7.35–7.59 (m, 6H), 8.16 (d, 1H).

Step G: 5-n-Butyl-4-[[2'-(N-t-butylsulfamoyl)biphenyl-4-yl]methyl]-2,4-dihydro-3H-1,2,4-triazol-3-one By the procedure of Example 9, Step C, [[2'-(N-t-butylsulfamoyl)biphenyl-4-yl)methyl]amine (from Step F) was reacted with ethyl valerimidate carbethoxyhydrazone (from Example 2, Step A) to give a 72% yield of the title compound as a white foam; satisfactory purity by TLC in 94:6 CH$_2$Cl$_2$—MeOH.

300 MHz NMR CDCl$_3$) $\delta$0.91 (t, 3H), 1.00 (s, 9H), 1.37 (sext, 2H), 1.62 (quint, 2H), 2.43 (t, 2H), 3.57 (s, 1H), 4.90 (s, 2H), 7.28 (d, 1H), 7.30–7.60 (m, 6H), 8.17 (d, 1H), 9.75 (s, 1H)

Step H: 5-n-Butyl-4-[[2'-(N-t-butylsulfamoyl)biphenyl-4-yl]methyl]-2,4-dihydro-2-isopropyl-3H-1,2,4-triazol-3-one To a suspension of 54 mg (1.35 mmole) of sodium hydride (60% in oil) in 1 ml of dry DMF was added 200 mg (0.452 mmole) of 5-n-butyl-4-[[2'-(N-t-butylsulfamoyl)biphenyl-4-yl]methyl]-2,4-dihydro-3H-1,2,4-triazol-3-one (from Step G). The resulting mixture was stirred under N$_2$ at room temperature for 2 hours. Then 270 μL (460 mg, 2.70 mmole) of isopropyl iodide was added dropwise, and the orange mixture was stirred at room temperature overnight. Next, the mixture was treated with H$_2$O and extracted 4× with ethyl acetate. The combined organic fractions were washed with brine, dried over MgSO$_4$, and filtered. The filtrate was concentrated in vacuo, and the residue was flash chromatographed twice on silica gel (elution with 1.5% MeOH in CH$_2$Cl$_2$) to yield 106 mg (48%) of the title compound; satisfactory purity by TLC in 98.5:1.5 CH$_2$Cl$_2$—MeOH; mass spectrum (FAB) m/e 485 (M+1)$^+$.

300 MHz NMR CDCl$_3$) $\delta$0.87 (t, 3H), 0.95 (s, 9H), 1.23–1.40 (m, 2H), 1.35 (d, 6H), 1.57 (quint, 2H), 2.40 (t, 2H), 3.50 (s, 1H), 4.48 (m, 1H), 4.85 (s, 2H), 7.20–7.33 (m, 3H), 7.40–7.58 (m, 4H), 8.14 (dd, 1H).

Step I: 5-n-Butyl-2,4-dihydro-2-isopropyl-4-[(2'-sulfamoylbiphenyl-4-yl)methyl]-3H-1,2,4-triazol-3-one Anisole (2 drops) was added to a solution of 5-n-butyl-4-[[2'-(N-t-butylsulfamoyl)biphenyl-4-yl]methyl]-2,4-dihydro-2-isopropyl-3H-1,2,4-triazol-3-one (from Step H) (97.5 mg; 0.201 mmole) in 2 ml of trifluoroacetic acid stirred under N$_2$ at room temperature. After 24 hours, the solution was concentrated in vacuo. Chromatography of the residue on silica gel (gradient elution with 1.5 to 2% MeOH in CH$_2$Cl$_2$, containing 0.2% concentrated ammonium hydroxide) afforded 67.4 mg (78%) of the title compound as a white solid; satisfactory purity by TLC in 98:2:0.2 CH$_2$Cl$_2$—MeOH-concd. NH$_4$OH; mass spectrum (FAB) m/e 429 (M+1)$^+$.

400 MHz NMR (CD$_3$OD) $\delta$0.88 (t, 3H), 1.28–1.42 (m, 2H), 1.36 (d, 6H), 1.55 (quint, 2H), 2.51 (t, 2H), 4.45 (m, 1H), 4.95 (s, 2H), 7.23–7.31 (m, 3H), 7.41 (dd, 2H), 7.55 (t, 1H), 7.58 (t, 1H), 8.10 (dd, 1H).

Step J: 4-[[2'-(N-Benzoylsulfamoyl)biphenyl-4-yl]methyl]-5-n-butyl-2,4-dihydro-2-isopropyl-3H-1,2,4-triazol-3-one To a solution of 52.7 mg (0.123 mmole) of 5-n-butyl-2,4-dihydro-2-isopropyl-4-[(2'-sulfamoylbiphenyl-4-yl)methyl]-3H-1,2,4-triazol-3-one (from Step I) in 1 ml of dry pyridine stirred at room temperature under argon was added 143 μL (173 mg; 1.23 mmole) of benzoyl chloride. After 12 hours at room temperature, the mixture was treated with saturated NaH$_2$PO$_4$ solution and extracted 3× with ethyl acetate. The combined organic extracts were washed with brine, dried over MgSO$_4$, filtered, and concentrated in vacuo. Flash chromatography of the residue on silica gel (elution with 4% MeOH and 0.2% ammonium hydroxide in CH$_2$Cl$_2$) gave 42.3 mg (69%) of the title compound as a white solid; satisfactory purity by TLC in 94:6:0.2 CH$_2$Cl$_2$—MeOH-concd. NH$_4$OH; mass spectrum (FAB) m/e 533 (M+1)$^+$.

400 MHz NMR (CD$_3$OD) $\delta$0.89 (t, 3H), 1.25–1.45 (m, 2H), 1.37 (d, 6H), 1.57 (quint, 2H), 2.49 (t, 2H), 4.46 (m, 1H), 4.89 (s, 2H), 7.13 (d, 2H), 7.24 (d, 1H), 7.28–7.41 (m, 4H), 7.46 (m, 1H), 7.56 (m, 4H), 8.26 (d, 1H).

EXAMPLE 13

4-[[2'-(N-Benzoylsulfamoyl)biphenyl-4-yl]methyl]-5-n-butyl-2-(2-chlorophenyl)-2,4-dihydro-3H-1,2,4-triazol-3-one Step A: 5-n-Butyl-4-[[2'-(N-t-butylsulfamoyl)biphenyl-4-yl]methyl]-2-(2-chlorophenyl)-2,4-dihydro-3H-1,2,4-triazol-3-one To a solution of 78 mg (0.310 mmole) of 5-n-butyl-2-(2-chlorophenyl)-2,4-dihydro-3H-1,2,4-triazol-3-one (from Example 5, Step A) in 620 $\mu$L of dry DMF was added 14.9 mg (0.372 mmole) of sodium hydride (60% in oil), and the mixture was stirred under $N_2$ at 50° C. for 1 hour, until gas evolution was complete. The resulting solution was cooled to room temperature and treated dropwise with a solution of 178 mg (0.465 mmole) of [2'-(N-t-butylsulfamoyl)biphenyl-4-yl]methyl bromide (from Example 12, Step D) in DMF. The mixture was stirred at 50° C. for 1.5 hours, by which time TLC (98:2 $CH_2Cl_2$—MeOH) indicated complete reaction. The mixture was quenched by addition of approximately 6 ml of $H_2O$ followed by extraction with 3×10 ml of EtOAc. The combined EtOAc extracts were washed with 2×15ml of $H_2O$ followed by 15 ml of brine. The organic phase was dried over $Na_2SO_4$, filtered, and concentrated. Column chromatography of the residue on silica gel (elution with 0.5% MeOH in $CH_2Cl_2$) yielded 130 mg (76%) of the title compound as a white, stiff foam, homogeneous by TLC in 98:2 $CH_2Cl_2$—MeOH; mass spectrum (FAB) m/e 553 $(M+1)^+$.

400 MHz NMR $CDCl_3$) $\delta$0.89 (t, 3H), 0.97 (s, 9H), 1.38 (m, 2H), 1.66 (m, 2H), 2.49 (t, 2H), 3.50 (s, 1H), 4.96 (s, 2H), 7.2–7.6 (m, 11H), 8.15 (d, 1H).

Step B: 5-n-Butyl-2-(2-chlorophenyl)-2,4-dihydro-4-[(2'-sulfamoylbiphenyl-4-yl)methyl]-3H-1,2,4-triazol-3-one A solution of 122 mg (0.221 mmole) of 5-n-butyl-4-[[2'-(N-t-butylsulfamoyl)biphenyl-4-yl]methyl]-2-(2-chlorophenyl)-2,4-dihydro-3H-1,2,4-triazol-3-one in 2.2 ml of anhydrous trifluoroacetic acid (TFA) containing 2 drops of anisole was stirred at room temperature under $N_2$ for 2 days. The TFA was removed under a gentle stream of $N_2$ followed by co-evaporation in vacuo 2× with toluene. The residue was chromatographed on a silica gel column (gradient elution with 0.5–2% MeOH in $CH_2Cl_2$). Concentration of the combined product fractions gave 98 mg (89%) of the title compound as a white solid, mp 140°–142° C.; satisfactory purity by TLC in 98:2 $CH_2Cl_2$—MeOH; mass spectrum (FAB) m/e 497 $(M+1)^+$.

400 MHz NMR $CDCl_3$) $\delta$0.89 (t, 3H), 1.38 (m, 2H), 1.65 (m, 2H), 2.51 (t, 2H), 4.22 (s, 2H), 4.96 (s, 2H), 7.3–7.6 (m, 11H), 8.14 (d, 1H).

Step C: 4-[[2'-(N-Benzoylsulfamoyl)biphenyl-4-yl]-5-n-butyl-2-(2-chlorophenyl)-2,4-dihydro-3H-1,2,4-triazol-3-one To a solution of 41.4 mg (0.0834 mmole) of 5-n-butyl-2-(2-chlorophenyl)-2,4-dihydro-4-[(2'-sulfamoylbiphenyl-4-yl)methyl]-3H-1,2,4-triazol-3-one (from Step B) in 1 ml of dry pyridine stirred at room temperature under argon was added 97 $\mu$l (117 mg, 0.836 mmole) of benzoyl chloride. The resulting solution was stirred at room temperature for 12 hours and then treated with saturated $NaH_2PO_4$ solution. The mixture was extracted 3× with ethyl acetate. The combined organic extracts were washed with brine, dried ($MgSO_4$), and concentrated in vacuo. The residue was flash chromatographed twice on silica gel (elution with 6–7% MeOH in $CH_2Cl_2$ containing 0.2–0.4% concd. $NH_4OH$) to give 30 mg (60%) of the title compound as a white solid; satisfactory purity by TLC in 94:6:0.2 $CH_2Cl_2$—MeOH-concd. $NH_4OH$; mass spectrum (FAB) m/e 601 $(M+1)^+$.

400 MHz NMR ($CDCl_3/CD_3OD$) $\delta$0.87 (t, 3H), 1.36 (sext, 2H), 1.64 (quint, 2H), 2.53 (t, 2H), 4.94 (s, 2H), 7.10–7.62 (m, 15H), 7.99 (dd, 1H), 8.27 (dd 1H).

EXAMPLE 14

5-n-Butyl-2-(2-chlorophenyl)-2,4-dihydro-4-[[2'-[N-(4-fluorobenzoyl)sulfamoyl]biphenyl-4-yl]methyl]-3H-1,2,4-triazol-3-one By the procedure of Example 13, Step C, 5-n-butyl-2-(2-chlorophenyl)-2,4-dihydro-4-[(2'-sulfamoylbiphenyl-4-yl)methyl]-3H-1,2,4-triazol-3-one (from Example 13, Step B) was reacted with 4-fluorobenzoyl chloride. Column chromatography on silica gel (gradient elution with 0.5–5% MeOH in $CH_2Cl_2$) afforded an 80% yield of the title compound as cream-colored crystals, mp 118°–120° C., satisfactory purity by TLC in 9:1 $CH_2Cl_2$—MeOH; mass spectrum (FAB) m/e 619 $(M+1)^+$ Analysis: ($C_{32}H_{28}ClFN_4O_4S.0.25CH_2Cl_2$) Calcd: C, 60.49; H, 4.49; N, 8.75. Found: C, 60.46; H, 4.18; N, 8.49.

400 MHz NMR $CDCl_3$) $\delta$0.88 (t, 3H), 1.38 (m, 2H), 1.66 (m, 2H), 2.52 (t, 2H), 4.86 (s, 2H), 6.95–7.65 (m, 15H), 8.39 (dd, 1H), 9.08 (br s, 1H).

EXAMPLE 15

5-n-Butyl-2-(2-chlorophenyl)-2,4-dihydro-4-[[2'-[N-(trifluoroacetyl)sulfamoyl]biphenyl-4-yl]methyl]-3H-1,2,4-triazol-3-one By the procedure of Example 13, Step C, 5-n-butyl-2-(2-chlorophenyl)-2,4-dihydro-4-[(2'-sulfamoylbiphenyl-4-yl)methyl]-3H-1,2,4-triazol-3-one (from Example 13, Step B) was reacted with trifluoroacetic anhydride. The crude product was column chromatographed twice on silica gel (gradient elution with 1–5% MeOH in $CH_2Cl_2$) to give a 43% yield of the title compound as cream-colored crystals, mp 163°–166° C.; satisfactory purity by TLC in 9:1 $CH_2Cl_2$—MeOH; mass spectrum (FAB) m/e 631 $(M+K)^+$.

300 MHz NMR $CDCl_3$) $\delta$0.96 (t, 3H), 1.47 (m, 2H), 1.78 (m, 2H), 2.71 (t, 2H), 4.72 (s, 2H), 7.1–7.6 (m, 11H), 8.20 (d, 1H).

EXAMPLE 16

4-[[2'-(N-Benzoylsulfamoyl)biphenyl-4-yl]methyl]-5-n-butyl-2,4-dihydro-2-[2-(trifluoromethyl)phenyl]-3H-1,2,4-triazol-3-one Step A: 5-n-Butyl-2,4-dihydro-2-[2-(trifluoromethyl)-phenyl]-3H-1,2,4-triazol-3-one Ethyl-N-carbethoxyvalerimidate (from Example 4, Step B) was reacted with 2-(trifluoromethyl)phenylhydrazine according to the procedure of Example 4, Step C. Flash chromatography of the crude product on silica gel (gradient elution with 0.5–2% MeOH in $CH_2Cl_2$) gave a 66% yield of the title compound as white crystals, mp 124°–126° C.; homogeneous by TLC in 19:1 $CH_2Cl_2$—MeOH; mass spectrum (FAB) m/e 286 $(M+1)^+$.

400 MHz NMR $CDCl_3$) $\delta$0.88 (t, 3H), 1.34 (m, 2H), 1.62 (m, 2H), 2.52 (t, 2H), 7.5–7.6 (m, 2H), 7.66 (dd, 1H), 7.79 (d, 1H), 11.75 (br s, 1H).

Step B: 5-n-Butyl-4-[[2'-(N-t-butylsulfamoyl)biphenyl-4-yl]methyl]-2,4-dihydro-2-[2-(trifluoromethyl)phenyl]-3H-1,2,4-triazol-3-one By the procedure of Example 13, Step A, 5-n-butyl-2,4-dihydro-2-[2-(trifluoromethyl)phenyl]-3H-1,2,4-triazol-3-one (from Step A) was alkylated with [2'-(N-t-butylsulfamoyl)biphenyl-4-yl]methyl bromide (from Example 12, Step D). Flash chromatography of the crude product on silica gel (gradient elution with 0.5–5% MeOH in $CH_2Cl_2$) gave a 61% yield of the title compound as cream-colored crystals, mp 168°–170° C.; satisfactory purity by TLC in 98:2 $CH_2Cl_2$—MeOH; mass spectrum (FAB) m/e 587 $(M+1)^+$.

400 MHz NMR $CDCl_3$) δ0.89 (t, 3H), 0.97 (s, 9H), 1.37 (m, 2H), 1.64 (m, 2H), 2.48 (t, 2H), 3.48 (s, 1H), 4.95 (s, 2H), 7.2–7.6 (m, 9H), 7.66 (dd, 1H), 7.78 (d, 1H), 8.15 (d, 1H).

Step C: 5-n-Butyl-2,4-dihydro-4-[(2'-sulfamoylbiphenyl-4-yl)methyl]-2-[2-(trifluoromethyl)phenyl]-3H-1,2,4-triazol-3-one The title compound was prepared according to the procedure of Example 13, Step B, and was obtained in 92% yield as white crystals, mp 74°–76° C.; satisfactory purity by TLC in 98:2 $CH_2Cl_2$—MeOH; mass spectrum (FAB) m/e 531 $(M+1)^+$.

400 MHz NMR $CDCl_3$) δ0.88 (t, 3H), 1.36 (m, 2H), 1.63 (m, 2H), 2.50 (t, 2H), 4.23 (br s, 2H), 4.95 (s, 2H), 7.3–7.6 (m, 9H), 7.65 (dd, 1H), 7.78 (d, 1H), 8.14 (d, 1H).

Step D: 4-[[2'-(N-Benzoylsulfamoyl)biphenyl)-4-yl]methyl]-5-n-butyl-2,4-dihydro-2-[2-(trifluoromethyl)phenyl]-3H-1,2,4-triazol-3-one The reaction of 5-n-butyl-2,4-dihydro-4-[(2'-sulfamoylbiphenyl-4-yl)methyl]-2-[2-(trifluoromethyl)phenyl]-3H-1,2,4-triazol-3-one (from Step C) with benzoyl chloride was carried out according to the method of Example 13, Step C. Flash chromatography of the crude product on silica gel (gradient elution with 0.5–5% MeOH in $CH_2Cl_2$) provided a 75% yield of the title compound as white crystals, mp 91°–93° C.; satisfactory purity by TLC 19:1 $CH_2Cl_2$—MeOH; mass spectrum (FAB) m/e 673 $(M+K)^+$.

Analysis: $(C_{33}H_{29}F_3N_4O_4S \cdot 0.33CH_2Cl_2)$ Calcd: C, 60.39; H, 4.51; N, 8.45. Found: C, 60.28; H, 4.49; N, 8.15.

400 MHz NMR $CDCl_3$) δ0.87 (t, 3H), 1.36 (m, 2H), 1.63 (m, 2H), 2.47 (t, 2H), 4.86 (s, 2H), 7.11 (d, 2H), 7.2–7.7 (m, 13H), 7.75 (d, 1H), 8.25 (br s, 1H), 8.39 (d, 1H).

EXAMPLE 17

5-n-Butyl-2,4-dihydro-4-[[2'-[N-(trifluoroacetyl)sulfamoyl]biphenyl-4-yl]methyl]-2-[2-(trifluoromethyl)phenyl]-3H-1,2,4-triazol-3-one By the procedure of Example 13, Step C, 5-n-butyl-2,4-dihydro-4-[(2'-sulfamoylbiphenyl-4-yl)methyl]-2-[2-(trifluoromethyl)phenyl]-3H-1,2,4-triazol-3-one (from Example 16, Step C) was reacted with trifluoroacetic anhydride. Column chromatography of the crude product on silica gel (gradient elution with 1–5% MeOH in $CH_2Cl_2$) afforded a 29% yield of the title compound as a cream-colored solid; mp 125°–127° C.; satisfactory purity by TLC in 9:1 $CH_2Cl_2$—MeOH; mass spectrum (FAB) m/e 665 $(M+K)^+$.

Analysis $(C_{28}H_{24}F_6N_4O_4S)$: Calcd: C, 51.45; H, 4.16; N, 8.57. Found: C, 51.71; H, 4.00; N, 8.28.

400 MHz NMR $(CD_3OD)$ δ0.90 (t, 3H), 1.39 (m, 2H), 1.62 (m, 2H), 2.58 (t, 2H), 5.01 (s, 2H), 7.2–7.6 (m, 8H), 7.71 (dd, 1H), 7.81 (dd, 1H), 7.89 (d, 1H), 8.16 (d, 1H).

EXAMPLE 18

5-n-Butyl-2,4-dihydro-4-[[2'-[N-(4-fluorobenzoyl)sulfamoyl]biphenyl-4-yl]methyl]-2-[2-(trifluoromethyl)phenyl]-3H-1,2,4-triazol-3-one The title compound was prepared in 93% yield by reaction of 5-n-butyl-2,4-dihydro-4-[(2'-sulfamoylbiphenyl-4-yl)methyl]-2-[2-(trifluoromethyl)phenyl]-3H-1,2,4-triazol-3-one (from Example 16, Step C) with 4-fluorobenzoyl chloride according to the procedure of Example 13, Step C. Column chromatography on silica gel (gradient elution with 0.5–5% MeOH in $CH_2Cl_2$) provided the material as cream-colored crystals, mp 120°–122° C.; satisfactory purity by TLC in 9:1 $CH_2Cl_2$—MeOH; mass spectrum (FAB) m/e 691 $(M+K)^+$.

Analysis $(C_{33}H_{28}F_4N_4O_4S \cdot H_2O)$: Calcd: C, 59.10; H, 4.51; N, 8.35. Found: C, 59.35; H, 4.24; N, 7.95.

400 MHz NMR $(CD_3OD)$ δ0.88 (t, 3H), 1.36 (m, 2H), 1.60 (m, 2H), 2.56 (t, 2H), 4.99 (s, 2H), 7.02 (dd, 2H), 7.15–7.65 (m, 9H), 7.72 (dd, 1H), 7.80 (dd, 1H), 7.90 (d, 1H), 8.05 (dd, 1H), 8.26 (d, 1H).

EXAMPLE 19

5-n-Butyl-2,4-dihydro-4-[[2'-(N-octanoylsulfamoyl)biphenyl-4-yl]methyl]-2-[2-(trifluoromethyl)phenyl]-3H-1,2,4-triazol-3-one By the procedure of Example 13, Step C, 5-n-butyl-2,4-dihydro-4-[(2'-sulfamoylbiphenyl-4-yl)methyl]-2-[2-(trifluoromethyl)phenyl]-3H-1,2,4-triazol-3-one (from Example 16, Step C) was reacted with octanoyl chloride. Flash chromatography of the crude product twice on silica gel (gradient elution with 0.3–3% and 0.5–2% MeOH in $CH_2Cl_2$) gave a 37% yield of the title compound as a gum, homogeneous by TLC in 19:1 $CH_2Cl_2$—MeOH; mass spectrum (FAB) m/e 657 $(M+1)^+$. 400 MHz NMR $CDCl_3$) δ0.81 (t, 3H), 0.89 (t, 3H), 1.1–1.3 (m, 8H), 1.39 (m, 4H), 1.66 (m, 2H), 1.88 (t, 2H), 2.55 (t, 2H), 4.92 (s, 2H), 7.26, (d, 2H), 7.35 (d, 2H), 7.5–7.7 (m, 6H), 7.78 (d, 1H), 8.20 (br s, 1H), 8.28 (d, 1H).

EXAMPLE 20

5-n-Butyl-4-[[2'-[N-(3-cyclopentylpropionyl)sulfamoyl]biphenyl-4-yl]methyl]-2,4-dihydro-2-[2-(trifluoromethyl)phenyl-3H-1,2,4-triazol-3-one By the procedure of Example 13, Step C, 5-n-butyl-2,4-dihydro-4-[(2'-sulfamoylbiphenyl-4-yl)methyl]-2-[2-(trifluoromethyl)phenyl]-3H-1,2,4-triazol-3-one (from Example 16, Step C) was reacted with 3-cyclopentylpropionyl chloride. Flash chromatography of the crude product on silica gel (elution with 0.5% and then 1% MeOH in $CH_2Cl_2$) afforded a 62% yield of the title compound as a glass, homogeneous by TLC in 19:1 $CH_2Cl_2$—MeOH; mass spectrum (FAB) m/e 655 $(M+1)^+$.

400 MHz NMR $CDCl_3$) δ0.89 (t, 3H), 1.3–1.7 (m, 15H), 1.92 (t, 2H), 2.54 (t, 2H), 4.93 (s, 2H), 7.27 (d, 2H), 7.35 (d, 2H), 7.5–7.7 (m, 6H), 7.78 (d, 1H), 8.08 (br s, 1H), 8.28 (d, 1H).

EXAMPLE 21

5-n-Butyl-4-[[2'-[N-(cyclopropanecarbonyl)sulfamoyl]-biphenyl-4-yl]methyl]-2,4-dihydro-2-[2-(trifluoromethyl)phenyl]-3H-1,2,4-triazol-3-one Following the procedure of Example 13, Step C, 5-n-butyl-2,4-dihydro-4-[(2'-sulfamoylbiphenyl-4-yl)methyl]-2-[2-(trifluoromethyl)phenyl]-3H-1,2,4-triazol-3-one (from Example 16, Step C) was reacted with cyclopropanecarbonyl chloride. Flash chromatography of the crude product on silica gel (gradient elution with 0.3–1% MeOH in $CH_2Cl_2$) gave a 51% yield of the title compound as white crystals, mp 187°–189° C.; satisfactory purity by TLC in 19:1 $CH_2Cl_2$—MeOH; mass spectrum (FAB) m/e 599 $(M+1)^+$.

Analysis ($C_{30}H_{29}F_3N_4O_4S.0.25H_2O$): Calcd: C, 59.79; H, 4.85; N, 9.30. Found: C, 59.82; H, 4.81; N, 8.90.

400 MHz NMR $CDCl_3$) $\delta 0.71$ (m, 0.84–0.92 (m, 5H, including t, 3H, centered at 0.89), 1.38 (m, 2H), 1.55–1.7 (m, 3H), 2.55 (t, 2H), 4.92 (s, 2H), 7.25–7.7 (m, 10H), 7.77 (d, 1H), 8.26 (d, 1H), 8.51 (br s, 1H).

EXAMPLE 22

5-n-Butyl-2,4-dihydro-4-[[2'-[N-(diphenylacetyl)sulfamoyl]biphenyl-4-yl]methyl]-2-[2-(trifluoromethyl)-phenyl]-3H-1,2,4-triazol-3-one By the procedure of Example 13, Step C, 5-n-butyl-2,4-dihydro-4-[(2'-sulfamoylbiphenyl-4-yl)methyl]-2-[2-(trifluoromethyl)phenyl]-3H-1,2,4-triazol-3-one (from Example 16, Step C) was reacted with diphenylacetyl chloride. The crude product was evaporated twice from toluene and flash chromatographed twice on silica gel (gradient elution with 0.1–1% MeOH in $CH_2Cl_2$ and then approx. 0.01–1% MeOH in $CH_2Cl_2$) to give a 73% yield of the title compound as off-white crystals, mp 144°–146° C.; homogeneous by TLC in 19:1 $CH_2Cl_2$—MeOH; mass spectrum (FAB) m/e 725 $(M+1)^+$.

Analysis ($C_{40}H_{35}F_3N_4O_4S$): Calcd: C, 66.29; H, 4.87; N, 7.73. Found: C, 66.53; H, 4.68; N, 7.46.

400 MHz NMR $CDCl_3$) $\delta 0.89$ (t, 3H), 1.38 (m, 2H), 1.64 (m, 2H), 2.50 (t, 2H), 4.58 (s, 1H), 4.85 (s, 2H), 6.95–7.65 (m, 20H), 7.78 (d, 1H), 8.31 (d, 1H), 8.38 (br s, 1H).

EXAMPLE 23

5-n-Butyl-2,4-dihydro-4-[[2'-[N-(4-morpholinecarbonyl)sulfamoyl]biphenyl-4-yl]methyl]-2-[2-(trifluoromethyl)phenyl]-3H-1,2,4-triazol-3-one To a solution of 51.1 mg (0.0964 mmole) of 5-n-butyl-2,4-dihydro-4-[(2'-sulfamoylbiphenyl-4-yl)methyl]-2-[2-(trifluoromethyl)phenyl]-3H-1,2,4-triazol-3-one (from Example 16, Step C) in 0.2 ml of dry THF was added 4.6 mg (0.116 mmole) of sodium hydride (60% in oil), and the mixture was allowed to stir at room temperature under $N_2$ for 4 hours. Next, 17 μl (21.6 mg, 0.145 mmole) of 4-morpholinecarbonyl chloride was added, and the solution was stirred under $N_2$ at room temperature overnight. The reaction was quenched by addition of 2 ml of $H_2O$ followed by extraction with 3×5 ml of ethyl acetate. The combined organic extracts were washed with 2×5 ml of $H_2O$ and then with 5 ml of brine. After co-evaporation twice from toluene, the crude product was flash chromatographed on silica gel (gradient elution with 0.3–10% MeOH in $CH_2Cl_2$) to give 16.1 mg of the title compound as a whitish glass; satisfactory purity by TLC in 19:1 and 9:1 $CH_2Cl_2$—MeOH; mass spectrum (FAB) m/e 682 $(M+K)^+$.

400 MHz NMR ($CD_3OD$) $\delta 0.90$ (t, 3H), 1.40 (m, 2H), 1.65 (m, 2H), 2.61 (t, 2H), 3.13 (br m, 4H), 3.43 (m, 4H), 5.02 (s, 2H), 7.25 (d, 1H), 7.3–7.6 (m, 7H), 7.62 (d, 1H), 7.71 (dd, 1H), 7.80 (dd, 1H), 7.89 (d, 1H), 8.18 (br s, 1H).

EXAMPLE 24

4-[[2'-[N-(2-Chlorobenzoyl)sulfamoyl]biphenyl-4-yl]methyl-2,4-dihydro-5-(4,4,4-trifluoro-n-butyl)-2-[2-(trifluoromethyl)phenyl]-3H-1,2,4-triazol-3-one Step A: 5,5,5,-Trifluorovaleronitrile A mixture of 882 mg (18 mmole) of sodium cyanide and 9 mL of DMSO was heated in an oil bath at 80° C. for 10 minutes until most of the solid had dissolved. The mixture was then removed from the oil bath and treated with 2.87 g (15 mmole) of 4,4,4-trifluorobutyl bromide. The mixture was heated to 110° C. for about 30 minutes and then cooled to room temperature. The mixture was partitioned between $H_2O$ and ether, and the aqueous layer was extracted with an additonal 2 portions of ether. The combined organic fractions were washed successively with 2N HCl (twice), $H_2O$ (twice), and brine. The ether phase was dried over anhydrous $Na_2SO_4$, filtered, and concentrated to yield 1.99 g (97%) of the title compound as a colorless liquid, suitable for use without further purification; IR (neat) $\nu_{CO}$ 2260 cm$^{-1}$.

400 MHz $^1H$ NMR ($CDCl_3$) $\delta 1.94$ (m, 2H), 2.26 (m, 2H), 2 46 (t, J=7.1 Hz, 2H).

Step B: Ethyl 5,5,5,-Trifluorovalerimidate

By the procedure of Example 4, Step A, 5,5,5-trifluorovaleronitrile (from Step A) was converted to the title compound, obtained in 73% yield as an oil.

200 MHz $^1H$ NMR $CDCl_3$) $\delta 1.27$ (t, J=7.1 Hz, 3H), 1.82 (m, 2H), 1.95–2.2 (m, 2H), 2.31 (t, J=7.4 Hz, 2H), 4.09 (br m, 2H), 6.92 (br s, 1H).

Step C: Ethyl N-Carbethoxy-5,5,5,-trifluorovalerimidate

By the procedure of Example 4, Step B, ethyl 5,5,5-trifluorovalerimidate (from Step B) was converted to the title compound, obtained in 63% yield as an oil.

200 MHz $^1H$ NMR $CDCl_3$) $\delta 1.22–1.35$ (m, 6H), 1.89 (m, 2H), 2.10 (m, 2H), 2.48 (t, J=7.3 Hz, 2H), 4.1–4.25 (m, 4H).

Step D: 2,4-Dihydro-2-(4,4,4-trifluoro-n-butyl)-2-[2-(trifluoromethyl)-phenyl-3H-1,2,4-triazol-3-one Reaction of ethyl N-carbethoxy-5,5,5,-trifluorovalerimidate (from Step C) with 2-(trifluoromethyl)phenylhydrazine according to the procedure of Example 4, Step C, afforded a 72% yield of the title compound as a white gum; jomogeneous by TLC in 95:5 $CH_2Cl_2$—MeOH; mass spectrum (FAB) m/e 340 $(M+1)^+$.

400 MHz $^1H$ NMR $CDCl_3$) $\delta 1.88$ (m, 2H), 2.08 (m, 2H), 2.56 (t, J=7.3 Hz, 2H), 7.50 (d, J=7.7 Hz, 1H), 7.58 (dd, J=7.7, 7.7 Hz, 1H), 7.68 (dd, J=7.7, 7.7 Hz, 1H), 7.80 (d, J=7.7 Hz, 1H), 12.10 (s, 1H).

Step E: 4-[[2'-(N-t-Butylsulfamoyl)biphenyl-4-yl]methyl]-2,4-dihydro-2-(4,4,4-trifluoro-n-butyl)-2-[2-(trifluoromethyl)phenyl-3H-1,2,4-triazol-3-one Alkylation of 2,4-dihydro-2-(4,4,4-trifluoro-n-butyl)-2-[2-(trifluoromethyl)phenyl-3H-1,2,4-triazol-3-one (from Step D) with [2'-(N-t-butylsulfamoyl)biphenyl-4-yl]methyl bromide (from Example 12, Step D) was accomplished by the procedure of Example 13, Step A. Purification of the crude product by flash chromatography on silica gel (gradient elution with 0.5–1% MeOH in CH$_2$Cl$_2$) gave a 98% yield of the title compound; homogeneous by TLC in 95:5 CH$_2$Cl$_2$—MeOH; mass spectrum (FAB) m/e 641 (M+1)$^+$.

400 MHz $^1$H NMR CDCl$_3$) δ0.99 (s, 9H), 1.94 (m, 2H), 2.18 (m, 2H), 2.58 (t, J=7.1 Hz, 2H), 3.52 (s, 1H), 4.95 (s, 2H), 7.27 (dd, J=7.5, 1.4 Hz, 1H), 7.35 (d, J=8.2 Hz, 2H), 7.4–7.6 (m, 6H), 7.68 (m, 1H), 7.80 (d, J=7.4 Hz, 1H), 8.15 (dd, J=7.9, 1.3 Hz, 1H).

Step F: 2,4-Dihydro-4-[(2'-sulfamoylbiphenyl-4-yl)methyl]-2-(4,4,4-trifluoro-n-butyl)-2-[2-(trifluoromethyl)-phenyl-3H-1,2,4-triazol-3-one Deprotection of 4-[[2'-(N-t-butylsulfamoyl)biphenyl-4-yl]methyl]-2,4-dihydro-2-(4,4,4-trifluoro-n-butyl)-2-[2-(trifluoromethyl)phenyl-3H-1,2,4-triazol-3-one (from Step E) with TFA according to the procedure of Example 76, Step G) afforded an 84% yield of the title compound; homogeneous by TLC in 95:5 CH$_2$Cl$_2$—MeOH; mass spectrum (FAB) m/e 585 (M+1)$^+$.

400 MHz $^1$H NMR CDCl$_3$) δ1.93 (m, 2H), 2.17 (m, 2H), 2.59 (t, J=7.3 Hz, 2H), 4.21 (s, 2H), 4.96 (s, 2H), 7.30 (dd, J=7.5, 1.3 Hz, 1H), 7.34 (d, J=8.1 Hz, 2H), 7.48–7.61 (m, 6H), 7.67 (m, 1H), 7.80 (d, J=7.7 Hz, 1H), 8.14 (dd, J=8.0, 1.3 Hz, 1H).

Step G: 4-[[2'-[N-(2-Chlorobenzoyl)sulfamoyl]biphenyl-4-yl]methyl]-2,4-dihydro-2-(4,4,4-trifluoro-n-butyl)-2-[2-(trifluoromethyl)phenyl-3H-1,2,4-triazol-3-one Reaction of 2,4-dihydro-4-[(2'-sulfamoylbiphenyl-4-yl)methyl]-2-(4,4,4-trifluoro-n-butyl)-2-[2-(trifluoromethyl)phenyl-3H-1,2,4-triazol-3-one (from Step F) with 2-chlorobenzoic acid (2 equivalents), CDI (2 equiv), and DBU (2 equiv) was carried out according to the method of Example 51. Flash chromatography of the crude product on silica gel (gradient elution with 0.5–0.8% MeOH in CH$_2$Cl$_2$) followed by semi-preparative reverse phase HPLC on a Zorbax C8 column (elution with 70:30 acetonitrile-H$_2$O containing 0.1% TFA) gave a 9% yield of the title compound as a solid, mp 93°–96° C.; TLC in 95:5 CH$_2$Cl$_2$—MeOH; mass spectrum (FAB) m/e 723 (M+1)$^+$.

400 MHz $^1$H NMR CDCl$_3$) δ1.91 (m, 2H), 2.17 (m, 2H), 2.54 (t, J=7.3 Hz, 2H), 4.88 (s, 2H), 7.16 (d, J=8.2 Hz, 2H), 7.26–7.41 (m, 6H), 7.53–7.70 (m, 6H), 7.80 (d, J=6.9 Hz, 1H), 8.37 (dd, J=7.9, 1.4 Hz, 1H), 8.60 (br s, 1H).

EXAMPLE 25

4-[[2'-(N-Benzoylsulfamoyl)biphenyl-4-yl]methyl]-2,4-dihydro-5-(4,4,4-trifluoro-n-butyl)-2-[2-(trifluoromethyl)phenyl]-3H-1,2,4-triazol-3-one The title compound was prepared by the methods of Example 24, except that benzoic acid was substituted for 2-chlorobenzoic acid in the final step. The material was obtained in 29% yield as a solid, mp 197°–199° C.; TLC in 95:5 CH$_2$Cl$_2$—MeOH; mass spectrum (FAB) m/e 689 (M+1)$^+$.

400 MHz $^1$H NMR CDCl$_3$) δ1.92 (m, 2H), 2.13 (m, 2H), 2.59 (t, J=7.1 Hz, 2H), 4.88 (s, 2H), 7.06 (d, J=8.3 Hz, 2H), 7.20–7.67 (m, 13H), 7.79 (d, J=7.3 Hz, 1H), 8.36 (d, J 8 Hz, 1H).

EXAMPLE 26

5-n-Butyl-2,4-dihydro-4-[4-(methoxycarbonyl)benzyl]-2-[2-(trifluoromethyl)phenyl]-3H-1,2,4-triazol-3-one Alkylation of 5-n-butyl-2,4-dihydro-2-[2-(trifluoromethyl)phenyl]-3H-1,2,4-triazol-3-one (from Example 16, Step A) with methyl 4-(bromomethyl)benzoate was carried out according to the procedure of Example 13, Step A. Purification of the crude product by flash chromatography on silica gel (gradient elution with 0.3–1% MeOH in CH$_2$Cl$_2$) provided a 53% yield of the title compound as a clear, glassy solid; homogeneous by TLC in 95:5 CH$_2$Cl$_2$—MeOH; mass spectrum (FAB) m/e 434 (M+1)$^+$.

Analysis: (C$_{22}$H$_{22}$F$_3$N$_3$O$_3$) Calcd: C, 60.96; H, 5.12; N, 9.69. Found: C, 61.19; H, 5.24; N, 9.45.

400 MHz $^1$H NMR CDCl$_3$) δ0.83 (t, J=7.3 Hz, 3H), 1.31 (m, 2H), 1.61 (m, 2H), 2.39 (t, J=7.7 Hz, 2H), 3.90 (s, 3H), 4.94 (s, 2H), 7.31 (d, J=8.1 Hz, 2H), 7.53 (m, 2H), 7.65 (m, 1H), 7.78 (d, J=7.3 Hz, 1H), 8.03 (d, J=8.1 Hz, 2H).

EXAMPLE 27

5-n-Butyl-2,4-dihydro-4-[[2'-(trifluoromethanesulfonamido)biphenyl-4-yl]methyl]-2-[2-(trifluoromethyl)-phenyl]-3H-1,2,4-triazol-3-one Step A: 4-Methyl-2'-nitrobiphenyl Under N$_2$, a clean, dry flask was charged with p-tolyltrimethyltin (from Example 12, Step B) (5.61 g, 0.022 mol), 2-bromonitrobenzene (4.04 g, 0.020 mol), anhydrous DMF (40 mL), and palladium(II) bis(triphenylphosphine)dichloride (140 mg, 0.2 mmol), heated at 110° C. and stirred for 4 h when TLC (4:1 hexane/EtOAc) indicated disappearance of starting materials. The nearly black reaction mixture was cooled to room temperature, poured into a solution made from 100 mL 1N KOH and 100 mL sat. NaCl, and extracted with 3×150 mL EtOAc. The combined, organic layers were washed with 100 mL 1N KOH and 100 mL sat. NaCl, and then dried over anhydrous Na$_2$SO$_4$. After filtration, the amber solution was evaporated to dryness and then flash chromatographed over 900 mL SiO$_2$, eluting with 2.5% EtOAc-hexane to give 4.109 g (96%) of the title compound as a light orange liquid, homogeneous on TLC (4/1 hex-EtOAc).

$^1$H NMR (400 MHz, CDCl$_3$, ppm) δ2.38 (s, 3H), 7.21 (m, 4H), 7.43 (m, 2H), 7.58 (m, 1H), 7.80 (dd, J=8.09, 1.34 Hz, 1H). Mass spectrum:EI (m/e):213 (M$^+$)

Step B: (2'-Nitrobiphenyl-4-yl)methyl bromide

4-Methyl-2'-nitrobiphenyl (from Step A) (2.173 g, 10.2 mmol) was dissolved in CCl$_4$ (100 mL) and heated to reflux with stirring. To this was added a bromine solution [prepared by diluting 11.2 ml (11.2 mmole) of commercial 1.0M solution in CCl$_4$ to a final volume of 40 mL with CCl$_4$] dropwise while a 100 W lamp was used to irradiate the refluxing reaction mixture. After completion of addition, the solution was cooled to room temperature, volatiles were removed, and the residue was flash chromatographed over 700 mL SiO$_2$, eluting with 1.5–4.0–10.0% EtOAc/hexane, to afford 2.68 g (90%) of the title compound, 85% pure as indicated by NMR (the remainder being the dibrominated material), but homogeneous on TLC (4/1 hex-EtOAc).

$^1$H NMR (400 MHz, CDCl$_3$, ppm) δ4.52 (s, 2H), 7.29 (m, 2H), 7.48 (m, 4H), 7.61 (m, 1H), 7.85 (dd, J=8.05, 1.26 Hz, 1H). Mass spectrum: FAB (m/e): 292 (M+1)$^+$ Step C: 5-n-Butyl-2,4-dihydro-4-[(2'-nitrobiphenyl-4-yl)methyl]-2-[2-(trifluoromethyl)phenyl]-3H-1,2,4-triazol-3-one By the procedure of Example 13, Step A, 5-n-butyl-2,4-dihydro-2-[2-(trifluoromethyl)phenyl]-3H-1,2,4-triazol-3-one (from Example 16, Step A) was alkylated with (2'-nitrobiphenyl-4-yl)methyl bromide (from Step B). Flash chromatography of the crude product on silica gel (gradient elution with 0.5–5% MeOH in CH$_2$Cl$_2$) gave a 91% yield of the title compound as a sticky foam; satisfactory purity by TLC in 98:2 CH$_2$Cl$_2$—MeOH; mass spectrum (FAB) m/e 497 (M+1)$^+$.

200 MHz NMR (CDCl$_3$) δ0.88 (t, 3H), 1.36 (m, 2H), 1.52 (m, 2H), 2.48 (t, 2H), 4.95 (s, 2H), 7.25–7.75 (m, 10H), 7.80 (d, 1H), 7.87 (d, 1H).

Step D: 4-[(2′-Aminobiphenyl-4-yl)methyl]-5-n-butyl-2,4-dihydro-2-[2-(trifluoromethyl)phenyl]-3H-1,2,4-triazol-3-one To a solution of 217 mg (0.438 mmole) of 5-n-butyl-2,4-dihydro-4-[(2′-nitrobiphenyl-4-yl)methyl]-2-[2-(trifluoromethyl)phenyl]-3H-1,2,4-triazol-3-one (from Step C) in 2.2 ml of THF stirred at 0° C. under N$_2$ was added dropwise a solution of 692 mg (3.07 mmole) of stannous chloride dihydrate in 1.2 ml of concentrated hydrochloric acid. After 15 minutes, the ice bath was removed, and the mixture was allowed to warm to room temperature. After 2 hours at room temperature, by which time TLC (98:2 CH$_2$Cl$_2$—MeOH) indicated complete disappearance of starting material, the reaction mixture was added to a mixture of 10.6 g of ice, 3 ml of 50% NaOH, and 6 ml of ether. The resulting mixture was stirred at 0° C. for about 1 hour and then extracted with 2×10 ml of ether and 1×10 ml of ethyl acetate. The combined organic extracts were washed with brine, dried over sodium sulfate, filtered, and concentrated. The crude product was flash chromatographed twice on silica gel (first elution with a gradient of 0.5–5% MeOH in CH$_2$Cl$_2$, second elution with 0.5% MeOH in CH$_2$Cl$_2$). Concentration of the product fractions afforded 95 mg (47%) of the title compound as a sticky foam; satisfactory purity by TLC (98:2 CH$_2$Cl$_2$—MeOH) for use in the next step; mass spectrum (FAB) m/e 467 (M+1)$^+$.

400 MHz NMR (CDCl$_3$) δ0.86 (t, 3H), 1.35 (m, 2H), 1.62 (m, 2H), 2.49 (t, 2H), 4.91 (s, 2H), 6.86 (m, 2H), 7.1–7.2 (m, 2H), 7.32 (d, 2H), 7.46 (d, 2H), 7.5–7.6 (m, 2H), 7.64 (dd, 1H), 7.78 (d, 1H).

Step E: 5-n-Butyl-2,4-dihydro-4-[[2′-(trifluoromethanesulfonamido)biphenyl-4-yl]methyl]-2-[2-(trifluoromethyl)phenyl]-3H-1,2,4-triazol-3-one A solution of 75 mg (0.161 mmole) of 4-[(2′-aminobiphenyl-4-yl)methyl]-5-n-butyl-2,4-dihydro-2-[2-(trifluoromethyl)phenyl]-3H-1,2,4-triazol-3-one (from Step D) in 1.0 ml of dry pyridine was treated with 135 μl (227 mg, 0.805 mmole) of trifluoromethanesulfonic anhydride. The resulting red solution was stirred under N$_2$ at room temperature for 4 hours. The reaction was quenched by addition of 7 ml of saturated KH$_2$PO$_4$ solution followed by extraction with 3×10 ml of ethyl acetate. The combined organic extracts were washed with 15 ml of brine, then dried over Na$_2$SO$_4$, filtered, and concentrated. The residue was taken up in a small volume of CH$_2$Cl$_2$ and shaken with 1 ml of 1N HCl. The organic layer was separated, dried (Na$_2$SO$_4$), filtered, and evaporated. The crude product was flash chromatographed on silica gel (gradient elution with 0.3–5% MeOH in CH$_2$Cl$_2$). Concentration of the fraction containing the high R$_f$ major product (TLC in 95:5 CH$_2$Cl$_2$—MeOH) gave 58 mg of the bis(trifluoromethanesulfonyl)amino derivative, which was dissolved in 580 μl of methanol and treated with 318 μl (0.795 mmole) of 2.5N NaOH. The solution was stirred at 50° C. for 4 hours and then concentrated. The residue was partitioned between 4 ml of CH$_2$Cl$_2$ and 1 ml of 1N HCl. The organic layer was dried over Na$_2$SO$_4$, filtered, and concentrated. Flash chromatography of the residue on silica gel (elution with 0.3% and then 0.5% MeOH in CH$_2$Cl$_2$) gave 30 mg (63%) of cream-colored crystals, mp 168°–170° C.; satisfactory purity by TLC in 95:5 CH$_2$Cl$_2$—MeOH; mass spectrum (FAB) m/e 599 (M+1)$^+$.

Analysis (C$_{27}$H$_{24}$F$_6$N$_4$O$_3$S): Calcd: C, 54.18; H, 4.04; N, 9.36. Found: C, 53.94; H, 3.74; N, 9.07.

400 MHz NMR (CDCl$_3$) δ0.87 (t, 3H), 1.36 (m, 2H), 1.64 (m, 2H), 2.49 (t, 2H), 4.95 (s, 2H), 6.82 (br s, 1H), 7.2–7.6 (m, 10H), 7.65 (dd, 1H), 7.78 (d, 1H).

EXAMPLE 28

5-n-Butyl-2-(α-carboxybenzyl)-2,4-dihydro-4-[[2′-(5-tetrazolyl)biphenyl-4-yl]methyl]-3H-1,2,4-triazol-3-one Step A: 5-n-Butyl-2-[α-(carbomethoxy)benzyl]-2,4-dihydro-4-[[2′-(N-trityltetrazol-5-yl)biphenyl-4-yl]methyl]-3H-1,2,4-triazol-3-one The alkylation of 5-n-butyl-2,4-dihydro-4-[[2′-(N-trityltetrazol-5-yl)biphenyl-4-yl]methyl]-3H-1,2,4-triazol-3-one (from Example 2, Step D) with methyl α-bromophenyl-acetate was carried out as described in Example 3, Step A, except 3 equivalents of the alkylating agent was used. After work-up, flash chromatography of the crude product over silica gel (50 mL for 0.24 mmole, elution with 0.5% MeOH/CH$_2$Cl$_2$) gave the title compound in 57% yield as an oil, homogeneous by TLC in 2% MeOH/CH$_2$Cl$_2$, mass spectrum (FAB) m/e 766 (M+1)$^+$.

300 MHz NMR (CDCl$_3$) δ0.80 (t, J=7.3 Hz, 3H), 1.18–1.25 (m, 2H), 1.44–1.61 (m, 2H), 2.21–2.28 (m, 2H), 3.75 (s, 3H), 4.69 (s, 2H), 6.05 (s, 1H), 6.88–7.60 (m, 27H), 7.90–7.93 (m, 1H).

Step B: 5-n-Butyl-2-[α-(carbomethoxy)benzyl]-2,4-dihydro-4-[[2′-(5-tetrazolyl)biphenyl-4-yl]methyl]-3H-1,2,4-triazol-3-one Deprotection of 5-n-butyl-2-[α-(carbomethoxy)benzyl]-2,4-dihydro-4-[[2′-(N-trityltetrazol-5-yl)biphenyl-4-yl]methyl]-3H-1,2,4-triazol-3-one in 67% aqueous acetic acid was accomplished by the procedure of Example 3, Step B, except the mixture was heated overnight at 65° C. After work-up, the residue was flash chromatographed over silica gel (30 mL for 0.14 mmole, elution with 4–10% MeOH/CH$_2$Cl$_2$) to give the title compound in 96% yield as an off-white foam, homogeneous by TLC in 9:1 CH$_2$Cl$_2$/MeOH, mass spectrum (FAB) m/e 524 (M+1)$^+$.

300 MHz NMR (CDCl$_3$) δ0.81 (t, J=7.3 Hz, 3H), 1.20–1.35 (m, 2H), 1.42–1.60 (m, 2H), 2.40–2.50 (m, 2H), 3.66 (s, 3H), 4.69 (s, 2H), 5.95 (s, 1H), 6.90–7.60 (m, 12H), 7.80–7.84 (m, 1H).

Step C: 5-n-Butyl-2-(α-(α-carboxybenzyl)-2,4-dihydro-4-[[2′-(5-tetrazolyl)biphenyl-4-yl]methyl]-3H-1,2,4-triazol-3-one The hydrolysis of 5-n-butyl-2-[α-(carbomethoxy)benzyl]-2,4-dihydro-4-[[2′-(5-tetrazolyl)biphenyl-4-yl]methyl]-3H-1,2,4-triazol-3-one using methanolic sodium hydroxide in THF was carried out as described in Example 7. After work-up, the residue was flash chromatographed over silica gel (gradient elution with 4–30% MeOH/CH$_2$Cl$_2$) to give the title compound in 50% yield. This material was re-acidified with 1N HCl to pH 1.5, and the compound re-isolated to give a foam, homogeneous by TLC in 10% MeOH/CH$_2$Cl$_2$, mass spectrum (FAB) m/e 510 (M+1)$^+$.

300 MHz NMR (CDCl$_3$) δ0.88 (t, J=7.3 Hz, 3H), 1.25–1.35 (m, 2H), 1.36–1.40 (m, 2H), 2.38–2.52 (m, 2H), 4.80 (s, 2H), 5.84 (s, 1H), 7.05–7.65 (m, 13H).

EXAMPLE 29

5-n-Butyl-2-cyanomethyl-2,4-dihydro-4-[[2'-(5-tetrazolyl)biphenyl-4-yl]methyl]-3H-1,2,4-triazol-3-one Step A: 5-n-Butyl-2-cyanomethyl-2,4-dihydro-4-[[2'-(N-trityltetrazol-5-yl)biphenyl-4-yl]methyl]-3H-1,2,4-triazol-3-one The alkylation of 5-n-butyl-2,4-dihydro-4-[[2'-(N-trityltetrazol-5-yl)biphenyl-4-yl]methyl]-3H-1,2,4-triazol-3-one (from Example 2, Step D) with bromoacetonitrile was carried out as described in Example 3, Step A. After work-up, the residue was flash chromatographed over silica gel (30 mL for 0.162 mmole, gradient elution using 0.5–2.0% MeOH/CH$_2$Cl$_2$ to give the desired compound in 58% yield, homogeneous by TLC in 2% MeOH/CH$_2$Cl$_2$, mass spectrum (FAB) m/e 657 (M+1)$^+$.

300 MHz NMR (CDCl$_3$) δ0.84 (t, J=7.3 Hz, 3H), 1.24–1.31 (m, 2H), 1.49–1.57 (m, 2H), 2.29 (t, J=7.5 Hz, 2H), 4.68 (s, 2H), 4.71 (s, 2H), 6.85–7.55 (m, 22H), 7.90–7.94 (m, 1H).

Step B: 5-n-Butyl-2-cyanomethyl-2,4-dihydro-4-[[2'-(5-tetrazolyl)biphenyl-4-yl]methyl]-3H-1,2,4-triazol-3-one Deprotection of 5-n-butyl-2-cyanomethyl-2,4-dihydro-4-[[2'-(N-trityltetrazol-5-yl)biphenyl-4-yl]methyl]-3H-1,2,4-triazol-3-one in 67% aqueous acetic acid was accomplished by the procedure of Example 3, Step B. After work-up, the residue was flash chromatographed over silica gel (15 mL for 0.082 mmole, gradient elution using 3–10% MeOH/CH$_2$Cl$_2$) to give a 32% yield of the desired material as a glassy solid, mp 86°–88° C., homogeneous by TLC in 10% MeOH/CH$_2$Cl$_2$, mass spectrum (FAB) m/e 415 (M+1)$^+$.

300 MHz NMR (CDCl$_3$) δ0.87 (t, J=7.3 Hz, 3H), 1.31–1.40 (m, 2H), 1.54–1.66 (m, 2H), 2.42 (t, J=7.5 Hz, 2H), 4.68 (s, 2H), 4.76 (s, 2H), 7.08–7.65 (m, 7H), 7.93–7.95 (m, 1H).

EXAMPLE 30

5-n-Butyl-2,4-dihydro-2-(1-phenylpropyl)-4-[[2'-(5-tetrazolyl)biphenyl-4-yl]methyl]-3H-1,2,4-triazol-3-one Step A: 5-n-Butyl-2,4-dihydro-2-(1-phenylpropyl)-4-[[2'-(N-trityltetrazol-5-yl)biphenyl-4-yl]methyl]-3H-1,2,4-triazol-3-one The alkylation of 5-n-butyl-2,4-dihydro-4-[[2'-(N-trityltetrazol-5-yl)biphenyl-4-yl]methyl]-3H-1,2,4-triazol-3-one (from Example 2, Step D) with 1-bromo-1-phenylpropane was carried out as described in Example 3, Step A. After work-up, the residue was flash chromatographed over silica gel (gradient elution using 0.2–1.0% MeOH/CH$_2$Cl$_2$) to give the desired material in 50% yield, homogeneous by TLC in 2% MeOH/CH$_2$Cl$_2$, mass spectrum (FAB) 736 (M+1)$^+$.

300 MHz NMR (CDCl$_3$) δ0.81 (t, J=7.3 Hz, 3H), 0.90 (t, J=7.4 Hz, 3H), 1.20–1.33 (m, 2H), 1.40–1.60 (m, 4H), 2.20–2.30 (m, 2H), 4.60–4.73 (m, 2H), 5.14–5.20 (m, 1H), 6.90–7.46 (m, 27H), 7.89–7.92 (m, 1H).

Step B: 5-n-Butyl-2,4-dihydro-2-(1-phenylpropyl)-4-[[2'-(5-tetrazolyl)biphenyl-4-yl]methyl]-3H-1,2,4-triazol-3-one Deprotection of 5-n-butyl-2,4-dihydro-2-(1-phenylpropyl)-4-[[2'-(N-trityltetrazol-5-yl)biphenyl-4-yl]methyl]-3H-1,2,4-triazol-3-one in 67% aqueous acetic acid was accomplished by the procedure of Example 3, Step B. After work-up, the residue was flash chromatographed over silica gel (15 mL for 0.065 mmole, gradient elution using 2–20% MeOH/CH$_2$Cl$_2$, mass spectrum (FAB) 494 (M+1)$^+$, mp 72°–75° C.

300 MHz NMR (CDCl$_3$) δ0.82–0.88 (m, 6H), 1.25–1.43 (m, 2H), 1.52–1.65 (m, 2H), 2.00–2.15 (m, 1H), 2.20–2.33 (m, 1H), 2.40 (t, J=7.2 Hz, 2H), 4.68–4.82 (m, 2H), 5.03–5.10 (m, 1H), 7.05–7.45 (m, 10H), 7.50–7.62 (m, 2H), 8.03–8.06 (m, 1H).

EXAMPLE 31

5-n-Butyl-2,4-dihydro-2-[1-(N-methylcarbamoyl)ethyl]-4-[[2'-(5-tetrazolyl)biphenyl-4-yl]methyl]-3H-1,2,4-triazol-3-one Step A: 5-n-Butyl-2,4-dihydro-2-[1-(carbomethoxy)ethyl]-4-[(2'-cyanobiphenyl-4-yl)methyl]-3H-1,2,4-triazol-3-one The alkylation of 5-n-butyl-4-[(2'-cyanobiphenyl-4-yl)methyl]-2,4-dihydro-3H-1,2,4-triazol-3-one (from Example 9, Step C) with methyl 2-bromopropionate was carried out as described in Example 3, Step A, except that no excess sodium hydride was used. After work-up, the residue was flash chromatographed over silica gel (eluted with 0.5% MeOH/CH$_2$Cl$_2$) to give the desired material in 84% yield as a colorless oil, homogeneous by TLC in 2% MeOH/CH$_2$Cl$_2$, mass spectrum (FAB) 419 (M+1)$^+$.

300 MHz NMR (CDCl$_3$) δ0.84 (t, J=7.3 Hz, 3H), 1.25–1.40 (m, 2H), 1.53–1.65 (m, 2H), 1.70 (d, J=7.4 Hz, 3H), 2.41 (m, 2H), 3.72 (s, 3H), 4.39 (s, 2H), 4.93 (q, J=4.5 Hz, 1H), 7.40–7.76 (m, 8H).

Step B: 5-n-Butyl-2,4-dihydro-2-[1-(N-methylcarbamoyl)ethyl]-4-[(2'-cyanobiphenyl-4-yl)methyl]-3H-1,2,4-triazol-3-one 5-n-Butyl-2,4-dihydro-2-[1-(carbomethoxyethyl]-4-[(2'-cyanobiphenyl-4-yl)methyl)-3H-1,2,4-triazol-3-one (100 mg, 0.239 mmole) was reacted with excess 40% aqueous methylamine (1.0 mL) in methanol under gentle reflux for 60 hours. After cooling to room temperature, volatiles were evaporated under reduced pressure, and the residue was flash chromatographed over silica gel (25 mL, gradient elution using 0.5–1.0% MeOH/CH$_2$Cl$_2$) to give 79 mg of the desired compound as a colorless oil, homogeneous by TLC in 5% MeOH/CH$_2$Cl$_2$, mass spectrum (FAB) 418 (M+1)$^+$.

300 MHz NMR CDCl$_3$) δ0.88 (t, J=4.2 Hz, 3H), 1.28–1.42 (m, 2H), 1.50–1.70 (m, 2H), 1.62 (d, J=7.3 Hz, 3H), 2.45 (m, 2H), 2.80 (d, J=4.2 Hz, 3H), 4.88 (s, 2H), 7.30–7.78 (m, 8H).

Step C: 5-n-Butyl-2,4-dihydro-2-[1-(N-methylcarbamoyl)ethyl]-4-[[2'-(5-tetrazolyl)biphenyl-4-yl]methyl)-3H-1,2,4-triazol-3-one The conversion of 5-n-butyl-2,4-dihydro-2-[1-(N-methylcarbamoyl)ethyl]-4-[(2'-cyanobiphenyl-4-yl)methyl]-3H-1,2,4-triazol-3-one to the corresponding tetrazole was accomplished by the procedure of Example 9, Step E, except that the mixture was stirred at 120° C. for 2 days. After work-up, the residue was taken up in CH2Cl2 and flash chromatographed over silica gel (15 mL for 0.19 mmole, gradient elution using 5–30% MeOH/CH$_2$Cl$_2$ to give the desired compound as a white powder in 43% yield, homogeneous by TLC in 30% MeOH/CH$_2$Cl$_2$, mass spectrum (FAB) 461 (M+1)$^+$, mp 153°–155° C.

300 MHz NMR (DMSO-d$_6$) δ0.81 (t, J=7.4 Hz, 3H), 1.20–1.35 (m, 2H), 1.40–1.55 (m, 2H), 1.46 (d, J=7.3 Hz, 3H), 2.38–2.45 (m, 2H), 2.50 (s, 1H), 2.58 (d, J=4.4 Hz, 3H), 4.62 (q, J=7.3 Hz, 1H), 4.80 (s, 2H), 7.05–7.20 (m, 3H), 7.40–8.00 (m, 5H).

EXAMPLE 32

5-n-Butyl-2,4-dihydro-2-phenacyl-4-[[2'-(5-tetrazolyl)-biphenyl-4-yl]methyl)-3H-1,2,4-triazol-3-one Step A: 5-n-Butyl-2,4-dihydro-2-phenacyl-4-[[2'-(N-trityltetrazol-5-yl)biphenyl-4-yl]methyl]-3H-1,2,4-triazol-3-one The alkylation of 5-n-butyl-2,4-dihydro-4-[[2'-(N-trityltetrazol-5-yl)biphenyl-4-yl]methyl]-3H- 1,2,4-triazol-3-one (from Example 2, Step D) with phenacyl bromide was carried out as described in Example 3, Step A, except that only 3 equivalents of the alkylating agent was used. After work-up, the residue was flash chromatographed over silica gel (25 mL for 0.162 mmole, gradient elution using 0.5–2.0% MeOH/CH$_2$Cl$_2$) to give the desired compound as a white foam in 81% yield, homogeneous by TLC in 2% MeOH/CH$_2$Cl$_2$, mass spectrum (FAB) 736 (M+1)+.

300 MHz NMR CDCl$_3$) δ0.80 (t, J=7.4 Hz, 3H), 1.18–1.30 (m, 2H), 1.45–1.57 (m, 2H), 2.27 (t, J=7.3 Hz. 2H), 4.74 (s, 2H), 5.24 (s, 2H), 6.80–7.60 (m, 25H), 7.88–8.00 (m, 3H).

Step B: 5-n-Butyl-2,4-dihydro-2-phenacyl-4-[[2'-(5-tetrazolyl)biphenyl-4-yl]methyl]-3H-1,2,4-triazol-3-one Deprotection of 5-n-butyl-2,4-dihydro-2-phenacyl-4-[[2'-(5-tetrazolyl)biphenyl-4-yl]methyl]-3H-1,2,4-triazol-3-one in 50% aqueous acetic acid was accomplished by the procedure of Example 3, Step B. After work-up, the residue was flash chromatographed over silica gel (15 mL for 0.082 mmole, gradient elution using 2–20% MeOH/CH$_2$Cl$_2$) to give the desired material as a white foam in 84% yield, homogeneous by TLC in 10% MeOH/CH$_2$Cl$_2$, mass spectrum (FAB) 494 (M+1)+, mp 89°–92° C.

300 MHz NMR CDCl$_3$) δ0.83 (t, J=7.2 Hz, 3H), 1.22–1.42 (m, 2H), 1.48–1.62 (m, 2H), 2.38 (t, J=7.4 Hz, 2H), 4.79 (s, 2H), 5.18 (s, 2H), 7.10–7.65 (m, 10H), 7.80–7.90 (m, 3H).

EXAMPLE 33

5-n-Butyl-2-(4-chlorophenoxymethyl)-2,4-dihydro-4-[[2'-(5-tetrazolyl)biphenyl-4-yl]methyl]-3H-1,2,4-triazol-3-one Step A: 5-n-Butyl-2-(4-chlorophenoxymethyl)-2,4-dihydro-4-[[2'-(N-trityltetrazol-5-yl)biphenyl-4-yl]methyl]-3H-1,2,4-triazol-3-one The alkylation of 5-n-butyl-2,4-dihydro-4-[[2'-(N-trityltetrazol-5-yl)biphenyl-4-yl]methyl]-3H-1,2,4-triazol-3-one (from Example 2, Step D) with α,4-dichloroanisole was carried out as described in Example 3, Step A, except that only 5 equivalents of the alkylating agent was used. After work-up, the residue was flash chromatographed over silica gel (25 mL for 0.162 mmole, gradient elution using 0.25–1.0% MeOH/CH$_2$Cl$_2$) to give the desired material as a colorless oil in 55% yield, homogeneous by TLC in 2% MeOH/CH$_2$Cl$_2$, mass spectrum (FAB) 758 (M+1)+.

300 MHz NMR CDCl$_3$) δ0.82 (t, J=7.4 Hz, 3H), 1.18–1.42 (m, 2H), 1.46–1.60 (m, 2H), 2.26 (t, J=7.7 Hz, 2H), 4.67 (s, 2H), 5.68 (s, 2H), 6.85–7.50 (m, 26H), 7.92–7.94 (m, 1H).

Step B: 5-n-Butyl-2-(4-chlorophenoxymethyl)-2,4-dihydro-4-[[2'-(5-tetrazolyl)biphenyl-4-yl]methyl]-3H-1,2,4-triazol-3-one Deprotection of 5-n-butyl-2,4-dihydro-4-[[2'-(N-trityltetrazol-5-yl)biphenyl-4-yl]methyl]-3H-1,2,4-triazol-3-one in 50% aqueous acetic acid was accomplished by the procedure of Example 3, Step B. After work-up, the residue was flash chromatographed over silica gel (15 mL for 0.07 mmole, gradient elution using 2–20% MeOH/CH$_2$Cl$_2$) to give the desired material as a foam in 69% yield, homogeneous by TLC in 10% MeOH/CH$_2$Cl$_2$, mass spectrum (FAB) m/e 516 (M+1)+.

300 MHz NMR CDCl$_3$) δ0.86 (t, J=7.3 Hz, 3H), 1.25–1.42 (m, 2H), 1.55–1.65 (m, 2H), 2.41 (t, J=7.6 Hz, 2H), 4.78 (s, 2H), 5.64 (s, 2H), 7.00–7.65 (m, 11H). 8.06–8.08 (m, 1H).

EXAMPLE 34

5n-Butyl-2,4-dihydro-2-(phenylthiomethyl)-4-[[2'-(5-tetrazolyl)biphenyl-4-yl]methyl]-3H-1,2,4-triazol-3-one Step A: 5-n-Butyl-2,4-dihydro-2-(phenylthiomethyl)-4-[[2'-(N-trityltetrazol-5-yl)biphenyl-4-yl]methyl]-3H-1,2,4-triazol-3-one The alkylation of 5-n-butyl-2,4-dihydro-4-[[2'-(N-trityltetrazol-5-yl)biphenyl-4-yl]methyl]-3H-1,2,4-triazol-3-one (from Example 2, Step D) with chloromethyl phenyl sulfide was carried out as described in Example 3, Step A, except that only 5 equivalents of the alkylating agent was used. After work-up, the residue was flash chromatographed over silica gel (25 mL for 0.162 mole, gradient elution using 0.25–1.0% MeOH/CH$_2$Cl$_2$) to give the desired material as a colorless oil in 17% yield, homogeneous by TLC in 2% MeOH/CH$_2$Cl$_2$, mass spectrum (FAB) m/e 740 (M+1)+.

300 MHz NMR (CDCl$_3$) δ0.81 (t, J=7.3 Hz, 3H), 1.16–1.32 (m, 2H), 1.40–1.55 (m, 2H), 2.23 (t, J=7.6 Hz, 2H), 4.63 (s, 2H), 5.21 (s, 2H), 6.80–7.55 (m, 27H), 7.90–7.93 (m, 1H).

Step B: 5-n-Butyl-2,4-dihydro-2-(phenylthiomethyl)-4-[[2'-(5-tetrazolyl)biphenyl-4-yl]methyl]-3H-1,2,4-triazol-3-one Deprotection of 5-n-butyl-2,4-dihydro-2-(phenylthiomethyl)-4-[[2'-(N-trityltetrazol-5-yl)biphenyl-4-yl]methyl]-3H-1,2,4-triazol-3-one in 50% aqueous acetic acid was accomplished by the procedure of Example 3, Step B. After work-up, the residue was flash chromatographed over silica gel (10 mL for 0.02 mmole, gradient elution using 2–10% MeOH/CH$_2$Cl$_2$) to give the desired material as an oil in 75% yield, homogeneous by TLC in 10% MeOH/CH$_2$Cl$_2$, mass spectrum (FAB) m/e 498 (M+1)+, mp 170° C. dec.

300 MHz NMR CDCl$_3$) δ0.84 (t, J=7.4 Hz, 3H), 1.20–1.45 (m, 2H), 1.48–1.65 (m, 2H), 2.35 (t, J=7.7 Hz, 2H), 4.69 (s, 2H), 5.09 (s, 2H), 6.95–7.65 (m, 12H), 7.95–7.99 (m, 1H).

EXAMPLE 35

2,4-Bis[[2'-(5-tetrazolyl)biphenyl-4-yl]methyl]-5-n-butyl-2,4-dihydro-3H-1,2,4-triazol-3-one Step A: 2,4-Bis[[2'-(N-trityltetrazol-5-yl)biphenyl-4-yl]methyl]-5-n-butyl-2,4-dihydro-3H-1,2,4-triazol-3-one The alkylation of 5-n-butyl-2,4-dihydro-4-[[2'-(N-trityltetrazol-5-yl)biphenyl-4-yl]methyl]-3H-1,2,4-triazol-3-one (from Example 2, Step D) with 5-[4'-(bromomethyl)-biphenyl-2-yl]-N-trityltetrazole (see Example 2, Step B) was carried out as described in Example 3, Step A, except that only 3 equivalents of the alkylating agent was used. After work-up, the residue was flash chromatographed over silica gel (25 mL for 0.162 mmole, gradient elution using 0.25–1.0% MeOH/CH$_2$Cl$_2$) to give the desired material as a white foam in 96% yield, homogeneous by TLC in 2% MeOH/CH$_2$Cl$_2$, mass spectrum (FAB) 1094 (M+1)$^+$.

300 MHz NMR CDCl$_3$) δ0.80 (t, J=7.3 Hz, 3H), 1.20–1.32 (m, 2H), 1.40–1.52 (m, 2H), 2.25 (t, J=7.4 Hz, 2H), 4.72 (s, 2H), 4.88 (s, 2H), 6.85–7.50 (m, 44H), 7.85–7.95 (m, 2H).

Step B: 2,4-Bis[[2'-(5-tetrazolyl)biphenyl-4-yl]methyl]-5-n-butyl-2,4-dihydro-3H-1,2,4-triazol-3-one Deprotection of 2,4-bis[[2'-(N-trityltetrazol-5-yl)biphenyl-4-yl]methyl]-5-n-butyl-2,4-dihydro-3H-1,2,4-triazol-3-one in 50% aqueous acetic acid was accomplished by the procedure of Example 3, Step B. After work-up, the residue was flash chromatographed over silica gel (15 mL for 0.091 mmole, gradient elution using 2–30% MeOH/CH$_2$Cl$_2$) to give the desired material as a solid in 91% yield, homogeneous by TLC in 10% MeOH/CH$_2$Cl$_2$, mass spectrum (FAB) m/e 610 (M+1)$^+$, mp 150°–151° C.

300 MHz NMR CDCl$_3$) δ0.85 (t, J=7.3 Hz, 3H), 1.25–1.42 (m, 2H), 1.50–1.65 (m, 2H), 2.41 (t, J=7.5 Hz, 2H), 4.64 (s, 2H), 4.80 (s, 2H), 6.95–7.70 (m, 14H), 7.85–8.00 (m, 2H).

EXAMPLE 36

5-n-Butyl-2-cyclopropyl-2,4-dihydro-4-[[2'-(5-tetrazolyl)biphenyl-4-yl]methyl]-3H-1,2,4-triazol-3-one Step A: 5-n-Butyl-2-cyclopropyl-4-[(2'-cyanobiphenyl-4-yl)methyl]-3H-2,4-dihydro-1,2,4-triazol-3-one The alkylation of 5-n-butyl-4-[[2'-cyanobiphenyl-4-yl]methyl]-2,4-dihydro-3H-1,2,4-triazol-3-one (from Example 9, Step C) with bromomethylcyclopropane was carried out as described in Example 3, Step A, except that no excess sodium hydride was used and that the reaction was run with 13 equivalents of the alkylating agent at 160° C. in a sealed tube for 40 hours. After work-up, the residue was flash chromatographed over silica gel (gradient elution using 1–5% MeOH/CH$_2$Cl$_2$) to give the desired material in 12% yield as a colorless oil, homogeneous by TLC in 5% MeOH/CH$_2$Cl$_2$, mass spectrum (FAB) 373 (M+1)$^+$.

300 MHz NMR CDCl$_3$) δ0.85 (t, J=7.3 Hz, 3H), 0.91–1.05 (m, 2H), 1.04–1.10 (m, 2H), 1.26–1.42 (m, 2H), 1.52–1.66 (m, 2H), 2.38 (t, J=7.6 Hz, 2H), 3.15–3.22 (m, 1H), 4.84 (s, 2H), 7.30–7.78 (m, 8H).

Step B: 5-n-Butyl-2-cyclopropyl-2,4-dihydro-4-[[2'-(5-tetrazolyl)biphenyl-4-yl]methyl]-3H-1,2,4-triazol-3-one The conversion of 5-n-butyl-2-cyclopropyl-4-[(2'-cyanobiphenyl-4-yl)methyl]-2,4-dihydro-3H-1,2,4-triazol-3-one to the corresponding tetrazole was accomplished by the procedure of Example 9, Step E, except that it was stirred at 120° C. for 2 days. After work-up, the residue was taken up in CH$_2$Cl$_2$ and flash chromatographed over silica gel (5 mL for 0.091 mmole, gradient elution using 2–10% MeOH/CH$_2$Cl$_2$) to give the desired compound as an oil in 34% yield, homogeneous by TLC in 10% MeOH/CH$_2$Cl$_2$, mass spectrum (FAB) 416 (M+1)$^+$.

300 MHz NMR CDCl$_3$) δ0.78–0.92 (m, 4H), 0.82 (t, J=7.3 Hz, 3H), 1.21–1.38 (m, 2H), 1.40–1.55 (m, 2H), 2.32 (t, J=7.6 Hz, 2H), 3.00–3.05 (m, 1H), 4.66 (s, 2H), 6.90–7.60 (m, 6H), 7.80–8.10 (m, 2H).

EXAMPLE 37

5-n-Butyl-2,4-dihydro-2-[3-(N-methyl-N-phenylcarbamoyloxy)propyl]-4-[[2'-(5-tetrazolyl)biphenyl-4-yl]methyl]-3H-1,2,4-triazol-3-one Step A: 3-Bromopropyl-N-methyl-N-phenylcarbamate At 0° C., to a vigorously stirred solution of 3-bromopropanol (139 mg, 1 mmole) and N-methyl-N-phenylcarbamyl chloride (170 mg, 1 mmole) in 1 mL dry THF, was added dropwise potassium t-butoxide in THF (1 mL of 1.0M solution), stirred at 0° C. for 30 minutes and then warmed to room temperature. When TLC indicated the disappearance of all starting material, the reaction mixture was cooled to 0° C., and 4 mL of water was added and the aqueous layer was extracted with 3×5 mL EtOAc. The organic layers were washed with brine and dried over sodium sulfate. After filtration and removal of volatiles, the residue was flash chromatographed over 30 mL of silica gel, eluting with 20/1 hexane/EtOAc to give 100 mg of a colorless oil, homogeneous by TLC in 5/1 hexane/EtOAc, mass spectrum (FAB) 273 (M+1)$^+$.

300 MHz NMR CDCl$_3$) δ2.11 (t, J=6.1 Hz, 2H), 3.25–3.43 (m, 2H), 3.28 (s, 3H), 7.15–7.30 (m, 3H), 7.30–7.40 (m, 2H).

Step B: 5-n-Butyl-2,4-dihydro-2-[3-(N-methyl-N-phenylcarbamoyloxy)propyl]-4-[[2'-(N-trityltetrazol-5-yl)biphenyl-4-yl]methyl]-3H-1,2,4-triazol-3-one The alkylation of 5-n-butyl-2,4-dihydro-4-[[2'-(N-trityltetrazol-5-yl)biphenyl-4-yl]methyl]-3H-1,2,4-triazol-3-one (from Example 2, Step D) with 3-bromopropyl-N-methyl-N-phenylcarbamate was carried out as described in Example 3, Step A, except that only 2.4 equivalents of the alkylating agent was used. After work-up, the residue was flash chromatographed over silica gel (35 mL for 0.162 mmole, gradient elution using 0.75–2.5% MeOH/CH$_2$Cl$_2$) to give the desired material as a white foam in 86% yield, mass spectrum (FAB) 809 (M+1)$^+$.

200 MHz NMR CDCl$_3$) δ0.83 (t, J=7.3 Hz, 3H), 1.18–1.38 (m, 2H), 1.40–1.60 (m, 2H), 2.00–2.18 (m,; 2H), 2.26 (t, J=7.5 Hz, 2H), 3.31 (s, 3H), 3.76–3.88 (m, 2H), 4.12–4.10 (m, 2H), 4.67 (s, 2H), 6.86–7.70 (m, 27H), 7.88–7.94 (m, 1H).

Step C: 5-n-Butyl-2,4-dihydro-2-[3-(N-methyl-N-phenylcarbamoyloxy)propyl]-4-[[2'-(5-tetrazolyl)biphenyl-4-yl]methyl]-3H-1,2,4-triazol-3-one Deprotection of 5-n-butyl-2,4-dihydro-2-[3-(N-methyl-N-phenylcarbamoyloxy)propyl]-4-[[2'-(N-trityltetrazol-5-yl)biphenyl-4-yl]methyl]-3H-1,2,4-triazol-3-one in 50% aqueous acetic acid was accomplished by the procedure of Example 3, Step B. After work-up, the residue was flash chromatographed over silica gel (35 mL for 0.13 mmole, gradient elution using 2–10% MeOH/CH$_2$Cl$_2$) to give the desired material as a foam in 68% yield, homogeneous by TLC in 10% MeOH/CH$_2$Cl$_2$, mass spectrum (FAB) m/e 567 (M+1)$^+$.

300 MHz NMR (CDCl$_3$) δ0.90 (t, J=7.3 Hz, 3H), 1.35–1.50 (m, 2H), 1.60–1.73 (m, 2H), 1.90–2.10 (m, 2H), 2.50 (t, J=7.4 Hz, 2H), 3.25 (s, 3H), 3.70–3.90 (m, 4H), 4.73 (s, 2H), 6.90–7.70 (m, 12H), 7.90–7.98 (m, 1H).

EXAMPLE 38

5-n-Butyl-2-[1-(carbomethoxy)isobutyl]-2,4-dihydro-4-[[2'-(5-tetrazolyl)biphenyl-4-yl]methyl]-3H-1,2,4-triazol-3-one Step A: Methyl 2-bromo-3-methylbutyrate 2-Bromo-3-methylbutyric acid (3.65 g, 20 mmole) was esterified in refluxing methanol containing 2 mL concentrated sulfuric acid for 22 hours. After cooling to room temperature, volatiles were evaporated and the residue was taken up in 50 mL of water and extracted with Et₂O. The ether layer was washed with 5% aq. NaHCO₃, water brine, and dried over Na₂SO₄. The desired material was obtained after filtration and removal of volatiles; homogeneous by TLC in 4/1 hexane/EtOAc.

300 MHz NMR CDCl₃) δ0.99 (t, J=6.6 Hz, 3H), 1.06 (t, J=6.6 Hz, 3H), 2.16–2.23 (m, 1H), 3.74 (s, 3H), 4.03 (m, 1H).

Step B: 5-n-Butyl-2-[1-(carbomethoxy)isobutyl]-2,4-dihydro-4-[[2'-(N-trityltetrazol-5-yl)biphenyl-4-yl]methyl]-3H-1,2,4-triazol-3-one The alkylation of 5-n-butyl-2,4-dihydro-4-[[2'-(N-trityltetrazol-5-yl)biphenyl-4-yl]methyl]-3H-1,2,4-triazol-3-one (from Example 2, Step D) with methyl 2-bromo-3-methylbutyrate was carried out as described in Example 3, Step A, except that only 5 equivalents of the alkylating agent was used. After work-up, the residue was flash chromatographed over silica gel (50 mL for 0.324 mmole, eluted using 0.5% MeOH/CH₂Cl₂) to give the desired material as a white foam in 56% yield, homogeneous by TLC in 5% MeOH/CH₂Cl₂.

300 MHz NMR (CDCl₃) δ0.80 (t, J=7.5 Hz, 3H), 0.95 (d, J=6.8 Hz, 3H), 1.04 (d, J=6.8 Hz, 3H), 1.18–1.26 (m, 2H), 1.34–1.50 (m, 2H), 2.25–2.31 (m, 2H), 2.55–2.69 (m, 1H), 3.71 (s, 3H), 4.62 (d, J=8.5 Hz, 1H), 4.70 (s, 2H), 6.90–7.48 (m, 22H), 7.89–7.92 (m, 1H).

Step C: 5-n-Butyl-2-[1-(carbomethoxy)isobutyl]-2,4-dihydro-4-[[2'-(5-tetrazolyl)biphenyl-4-yl ]methyl]-3H-1,2,4-triazol-3-one Deprotection of 5-n-butyl-2-[1-(carbomethoxy)isobutyl]-2,4-dihydro-4-[[2'-(5-tetrazolyl)biphenyl-4-yl]methyl]-3H-1,2,4-triazol-3-one in 50% aqueous acid was accomplished by the procedure of Example 3, Step B. After work-up, the residue was flash chromatographed over silica gel (20 mL for 0.162 mmole, gradient elution using 2–10% MeOH/CH₂Cl₂) to give the desired material as a foam in 75% yield, homogeneous by TLC in 10% MeOH/CH₂Cl₂, mass spectrum (FAB) m/e 490 (M+1)+.

300 MHz NMR CDCl₃) δ0.84 (t, J=7.3 Hz, 3H), 0.89 (d, J=6.8 Hz, 3H), 0.96 (d, J=6.8 Hz, 3H), 2.38–2.41 (m, 2H), 2.43–2.58 (m, 1H), 3.66 (s, 3H), 4.46 (d, J=8.4 Hz, 1H), 4.74 (s, 2H), 7.07–7.11 (m, 4H), 7.39–7.60 (m, 3H), 7.88–7.90 (m, 1H).

EXAMPLE 39

5-n-Butyl-2-(1-carboxyisobutyl)-2,4-dihydro-4-[[2'-(5-tetrazolyl)biphenyl-4-yl]methyl]-3H-1,2,4-triazol-3-one The hydrolysis of 5-n-butyl-2-[1-(carbomethoxy)isobutyl]-2,4-dihydro-4-[[2'-(5-tetrazolyl)biphenyl-4-yl]methyl]-3H-1,2,4-triazol-3-one (from Example 38) using methanolic sodium hydroxide in THF was carried out as described in Example 7. The material obtained after work-up (71%) was homogeneous by TLC in 10% MeOH/CH₂Cl₂, mass spectrum (FAB) m/e 475 (M+1)+.

400 MHz NMR (CD₃OD) δ0.86(t, J=7.3 Hz, 3H), 0.98(d, J=6.8 Hz, 3H), 1.07(d, J=6.8 Hz, 3H), 1.29–1.35(m,2H), 1.48–1.54(m, 2H), 2.43(t, J=7.2 Hz, 2H), 2.56–2.59(m, 1H), 4.53(d, J=8.1 Hz, 1H), 4.90(s, 2H), 7.11–7.19(m, 4H), 7.54–7.69(m,4H).

EXAMPLE 40

5-Cyclopropyl-2,4-dihydro-2-(2-nitrophenyl)-4-[[2'-(5-tetrazolyl)biphenyl-4-yl]methyl]-3H-1,2,4-triazol-3-one Step A: Ethyl N-(carbethoxy)cyclopropanecarboximidate An ether solution of 4.0 g (35.4 mmole) of ethyl cyclopropanecarboximidate [free base, obtained from the corresponding hydrochloride salt by the procedure described in Example 4, Step A. The imidate hydrochloride salt was prepared from cyclopropyl cyanide, ethanol and HCl gas as described by A. J. Hill and I. Rabinowitz, J. Am. Chem. Soc., 48, 734 (1926)] was treated with 5.07 mL (37.2 mmole) of triethylamine and 3.49 mL (36.5 mmole) of ethyl chloroformate according to the procedure of Example 4, Step B. After work-up, the crude material was flash chromatographed over silica gel (275 mL, eluted with 1% MeOH/CH₂Cl₂, to give 3.15 g of clear liquid, homogeneous by TLC in 2% MeOH/CH₂Cl₂, mass spectrum (EI) m/e 185 (M)+.

200 MHz NMR (CDCl₃) δ0.84–0.90(m, 2H), 1.03–1.11(m, 2H), 1.21(t, J=7.1 Hz, 3H), 1.33(t, J=7.1 Hz, 3H), 1.75–1.89(m, 1H), 4.10(q, J=7.1 Hz, 2H), 4.23(q, J=7.1 Hz, 2H).

Step B: 5-Cyclopropyl-2,4-dihydro-2-(2-nitrophenyl)-3H-1,2,4-triazol-3-one

By the procedure of Example 4, Step C, 2-nitrophenylhydrazine was reacted with ethyl N-(carbethoxy)cyclopropanecarboximidate. After work-up, the residue was purified by flash chromatography on silica gel (150 mL for 2.0 mmole, eluted with 1.5% MeOH/CH₂Cl₂) to give the desired material as a yellow foam in 69% yield, homogeneous by TLC in 5% MeOH/CH₂Cl₂, mass spectrum (FAB) m/e 247 (M+1)+.

300 MHz NMR (CDCl₃) δ0.98–1.04(m, 4H), 1.79–1.86(m, 1H), 7.42–7.48(m,1H), 7.64–7.72(m, 2H), 7.91–7.94(m, 1H), 11.63(s, 1H).

Step C: 5-Cyclopropyl-2,4-dihydro-2-(2-nitrophenyl)-4-[[2'-(N-trityltetrazol-5-yl)biphenyl-4-yl]methyl]-3H-1,2,4-triazol-3-one The alkylation of 5-cyclopropyl-2,4-dihydro-2-(2-nitrophenyl)-3H-1,2,4-triazol-3-one with 5-[4'-bromomethyl)biphenyl-2-yl]-N-trityltetrazole (see Example 2, Step B) was carried out as described in Example 4, Step D, except that a 20% excess of sodium hydride and 20% excess of the alkylating agent were used. After work-up, the crude product mixture was flash chromatographed on silica gel (124 mL for 0.467 mmole, eluted with 0.5% MeOH/CH₂Cl₂) to give a 59% yield of the desired material as a yellow foam, homogeneous by TLC in 2% MeOH/CH₂Cl₂, mass spectrum (FAB) m/e 723 (M+1)+.

300 MHz NMR (CDCl₃) δ0.76–0.79(m, 2H), 0.86–0.89(m, 2H), 1.85–1.95(m, 1H), 4.86(s, 2H), 6.83–7.75(m, 26H), 7.90–7.93(m,1H).

Step D: 5-Cyclopropyl-2,4-dihydro-2-(2-nitrophenyl)-4-[[2'-(5-tetrazolyl)biphenyl-4-yl]methyl]-3H-1,2,4-triazol-3-one Deprotection of 5-cyclopropyl-2,4-dihydro-2-(2-nitrophenyl)-4-[[2'-(5-tetrazolyl)biphenyl-4-yl]methyl]-3H-1,2,4-triazol-3-one in 50% aqueous acetic acid was accomplished by the procedure of Example 3, Step B, except that the mixture was heated at 65° overnight. After work-up, the residue was flash chromatographed over silica gel (25 mL for 0.139 mmole, gradient elution using 2–20% MeOH/CH₂Cl₂) to give the desired material as a foam in 34% yield, homogeneous by TLC in 10% MeOH/CH₂Cl₂, mass spectrum (FAB) m/e 481 (M+1)+.

300 MHz NMR (CDCl₃) δ0.96–1.00(m, 4H), 1.60–1.66(m, 1H), 5.00(s, 2H), 7.15–7.70(m, 10H), 7.90–8.48(m, 2H).

EXAMPLE 41

2-(2-Chlorophenyl)-2,4-dihydro-5-(3-methylbutyl)-4-[[2'-(5-tetrazolyl)biphenyl-4-yl]methyl]-3H-1,2,4-triazol-3-one Step A: Ethyl N-carbethoxy-4-methylvalerimidate A methylene chloride solution of 1.29 g (9.0 mmole) of ethyl 4-methylvalerimidate [free base, obtained from the corresponding hydrochloride salt by the procedure described in Example 4, Step A. The imidate hydrochloride salt was prepared from 4-methylvaleronitrile, ethanol and HCl gas as described by A. J. Hill and I. Rabinowitz, *J. Am. Chem. Soc.*, 48, 734 (1926) was treated with 1.0 g (9.9 mmole) of triethylamine and 0.986 g (9.09 mmole) of ethyl chloroformate according to the procedure of Example 4, Step B. After work-up, the crude material (344 mg) was used without further purification in the next step.

300 MHz NMR (CDCl$_3$) δ0.84–0.87(m, 9H), 1.21–1.32(m, 4H), 1.35–1.55(m, 2H), 2.15–2.41(m, 2H), 4.02–4.20(m, 4H).

Step B: 2-(2-Chlorophenyl)-2,4-dihydro-5-(3-methylbutyl)-3H-1,2,4-triazol-3-one

By the procedure of Example 4, Step C, 2-chlorophenylhydrazine (generated from the hydrochloride by partitioning between ether and 1N Na$_2$CO$_3$) was reacted with ethyl N-carbethoxy-4-methylvalerimidate. After work-up, the residue was purified by flash chromatography on silica gel (150 mL for 2.0 mmole, eluted with 1.5% MeOH/CH$_2$Cl$_2$ to give the desired material as a yellow foam in 69% yield, homogeneous by TLC in 5% MeOH/CH$_2$Cl$_2$, mass spectrum (FAB) m/e 247 (M+1)$^+$.

300 MHz NMR (CDCl$_3$) δ0.87(s, 3H), 0.88(s, 3H), 1.53–1.58(m, 3H), 2.53(t, J=7.9Hz, 2H), 7.33–7.53(m, 4H).

Step C: 2-(2-Chlorophenyl)-2,4-dihydro-5-(3-methylbutyl)-4-[[2'-(N-trityltetrazol-5-yl)biphenyl-4-yl]methyl]-3H-1,2,4-triazol-3-one The alkylation of 2-(2-chlorophenyl)-2,4-dihydro-5-(3-methylbutyl)-3H-1,2,4-triazol-3-one with 5-[4'-(bromomethyl)biphenyl-2-yl]-N-trityltetrazole (see Example 2, Step B) was carried out as described in Example 4, Step D, except that a 20% excess of sodium hydride and 50% excess of the alkylating agent were used. After work-up, the crude product mixture was flash chromatographed on silica gel (72 mL for 0.354 mmol, eluted with 0.3% MeOH/CH$_2$Cl$_2$) to give a 39% yield of the desired material, mass spectrum (FAB) m/e 742 (M+1)$^+$.

400 MHz NMR CDCl$_3$) δ0.85(s, 3H), 0.87(s, 3H), 1.49–1.62(m, 3H), 2.39(m,2H), 4.82(s, 2H), 6.80–7.60 (m, 26H), 7.95(m, 1H).

Step D: 2-(2-Chlorophenyl)-2,4-dihydro-5-(3-methylbutyl)-4-[[2'-(5-tetrazolyl)biphenyl-4-yl]methyl-3H-1,2,4-triazol-3-one Deprotection of 2-(2-chlorophenyl)-2,4-dihydro-5-(3-methylbutyl)-4-[[2'-(N-trityltetrazol-5-yl)biphenyl-4-yl]methyl]-3H-1,2,4-triazol-3-one in 50% aqueous acetic acid was accomplished by the procedure of Example 3, Step B. After work-up, the residue was flash chromatographed over silica gel (14 mL for 0.123 mmole, gradient elution using 2–10% MeOH/CH$_2$Cl$_2$) to give the desired compound in 88% yield, homogeneous by TLC in 10% MeOH/CH$_2$Cl$_2$, mass spectrum (FAB) m/e 500 (M+1)$^+$.

300 MHz NMR (CDCl$_3$) δ0.85(s, 3H), 0.87(s, 3H), 1.50–1.70(m, 3H), 2.49(t, J=7.1 Hz, 2H), 4.87 (s, 2H), 7.10–7.65(m, 11H), 7.93–8.03(m, 1H).

EXAMPLE 42

2-[4-(Benzyloxy)phenyl]-5-n-butyl-2,4-dihydro-4-[[2'-(5-tetrazolyl)biphenyl-4-yl]methyl]-3H-1,2,4-triazol-3-one Step A: 2-[4-(Benzyloxy)phenyl]-5-n-butyl-2,4-dihydro-3H-1,2,4-triazol-3-one By the procedure of Example 4, Step C, p-(benzyloxy)phenylhydrazine [generated from the hydrochloride by partitioning between ether and 1N Na$_2$CO$_3$. The p-(benzyloxy)phenylhydrazine hydrochloride was prepared from the corresponding aniline according to H. Stroh and G. Westphal, *Chem. Ber.*, 96, 184 (1963)] was reacted with ethyl N-carbethoxyvalerimidate (from Example 4, Step B). After work-up, the residue was purified by flash chromatography on silica gel to give a 9% yield of the desired compound, homogeneous by TLC in 19.1 CH$_2$Cl$_2$/CH$_3$OH; mass spectrum (FAB) m/e 324 (M+1)$^+$.

200 MHz NMR (CDCl$_3$) δ: 0.98(t, J=7.1 Hz, 3H), 1.44(m, 2H), 1.72(m, 2H), 2.63(t, J=7.3 Hz, 2H), 5.11(s, 2H), 7.02–7.07(m, 2H), 7.30–7.58(m, 4H), 7.77–7.90(m, 2H), 11.66(s, 1H).

Step B: 2-[4-(Benzyloxy)phenyl]-5-n-butyl-2,4-dihydro-4-[[2'-(N-trityltetrazol-5-yl)biphenyl-4-yl]-methyl]-3H-1,2,4-triazol-3-one The alkylation of 2-[4-(benzyloxy)phenyl]-5-n-butyl-2.4-dihydro-3H-1,2,4-triazol-3-one with 5-[4'-(bromomethyl)biphenyl-2-yl]-N-trityltetrazole (see Example 2, Step B) was carried out as described in Example 4, Step D. After work-up, flash chromatography over silica gel using 0.4–0.5% MeOH/CH$_2$Cl$_2$ gave an 81% yield of the product, homogeneous by TLC in 1% MeOH/CH$_2$Cl$_2$; mass spectrum (FAB) m/e 800 (M+1)$^+$.

200 MHz NMR (CDCl$_3$) δ: 0.86(t, J=7.1 Hz, 3H), 1.20–1.40 (m, 2H), 2.38(t, J=7.5 Hz, 2H), 4.78 (s, 2H), 5.10 (s, 2H), 6.80–7.56(m, 29H), 7.80–7.96 (m, 3H),.

Step C: 2-[4-(Benzyloxy)phenyl]-5-n-butyl-2,4-dihydro-4-[[2'-(5-tetrazolyl)biphenyl-4-yl]methyl]-3H-1,2,4-triazol-3-one Deprotection of 2-[4-(benzyloxy)phenyl]-5-n-butyl-2,4-dihydro-4-[[2'-(N-trityltetrazol-5-yl)biphenyl-4-yl]methyl]-3H-1,2,4-triazol-3-one in 75% aqueous acetic acid was accomplished by the procedure of Example 5, Step C, except that the mixture was kept at 60° C. overnight. After work-up, the residue was flash chromatographed over silica gel (10 mL for 0.05 mmole; gradient elution with 2–5–10% methanol in CH$_2$Cl$_2$) to give a 43% yield of the title compound as a glassy solid, homogeneous by TLC in 10% MeOH/CH$_2$Cl$_2$; mass spectrum (FAB) m/e 558 (M+1)$^+$.

300 MHz NMR (CDCl$_3$) δ: 0.88(t, J=7.2 Hz, 3H), 1.33–1.41 (m, 2H), 1.60–1.70(m, 2H), 2.46(t, J=7.5H, 2H), 4.80 (s, 2H), 5.05(s, 2H), 6.90–7.60(m, 14H), 7.66–7.76(m, 2H), 7.91–7.94(m, 2H).

EXAMPLE 43

5-n-Butyl-4-[[2'-[N-[(S)-2,2-dimethylcyclopropanecarbonyl]sulfamoyl]biphenyl-4-yl]methyl]-2,4-dihydro-2-[2-(trifluoromethyl)phenyl]-3H-1,2,4-triazol3-one A solution of (S)-2,2-dimethylcyclopropanecarboxylic acid (194 mg, 1.70 mmol), and carbonyldiimidazole (275 mg, 1.70 mmol) in THF was stirred at 50° C. for 3 hrs. To this was added dropwise a solution of DBU (258 mg, 1.7 mmol) and 5-n-butyl-2,4-dihydro-4-[(2'-sulfamoylbiphenyl-4-yl)methyl]-2-[2-(trifluoromethyl)phenyl]-3H-1,2,4-triazol-3-one (300 mg, 0.57 mmol) (from Example 16, Step C) in THF. After stirring at 50° C. overnight, the reaction mixture was quenched by addition of 5% citric acid and extracted with EtOAc. The organic layers were combined and washed with water, 5% $NaHCO_3$, and brine, and dried over anhydrous $Na_2SO_4$. The crude material obtained after filtration and evaporation of volatiles was flash chromatographed over 60 mL silica gel (gradient elution using 0.5–5.0% $MeOH/CH_2Cl_2$) to afford the title compound in 74% yield (263 mg) as a white solid, homogeneous by TLC in 5% $MeOH/CH_2Cl_2$; mass spectrum (FAB) m/e 627 $(M+1)^+$, 649 $(M+Na)^+$; mp 93°–95° C.

Analysis $C_{32}H_{33}F_3N_4O_4S.0.25\ H_2O$ Calcd: C, 60.89; H, 5.35; N, 8.88. Found: C, 60.68; H, 5.35; N, 8.88.

400 MHz NMR ($CDCl_3$) δ0.75(dd, J=7.5 Hz, 4.0 Hz, 1H), 0.89(t, J=7.4 Hz, 3H) 0.96(s, 3H), 0.99(s, 3H), 1.01–1.08(m, 2H), 1.35–1.41(m, 2H), 1.62–1.70(m, 2H), 2.54 (t, J=7.4 Hz, 2H), 4.95(s, 2H), 7.27–7.38(m, 5H), 7.52–7.79(m, 6H), 7.92(s, br, 1H), 8.27(dd, J=7.9 Hz, 1.3 Hz, 1H)

EXAMPLE 44

5-n-Butyl-2,4-dihydro-4-[[2'-[N-[p-(methylsulfonyl)benzoyl]sulfamoyl]-biphenyl-4-yl]methyl]-2-[2-(trifluoromethyl)phenyl]-3H-1,2,4-triazol-3-one The title compound was prepared from 5-n-butyl-2,4-dihydro-4-[(2'-sulfamoylbiphenyl-4-yl)methyl]-2-[2-(trifluoromethyl)phenyl]-3H-1,2,4-triazol-3-one (from Example 16, Step C), according to the procedure of Example 43 except that p-(methylsulfonyl)benzoic acid was used as the acid. The crude product was purified by flash chromatography (gradient elution using 0.5–10% $MeOH/CH_2Cl_2$) to afford a 60% yield of the desired compound as a white solid, homogeneous by TLC in 5% $MeOH/CH_2Cl_2$; mass spectrum (FAB) m/e 735 $(M+Na)^+$, 751 $(M+K)^+$; mp 131°–133° C.

400 MHz NMR ($CDCl_3$) δ0.85(t, J=7.3 Hz, 3H), 1.43(m, 2H), 1.60(m, 2H), 2.48(t, J=7.6 Hz, 2H), 2.98(s, 3H), 4.78(s, 2H), 7.12–7.35(m, 5H), 7.42–7.85(m, 10H), 8.35(d, J=7.7 Hz, 1H).

EXAMPLE 45

5-n-Butyl-2,4-dihydro-4-[[2'-(N-pivaloylsulfamoyl)biphenyl-4-yl]methyl]-2-[2-(trifluoromethyl)phenyl]-3H-1,2,4-triazol-3-one The title compound was prepared from 5-n-butyl-2,4-dihydro-4-[(2'-sulfamoylbiphenyl-4-yl)methyl]-2-[2-(trifluoromethyl)phenyl]-3H-1,2,4-triazol-3-one (from Example 16, Step C), according to the procedure of Example 43 except that pivalic acid was used as the acid. Excess pivalic acid was removed by 10% aq. $KHCO_3$. The crude product was purified by flash chromatography (gradient elution using 1–5% $MeOH/CH_2Cl_2$) to afford a 86% yield of the desired compound as a white solid, homogeneous by TLC in 5% $MeOH/CH_2C_2$; mass spectrum (FAB) m/e 615 $(M+1)^+$; mp 176°–178° C.

Analysis $C_{31}H_{33}F_3N_4O_4S$ Calcd: C, 60.57; H, 5.41; N, 9.11. Found: C, 60.27; H, 5.55; N, 8.86.

400 MHz NMR ($CDCl_3$) δ0.88(t, J=7.2 Hz, 3H), 0.96(s, 9H), 1.40(m, 2H), 1.65(m, 2H), 2.51(t, J=7.2 Hz, 2H), 4.93(s, 2H), 7.26–7.42(m, 5H), 7.53–7.79(m, 6H), 8.31(dd, J=8.0 Hz, 1.4 Hz, 1H).

EXAMPLE 46

5-n-Butyl-4-(4-carboxybenzyl)-2,4-dihydro-2-[2-(trifluoromethyl)phenyl]-3H-1,2,4-triazol-3-one A solution of 25 mg (0.0577 mmole) of 5-n-butyl-2,4-dihydro-4-[4-(methoxycarbonyl)benzyl]-2-[2-(trifluoromethyl)phenyl]-3H-1,2,4-triazol-3-one (from Example 26) in 0.25 mL of THF was treated with 0.25 mL of 1N sodium hydroxide in methanol, and the resulting solution was stirred overnight at 60° C. Volatiles were removed by evaporation, and the residue was taken up in 1 mL of methanol and acidified to pH 1.5 by addition of 1N HCl in methanol. The mixture was concentrated to dryness. The residue was leached with chloroform. The $CHCl_3$ solution was dried over anhydrous sodium sulfate, filtered through Celite, and concentrated in vacuo to give 23 mg (96%) of the title compound as a colorless, glassy solid; homogeneous by TLC in 9:1 $CH_2Cl_2$—MeOH; mass spectrum (FAB) m/e 420 $(M+1)^+$.

400 MHz $^1$H NMR ($CDCl_3$) δ0.84 (t, J=7.3 Hz, 3H), 1.33 (m, 2H), 1.59 (m, 2H), 2.42 (t, J=7.6 Hz, 2H), 4.97 (s, 2H), 7.35 (d, J=8.1 Hz, 2H), 7.55 (m, 2H), 7.66 (m, 1H), 7.79 (d, J=8.1 Hz, 1H), 8.09 (d, J=8.1 Hz, 2H).

EXAMPLE 47

5-n-Butyl-2,4-dihydro-4-[[2'-[N-(N-isopropylcarbamoyl)sulfamoyl]biphenyl-4-yl]methyl]-2-[2-(trifluoromethyl]phenyl-3H-1,2,4-triazol-3-one A solution of 5-n-butyl-2,4-dihydro-4-[(2'-sulfamoylbiphenyl-4-yl)methyl]-2-[2-(trifluoromethyl)phenyl]-3H-1,2,4-triazol-3-one (100 mg, 0.19 mmol) (from Example 16, Step C), triethylamine (0.35 mL, 0.38 mmol), and isopropyl isocyanate (0.186 mL, 1.9 mmol), in DMF (0.2 mL) was stirred at 74° C. overnight. After cooling to room temperature, the reaction mixture was quenched by addition of water and extracted with EtOAc. The EtOAc layer was washed with 2N HCl, water, and brine, and dried over anhydrous $Na_2SO_4$. The crude material obtained after filtration and evaporation of volatiles was flash chromatographed over 30 mL silica gel (gradient elution using 0.5–5.0% $MeOH/CH_2Cl_2$) to afford a cream colored solid which was obtained in 41% yield (48 mg) as a solid, homogeneous by TLC in 5% $MeOH/CH_2Cl_2$; mass spectrum (FAB) m/e 654 $(M+1)^+$; mp 78°–80° C.

400 MHz NMR ($CDCl_3$) δ0.89 (t, J=7.3 Hz, 3H), 0.96 (d, J=6.6 Hz, 6H), 1.34–1.43 (m, 2H), 1.62–1.70 (m, 2H), 2.54 (t, J=7.6 Hz, 2H), 3.70 (m, 1H), 4.94 (s, 2H), 5.82 (d, J=7.7 Hz, 1H), 6.53 (s, br, 1H), 7.28–7.42 (m, 5H), 7.50–7.80 (m, 6H), 8.13 (dd, J=8.0 Hz, 1.2 Hz, 1H).

EXAMPLE 48

4-[[2'-[N-(Benzoxazol-2-yl)sulfamoyl]biphenyl-4-yl]methyl-4-yl]methyl-5-n-butyl-2,4-dihydro-2-[2-(trifluoromethyl)phenyl]-3H-1,2,4-triazol-3-one Step A: 2-[[2'-[N-[[Bis(methylthio)methylene]amino]sulfonyl]biphenyl-4-yl]methyl]-5-n-butyl-2,4-dihydro-2-[2-(trifluoromethyl)phenyl]-3H-1,2,4-triazol-3-one To a mixture of 5-n-butyl-2,4-dihydro-4-[(2'-sulfamoylbiphenyl-4-yl)methyl]-2-[2-(trifluoromethyl)phenyl]-3H-1,2,4-triazol-3-one (265 mg, 0.50 mmol) (from Example 16, Step C) and sodium hydride (13.2 mg, 0.55 mmol) in DMF (1.2 mL) which had been stirring at room temperature for 10 minutes, was added carbon disulfide (20.9 mg, 0.275 mmol) and stirring was continued for 30 minutes. The above NaH/CS$_2$ treatment was then repeated. Subsequently, the reaction mixture was cooled to 0° C. and methyl iodide (213 mg, 1.5 mmol) was added dropwise. The somewhat discolored reaction mixture was stirred overnight at room temperature and then quenched by addition of 8 g ice/water mixture and extracted with EtOAc (3×8 mL). The combined organic layers were washed with water (2×10 mL), and brine (1×10 mL), and dried (Na$_2$SO$_4$). After filtration and removal of volatiles, the residue was flash chromatographed over 80 mL silica gel (eluted with 0.5% MeOH/CH$_2$Cl$_2$) to give 257 mg (81%) of the desired material as a white foam, homogeneous on TLC (5% MeOH/CH$_2$Cl$_2$); mass spectrum (FAB) m/e 635 (M+1)$^+$.

400 MHz NMR (CDCl$_3$) δ0.89 (t, J=7.3 Hz, 3H), 1.34–1.38 (m, 2H), 1.62–1.66 (m, 2H), 2.24 (s, 6H), 2.48 (t, J=7.7 Hz, 2H), 4.92 (s, 2H), 7.25–7.30 (m, 3H), 7.45–7.79 (m, 8H), 8.25 (dd, J=8.0 Hz, 1.3 Hz, 1H).

Step B: 4-[[2'-[N-(Benzoxazol-2-yl)sulfamoyl]biphenyl-4-yl]methyl]-5-n-butyl-2,4-dihydro-2-[2-(trifluoromethyl)phenyl]-3H-1,2,4-triazol-3-one A mixture of o-aminophenol (14.2 mg, 0.13 mmol) and sodium hydride (6.24 mg, 0.26 mmol) in DMF (1 mL) was stirred at room temperature for 1.5 hours. To this was added dropwise a solution of 5-n-butyl-2,4-dihydro-4-[[2'-[N-[[[bis(methylthio)methylene]amino]sulfonyl]biphenyl-4-yl]methyl]-2-[ 2-(trifluoromethyl)phenyl]-3H-1,2,4-triazol-3-one (75 mg, 0.12 mmol) (from Step A), dissolved in DMF. This mixture was heated at 110° C. overnight. After cooling to room temperature, water (3 mL), 1N HCl (0.5 mL), and EtOAc (5 mL) were added. The phases were separated and the aqueous phase was further extracted with EtOAc (2×3 mL). The combined organic layers were washed with water, and brine, and dried over Na$_2$SO$_4$. The residue obtained after filtration and removal of volatiles was flash chromatographed over 15 mL silica gel (eluted using 0.5–1.0% MeOH/CH$_2$Cl$_2$) to give 43 mg (57%) of an off-white stiff foam, homogeneous on TLC (5% MeOH/CH$_2$Cl$_2$); mass spectrum (FAB) m/e 648 (M+1)$^+$. m.p. 109°–111° C.

400 MHz NMR (CDCl$_3$) δ0.83 (t, J=7.6 Hz, 3H), 1.25–1.32 (m, 2 h), 1.48–1.55 (m, 2H), 2.31 (t, J=7.5 Hz, 2H), 4.24 (s, 2H), 6.91–6.93 (m, 2H), 7.11–7.36 (m, 6H), 7.50–7.79 (m, 7H), 8.27 (dd, J=7.3 Hz, 1.9 Hz, 1H), 9.53 (s, br, 1H).

EXAMPLE 49

4-[[2'-(N-Benzoylsulfamoyl)biphenyl-4-yl]methyl]-2,4-dihydro-5-[(2-methylcyclopropyl)methyl]-2-[2-(trifluoromethyl)phenyl]-3H-1,2,4-triazol-3-one Step A: 2-Methyl-1-(chloromethyl)cyclopropane At 0° C., to a solution of 6.02 g (72.0 mmol) 2-methylcyclopropanemethanol and 5.6 mL (72.0 mmol) pyridine in 15 mL chloroform was added dropwise a solution of 5.2 mL (72.0 mmol) thionyl chloride dissolved in 30 mL chloroform. The reaction mixture was allowed to warm up to room temperature slowly and then refluxed for 1 hour. After cooling to room temperature, volatiles were removed under reduced pressure and ether was added. The material obtained after filtration and removal of most of the solvent was used in the next step without further purification.

400 MHz NMR (CDCl$_3$) δ0.41 (m, 1H), 0.48 (m, 1H), 0.73 (m, 1H), 0.91 (m, 1H), 1.05 (d, J=6.0 Hz, 3H), 3.41 (m, 2H).

Step B: (2-Methylcyclopropane)acetonitrile

A mixture of 258 mg (5.26 mmol) sodium cyanide and 2.5 mL DMSO was heated to 80° C. and then removed from the oil bath. To this mixture was added dropwise 0.50 mL of crude 2-methyl-2-(chloromethyl)cyclopropane (from Step A), and the resulting mixture was heated to 110° C., removed from the oil bath, cooled to room temperature, diluted with water, and extracted with ether (2×20 mL). The organic layers were combined and washed with 2H HCl, and water, and dried over anhydrous sodium sulfate. After filtration and removal of volatiles, the title compound was obtained as a brown liquid (340 mg) which was used in the next step without further purification.

IR (neat): cm$^{-1}$ 2240(w)

400 MHz NMR (CDCl$_3$) δ0.37 (m, 1H), 0.46 (m, 1H), 0.70 (m, 2H), 1.03 (d, J=5.8 Hz, 3H), 2.32 (d, J=7.0 Hz, 2H).

Step C: Ethyl (2-methylcyclopropane)acetimidate (Free Base)

The title compound was prepared from (2-methylcyclopropane)acetonitrile (from Step B) according to the procedure of Example 4, Step A, to give a 63% yield of the desired material as a colorless oil. The material obtained from the ether extraction was used without further purification in the next step.

400 MHz NMR (CDCl$_3$) δ0.26–0.32 (m, 2H), 0.49–0.55 (m, 2H), 1.03 (d, J=5.5 Hz, 3H), 1.24 (t, J=7.0 Hz, 3H), 2.09 (d, J=6.6 Hz, 2H), 4.09 (q, J=7.0 Hz, 2H).

Step D: Ethyl N-Carbethoxy-(2-methylcyclopropane)acetimidate

The title compound was prepared from ethyl (2-methylcyclopropane)acetimidate (1.0 eq.) (from Step C), triethylamine (2.6 eq.), and ethyl chloroformate (2.5 eq.) according to the procedure of Example 4, Step B. The crude material was purified by flash chromatography over silica gel (eluting with 1% MeOH/CH$_2$Cl$_2$) to give a 44% yield of the desired material as a colorless oil, homogeneous by TLC in 2% MeOH/CH$_2$Cl$_2$.

400 MHz NMR (CDCl$_3$) δ0.20 (m, 1H), 0.30 (m, 1H), 0.55 (m, 1H), 0.68 (m, 1H), 0.97 (d, J=6.0 Hz, 3H), 1.20–1.35 (m, 6H), 2.23 (dd, J=7.1 Hz, 2H), 4.09–4.20 (m, 4H).

Step E: 2,4-Dihydro-5-[(2-methylcylopropyl)methyl]-2-[2-(trifluoromethyl)phenyl]-3H-1,2,4-triazol-3-one The title compound was prepared from ethyl N-carbethoxy-(2-methylcyclopropane)acetimidate (from Step D) and o-(trifluoromethyl)phenylhydrazine according to the procedure of Example 4, Step C. The crude material was purified by flash chromatography over silica gel (gradient elution using 0.5–5.0% MeOH/CH$_2$Cl$_2$; mass spectrum (FAB) m/e 298 (M+1)$^+$, 320 (M+Na)$^+$; mp 117°–120° C.

400 MHz NMR (CDCl$_3$) δ0.30 (m, 1H), 0.37 (m, 1H), 0.61 (m, 1H), 0.72 (m, 1H), 2.35–2.52 (m, 2H), 7.49–7.82 (m, 4H), 11.53 (s, br, 1H).

Step F: 4-[[2'-(N-t-Butylsulfamoyl)biphenyl-4-yl]methyl]-2,4-dihydro-5-[(2-methylcyclopropyl)methyl]-2-[2-(trifluoromethyl)phenyl]-3H-1,2,4-triazol-3-one.

The title compound was prepared from 2,4-dihydro-5-[(2-methylcylopropyl)methyl]-2-[2-(trifluoromethyl)phenyl]-3H-1,2,4-triazol-3-one (from Step E) and [2'-(N-t-butylsulfamoyl)biphenyl-4-yl]methyl bromide (from Example 12, Step D) according to the procedure of Example 13, Step A. The crude material was purified by flash chromatography over silica gel (gradient elution using 0.3–1.0% MeOH/CH$_2$Cl$_2$) to give a 64% yield of the desired material as a cream-colored solid, homogeneous by TLC in 2% MeOH/CH$_2$Cl$_2$; mass spectrum (FAB) m/e 599 (M+1)$^+$; mp 128°–130° C.

400 MHz NMR ((CDCl$_3$) δ0.33 (m, 2H), 0.69 (m, 1H), 0.69 (m, 1H), 0.98 (s, 9H), 0.99 (d, J=6.2 Hz, 3H), 2.42 (dd, J=6.8 Hz, 3.3 Hz, 2H), 3.49 (s, 1H), 4.98 (s, 2H), 7.26–7.80 (m, 11H), 8.15 (d, J=7.3 Hz, 1H).

Step G: 2,4-Dihydro-5-[(2-methylcylopropyl)methyl]-4-[(2'-sulfamoylbiphenyl-4-yl)methyl]-2-[2-(trifluoromethyl)phenyl]-3H-1,2,4-triazol-3-one The title compound was prepared from 4-[[2'-(N-t-butylsulfamoyl)biphenyl-4-yl]methyl]-2,4-dihydro-5-[(2-methylcylopropyl)methyl]-2-[2-(trifluoromethyl)phenyl]-3H-1,2,4-triazol-3-one (from Step F) according to the procedure of Example 13, Step B. The crude material was purified by flash chromatography over silica gel (gradient elution using 0.5–5.0% MeOH/CH$_2$Cl$_2$) to give a 58% yield of the desired material as a white solid, homogeneous by TLC in 2% MeOH/CH$_2$Cl$_2$, mass spectrum (FAB) m/e 543 (M+1)$^+$; mp 84°–86° C.

400 MHz NMR (CDCl$_3$) δ0.35 (m, 2H), 0.58 (m, 1H), 0.65 (m, 1H), 0.98 (d, J=6.0 Hz, 3H), 2.44 (d, J=7.0 Hz, 2H), 4.22 (s, 2H), 4.99 (s, 2H), 7.29–7.80 (m, 11H), 8.14 (dd, J=8.0 Hz, 1.2 Hz, 1H).

Step H: 4-[[2'-[N-Benzoylsulfamoyl]biphenyl-4-yl]-2,4-dihydro-5-[(2-methylcyclopropyl)methyl]-2-[2-(trifluoromethyl)phenyl]-3H-1,2,4-triazol-3-one The title compound was prepared from 2,4-dihydro-5-[(2-methylcyclopropyl)methyl]-4-[(2'-sulfamoylbiphenyl-4-yl)methyl]-2-[2-(trifluoromethyl)phenyl]-3H-1,2,4-triazol-3-one (from Step G) and benzoic acid according to the procedure of Example 43. The crude material was purified by flash chromatography over silica gel (gradient elution using 0.5–5.0% MeOH/CH$_2$Cl$_2$) to give a 64% of the desired material as a white solid, homogeneous by TLC (5% MeOH/CH$_2$Cl$_2$); mass spectrum (FAB) m/e 647 (M+1)$^+$; mp 123°–125° C.

400 MHz NMR (CD$_3$OD) δ0.27 (m, 1H), 0.35 (m, 1H), 0.58 (m, 1H), 0.70 (m, 1H), 0.97 (d, J=5.9 Hz, 3H), 2.50 (m, 2H), 5.00 (s, 2H), 7.16–7.95 (m, 11H), 8.27 (d, J=7.9 Hz, 1H).

EXAMPLE 50

5-n-Butyl-2,4-dihydro-4-[[2'-[N-(4-nitrophenyl)sulfamoyl]biphenyl-4-yl]methyl]-2-[2-(trifluoromethyl)phenyl]-3H-1,2,4-triazol-3-one To a mixture of 5-n-butyl-2,4-dihydro-4-[(2'-sulfamoylbiphenyl-4-yl)methyl]-2-[2-(trifluoromethyl)phenyl]-3H-1,2,4-triazol-4-one (100 mg, 0.19 mmol) (from Example 16, Step C) and sodium hydride (4.5 mg, 0.19 mmol) in DMF, (0.5 mL) which had been stirring at room temperature for 2 h, was added dropwise a solution of 4-fluoro-nitrobenzene (27 mg, 0.19 mmol) dissolved in 0.3 mL DMF. The yellow reaction mixture was stirred at 60° C. for 29 hours. After cooling to room temperature, water and EtOAc were added and the phases were separated. After two more extractions with EtOAc, the organic layers were combined and washed twice with water, and brine, and then dried over Na$_2$SO$_4$. The crude product obtained after filtration and evaporation of volatiles was flash chromatographed over silica gel (gradient elution using 0.3–5.0% MeOH/CH$_2$Cl$_2$) to afford 53 mg (43%) of the title compound as an off-white solid, homogeneous by TLC in 5% MeOH/CH$_2$Cl$_2$; mass spectrum (FAB) m/e 652 (M+1)$^+$; mp 186°–187° C.

400 MHz NMR (CDCl$_3$) δ0.91 (t, J=7.3 Hz, 3H), 1.41 (m, 2H), 1.70 (m, 2H), 2.58 (t, J=7.4 Hz, 2H), 5.00 (s, 2H), 6.50 (s, 1H), 6.75 (dd, J=7.1 Hz, 2.1 Hz, 2H), 7.23–7.32 (m, 5H), 7.54–7.82 (m, 6H), 7.97 (dd, J=7.0 Hz, 2.1 Hz, 2H), 8.28 (dd, J=7.8 Hz, 1.4 Hz, 1H).

Additional 5-alkyl-2-aryl-2,4-dihydro-4-[[2'-(N-substituted-sulfamoyl)biphenyl-4-yl]methyl]-3H-1,2,4-triazol-3-ones prepared by the methods described in the foregoing Examples are tabulated below:

TABLE III

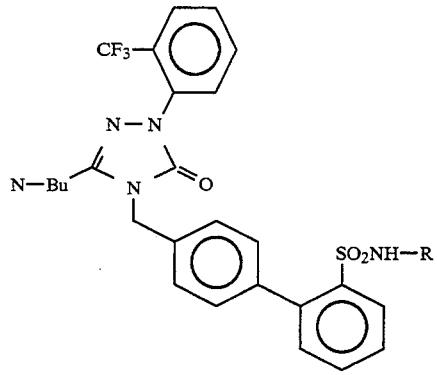

| R | mp | formula | Analysis | | |
|---|---|---|---|---|---|
| | | | C | H | N |
| (1) 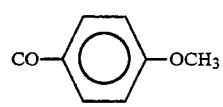 | 130–132° C. | C$_{34}$H$_{31}$F$_3$N$_4$O$_5$S.H$_2$O | calcd: 59.82<br>found: 59.75 | 4.87<br>4.71 | 8.21<br>8.14 |

TABLE III-continued

| | R | mp | formula | | Analysis | | |
|---|---|---|---|---|---|---|---|
| | | | | | C | H | N |
| (2) | CH₃, CH₃, CH₃, CH₃ cyclopropyl-CO- | 97–100° C. | C₃₄H₃₇F₃N₄O₄S | calcd: found: | 62.40 62.27 | 5.70 5.53 | 8.56 8.37 |
| (3) | CO-cyclopropyl-phenyl (trans) | 119–121° C. | C₃₆H₃₃F₃N₄O₄S.H₂O | calcd: found: | 62.42 62.17 | 5.09 4.76 | 8.09 7.84 |
| (4) | CO-CH₃,Cl,Cl cyclopropyl | 189–191° C. | C₃₁H₂₉Cl₂F₃N₄O₄S | calcd: found: | 54.60 54.63 | 4.29 4.07 | 8.22 7.96 |
| (5) | CO-cyclopropyl-phenyl | 120–122° C. | C₃₆H₃₃F₃N₄O₄S.1.75H₂O | calcd: found: | 61.22 61.14 | 5.21 4.86 | 7.93 7.70 |
| (6) | CO-C₆H₄-N(CH₃)₂ | 229–231° C. | C₃₅H₃₄F₃N₅O₄S.0.75H₂O | calcd: found: | 60.81 60.89 | 5.18 5.09 | 10.13 10.12 |
| (7) | CH₃-C₆H₄-CO- | 93–95° C. | C₃₄H₃₁F₃N₄O₄S | calcd: found: | 62.95 62.66 | 4.82 4.95 | 8.64 8.44 |
| (8) | CO-C₆H₄-CN | 193–195° C. | C₃₄H₂₈F₃N₅O₄S.1.5H₂O | calcd: found: | 59.47 59.11 | 4.55 4.14 | 10.20 9.90 |
| (9) | COCH(CH₃)₂ | 93–95° C. | C₃₀H₃₁F₃N₄O₄S.0.5 H₂O | calcd: found: | 59.10 59.04 | 5.29 5.23 | 9.19 9.10 |
| (10) | CF₃-C₆H₄-CO- | 197–199° C. | C₃₄H₂₈F₆N₄O₄S.0.25H₂O | calcd: found: | 57.70 57.93 | 4.06 3.98 | 7.92 7.80 |

TABLE III-continued

| | R | mp | formula | | Analysis C | H | N |
|---|---|---|---|---|---|---|---|
| (11) | COCH₂-Ph | 171–173° C. | C₃₄H₃₁F₃N₄O₄S | calcd: found: | 62.95 62.67 | 4.82 4.90 | 8.64 8.48 |
| (12) | CO-cyclopropyl-CH₃ | 94–96° C. | C₃₁H₃₁F₃N₄O₄S | calcd: found: | 60.80 60.53 | 5.10 5.06 | 9.14 9.12 |
| (13) | CO-cyclopropyl-F,F | 178–180° C. | C₃₀H₂₇F₅N₄O₄S | calcd: found: | 56.78 56.54 | 4.29 4.10 | 8.83 8.55 |
| (14) | CO-cyclobutyl | 184–185° C. | C₃₁H₃₁F₃N₄O₄S·H₂O· 0.05 CHCl₃ | calcd: found: | 58.58 58.44 | 5.23 4.88 | 8.80 8.68 |
| (15) | CO-cyclopentyl | 95–97° C. | C₃₂H₃₃F₃N₄O₄S·0.2 H₂O | calcd: found: | 60.98 60.91 | 5.34 5.12 | 8.89 8.92 |
| (16) | COCH₂C(CH₃)₃ | 94–96° C. | C₃₂H₃₅F₃N₄O₄S | calcd: found: | 61.13 60.93 | 5.61 5.52 | 8.91 8.75 |
| (17) | CONH-Ph(F,F) | 151–153° C. | C₃₃H₂₈F₅N₅O₄S | calcd: found: | 57.80 57.57 | 4.12 4.33 | 10.20 10.09 |
| (18) | CONH-Ph-F | 105–107° C. | C₃₃H₂₉F₄N₅O₄S | calcd: found: | 59.40 59.12 | 4.38 4.31 | 10.50 10.27 |
| (19) | CONH-Ph-NO₂ | 140–142° C. | C₃₃H₂₉F₃N₆O₆S·0.5H₂O | calcd: found: | 56.33 55.96 | 4.30 3.89 | 11.94 11.80 |
| (20) | CON(CH₃)₂ | 148–150° C. | C₂₉H₃₀F₃N₅O₄S· 0.5H₂O·0.25CH₂Cl₂ | calcd: found: | 55.60 55.96 | 5.02 4.70 | 11.08 10.73 |
| (21) | CO-furyl | 194–195° C. | C₃₁H₂₇F₃N₄O₅S | calcd: found: | 59.61 59.69 | 4.36 4.31 | 8.97 8.78 |

TABLE III-continued

[Structure: biphenyl compound with CF3-phenyl-N-N, N-Bu, N, =O, benzyl linker to biphenyl-SO2NH-R]

| | R | mp | formula | | Analysis C | H | N |
|---|---|---|---|---|---|---|---|
| (22) | [furan-CO-] | 125–127° C. | C₃₁H₂₇F₃N₄O₅S | calcd: found: | 59.61 59.61 | 4.36 4.48 | 8.97 8.59 |
| (23) | [thiophen-2-yl CO-] | >110° C. (gradual) | C₃₁H₂₇F₃N₄O₄S₂ | calcd: found: | 58.11 57.94 | 4.25 4.28 | 8.75 8.54 |
| (24) | [thiophen-3-yl CO-] | 123–126° C. | C₃₁H₂₇F₃N₄O₄S₂ | calcd: found: | 58.11 58.10 | 4.29 4.35 | 8.75 8.47 |
| (25) | [N-methylpyrrole-CO-] | >115° C. (gradual) | C₃₂H₃₀F₃N₅O₄S | calcd: found: | 60.27 60.08 | 4.74 5.04 | 10.99 10.61 |
| (26) | [tetrahydrofuran-2-yl CO-] | 149–151° C. | C₃₁H₃₁F₃N₄O₅S·0.5H₂O | calcd: found: | 58.39 58.47 | 5.06 4.86 | 8.79 8.58 |
| (27) | [tetrahydrofuran-3-yl CO-] | 154–155° C. | C₃₁H₃₁F₃N₄O₅S·0.5H₂O | calcd: found: | 58.39 58.43 | 5.06 4.94 | 8.79 8.65 |
| (28) | COCH₂OCH₃ | 150–151° C. | C₂₉H₂₉F₃N₄O₅S·0.5 C₄H₁₀O (ether) | calcd: found: | 58.27 58.65 | 5.36 4.97 | 8.76 8.70 |
| (29) | CO(CH₂)₂OCH₃ | >65° C. (gradual) | C₃₀H₃₁F₃N₄O₅S·0.5 H₂O | calcd: found: | 57.59 57.67 | 5.16 5.07 | 8.96 8.80 |
| (30) | CO(CH₂)₂CON(CH₃)₂ | >80° C. (gradual) | C₃₂H₃₄F₃N₅O₅S·0.75 CH₂Cl₂ | calcd: found: | 54.52 54.13 | 4.96 4.87 | 9.71 9.56 |
| (31) | COCH₂SO₂CH₃ | >75° C. (gradual) | C₂₉H₂₉F₃N₄O₆S₂·1.5 CH₂Cl₂ | calcd: found: | 47.08 47.21 | 4.15 3.96 | 7.20 7.37 |
| (32) | COCON(CH₃)₂ | >175° C. (gradual) | C₃₀H₃₀F₃N₅O₅S | calcd: 668.1557 for (M+K)⁺ found: 668.1528 by high resolution FAB—MS | | | |
| (33) | CO(CH₂)₂SO₂CH₃ | 168–171° C. | C₃₀H₃₁F₃N₄O₅S₂·0.75H₂O | calcd: found: | 53.15 52.74 | 4.83 4.70 | 8.26 8.21 |
| (34) | CO(CH₂)₂SCH₃ | >65° C. (gradual) | C₃₀H₃₁F₃N₄O₄S₂·0.5H₂O | calcd: found: | 56.14 55.79 | 5.03 4.97 | 8.73 8.48 |
| (35) | COCH₂OCH₂CH₃ | 151–152° C. | C₃₀H₃₁F₃N₄O₅S·0.1H₂O | calcd: found: | 58.26 57.96 | 5.09 5.01 | 9.06 8.77 |
| (36) | [pyridine-CO-] | >110° C. (gradual) | C₃₂H₂₈F₃N₅O₄S | calcd: 635.1814 molecular weight found: 635.1858 by high resolution FAB—MS | | | |

TABLE III-continued

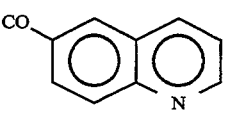

| | R | mp | formula | | Analysis | | |
|---|---|---|---|---|---|---|---|
| | | | | | C | H | N |
| (37) | 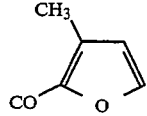 | >175° C. (gradual) | C$_{36}$H$_{30}$F$_3$N$_5$O$_4$S. 0.7 CH$_2$Cl$_2$ | calcd: found: | 59.15 58.91 | 4.25 4.30 | 9.40 9.49 |
| (38) | 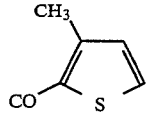 | >95° C. (gradual) | C$_{32}$H$_{29}$F$_3$N$_4$O$_5$S. 0.2H$_2$O.0.3 C$_4$H$_{10}$O (ether) | calcd: found: | 60.61 59.63 | 4.91 5.00 | 8.43 8.13 |
| (39) | 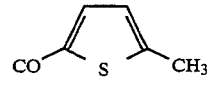 | >145° C. (gradual) | C$_{32}$H$_{29}$F$_3$N$_4$O$_4$S$_2$. 1.5H$_2$O.0.7 CH$_2$Cl$_2$ | calcd: found: | 54.92 55.07 | 4.43 4.39 | 7.84 7.51 |
| (40) | 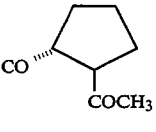 | >125° C. (gradual) | C$_{32}$H$_{29}$F$_3$N$_4$O$_4$S$_2$. 0.25 CH$_2$Cl$_2$ | calcd: found: | 57.30 57.69 | 4.40 4.77 | 8.29 7.93 |
| (41) | 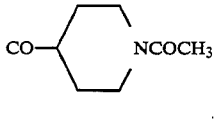 | >90° C. (gradual) | C$_{33}$H$_{34}$F$_3$N$_5$O$_5$S.1.5H$_2$O. 0.2 C$_4$H$_{10}$O (ether) | calcd: found: | 57.05 57.23 | 5.52 5.13 | 9.84 9.49 |
| (42) | 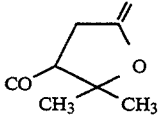 | >105° C. (gradual) | C$_{34}$H$_{36}$F$_3$N$_5$O$_5$S. 0.5C$_4$H$_{10}$O (ether) | calcd: found: | 57.84 57.80 | 5.96 5.49 | 9.64 9.30 |
| (43) | 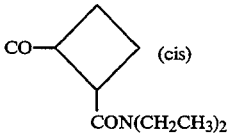 | >150° C. (gradual) | C$_{33}$H$_{33}$F$_3$N$_4$O$_6$S. 0.75 CH$_2$Cl$_2$ | calcd: found: | 55.20 55.05 | 4.74 4.48 | 7.63 7.60 |
| (44) | 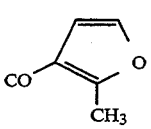 | >75° C. (gradual) | C$_{36}$H$_{40}$F$_3$N$_5$O$_5$S.H$_2$O | calcd: found: | 59.25 59.30 | 5.80 5.59 | 9.60 9.21 |
| (45) |  | 154–157° C. | C$_{32}$H$_{29}$F$_3$N$_4$O$_5$S.0.75H$_2$O | calcd: found: | 58.93 58.64 | 4.71 4.73 | 8.59 8.52 |

TABLE III-continued

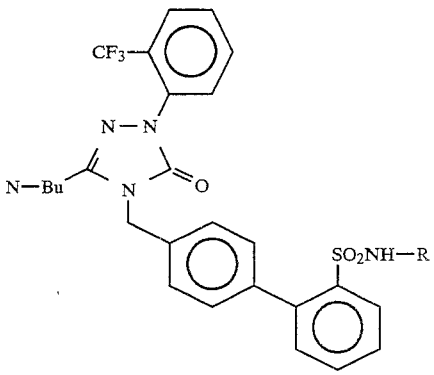

| | R | mp | formula | | Analysis C | H | N |
|---|---|---|---|---|---|---|---|
| (46) | 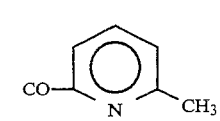 | 220–223° C. | C$_{33}$H$_{31}$F$_3$N$_4$O$_5$S. 0.75H$_2$O | calcd: found: | 59.50 59.64 | 4.92 4.96 | 8.41 8.26 |
| (47) | COC(CH$_3$)$_2$OCH$_2$CH$_3$ | >50° C. (gradual) | C$_{32}$H$_{35}$F$_3$N$_4$O$_6$S. 1.2 H$_2$O | calcd: found: | 57.72 57.53 | 5.60 5.29 | 8.41 8.01 |
| (48) | 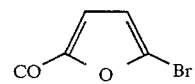 | >65° C. (gradual) | C$_{33}$H$_{30}$F$_3$N$_5$O$_4$S. 1.25 H$_2$O. 0.5 C$_4$H$_{10}$O (ether) | calcd: found: | 59.27 58.93 | 5.32 4.93 | 9.88 9.72 |
| (49) | 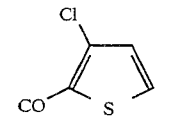 | >125° C. (gradual) | C$_{31}$H$_{26}$BrF$_3$N$_4$O$_5$S.H$_2$O | calcd: found: | 51.60 51.44 | 3.91 3.53 | 7.77 7.59 |
| (50) | 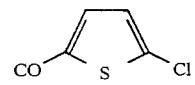 (K salt) | >200° C. (gradual) | C$_{31}$H$_{29}$ClF$_3$KN$_4$O$_4$S$_2$. 0.3 C$_4$H$_{10}$O (ether) | calcd: found: | 52.59 52.79 | 3.84 3.60 | 7.62 7.77 |
| (51) | 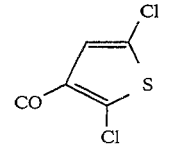 | >125° C. (gradual) | C$_{31}$H$_{26}$ClF$_3$N$_4$O$_4$S$_2$. 0.5 H$_2$O | calcd: found: | 54.42 54.76 | 3.99 4.39 | 8.19 7.79 |
| (52) | 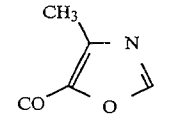 | >130° C. (gradual) | C$_{31}$H$_{25}$Cl$_2$F$_3$N$_4$O$_4$S$_2$. 0.7 CH$_2$Cl$_2$ | calcd: found: | 49.51 49.46 | 3.46 3.42 | 7.29 7.19 |
| (53) | 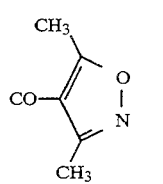 | >155° C. (gradual) | C$_{31}$H$_{25}$Cl$_2$F$_3$N$_4$O$_5$S. 0.9 CH$_2$Cl$_2$ | calcd: found: | 51.41 51.34 | 3.56 3.51 | 7.61 7.57 |
| (54) |  | 142–143° C. | C$_{32}$H$_{30}$F$_3$N$_5$O$_5$S | calcd: found: | 58.80 58.52 | 4.63 4.62 | 10.72 10.60 |

TABLE III-continued

[Structure: 1,2,4-triazolinone with N-Bu, N-N-(2-trifluoromethylphenyl), N-CH2-biphenyl-SO2NH-R]

| | R | mp | formula | | Analysis C | H | N |
|---|---|---|---|---|---|---|---|
| (55) | CO-[4-methyl-3-ethyl-isoxazol-4-yl] (CH3, CH2CH3 on isoxazole) | >75° C. (gradual) | C33H32F3N5O5S. 0.25 H2O | calcd: found: | 58.96 58.79 | 4.87 4.89 | 10.42 10.31 |
| (56) | CO-[4-methyl-oxazol-5-yl] | >155° C. (gradual) | C31H28F3N5O5S. H2O.0.4 CH2Cl2 | calcd: found: | 54.53 54.25 | 4.49 4.43 | 10.13 10.49 |
| (57) | CO-benzofuran-2-yl | 124–127° C. | C35H29F3N4O5S.H2O 0.2 C4H10O (ether) | calcd: found: | 60.77 60.85 | 4.70 4.68 | 7.92 7.58 |
| (58) | CO-(1-methylcyclopropyl) | 193–195° C. | C31H31F3N4O4S. 0.25 H2O | calcd: found: | 60.33 60.29 | 5.14 4.98 | 9.08 8.83 |
| (59) | CO-(1,3-dithiolan-2-yl) | >75° C. (gradual) | C30H29F3N4O4S. 0.5 H2O | calcd: found: | 53.64 53.62 | 4.50 4.23 | 8.34 7.99 |
| (60) | CO-[5-methyl-2-trifluoromethyl-furan-3-yl] | 218–219° C. | C33H28F6N4FO5S | calcd: found: | 56.09 55.81 | 3.99 3.74 | 7.93 7.76 |
| (61) | CO-benzothiophen-2-yl | 177–179° C. | C35H29F3N4O4S2. 0.4 CH2Cl2 | calcd: found: | 58.67 58.64 | 4.14 3.85 | 7.73 7.68 |
| (62) | CO-(3-methyl-benzofuran-2-yl) | 103–106° C. | C36H31F3N4O5 | calcd: found: | 62.78 62.58 | 4.54 4.29 | 8.14 8.01 |

TABLE III-continued
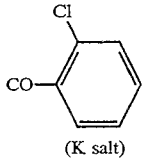
| R | mp | formula | | Analysis C | H | N |
|---|---|---|---|---|---|---|
| (63) 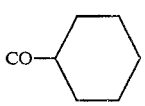 (K salt) | 168–170° C. | C₃₃H₂₈ClF₃KN₄O₄S | calcd: found: | 59.24 58.99 | 4.22 4.32 | 8.37 8.11 |
| (64) 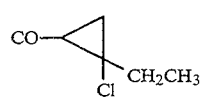 | 101–103° C. | C₃₃H₃₅F₃N₄O₄S | calcd: found: | 61.86 61.63 | 5.51 5.38 | 8.74 8.52 |
| (65) 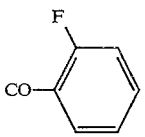 | 90–92° C. | C₃₃H₃₅F₃N₄O₄S | calcd: found: | 61.86 61.74 | 5.51 5.61 | 8.74 8.49 |
| (66) 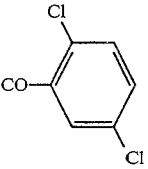 | 98–100° C. | C₃₃H₂₈F₄N₄O₄S. 0.25 H₂O | calcd: found: | 60.31 60.06 | 4.37 4.12 | 8.53 8.33 |
| (67) 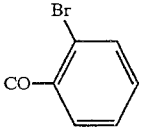 | 142–145° C. | C₃₃H₂₇Cl₂F₃N₄O₄S | calcd: found: | 55.62 55.33 | 3.96 3.56 | 7.86 7.65 |
| (68) 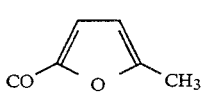 | 90–93° C. | C₃₃H₂₈BrF₃N₄O₄S. 0.25 H₂O | calcd: found: | 55.20 54.98 | 4.00 3.78 | 7.80 7.54 |
| (69) 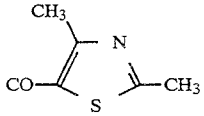 | 210–211° C. | C₃₂H₂₉F₃N₄O₅S | calcd: found: | 60.18 59.89 | 4.58 4.55 | 8.77 8.62 |
| (70)  | 176–177° C. | C₃₂H₃₀F₃N₅O₄S₂. 0.5H₂O | calcd: found: | 56.63 56.65 | 4.60 4.38 | 10.32 10.25 |

TABLE III-continued

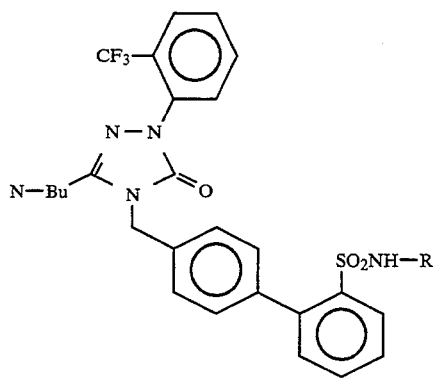

| | R | mp | formula | | Analysis | | |
|---|---|---|---|---|---|---|---|
| | | | | | C | H | N |
| (71) | cyclopentyl-phenyl-CO- | 159–161° C. | $C_{38}H_{37}F_3N_4O_4S$ | calcd: | 64.94 | 5.31 | 7.97 |
| | | | | found: | 65.06 | 5.24 | 7.78 |
| (72) | 4-(CO$_2$CH$_3$)-phenyl-CO- | 123–125° C. | $C_{35}H_{31}F_3N_4O_6S \cdot$ | calcd: | 59.91 | 4.60 | 7.98 |
| | | | $0.5H_2O$ | found: | 59.90 | 4.39 | 7.88 |
| (73) | trans-2-CON(CH$_3$)$_2$-cyclohexyl-CO- | >85° C. (gradual) | $C_{36}H_{40}F_3N_5O_5S \cdot$ | calcd: | 60.14 | 5.72 | 9.74 |
| | | | $0.4H_2O$ | found: | 59.83 | 5.64 | 9.76 |
| (74) | cis-2-CON(CH$_3$)$_2$-cyclohexyl-CO- | >85° C. (gradual) | $C_{36}H_{40}F_3N_5O_5S \cdot$ | calcd: | 60.95 | 6.06 | 9.35 |
| | | | $0.5C_4H_{10}O(ether)$ | found: | 61.33 | 6.22 | 9.63 |
| (75) | cis-2-CON(CH$_3$)$_2$-cyclobutyl-CO- | >85° C. (gradual) | $C_{34}H_{36}F_3N_5O_5S \cdot$ | calcd: | 60.18 | 6.04 | 9.33 |
| | | | $0.9C_4H_{10}O(ether)$ | found: | 60.17 | 5.67 | 9.28 |
| (76) | 2-(4-methylphenyl)-thien-3-yl-CO- | 174–175° C. | $C_{38}H_{33}F_3N_4O_4S_2$ | calcd: | 62.45 | 4.55 | 7.67 |
| | | | | found: | 62.41 | 4.53 | 7.56 |

TABLE III-continued

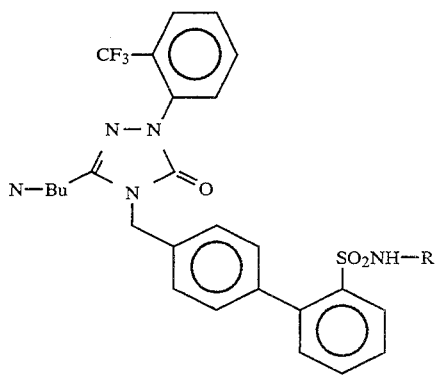

| (No.) | R | mp | formula | Analysis calcd/found C | H | N |
|---|---|---|---|---|---|---|
| (77) | CO-biphenyl(2-Ph) | 104–106° C. | C$_{39}$H$_{33}$F$_3$N$_4$O$_4$S | calcd: 65.90<br>found: 65.63 | 4.68<br>4.45 | 7.88<br>7.97 |
| (78) | CO-(3-Br-thiophen-2-yl) | >200° C. (gradual) | C$_{31}$H$_{26}$BrF$_3$N$_4$O$_4$S$_2$·1.2H$_2$O | calcd: 50.37<br>found: 49.93 | 3.60<br>3.25 | 7.58<br>7.40 |
| (79) | CO-(2,5-diBr-thiophen-3-yl) | >165° C. (gradual) | C$_{31}$H$_{25}$Br$_2$F$_3$N$_4$O$_4$S$_2$·H$_2$O | calcd: 45.60<br>found: 45.37 | 3.33<br>2.96 | 6.86<br>6.82 |
| (80) | CO-(4,5-diBr-thiophen-2-yl) | >180° C. (gradual) | C$_{31}$H$_{25}$Br$_2$F$_3$N$_4$O$_4$S$_2$·0.8CH$_2$Cl$_2$ | calcd: 44.08<br>found: 43.93 | 3.09<br>2.79 | 6.47<br>6.36 |
| (81) | CO-(2-benzyl-phenyl) | 216–218° C. | C$_{40}$H$_{35}$F$_3$N$_4$O$_4$S | calcd: 66.28<br>found: 66.14 | 4.87<br>4.62 | 7.73<br>7.63 |
| (82) | CO-(4-CF$_3$-phenyl) | 176–178° C. | C$_{34}$H$_{28}$F$_6$N$_4$O$_4$S | calcd: 703.1814 for (M+H)$^+$<br>found: 703.1826 by high resolution FAB—MS | | |
| (83) | CO-(4-Cl-phenyl) | 166–168° C. | C$_{33}$H$_{28}$ClF$_3$N$_4$O$_4$S | calcd: 669.1550 for (M+H)$^+$<br>found: 669.1534 by high resolution FAB—MS | | |

TABLE III-continued

| R | mp | formula | Analysis C | H | N |
|---|---|---|---|---|---|
| (84) 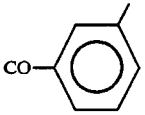 (CF₃-phenyl-CO) | 163–165° C. | C₃₄H₂₈F₆N₄O₄S | calcd: 741.1373 for (M+K)⁺ found: 741.1376 by high resolution FAB—MS | | |
| (85) 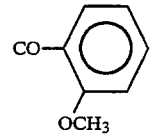 (Cl-phenyl-CO) | 173–175° C. | C₃₃H₂₈ClF₃N₄O₄S | calcd: 669.1550 for (M+H)⁺ found: 669.1563 by high resolution FAB—MS | | |
| (86)  (OCH₃-phenyl-CO) | 68–70° C. | C₃₄H₃₁F₃N₄O₅S | calcd: 665.2045 for (M+H)⁺ found: 665.2062 by high resolution FAB—MS | | |
| (87) 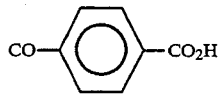 (cyclopropyl-CO) | 93–95° C. | C₃₆H₃₉F₃N₄O₄S | calcd: 681.2722 for (M+H)⁺ found: 681.2719 by high resolution FAB—MS | | |
| (88) 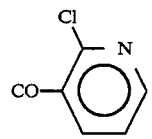 (HO₂C-phenyl-CO) | 136–139° C. | C₃₄H₂₉F₃N₄O₆S·0.75H₂O | calcd: 59.00 found: 59.05 | 4.44 4.18 | 8.09 8.07 |
| (89) 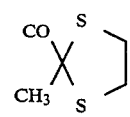 (Cl-pyridyl-CO) | >130° C. (gradual) | C₃₂H₂₇ClF₃N₅O₄S·1.4H₂O | calcd: 55.28 found: 54.95 | 4.32 4.01 | 10.07 9.88 |
| (90) 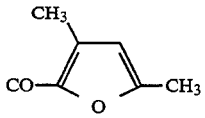 (dithiane-CO) | >75° C. (gradual) | C₃₁H₃₁F₃N₄O₄S | calcd: 677.1583 for (M+H)⁺ found: 677.1542 by high resolution FAB—MS | | |
| (91) (dimethylfuryl-CO) | 110–112° C. | C₃₃H₃₁F₃N₄O₅S·0.6H₂O | calcd: 59.74 found: 59.50 | 4.89 4.77 | 8.45 8.23 |
| (92) CONHC(CH₃)₃ | 79–82° C. | C₃₁H₃₄F₃N₅O₄S | calcd: 630.2362 for (M+H)⁺ found: 630.2385 by high resolution FAB—MS | | |

TABLE III-continued

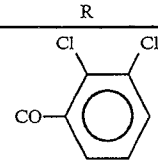

| R | mp | formula | | Analysis | | |
|---|---|---|---|---|---|---|
| | | | | C | H | N |
| (93) ![structure with Cl, Cl, CO-phenyl] | >120° C. (gradual) | $C_{33}H_{27}Cl_2F_3N_4O_4S \cdot H_2O$ | calcd: found: | 54.93 54.87 | 4.05 3.75 | 7.76 7.82 |

EXAMPLE 51

4-[[2'-(N-Benzoylsulfamoyl)biphenyl-4-yl]methyl]-5-n-butyl-2,4-dihydro-2-[2-(trifluoromethyl)phenyl]-3H-1,2,4-triazol-3-one A solution of 145 mg (1.18 mmole) of benzoic acid and 192 mg (1.18 mmole) of 1,1'-carbonyldiimidazole in 1 mL of THF was stirred under $N_2$ at 55° C. for 2 hours. Then a solution of 157 mg (0.296 mmole) of 5-n-butyl-2,4-dihydro-4-[(2'-sulfamoylbiphenyl-4-yl)methyl]-2-[2-(trifluoromethyl)phenyl]-3H-1,2,4-triazol-3-one (from Example 16, Step C) and 133 mL (135 mg, 0.888 mmole) of 1,8-diazabicyclo[5.4.0]undec-7-ene (DBU) in 1 mL of THF was added dropwise. After being stirred overnight at 55° C., the mixture was partitioned between ethyl acetate and 5% citric acid (aqueous). The organic layer was washed with $H_2O$ and then with saturated NaCl solution. The ethyl acetate phase was then dried over $Na_2SO_4$, filtered, and concentrated in vacuo. Flash chromatography of the residue as in Example 16, Step D, gave 159 mg (85%) of the title compound, homogeneous by TLC in 98:2 $CH_2Cl_2$—MeOH and comparable in physical properties to the product made according to Example 16, Step D.

EXAMPLE 52

4-[[2'-(N-Benzoylsulfamoyl)biphenyl-4-yl]methyl]-5-n-butyl-2,4-dihydro-2-[2-(trifluoromethyl)phenyl]-3H-1,2,4-triazol-3-one, potassium salt A 13.8 g (21.8 mmole) sample of 4-[[2'-(N-benzoylsulfamoyl)biphenyl-4-yl]methyl]-5-n-butyl-2,4-dihydro-2-[2-(trifluoromethyl)phenyl]-3H-1,2,4-triazol-3-one (prepared according to Example 16 or Example 51) was dissolved in a mixture of 100 mL of methanol and 100 mL of THF and stirred under $N_2$ as 218 mL (21.8 mL) of 1N KOH in methanol was added. The resulting solution was stirred for 1 hour and then concentrated to dryness. The residue was dissolved in 150 mL of THF and stirred vigorously as 1650 mL of hexane was added gradually, resulting in precipitation. The solid was collected on a filter and dried to give 13.8 g (94%) of the title compound as a white solid, which had high purity by HPLC ($C_{18}$ reverse phase, elution with 40:60:1 $H_2O$-acetonitriletrifluoroacetic acid).

Analysis: ($C_{33}H_{29}F_3KN_4O_4S$) Calcd: C, 58.92; H, 4.20; N, 8.32; K, 5.81. Found: C, 58.76; H, 4.29; N, 8.17; K, 5.93.

400 MHz NMR (CD$_3$OD) δ0.90 (t, J=7.3 Hz, 3H), 1.40 (m, 2H), 1.62 (m, 2H), 2.56 (t, J=7.5 Hz, 2H), 4.97 (s, 2H), 7.14–7.19 (m, 3H), 7.24 (dd, J=7.2 Hz, 7.3 Hz, 2H), 7.34 (dd, J≈7 Hz, 7 Hz, 1H), 7.41 (d, J=8.2 Hz, 2H), 7.49 (m, 2H), 7.59–7.65 (m, 3H), 7.71 (dd, J=7.0 Hz, 7.0 Hz, 1H), 7.81 (dd, J=6.6 Hz, 6.7 Hz, 1H), 7.88 (d, J=6.7 Hz, 1H), 8.26 (m, 1H).

EXAMPLE 53

5-n-Butyl-2,4-dihydro-4-[[2'-[N-(2-norbornanecarbonyl)sulfamoyl]biphenyl-4-yl]methyl]-2-[2-(trifluoromethyl)phenyl]-3H-1,2,4-triazol-3-one A solution of 53 mg (0.375 mmole) of 2-norbornanecarboxylic acid and 61 mg (0.375 mmole) of 1,1'-carbonyldiimidazole (CDI) in 1.5 mL THF was stirred under $N_2$ at 65° C. for 3 hours. Then a solution of 100 mg (0.189 mmole) of 5-n-butyl-2,4-dihydro-4-[(2'-sulfamoylbiphenyl-4-yl)methyl]-2-[2-(trifluoromethyl)phenyl]-3H-1,2,4-triazol-3-one (from Example 16, Step C) and 56.5 mL (57.5 mg, 0.378 mmole) of DBU in 1.4 mL of THF was added dropwise. After being stirred overnight at 55° C., the mixture was partitioned between ethyl acetate and 5% citric acid (aqueous). The organic layer was washed with water and then with saturated NaCl solution. The ethyl acetate phase was then dried over anhydrous $Na_2SO_4$, filtered, and concentrated in vacuo. Flash chromatography of the residue (eluting with 1% MeOH in $CH_2Cl_2$) gave 30 mg (24%) of the pure product as a glassy foam, mp 89°–92° C., homogeneous by TLC in 95:5 $CH_2Cl_2$—MeOH; mass spectrum (FAB) m/e 653 (M+1)$^+$.

400 MHz NMR (CDCl$_3$) δ0.89 (t, J=7.4 Hz, 3H), 1.02 (m, 2H), 1.12–1.85 (m, 12H), 2.18 (m, 1H), 2.53 (m, 2H), 2.80 (m, 1H), 4.95 (s, 2H), 5.95 (m, 1H), 7.20–7.82 (m, 11H), 8.29 (d, J=8.0 Hz, 1H).

EXAMPLE 54

5-n-Butyl-4-[[2'-[N-(cycloheptanecarbonyl)sulfamoyl]-biphenyl-4-yl]methyl]-2,4-dihydro-2-[2-(trifluoromethyl)phenyl]-3H-1,2,4-triazol-3-one The title compound was prepared from cycloheptanecarboxylic acid (2.0 equivalents), CDI (2.0 equivalents), 5-n-butyl-2,4-dihydro-4-[(2'-sulfamoylbiphenyl-4-yl)methyl]-2-[2-(trifluoromethyl)phenyl]-3H-1,2,4-triazol-3-one (from Example 16, Step C) (1.0 equivalent), and DBU (2.0 equivalents) according to the procedure of Example 7, to give a 69% yield of the desired material after flash chromatography, as a glassy solid, mp 146°–149° C., homogeneous by TLC in 95:5 $CH_2Cl_2$—MeOH; mass spectrum (FAB) m/e 655 $(M+1)^+$.

400 MHz NMR ($CDCl_3$) d 0.87 (t, J=7.4 Hz, 3H) 1.20–1.80 (m, 14H), 1.94 (m, 2H), 2.50 (m, 3H), 4.87 (s, 2H), 7.23–7.79 (m, 11H), 8.29 (d, J=6.5 Hz, 1H).

EXAMPLE 55

5-n-Butyl-4-[[2'-[N-(2-chlorobenzoyl)sulfamoyl]biphenyl-4-yl]methyl]-2,4-dihydro-2-[4-nitro-2-(trifluoromethyl)phenyl}-3H-1,2,4-triazol-3-one Step A: 5-n-Butyl-2,4-dihydro-2-[4-nitro-2-(trifluoromethyl)phenyl]-3H-1,2,4-triazol-3-one By the procedure of Example 4, Step C, 4-nitro-2-(trifluoromethyl)phenylhydrazine [generated from the hydrochloride which was prepared from 4-nitro-2-(trifluoromethyl)aniline according to H. Stroh and G. Westphal, Chem. Ber., 96, 184 (1963), by partitioning between ether and 1N sodium carbonate] was reacted with ethyl N-carbethoxyvalerimidate (Example 4, Step B). After work-up, the residue was purified by flash chromatography on silica gel (gradient elution with 0.5–5.0% methanol in $CH_2Cl_2$) to give a 27% yield of the title compound as an orange solid, mp 126°–128° C., homogeneous by TLC (19:1 $CH_2Cl_2$—MeOH); mass spectrum (FAB) m/e 331 $(M+1)^+$.

400 MHz $^1$H NMR ($CDCl_3$) δ0.91 (t, J=7.3 Hz, 3H), 1.38 (m, 2H), 1.66 (m, 2H), 2.57 (t, J=7.6 Hz, 2H), 7.83 (d, J=8.8 Hz, 1H), 8.50 (dd, J=8.8, 2.6 Hz, 1H), 8.67 (d, J=2.6 Hz, 1H), 11.25 (br s, 1H).

Step B: 5-n-Butyl-4-[[2'-(N-t-butylsulfamoyl)biphenyl-4-yl]methyl]-2,4-dihydro-2-[4-nitro-2-(trifluoromethyl)-phenyl]-3H-1,2,4-triazol-3-one By the procedure of Example 13, Step A, 5-n-butyl-2,4-dihydro-2-[4-nitro-2-(trifluoromethyl)phenyl]-3H-1,2,4-triazol-3-one (from Step A) was alkylated with [2'-(N-t-butylsulfamoyl)biphenyl-4-yl]-methyl bromide (from Example 12, Step D). Flash chromatography of the crude product on silica gel (gradient elution with 0.5–5.0% MeOH in $CH_2Cl_2$) gave an 88% yield of the title compound as an orange solid, mp >78° C. (gradual), homogeneous by TLC (98:2 $CH_2Cl_2$—MeOH), mass spectrum (FAB) m/e 632 $(M+1)^+$.

400 MHz $^1$H NMR ($CDCl_3$) δ0.90 (t, J=7.4 Hz, 3H), 0.98 (s, 9H), 1.40 (m, 2H), 1.66 (m, 2H), 2.50 (t, J=7.5 Hz, 2H), 3.47 (s, 1H), 4.95 (s, 2H), 7.25–7.60 (m, 7H), 7.92 (d, J=9.1 Hz, 1H), 8.15 (dd, J=7.9, 1.4 Hz, 1H) 8.48 (dd, J=8.9, 2.6 Hz, 1H), 8.66 (d, J=2.5 Hz, 1H).

Step C: 5-n-Butyl-2,4-dihydro-2-[4-nitro-2-(trifluoromethyl)phenyl]-4-[(2'-sulfamoylbiphenyl-4-yl)methyl]-3H-1,2,4-triazol-3-one The title compound was prepared from 5-n-butyl-4-[[2'-(N-t-butylsulfamoyl)biphenyl-4-yl]methyl]-2,4-dihydro-2-[4-nitro-2-(trifluoromethyl)phenyl]-3H-1,2,4-triazol-3-one (from Step B) according to the procedure of Example 13, Step B, and was obtained in 69% yield as a cream-colored solid, mp 218°–220° C., homogenous by TLC (19:1 $CH_2Cl_2$—MeOH); mass spectrum (FAB) m/e 576 $(M+1)^+$.

400 MHz $^1$H NMR ($CDCl_3$) δ0.89 (t, J=7.3 Hz, 3H), 1.38 (m, 2H), 1.65 (m, 2H), 2.52 (t, J=7.5 Hz, 2H), 4.20 (s, 2H), 4.96 (s, 2H), 7.25–7.61 (m, 7H), 7.92 (d, J=8.9 Hz, 1H), 8.14 (dd, J=7.6, 1.0 Hz, 1H), 8.48 (dd, J=8.8, 2.5 Hz, 1H), 8.66 (d, J=2.5 Hz, 1H).

Step D: 5-n-Butyl-4-[[2'-[N-(2-chlorobenzoyl)sulfamoyl]biphenyl-4-yl]methyl]-2,4-dihydro-2-[4-nitro-2-(trifluoromethyl)phenyl]-3H-1,2,4-triazol-3-one The title compound was prepared from 2-chlorobenzoic acid (2.0 equivalents), CDI (2.0 equiv), 5-n-butyl-2,4-dihydro-2-(4-nitro-2-trifluoromethyl)phenyl-4-[(2'-sulfamoylbiphenyl-4-yl)methyl]-3H-1,2,4-triazol-3-one (from Step C) (1.0 eq), and DBU (2.0 equiv) according to the procedure of Example 51, to give a 43% yield of the desired material after flash chromatography, as a glassy solid, mp 179°–181° C., homogeneous by TLC in 95:5 $CH_2Cl_2$—MeOH; mass spectrum (FAB) m/e 714 $(M+1)^+$.

Analysis ($C_{33}H_{27}ClF_3N_5O_6S$) Calcd: C, 55.50; H, 3.81; N, 9.81. Found: C, 55.60; H, 4.03; N, 9.66.

400 MHz NMR ($CDCl_3$) δ0.89 (t, J=7.3 Hz, 3H) 1.37 (m, 2H), 1.64 (m, 2H), 2.47 (t, J=7.5 Hz, 2H), 4.88 (s, 2H), 7.17–7.70 (m, 10H), 7.91 (d, J=8.9 Hz, 1H), 8.36 (d, J=7.9, 1.5 Hz, 1H), 8.43 (s, 1H), 8.49 (dd, J=8.8, 2.6 Hz, 1H), 8.67 (d, J=2.6 Hz, 1H)

EXAMPLE 56

2-[4-Amino-2-(trifluoromethyl)phenyl]-5-n-butyl-4-[[2'-[N-(2-chlorobenzoyl)sulfamoyl]biphenyl-4-yl]methyl]-2,4-dihydro-3H-1,2,4-triazol-3-one At 0° C., under nitrogen, to a solution of 82 mg (0.115 mmole) of 5-n-butyl-4-[(2'-[N-(2-chlorobenzoyl)sulfamoylbiphenyl-4-yl)methyl]-2,4-dihydro-2-(4-nitro-2-trifluoromethyl)phenyl-3H-1,2,4-triazol-3-one (from Example 55, Step D) dissolved in 1 mL of THF was added dropwise 182 mg (0.805 mmole) of stannous chloride, dissolved in 2.2 mL of concentrated HCl. After stirring at 0° C. for 15 minutes the ice/water bath was removed, and stirring continued for 30 min. The reaction mixture was poured onto a mixture of 2.8 g ice, 0.8 mL of 50% NaOH, and 1.6 mL of EtOAc. After stirring for 15 min, the phases were separated and the aqueous phase was reextracted with EtOAc twice. The combined organic layer was washed with brine, dried over sodium sulfate, filtered, and evaporated. Flash chromatography of the crude residue over silica gel (gradient elution using 0.5–2.0% MeOH/$CH_2Cl_2$) gave 53 mg (67%) of a cream-colored solid, mp 134°–136° C., homogeneous by TLC (9:1 MeOH/$CH_2Cl_2$), mass spectrum (FAB) m/e 684 $(M+1)^+$.

Analysis ($C_{33}H_{29}ClF_3N_5O_4S.0.5\ H_2O$) Calcd: C, 57.20; H, 4.36; N, 10.10. Found: C, 57.04; H, 4.48; N, 9.77.

400 MHz NMR ($CD_3OD$) δ0.87 (t, J=7.4 Hz, 3H) 1.35 (m, 2H), 1.56 (m, 2H), 2.52 (t, J=7.5 Hz, 2H), 4.99 (s, 2H), 6.89–7.71 (m, 14H), 8.29 (d, J=8.0, 1.3 Hz, 1H)

EXAMPLE 57

5-n-Butyl-4-[[2'-[N-(2-chlorobenzoyl)sulfamoyl]biphenyl-4-yl]methyl]-2,4-dihydro-2-[4-(propionylamino)-2-(trifluoromethyl)phenyl]-3H-1,2,4-triazol-3-one At room temperature, under $N_2$, a solution of 45 mg (0.066 mmole) of 2-[4-amino-2-(trifluoromethyl)phenyl]-5-n-butyl-4-[[2'-[N-(2-chlorobenzoyl)sulfamoyl]biphenyl-4-yl]methyl]-2,4-dihydro-3H-1,2,4-triazol-3-one (from Example 56) in DMF (0.5 mL) was stirred with 1.7 mg (0.072 mmole) of sodium hydride for 3 h. Subsequently, 9.1 mg (0.099 mmole) of propionyl chloride was added and the resulting reaction mixture was stirred at 50° C. overnight. The reaction was quenched by addition of water. The organic material was extracted with EtOAc and washed with water and brine, then dried over sodium sulfate. After filtration and removal of volatiles, the crude product was flash chromatographed over silica gel (gradient elution with 0.5–5% MeOH/$CH_2Cl_2$) to afford the desired material as a cream-colored solid, mp 204°–206° C., homogeneous by TLC (9:1 MeOH/$CH_2Cl_2$), mass spectrum (FAB) m/e 741 $(M+1)^+$.

400 MHz $^1$H NMR (CDCl$_3$) δ0.87 (t, J=7.3 Hz, 3H), 1.19 (t, J=7.5 Hz, 3H), 1.34 (m, 2H), 1.61 (m, 2H), 2.37 (q, J=7.5 Hz, 2H), 2.47 (t, J=7.6 Hz, 2H), 4.92 (s, 2H), 6.37 (s, br, 1H), 7.14–7.75 (m, 12H), 7.89 (s, 1H), 8.19 (s, 1H), 8.36 (d, J=7.1 Hz, 1H), 8.63 (s, br, 1H).

EXAMPLE 58

2-[4-(Benzylamino)-2-(trifluoromethyl)phenyl]-5-n-butyl-4-[[2'-[N-(2-chlorobenzoyl)sulfamoyl]biphenyl-4-yl]methyl]-2,4-dihydro-3H-1,2,4-triazol-3-one A solution of 70 mg (0.093 mmole) of 2-[4-amino-2-(trifluoromethyl)phenyl]-5-n-butyl-4-[[2'-[N-(2-chlorobenzoyl)sulfamoyl]biphenyl-4-yl]methyl]-2,4-dihydro-3H-1,2,4-triazol-3-one (from Example 56), 33 mg (0.31 mmole) of benzaldehyde, 2.1 mL of piperidine, and 2.5 mL of isopropanol was stirred at 95° C. overnight. The crude material obtained after cooling and evaporation of volatiles was dissolved in 2.2 mL MeOH, charged with 1.3 mL of a 1M solution of sodium cyanoborohydride in THF (1.3 mmole), and stirred at room temperature for 2 hours. Water (160 mL) was added at 0° C., and the resulting mixture stirred at 0° C. for 2 hours. After evaporation of volatiles, the crude product was flash chromatographed over silica gel (gradient elution with 0.5–5.0% MeOH/$CH_2Cl_2$) to afford 27 mg (38%) of the desired product as a cream-colored solid, mp >107° C. (gradual), homogeneous by TLC (9:1MeOH/$CH_2Cl_2$), mass spectrum (FAB) m/e 774 $(M+1)^+$.

Analysis: ($C_{40}H_{35}ClF_3N_5O_4S$.2 $CH_2Cl_2$) Calcd: C, 53.66; H, 4.18; N, 7.45. Found: C, 53.80; H, 3.89; N, 7.47.

400 MHz $^1$H NMR (CD$_3$OD) δ0.87 (t, J=7.3 Hz, 3H), 1.33 (m, 2H), 1.57 (m, 2H), 2.51 (t, J=7.5 Hz, 2H), 4.41 (s, 2H), 4.98 (s, 2H), 6.82–7.73 (m, 19H), 8.29 (dd, J=8.1, 1.4 Hz, 1H).

EXAMPLE 59

5-n-Butyl-4-[[2'-[N-(2-chlorobenzoyl)sulfamoyl]biphenyl-4-yl]methyl]-2-(2-chloro-5-nitrophenyl)-2,4-dihydro-3H-1,2,4-triazol-3-one Step A: 5-n-Butyl-2-(2-chloro-5-nitrophenyl)-2,4-dihydro-3H-1,2,4-triazol-3-one By the procedure of Example 4, Step C, 2-chloro-5-nitrophenylhydrazine [generated from the hydrochloride, which was prepared from 2-chloro-5-nitroaniline according to H. Stroh and G. Westphal, *Chem. Ber.* 96, 184 (1963), by partitioning between ether and 1N sodium carbonate] was reacted with ethyl N-carbethoxyvalerimidate (from Example 4, Step B). Enough THF was added to the reaction mixture to ensure dissolution of all starting material. After work-up, the residue was purified by flash chromatography on silica gel (gradient elution with 0.5–5.0% methanol in $CH_2Cl_2$) to give a 19% yield of the title compound as an orange solid, mp 145°–147° C., homogeneous by TLC (19:1 $CH_2Cl_2$—MeOH), mass spectrum (FAB) m/e 297 $(M+1)^+$.

400 MHz $^1$H NMR (CDCl$_3$) δ0.91 (t, J=7.3 Hz, 3H), 1.39 (m, 2H), 1.67 (m, 2H), 2.58 (t, J=7.7 Hz, 2H), 7.70 (d, J=8.9 Hz, 1H), 8.22 (dd, J=8.8, 2.6 Hz, 1H), 8.38 (d, J=2.6 Hz, 1H), 11.62 (s, 1H).

Step B: 5-n-Butyl-4-[[2'-(N-t-butylsulfamoyl)biphenyl-4-yl]methyl]-2-(2-chloro-5-nitrophenyl)-2,4-dihydro-3H-1,2,4-triazol-3-one By the procedure of Example 13, Step A, 5-n-butyl-2-(2-chloro-5-nitrophenyl)-2,4-dihydro-3H-1,2,4-triazol-3-one (from Step A) was alkylated with [2'-(N-t-butylsulfamoyl)biphenyl-4-yl]methyl bromide (from Example 12, Step D). Flash chromatography of the crude product on silica gel (gradient elution with 0.5–5.0% MeOH in $CH_2Cl_2$) gave an 83% yield of the title compound as an orange solid, mp >75° C. (gradual), homogeneous by TLC (98:2 $CH_2Cl_2$—MeOH), mass spectrum (FAB) m/e 598 $(M+1)^+$.

400 MHz $^1$H NMR (CDCl$_3$) δ0.91 (t, J=7.4 Hz, 3H), 0.98 (s, 9H), 1.40 (m, 2H), 1.66 (m, 2H), 2.52 (t, J=7.6 Hz, 2H), 3.49 (s, 1H), 4.96 (s, 2H), 7.25–7.60 (m, 7H), 7.69 (d, J=8.8 Hz, 1H), 8.15 (dd, J=7.7, 1.5 Hz, 1H) 8.21 (dd, J=8.8, 2.6 Hz, 1H), 8.39 (d, J=2.6 Hz, 1H)

Step C: 5-n-Butyl-2-(2-chloro-5-nitrophenyl)-2,4-dihydro-4-[(2'-sulfamoylbiphenyl-4-yl)methyl]-3H-1,2,4-triazol-3-one The title compound was prepared from 5-n-butyl-4-[[2'-(N-t-butylsulfamoyl)biphenyl-4-yl]methyl]-2-(2-chloro-5-nitrophenyl)-2,4-dihydro-3H-1,2,4-triazol-3-one (from Step B) according to the procedure of Example 13, Step B, and was obtained in 79% yield as a pale yellow solid after flash chromatographic purification, mp >90° C. (gradual), homogenous by TLC (19:1 $CH_2Cl_2$—MeOH); mass spectrum (FAB) m/e 542 $(M+1)^+$.

400 MHz $^1$H NMR (CDCl$_3$) δ0.90 (t, J=7.4 Hz, 3H), 1.39 (m, 2H), 1.67 (m, 2H), 2.53 (t, J=7.6 Hz, 2H), 4.23 (s, 2H), 4.96 (s, 2H), 7.25–7.61 (m, 7H), 7.69 (d, J=8.8 Hz, 1H), 8.14 (dd, J=7.9, 1.2 Hz, 1H), 8.20 (dd, J=8.8, 2.6 Hz, 1H), 8.39 (d, J=2.6 Hz, 1H).

Step D: 5-n-Butyl-4-[[2'-[N-(2-chlorobenzoyl)sulfamoyl]biphenyl-4-yl]methyl]-2-(2-chloro-5-nitrophenyl)-2,4-dihydro-3H-1,2,4-triazol-3-one The title compound was prepared from 5-n-butyl-2-(2-chloro-5-nitrophenyl)-2,4-dihydro-4-[(2'-sulfamoylbiphenyl-4-yl)methyl]-3H-1,2,4-triazol-3-one (from Step C) and 2-chlorobenzoic acid (2 eq), CDI (2 eq), and DBU (2 eq) according to the procedure of Example 51 to give a 48% yield of the desired material as a cream-colored solid after flash chromatography, mp >160° C. (gradual), homogeneous by TLC in 95:5 $CH_2Cl_2$—MeOH; mass spectrum (FAB) m/e 681 $(M+1)^+$.

400 MHz $^1$H NMR (CD$_3$OD) δ0.90 (t, J=7.3 Hz, 3H), 1.39 (m, 2H), 1.63 (m, 2H), 2.58 (t, J=7.4 Hz, 2H), 5.02 (s, 2H), 7.12–7.64 (m, 11H), 7.90 (dd, J=8.9, 2.8 Hz, 1H), 8.29 (dd, J=7.9, 1.2 Hz, 1H), 8.35 (dd, J=8.8, 2.6 Hz, 1H), 8.44 (d, J=2.7 Hz, 1H).

EXAMPLE 60

2-(5-Amino-2-chlorophenyl)-5-n-butyl-4-[[2'-[N-(2-chlorobenzoyl)sulfamoyl]biphenyl-4-yl]methyl]-2,4-dihydro-3H-1,2,4-triazol-3-one This material was prepared from 5-n-butyl-4-[[2'-[N-(2-chlorobenzoyl)sulfamoyl]biphenyl-4-yl]methyl]-2-(2-chloro-5-nitrophenyl)-2,4-dihydro-3H-1,2,4-triazol-3-one (from Example 59, Step D) and stannous chloride dihydrate according to the procedure of Example 56. The crude product was flash chromatographed over silica gel to afford the title compound in 70% yield as a cream-colored solid, mp 155°–157° C., homogeneous by TLC (9:1 MeOH/$CH_2Cl_2$), mass spectrum (FAB) m/e 651 $(M+1)^+$.

400 MHz $^1$H NMR ($CD_3OD$) δ0.88 (t, J=7.4 Hz, 3H), 1.36 (m, 2H), 1.59 (m, 2H), 2.54 (t, J=7.4 Hz, 2H), 5.00 (s, 2H), 6.75–6.79 (m, 2H), 7.10–7.65 (m, 12H), 8.29 (dd, J=8.0, 1.3 Hz, 1H).

EXAMPLE 61

5-n-Butyl-4-[[2'-[N-(2-chlorobenzoyl)sulfamoyl]biphenyl-4-yl]methyl]-2-[2-chloro-5-(propionylamino)-phenyl]-2,4-dihydro-3H-1,2,4-triazol-3-one At room temperature, under $N_2$, a solution of 59 mg (0.091 mmole) of 2-(5-amino-2-chlorophenyl)-5-n-butyl-4-[[2'-[N-(2-chlorobenzoyl)sulfamoyl]biphenyl-4-yl]methyl]-2,4-dihydro-3H-1,2,4-triazol-3-one (from Example 60) in DMF was stirred with 2.4 mg (0.10 mmole) of sodium hydride for 3 hours. Subsequently, 25 mg (0.18 mmole) of propionyl bromide was added and the resulting reaction mixture was stirred at 50° C. overnight. The reaction was quenched by addition of water. The organic material was extracted with EtOAc, washed with water and brine, and dried over sodium sulfate. After filtration and removal of volatiles, the crude product was flash chromatographed over silica gel (gradient elution with 1–5% MeOH/$CH_2Cl_2$) to afford 26 mg (40%) of the desired material as a cream-colored solid, mp 160°–162° C., homogeneous by TLC (9:1 MeOH/$CH_2Cl_2$), mass spectrum (FAB) m/e 707 $(M+1)^+$.

400 MHz $^1$H NMR ($CD_3OD$) δ0.89 (t, J=7.3 Hz, 3H), 1.18 (t, J=7.6 Hz, 3H), 1.36 (m, 2H), 1.61 (m, 2H), 2.39 (q, J=7.6 Hz, 2H), 2.56 (t, J=7.4 Hz, 2H), 5.01 (s, 2H), 7.12–7.69 (m, 13H), 7.93 (d, J=3.9 Hz, 1H), 8.29 (d, J=8.0 Hz, 1H).

EXAMPLE 62

5-n-Butyl-4-[[2'-[N-(2-chlorobenzoyl)sulfamoyl]biphenyl-4-yl]methyl]-2-[2-chloro-5-(valerylamino)phenyl]-2,4-dihydro-3H-1,2,4-triazol-3-one The title compound was prepared from 2-(5-amino-2-chlorophenyl)-5-n-butyl-4-[[2'-[N-(2-chlorobenzoyl)sulfamoyl]biphenyl-4-yl]methyl]-2,4-dihydro-3H-1,2,4-triazol-3-one (from Example 60), sodium hydride, and valeryl chloride according the procedure of Example 57. The crude product was flash chromatographed over silica gel (gradient elution with 0.5–2.0% MeOH/$CH_2Cl_2$) to give the desired compound as a cream-colored solid in 48% yield, mp >110° C. (gradual), homogeneous by TLC (9:1 MeOH/$CH_2Cl_2$), mass spectrum (FAB) m/e 734 $(M+1)^+$.

400 MHz $^1$H NMR ($CD_3OD$) δ0.89 (t, J=7.3 Hz, 3H), 0.95 (t, J=7.4 Hz, 3H), 1.39 (m, 4H), 1.61 (m, 4H), 2.38 (t, J=7.4 Hz, 2H), 2.56 (t, J=7.4 Hz, 2H), 5.01 (s, 2H), 7.10–7.68 (m, 13H), 7.91 (d, J=2.4 Hz, 1H), 8.29 (dd, J=8.0, 1.3 Hz, 1H).

EXAMPLE 63

5-n-Butyl-4-[[2'-[N-(2-chlorobenzoyl)sulfamoyl]biphenyl-4-yl]methyl]-2-[2-chloro-5-[(propoxycarbonyl)amino]phenyl]-2,4-dihydro-3H-1,2,4-triazol-3-one At room temperature, under $N_2$, a solution of 20 mg (0.031 mmole) of 2-(5-amino-2-chlorophenyl)-5-n-butyl-4-[[2'-[N-(2-chlorobenzoyl)sulfamoyl]biphenyl-4-yl]methyl]-2,4-dihydro-3H-1,2,4-triazol-3-one (from Example 60), 3.8 mg (0.031 mmole) of DMAP, 18.9 mg (0.154 mmole) of propyl chloroformate, and 1 mL pyridine was stirred overnight. After quenching with methanol and water, the organic material was extracted with EtOAc, washed with water and brine, and dried over sodium sulfate. The crude product obtained after filtration and removal of volatiles was flash chromatographed over silica gel (gradient elution with 0.5–5% MeOH/$CH_2Cl_2$) to give 15 mg (65%) of the desired compound as a white solid, mp >119° C. (gradual), homogeneous by TLC (9:1 MeOH/$CH_2Cl_2$), mass spectrum (FAB) m/e 736 $(M+1)^+$.

Analysis: ($C_{36}H_{35}Cl_2N_5O_6S$.0.5 $CH_2Cl_2$) Calcd: C, 56.34; H, 4.66; N, 9.00. Found: C, 56.26; H, 4.42; N, 8.68.

400 MHz $^1$H NMR ($CD_3OD$) δ0.89 (t, J=7.3 Hz, 3H), 0.99 (t, J=7.4 Hz, 3H), 1.37 (m, 2H), 1.61 (m, 2H), 1.69 (m, 2H), 2.55 (t, J=7.8 Hz, 2H), 4.09 (t, J=6.5 Hz, 2H), 5.01 (s, 2H), 7.13–7.75 (m, 14H), 8.28 (d, J=8.0 Hz, 1H).

EXAMPLE 64

5-n-Butyl-4-[[2'-[N-(2-chlorobenzoyl)sulfamoyl]biphenyl-4-yl]methyl]-2-[2-chloro-5-($N^3$-propylureido)-phenyl]-2,4-dihydro-3H-1,2,4-triazol-3-one At room temperature, under $N_2$, a solution of 34 mg (0.052 mmole) of 2-(5-amino-2-chlorophenyl)-5-n-butyl-4-[[2'-[N-(2-chlorobenzoyl)sulfamoyl]biphenyl-4-yl]methyl]-2,4-dihydro-3H-1,2,4-triazol-3-one (from Example 60), 6.4 mg (0.052 mmole) of DMAP, 23 mg (0.26 mmole) of propyl isocyanate, and 1 mL of pyridine was stirred overnight. After quenching with water, the organic material was extracted with EtOAc, washed with water and brine, and dried over sodium sulfate. The crude product obtained after filtration and removal of volatiles was flash chromatographed over silica gel (gradient elution with 0.5–5% MeOH/$CH_2Cl_2$) to give 23 mg (61%) of the desired compound as a white solid, mp >208° C. (gradual), homogeneous by TLC (9:1 MeOH/$CH_2Cl_2$), mass spectrum (FAB) m/e 773 $(M+K)^+$.

Analysis: ($C_{36}H_{36}Cl_2N_6O_5S$.0.5 $CH_2Cl_2$) Calcd: C, 56.34; H, 4.79; N, 10.80. Found: C, 56.22; H, 4.68; N, 10.86.

400 MHz $^1$H NMR ($CD_3OD$) δ0.91 (m, 6H), 1.38 (m, 2H), 1.51 (m, 2H), 1.61 (m, 2H), 2.55 (t, J=7.8 Hz, 2H), 3.12 (m, 2H), 4.99 (s, 2H), 7.12–7.70 (m, 14H), 8.28 (dd, J=7.9, 1.2 Hz, 1H).

Additional 2-[5-(acylamino)-2-chlorophenyl]-5-n-butyl-4-[[2'-[N-(2-chlorobenzoyl)sulfamoyl]biphenyl-4-yl]methyl]-2,4-dihydro-3H-1,2,4-triazol-3-ones prepared by the methods described in the foregoing examples are tabulated below:

TABLE IV

| | V₂ | mp | Formula | | Analysis C | H | N |
|---|---|---|---|---|---|---|---|
| (1) | NH(CH₂)₃CH₃ | 110–112° C. | C₃₅H₃₅Cl₂N₅O₄S· 0.33H₂O | calcd found | 60.17 59.88 | 5.15 4.82 | 10.02 9.98 |
| (2) | NHCO—Ph | >147° C. (gradual) | C₃₉H₃₃Cl₂N₅O₅S· H₂O | calcd found | 60.62 60.39 | 4.33 4.19 | 9.06 8.67 |
| (3) | NHCH₂—Ph | 113–115° C. | C₃₉H₃₅Cl₂N₅O₄S· 0.33H₂O | calcd found | 62.73 62.61 | 4.81 4.54 | 9.38 9.23 |
| (4) | NHCOCH₂—Ph | 157–160° C. | C₄₀H₃₅Cl₂N₅O₅S· 0.5CH₂Cl₂ | calcd found | 59.97 60.25 | 4.47 4.38 | 8.63 8.63 |
| (5) | NHCOCH₂CH(CH₃)₂ | 163–165° C. | C₃₇H₃₇Cl₂N₅O₅S· 0.33CH₂Cl₂ | calcd found | 58.77 58.97 | 4.98 5.06 | 9.18 8.92 |
| (6) | NHCOCH(CH₃)₂ | 158–160° C. | C₃₆H₃₅Cl₂N₅O₅S· 0.25CH₂Cl₂ | calcd found | 58.69 58.45 | 4.82 4.89 | 9.44 9.13 |
| (7) | NHCOCH₂C(CH₃)₃ | 173–175° C. | C₃₈H₃₉Cl₂N₅O₅S· 0.5CH₂Cl₂ | calcd found | 58.45 58.46 | 5.10 4.93 | 8.85 8.99 |
| (8) | NHCO(CH₂)₂—Ph | 159–161° C. | C₄₁H₃₇Cl₂N₅O₅S· 0.25CH₂Cl₂ | calcd found | 61.63 61.58 | 4.70 4.69 | 8.71 8.56 |
| (9) | NHCOCH₃ | 190–192° C. | C₃₄H₃₁Cl₂N₅O₅S· 0.6CH₂Cl₂ | calcd found | 55.89 55.99 | 4.37 4.27 | 9.42 9.44 |
| (10) | NHCO—cyclopropyl | 190–192° C. | C₃₆H₃₃Cl₂N₅O₅S· 0.6CH₂Cl₂ | calcd found | 57.12 57.29 | 4.48 4.20 | 9.10 9.15 |
| (11) | NHCOC(CH₃)₃ | 167–169° C. | C₃₉H₃₇Cl₂N₅O₅S· 0.33CH₂Cl₂ | calcd found | 58.77 58.83 | 4.98 4.94 | 9.18 9.19 |

EXAMPLE 65

5-n-Butyl-2-[5-(N-n-butylcarbamoyl)-2-chlorophenyl]-4-[[2′-[N-(2-chlorobenzoyl)sulfamoyl]biphenyl-4-yl]methyl]-2,4-dihydro-3H-1,2,4-triazol-3-one Step A: 5-n-Butyl-2-[5-(carbomethoxy)-2-chlorophenyl]-2,4,dihydro-3H-1,2,4-triazol-3-one By the procedure of Example 4, Step C, 5-(carbomethoxy)-2-chlorophenylhydrazine [generated from the hydrochloride, which was prepared from 5-(carbomethoxy)-2-chloroaniline according to H. Stroh and G. Westphal, *Chem. Ber.* 9.6, 184 (1963), by partitioning between EtOAc and 1N sodium carbonate] was reacted with ethyl N-carbethoxyvalerimidate (from Example 4, Step B). After work-up, the residue was purified by flash chromatography on silica gel (gradient elution with 0.5–10% methanol in $CH_2Cl_2$) to give a 34% yield of the title compound as an orange gum, homogeneous by TLC (19:1 $CH_2Cl_2$—MeOH), mass spectrum (FAB) m/e 310 (M+1)⁺.

400 MHz ¹H NMR (CDCl₃) δ0.88 (t, J=7.3 Hz, 3H), 1.34 (m, 2H), 1.64 (m, 2H), 2.54 (t, J=7.5 Hz, 2H), 3.85 (s, 3H), 7.58 (d, J=8.5 Hz, 1H), 8.01 (dd, J=8.4, 2.1 Hz, 1H), 8.14 (d, J=2.0 Hz, 1H), 11.93 (s, 1H).

Step B: 5-n-Butyl-4-[[2'-(N-t-butylsulfamoyl)biphenyl-4-yl]methyl]-2-[5-(carbomethoxy)-2-chlorophenyl]-2,4-dihydro-3H-1,2,4-triazol-3-one By the procedure of Example 13, Step A, 5-n-butyl-2-[5-(carbomethoxy)-2-chlorophenyl]-2,4-dihydro-3H-1,2,4-triazol-3-one (from Step A) was alkylated with [2'-(N-t-butylsulfamoyl)biphenyl- 4-yl]methyl bromide (from Example 12, Step D). Flash chromatography of the crude product on silica gel (gradient elution with 0.5–5.0% MeOH in CH$_2$Cl$_2$) gave an 85% yield of the title compound as a white solid, mp 65°–67° C., homogeneous by TLC (98:2 CH$_2$Cl$_2$—MeOH), mass spectrum (FAB) m/e 555 [M-(t-Bu)]+.

400 MHz $^1$H NMR (CDCl$_3$) δ0.90 (t, J=7.1 Hz, 3H), 0.98 (s, 9H), 1.38 (m, 2H), 1.64 (m, 2H), 2.50 (m, 2H), 3.50 (s, 1H), 3.90 (s, 3H), 4.96 (s, 2H), 7.26–7.62 (m, 8H), 7.99–8.20 (m, 3H).

Step C: 5-n-Butyl-2-[5-(carbomethoxy)-2-chlorophenyl]-2,4-dihydro-4-[(2'-sulfamoylbiphenyl-4-yl)methyl]-3H-1,2,4,-triazol-3-one.

The title compound was prepared from 5-n-butyl-4-[[2'-(N-t-butylsulfamoyl)biphenyl-4-yl]methyl]-2-[5-(carbomethoxy)-2-chlorophenyl]-2,4-dihydro-3H-1,2,4-triazol-3-one (from Step B) according to the procedure of Example 13, Step B, and was obtained in 65% yield as a white solid after flash chromatography, mp 182°–184° C., homogenous by TLC (19:1 CH$_2$Cl$_2$—MeOH); mass spectrum (FAB) m/e 555 (M+1)+.

400 MHz $^1$H NMR (CDCl$_3$) δ0.89 (t, J=7.2 Hz, 3H), 1.40 (m, 2H), 1.66 (m, 2H), 2.51 (t, J=7.5 Hz, 2H), 3.90 (s, 3H), 4.21 (s, 2H), 4.96 (s, 2H), 7.30–7.61 (m, 9H), 8.00 (dd, J=8.4, 2.1 Hz, 1H), 8.15 (m, 1H).

Step D: 5-n-Butyl-2-[5-(carbomethoxy)-2-chlorophenyl]-4-[[2'-[N-(2-chlorobenzoyl)sulfamoyl]biphenyl-4-yl]methyl]-2,4-dihydro-3H-1,2,4-triazol-3-one The title compound was prepared from 5-n-butyl-2-[5-(carbomethoxy)-2-chlorophenyl]-2,4-dihydro- 4-[(2'-sulfamoylbiphenyl-4-yl)methyl]-3H-1,2,4-triazol-3-one (from Step C) and 2-chlorobenzoic acid (2 equivalents), CDI (2 equiv), and DBU (2 equiv) according to the procedure of Example 51 to give an 88% yield of the desired material as a white solid after flash chromatography, mp 98°–101° C., homogeneous by TLC in 95:5 CH$_2$Cl$_2$—MeOH; mass spectrum (FAB) m/e 693 (M+1)+.

Analysis: (C$_{34}$H$_{30}$Cl$_2$N$_4$O$_6$S.0.5 H$_2$O) Calcd: C, 58.12; H, 4.45; N, 7.97. Found: C, 57.95; H, 4.38; N, 7.84.

400 MHz $^1$H NMR (CDCl$_3$) δ0.90 (t, J=7.2 Hz, 3H), 1.39 (m, 2H), 1.63 (m, 2H), 2.47 (t, J=7.6 Hz, 2H), 3.91 (s, 3H), 4.88 (s, 2H), 7.19–7.69 (m, 11H), 8.00 (dd, J=8.4, 2.3 Hz, 1H), 8.15 (d, J=2.0 Hz, 1H), 8.36 (dd, J=7.8, 1.5 Hz, 1H), 8.45 (s, 1H).

Step E: 5-n-Butyl-2-[5-(N-n-butylcarbamoyl)-2-chlorophenyl]-4-[[2'-[N-(2-chlorobenzoyl)sulfamoyl]biphenyl-4-yl]methyl]-2,4-dihydro-3H-1,2,4-triazol-3one A solution of 100 mg (0.14 mmole) of 5-n-butyl-2-[5-(carbomethoxy)-2-chlorophenyl]-4-[[2'-[N-(2-chlorobenzoyl)sulfamoyl]biphenyl-4-yl]methyl]-2,4-dihydro-3H-1,2,4-triazol-3-one (from Step D), in 1 mL of n-butylamine was stirred at 65° C. overnight. After removal of excess n-butylamine, the crude product was flash chromatographed over silica gel (gradient elution with 0.5–5.0% MeOH/CH$_2$Cl$_2$) to give 96 mg (91%) of the desired product as a white solid, mp >155° C. (gradual), homogeneous by TLC in 95:5 CH$_2$Cl$_2$—MeOH; mass spectrum (FAB) m/e 734 (M+1)+.

Analysis: (C$_{37}$H$_{37}$Cl$_2$N$_5$O$_5$S.0.33 CH$_2$Cl$_2$) Calcd: C, 58.77; H, 4.98; N, 9.18. Found: C, 58.60; H, 4.69; N, 8.80.

400 MHz $^1$H NMR (CD$_3$OD) δ0.90 (t, J=7.3 Hz, 3H), 0.96 (t, J=7.4 Hz, 3H), 1.39 (m, 4H), 1.62 (m, 4H), 2.58 (t, J=7.5 Hz; 2H), 3.37 (t, J=7.2 Hz, 2H), 5.02 (s, 2H), 7.11–7.73 (m, 12H), 7.93 (dd, J=8.4, 2.2 Hz, 1H), 7.98 (d, J=2.2 Hz, 1H), 8.28 (d, J=8.0 Hz, 1H).

EXAMPLE 66

5-n-Butyl-4-[[2'-[N-(2-chlorobenzoyl)sulfamoyl]biphenyl-4-yl]methyl]-2-[3-(propionylamino)phenyl]-2,4-dihydro-3H-1,2,4-triazol-3-one Step A: 5-n-Butyl-2,4-dihydro-2-(3-nitrophenyl)-3H-1,2,4-triazol-3-one By the procedure of Example 4, Step C, 3-nitrophenylhydrazine [generated from the hydrochloride by partitioning between EtOAc and 1N sodium carbonate] was reacted with ethyl N-carbethoxyvalerimidate (from Example 4, Step B). After work-up, the residue was purified by flash chromatography on silica gel (gradient elution with 0.5–1.0% methanol in CH2Cl2) to give a 75% yield of the title compound as a tan solid, homogeneous by TLC (98:2 CH$_2$Cl$_2$—MeOH), mass spectrum (FAB) m/e 263 (M+1)+ mp 158°–159° C.,.

200 MHz $^1$H NMR (CDCl$_3$) δ1.00 (t, J=7.2 Hz, 3H), 1.46 (m, 2H), 1.75 (m, 2H), 2.69 (t, J=7.5 Hz, 2H), 7.60 (t, J=8.2 Hz, 1H), 8.06 (m, 1H), 8.36 (m, 1H), 8.92 (m, 1H), 11.55 (s, 1H).

Step B: 5-n-Butyl-4-[[2'-(N-t-butylsulfamoyl)biphenyl-4-yl]methyl]-2,4-dihydro-2-(3-nitrophenyl)-3H-1,2,4-triazol-3-one By the procedure of Example 13, Step A, 5-n-butyl-2,4-dihydro-2-(3-nitrophenyl)-3H-1,2,4-triazol-3-one (from Step A) was alkylated with [2'-(N-t-butylsulfamoyl)biphenyl-4-yl]methyl bromide (from Example 12, Step D). Flash chromatography of the crude product on silica gel (gradient elution with 0.5–1.0% MeOH in CH$_2$Cl$_2$) gave a 74% yield of the title compound as an off-white solid, mp 164°–165° C., homogeneous by TLC (19:1 CH$_2$Cl$_2$—MeOH), mass spectrum (FAB) m/e 564 (M+1)+.

400 MHz $^1$H NMR (CDCl$_3$) δ0.94 (t, J=7.3 Hz, 3H), 0.98 (s, 9H), 1.41 (m, 2H), 1.70 (m, 2H), 2.53 (t, J=7.6 Hz, 2H), 3.50 (s, 1H), 4.94 (s, 2H), 7.26–7.60 (m, 7H), 8.03 (m, 1H), 8.14 (dd, J=8.0, 0.8 Hz, 1H) 8.45 (m, 1H), 8.87 (m, 1H).

Step C: 5-n-Butyl-2,4-dihydro-2-(3-nitrophenyl)-4-[(2'-sulfamoylbiphenyl-4-yl)methyl]-3H-1,2,4-triazol-3-one The title compound was prepared from 5-n-butyl-4-[[2'-(N-t-butylsulfamoyl)biphenyl-4-yl]methyl]-2,4-dihydro-2-(3-nitrophenyl)-3H-1,2,4-triazol-3-one (from Step B) according to the procedure of Example 13, Step B, and was obtained in 94% yield as a pale yellow solid after flash chromatography, mp 73°–76° C., homogenous by TLC (19:1 CH$_2$Cl$_2$—MeOH); mass spectrum (FAB) m/e 508 (M+1)+.

400 MHz $^1$H NMR (CDCl$_3$) δ0.93 (t, J=7.3 Hz, 3H), 1.43 (m, 2H), 1.70 (m, 2H), 2.55 (t, J=7.4 Hz, 2H), 4.29 (s, 2H), 4.95 (s, 2H), 7.27–7.59 (m, 8H), 8.03 (m, 1H), 8.11 (dd, J=8.0, 1.3 Hz, 1H), 8.43 (m, 1H), 8.86 (m, 1H).

Step D: 5-n-Butyl-4-[[2'-[N-(2-chlorobenzoyl)sulfamoyl]biphenyl-4-yl]methyl]-2,4-dihydro-2-(3-nitrophenyl)-3H-1,2,4-triazol-3-one The title compound was prepared from 5-n-butyl-2,4-dihydro-2-(3-nitrophenyl)-4-[(2'-sulfamoylbiphenyl-4-yl)methyl]-3H-1,2,4-triazol-3-one (from Step C) and 2-chlorobenzoic acid (2.5 equivalents), CDI (2.5 equiv), and DBU (2.5 equiv) according to the procedure of Example 51 to give a 95% yield of the desired material as a cream-colored solid after flash chromatography, mp 92°–95° C., homogeneous by TLC in 95:5 $CH_2Cl_2$—MeOH; mass spectrum (FAB) m/e 645 $(M+1)^+$.

Analysis: $(C_{32}H_{28}ClN_5O_6S.0.4\ CH_2Cl_2)$ Calcd: C, 57.22; H, 4.27; N, 10.30. Found: C, 57.57; H, 4.14; N, 10.04.

400 MHz $^1$H NMR (CDCl$_3$) δ0.94 (t, J=7.3 Hz, 3H), 1.43 (m, 2H), 1.69 (m, 2H), 2.52 (t, J=7.4 Hz, 2H), 4.87 (s, 2H), 7.19–7.36 (m, 8H), 7.56–7.66 (m, 4H), 8.03 (m, 1H), 8.34 (dd, J=7.9, 1.3 Hz, 1H), 8.42 (m, 1H), 8.62 (s, 1H), 8.86 (m, 1H).

Step E: 2-(3-Aminophenyl)-5-n-butyl-4-[[2'-[N-(2-chlorobenzoyl)sulfamoyl]biphenyl-4-yl]methyl]-2,4-dihydro-3H-1,2,4-triazol-3-one This material was prepared from 5-n-butyl-4-[[2'-[N-(2-chlorobenzoyl)sulfamoyl]biphenyl-4-yl]methyl]-2,4-dihydro-2-(3-nitrophenyl)-3H-1,2,4-triazol-3-one (from Example 59, Step D) and stannous chloride dihydrate according to the procedure of Example 56. The crude product was flash chromatographed over silica gel to afford the title compound in 95% yield as a cream-colored solid, mp 137°–139° C., homogeneous by TLC (9:1 MeOH/$CH_2Cl_2$), mass spectrum (FAB) m/e 616 $(M+1)^+$.

Analysis: $(C_{32}H_{30}ClN_5O_4S.0.5\ H_2O.0.25\ CH_2Cl_2)$ Calcd: C, 59.93; H, 4.91; N, 10.84. Found: C, 59.86; H, 4.52; N, 11.03.

400 MHz $^1$H NMR (CDCl$_3$) δ0.90 (t, J=7.2 Hz, 3H), 1.38 (m, 2H), 1.64 (m, 2H), 2.47 (t, J=7.6 Hz, 2H), 4.80 (s, 2H), 6.45 (d, J=6.8 Hz, 1H), 6.75–6.79 (m, 2H), 7.00–7.60 (m, 14H), 8.28 (d, J=7.1 Hz, 1H).

Step F: 5-n-Butyl-4-[[2'-[N-(2-chlorobenzoyl)sulfamoyl]biphenyl-4-yl]methyl]-2,4-dihydro-2-[3-(propionylamino)phenyl]-3H-1,2,4-triazol-3-one This material was prepared from 2-(3-aminophenyl)-5-n-butyl-4-[[2'-[N-(2-chlorobenzoyl)sulfamoyl]biphenyl-4-yl]methyl]-2,4-dihydro-3H-1,2,4-triazol-3-one (from Step E), sodium hydride, and propionyl bromide according to the procedure of Example 61. The crude product was flash chromatographed over silica gel to afford the title compound in 60% yield as a cream-colored solid, mp 105°–107° C., homogeneous by TLC (9:1 MeOH/$CH_2Cl_2$), mass spectrum (FAB) m/e 672 $(M+1)^+$.

Analysis: $(C_{35}H_{34}ClN_5O_5S.0.3\ CH_2Cl_2)$ Calcd: C, 60.77; H, 5.00; N, 10.04. Found: C, 60.46; H, 4.75; N, 9.70.

400 MHz 1H NMR (CDCl$_3$) δ0.93 (t, J=7.3 Hz, 3H), 1.24 (t, J=7.6 Hz, 3H), 1.43 (m, 2H), 1.68 (m, 2H), 2.38 (q, J=7.6 Hz, 2H), 2.51 (t, J=7.6 Hz, 2H), 4.82 (s, 2H), 7.17–7.72 (m, 14H), 8.03 (d, J=1.6 Hz, 1H), 8.35 (dd, J=7.8, 1.6 Hz, 1H), 8.76 (s, 1H).

EXAMPLE 67

5-n-Butyl-4-[[2'-[N-(2-chlorobenzoyl)sulfamoyl]biphenyl-4-yl]methyl]-2,4-dihydro-2-[3-(valerylamino)phenyl]-3H-1,2,4-triazol-3-one This material was prepared from 2-(3-aminophenyl)-5-n-butyl-4-[[2'-[N-(2-chlorobenzoyl)sulfamoyl]biphenyl-4-yl]methyl]-2,4-dihydro-3H-1,2,4-triazol-3-one (from Example 66, Step E), sodium hydride, and valeryl chloride according to the procedure of Example 62. The crude product was flash chromatographed over silica gel to afford the title compound in 67% yield as a cream-colored solid, mp 102°–105° C., homogeneous by TLC (9:1 MeOH/$CH_2Cl_2$), mass spectrum (FAB) m/e 700 $(M+1)^+$.

Analysis: $(C_{37}H_{38}ClN_5O_5S.0.25\ CH_2Cl_2)$ Calcd: C, 62.01; H, 5.38; N, 9.71. Found: C, 62.17; H, 5.32; N, 9.34.

400 MHz $^1$H NMR (CDCl$_3$) δ0.93 (t, J=7.4 Hz, 6H), 1.39 (m, 4H), 1.66 (m, 4H), 2.34 (t, J=7.3 Hz, 2H), 2.51 (t, J=7.6 Hz, 2H), 4.82 (s, 2H), 7.17–7.72 (m, 14H), 8.02 (d, J=1.9 Hz, 1H), 8.36 (dd, J=7.9, 1.4 Hz, 1H), 8.77 (s, 1H).

EXAMPLE 68

5-n-Butyl-4-[[2'-[N-(2-chlorobenzoyl)sulfamoyl]-5'-n-propylbiphenyl-4-yl]methyl]-2,4-dihydro-2-[2-(trifluoromethyl]-3H-1,2,4-triazol-3-one Step A: N-t-butyl-4-n-propylbenzenesulfonamide To a solution of 4-n-propylbenzenesulfonyl chloride (Lancaster) in anhydrous $CH_2Cl_2$ (0.5M solution) cooled to 0° C. under N$_2$ was added t-butylamine (2.2 equiv) slowly through a dropping funnel. After complete addition, the reaction was stirred at room temperature for 12 hours. The $CH_2Cl_2$ was removed under reduced pressure, and the residue was extracted into ether and washed with 2N NaOH, H$_2$O and brine. The organic phase was dried over anhydrous MgSO$_4$ and concentrated in vacuo to afford the titled product; R$_f$=0.46 (3:1 hexane-EtOAc).

$^1$H NMR (200 MHz, (CDCl$_3$) δ0.93 (t, 3H), 1.22 (s, 9H), 1.62 (m, 2H), 2.65 (t, 2H), 4.67 (bs, 1H), 7.27 (d, 2H), 7.79 (d, 2H).

Step B: 2-(N-t-butylsulfamoyl)-5-n-propylphenylboronic acid.

To a solution of 2.85 g (11.2 mmol) of N-t-butyl-4-n-propylbenzenesulfonamide (from Step A) in anhydrous THF (20 mL) cooled to −40° C. under N$_2$ was added 2.5M n-BuLi solution (11.2 mL, 2.5 equiv). The mixture was warmed to room temperature and stirred for 2 hours. To the mixture, containing the bright red dianion at 0° C., was added triisopropyl borate (3.9 mL, 1.5 equiv). The next day, 2N HCl (3 mL) was added and the mixture was stirred for 1 hour. The solvent was removed under reduced pressure and the residue was extracted with ethyl acetate. The organic solution was washed with 2N HCl, H$_2$O and brine. The organic phase was dried over anhydrous MgSO$_4$ and concentrated in vacuo to afford the titled compound; R$_f$=0.5 (1:1 EtOAc-hexane). The material was used in the next step without further purification.

Step C: [2'-(N-t-Butylsulfamoyl)-5'n-propylbiphenyl-4-yl]methanol

To a solution of 2.80 g (9.36 mmol) of 2-(N-t-butylsulfamoyl)-5-n-propylphenylboronic acid (from Step B) and 4-bromobenzyl alcohol (5.25 g, 3 equiv) in toluene (125 mL) was added 1.25N NaOH (32 mL), EtOH (86 mL) and tetrakis(triphenylphosphine)palladium(0) (325 mg, 3 mol %). The mixture was stirred at 100° C. under N$_2$ for 3 hours. The reaction was concentrated and the residue was extracted with ethyl acetate. The organic solution was washed with 1N NaOH, H$_2$O and brine. Next, the organic phase was dried over anhydrous MgSO$_4$ and concentrated in vacuo. The product was purified by flash chromatography, eluting with 2:1 hexane-EtOAc, to provide the titled compound; R$_f$=0.42 (1:1 EtOAc-hexane).

$^1$H NMR (400 MHz, CDCl$_3$) δ0.92 (t, 3H), 0.98 (s, 9H), 1.63 (m, 2H), 1.83 (bs, 1H), 2.63 (t, 2H), 3.57 (bs,

1H), 4.74 (s, 2H), 7.07 (d, 1H), 7.23 (dd, 1H), 7.42 (d, 2H), 7.49 (d, 2H), 8.02 (d, 1H).

Step D: 5-n-Butyl-4-[[2'-(N-t-butylsulfamoyl)-5'-n-propylbiphenyl-4-yl]methyl]-2,4-dihydro-2-[2-(trifluoromethyl)phenyl]-3H-1,2,4-triazol-3-one Under nitrogen, to a solution of 110 mg (0.386 mmole) of 5-n-butyl-2,4-dihydro-2-[2-(trifluoromethyl)-phenyl]-3H-1,2,4-triazol-3-one (from Example 16, Step A), 100 mg (0.257 mmole) of [2'-(N-t-butylsulfamoyl)-5'-n-propylbiphenyl-4-yl]methanol (from Step C), and 101 mg (0.386 mmole) of triphenylphosphine in 1.2 mL of THF at −10° C., was added dropwise 78 mg (0.386 mmole) of diisopropyl azodicarboxylate. The reaction mixture was warmed up to room temperature, stirred overnight, and concentrated in vacuo. The crude product thus obtained was flash chromatographed over 40 mL of silica gel (gradient elution, 5:1 to 3:1 hexane/ethyl acetate) to afford a foam, homogeneous by TLC (1:1 hexane-EtOAc); mass spectrum (FAB) m/e 629 (M+1)+.

400 MHz NMR (CDCl$_3$) δ0.89 (t, J=7.2 Hz, 3H), 0.93 (t, J=7.2 Hz, 3H), 0.97 (s, 9H), 1.38 (m, 2H), 1.64 (m, 4H), 2.46 (t, J=7.9 Hz, 2H), 2.63 (t, J=7.6 Hz, 2H), 3.46 (s, 1H), 4.94 (s, 2H), 7.06–7.79 (m, 10H), 8.04 (d, J=8.3 Hz, 1H).

Step E: 5-n-Butyl-2,4-dihydro-4-[(2'-sulfamoyl-5'-n-propylbiphenyl-4-yl)methyl]-2-[2-(trifluoromethyl)-phenyl]-3H-1,2,4-triazol-3-one The title compound was prepared from 5-n-butyl-4-[[2'-(N-t-butylsulfamoyl)-5'-n-propylbiphenyl-4-yl]methyl]-2-[2-(trifluoromethyl)phenyl]-3H-1,2,4-triazol-3-one (from Step D) according to the procedure of Example 13, Step B. The crude product was flash chromatographed over silica gel (gradient elution with 0.5–1.0% MeOH in CH$_2$Cl$_2$), to provide the titled compound; homogeneous by TLC in 19:1 CH$_2$Cl$_2$—MeOH; mass spectrum (FAB) m/e 573 (M+1)+.

400 MHz NMR (CDCl$_3$) δ0.87 (t, J=7.3 Hz, 3H), 0.93 (t, J=7.3 Hz, 3H), 1.35 (m, 2H), 1.64 (m, 4H), 2.49 (t, J=7.6 Hz, 2H), 2.63 (t, J=7.5 Hz, 2H), 4.31 (s, 2H), 4.94 (s, 2H), 7.09–7.78 (m, 10H), 7.99 (d, J=8.1 Hz, 1H).

Step F: 5-n-Butyl-4-[[2'-[N-(2-chlorobenzoyl)sulfamoyl]-5'-n-propylbiphenyl-4-yl]methyl]-2,4-dihydro-2-[2-(trifluoromethyl)phenyl]-3H-1,2,4-triazol-3-one The title compound was prepared from 5-n-butyl-2,4-dihydro-2-[2-(trifluoromethyl)phenyl]-4-[(2'-sulfamoyl-5'-propylbiphenyl-4-yl)methyl]-3H-1,2,4-triazol-3-one (from Step E) and 2-chlorobenzoic acid (2.0 equivalents), CDI (2.0 equiv), and DBU (2.0 equiv) according to the procedure of Example 51 to give an 86% yield of the desired material as a cream-colored solid after flash chromatography, mp 67°–69° C.; homogeneous by TLC in 9:1 CH$_2$Cl$_2$—MeOH; mass spectrum (FAB) m/e 711 (M+1)+.

400 MHz $^1$H NMR (CDCl$_3$) δ0.88 (t, J=7.3 Hz, 3H), 0.94 (t, J=7.3 Hz, 3H), 1.35 (m, 2H), 1.63 (m, 4H), 2.46 (t, J=7.6 Hz, 2H), 2.66 (t, J=7.9 Hz, 2H), 4.89 (s, 2H), 7.08–7.80 (m, 14H), 8.25 (d, J=8.3 Hz, 1H), 8.65 (s, 1H).

EXAMPLE 69

5-n-Butyl-2-[5-(butyrylamino)-2-chlorophenyl]-4-[[2'-[N-(2-chlorobenzoyl)-sulfamoyl]biphenyl-4-yl]methyl]-2,4-dihydro-3H-1,2,4-triazol-3-one A mixture of 100 mg (0.154 mmole) of 2-(5-amino-2-chlorophenyl)-5-n-butyl-4-[[2'-[N-(2-chlorobenzoyl)sulfamoyl]biphenyl-4-yl]methyl]-2,4-dihydro-3H-1,2,4-triazol-3-one (from Example 60), 18.8 mg (0.154 mmole) of 4-(dimethylamino)pyridine (DMAP), 80 μL (82 mg, 0.77 mmole) of butyryl chloride, and 1 mL of pyridine was stirred at room temperature overnight. Work-up of the reaction as in Example 57 provided a 65% yield of the title compound as a white solid, mp >130° C., homogeneous by TLC (9:1 MeOH-CH$_2$Cl$_2$), mass spectrum (FAB) m/e 758 (M+K)+.

400 MHz $^1$H NMR (CD$_3$OD) δ0.89 (t, J=7.3 Hz, 3H), 0.99 (t, J=7.5 Hz, 3H), 1.37 (m, 2H), 1.61 (m, 2H), 1.71 (m, 2H), 2.35 (t, J=7.4 Hz, 2H), 2.56 (t, J=7.5 Hz, 2H), 5.01 (s, 2H), 7.11 (d, J=7.6 Hz, 1H), 7.23 (m, 1H), 7.29–7.36 (m, 5H), 7.51–7.67 (m, 6H), 7.91 (d, J=2.5 Hz, 1H), 8.29 (dd, J=8.0, 1.3 Hz, 1H).

EXAMPLE 70

5-n-Butyl-2-[5-(N-n-butyl-N-methylcarbamoyl)-2-chlorophenyl]-4-[[2'-[N-(2-chlorobenzoyl)sulfamoyl]-biphenyl-4-yl]methyl]-2,4-dihydro-3H-1,2,4-triazol-3-one Step A: 5-n-Butyl-2-(5-carboxy-2-chlorophenyl)-4-[[2'-[N-(2-chlorobenzoyl)sulfamoyl]biphenyl-4-yl]methyl]-2,4-dihydro-3H-1,2,4-triazol-3-one A solution of 71 mg (0.102 mmole) of 5-n-butyl-2-[5-(carbomethoxy)-2-chlorophenyl]-4-[[2'-[N-(2-chlorobenzoyl)-sulfamoyl]-biphenyl-4-yl]methyl]-2,4-dihydro-3H-1,2,4-triazol-3-one (from Example 65, Step D) in 0.7 mL (0.7 mmole) of 1N NaOH (methanolic) was stirred at 60° C. overnight and then concentrated to dryness. The residue was dissolved in 1 mL of methanol, acidified to approximately pH 1.5 by addition of 1N HCl (methanolic), and again concentrated. The residue was dissolved in CHCl$_3$, dried over Na$_2$SO$_4$, and filtered through Celite. Evaporation of the solvent yielded 58 mg (84%) of the title compound as a white solid; nearly homogeneous by TLC in 9:1 CH$_2$Cl$_2$—MeOH; mass spectrum (FAB) m/e 679 (M+1)+.

400 MHz $^1$H NMR (CDCl$_3$) δ0.90 (t, J=7.3 Hz, 3H), 1.39 (m, 2H), 1.67 (m, 2H), 2.50 (t, J=7.7 Hz, 2H), 4.91 (s, 2H), 7.19–7.68 (m, 11H), 8.00 (dd, J=8.4, 1.9 Hz, 1H), 8.13 (d, J=2.0 Hz, 1H), 8.37 (dd, J=7.9, 1.5 Hz, 1H), 8.77 (br s, 1H).

Step B: 5-n-Butyl-2-[5-(N-n-butyl-N-methylcarbamoyl)-2-chlorophenyl]-4-[[2'-[N-(2-chlorobenzoyl)-sulfamoyl]biphenyl-4-yl]methyl]-2,4-dihydro-3H-1,2,4-triazol-3-one A solution of 40 mg (0.0589 mmole) of 5-n-butyl-2-(5-carboxy-2-chlorophenyl)-4-[[2'-[N-(2-chlorobenzoyl)-sulfamoyl]biphenyl-4-yl]methyl]-2,4-dihydro-3H-1,2,4-triazol-3-one (from Step A) and 51.3 μL (38.1 mg, 0.295 mmole) of N,N-diisopropylethylamine in 1 mL of CH$_2$Cl$_2$ and 0.3 μL of DMF was stirred at 0° C. under protection from moisture as 27.9 mL (20.5 mg, 0.236 mmole) of N-methylbutylamine was added, followed by 52.1 mg (0.118 mmole) of BOP reagent. The solution was stirred at 0° C. overnight and then concentrated. The residue was reconcentrated twice from toluene. It was then taken up in CH$_2$Cl$_2$ and washed successively twice with 5% citric acid (aqueous), twice with 5% NaHCO$_3$ (aqueous), and then with brine. The organic phase was dried over Na$_2$SO$_4$, filtered, and concentrated. The residue was flash chromatographed on silica gel (gradient elution with 1–5% MeOH in CH$_2$Cl$_2$) and then further purified by HPLC on a semi-preparative Zorbax C8 reverse phase column (elution with 60:40 acetonitrile-H$_2$O) to give a 36% yield of the title compound as a colorless, glassy solid, mp >90° C. (gradual); mass spectrum (FAB) m/e 748 (M+1)+. By NMR the material appeared to exist as a mixture of amide rotamers in a ratio of approximately 1:1.

Analysis: ($C_{38}H_{39}Cl_2N_5O_5S.0.6CH_2Cl_2$) Calcd: C, 57.98; H, 5.07; N, 8.76. Found: C, 58.36; H, 5.02; N, 8.42.

400 MHz $^1$H NMR ($CD_3OD$) δ0.90 (t, J=7.4 Hz, 6H), 1.38 (m, 4H), 1.62 (m, 4H), 2.57 (t, J=7.5 Hz, 2H), 3.00 and 3.06 (s, total 3H), 3.30 (partially obscured) and 3.54 (t, J=7.3 Hz, total 2H), 5.02 (s, 2H), 7.14 (dd, J=7.0, 0.9 Hz, 1H), 7.29–7.75 (m, 13H), 8.30 (dd, J=8.0, 1.3 Hz, 1H).

EXAMPLE 71

5-n-Butyl-2-[2-chloro-5-(propionylamino)phenyl]-2,4-dihydro-4-[[2'-[N-(2-phenoxybenzoyl)sulfamoyl]biphenyl-4-yl]methyl]-3H-1,2,4-triazol-3-one Step A: 5-n-Butyl-2-[2-chloro-5-nitrophenyl]-2,4-dihydro-4-[[2'-[N-(2-phenoxybenzoyl)sulfamoyl]biphenyl-4-yl]methyl]-3H-1,2,4-triazol-3-one The title compound was prepared from 5-n-butyl-2-(2-chloro-5-nitrophenyl)-2,4-dihydro-4-[(2'-sulfamoyl-biphenyl-4-yl)methyl]-3H-1,2,4-triazol-3-one (from Example 59, Step C) and 2-phenoxybenzoic acid (2.5 equivalents), CDI (2.5 equiv), and DBU (2.5 equiv) according to the procedure of Example 51. Flash chromatography of the crude product on silica gel (gradient elution with 0.5–1% MeOH in $CH_2Cl_2$) gave a 55% yield of the desired material as a stiff foam, homogeneous by TLC in 95:5 $CH_2Cl_2$—MeOH; mass spectrum (FAB) m/e 738 (M+1)$^+$.

400 MHz $^1$H NMR ($CDCl_3$) δ0.87 (t, J=7.4 Hz, 3H), 1.34 (m, 2H), 1.57 (m, 2H), 2.41 (t, J=7.6 Hz, 2H), 4.79 (s, 2H), 6.75 (d, J=8.4 Hz, 1H), 7.0–7.7 (m, 15H), 8.07 (dd, J=7.9, 1.8 Hz, 1H), 8.20 (dd, J=8.8, 2.2 Hz, 1H), 8.37 (d, J=2.6 Hz, 1H), 8.41 (dd, J=7.6, 1.6 Hz, 1H), 9.64 (s, 1H).

Step B: 2-[5-Amino-2-chlorophenyl]-5-n-butyl-2,4-dihydro-4-[[2'-[N-(2-phenoxybenzoyl)sulfamoyl]biphenyl-4-yl]methyl]-3H-1,2,4-triazol-3-one Reduction of 5-n-butyl-2-[2-chloro-5-nitrophenyl]-2,4-dihydro-4-[[2'-[N-(2-phenoxybenzoyl)sulfamoyl]-biphenyl-4-yl]methyl]-3H-1,2,4-triazol-3one (from Step A) with stannous chloride according to the procedure of Example 56 gave a 78% yield of the title compound as a foam, homogeneous by TLC in 95:5 $CH_2Cl_2$—MeOH; mass spectrum (FAB) m/e 708 (M+1)$^+$.

400 MHz $^1$H NMR ($CD_3OD$) δ0.88 (t, J=7.3 Hz, 3H), 1.36 (m, 2H), 1.60 (m, 2H), 2.54 (t, J=7.5 Hz, 2H), 4.99 (s, 2H), 6.73–7.52 (m, 19H), 8.18 (d, J=7.9 Hz, 1H).

Step C: 5-n-Butyl-2-[2-chloro-5-(propionylamino)-phenyl]-2,4-dihydro-4-[[2'-[N-(2-phenoxybenzoyl)sulfamoyl]biphenyl-4-yl]methyl]-3H-1,2,4-triazol-3-one By the procedure of Example 69, 2-[5-amino-2-chlorophenyl]-5-n-butyl-2,4-dihydro-4-[[2'-[N-(2-phenoxybenzoyl)sulfamoyl]biphenyl-4-yl]methyl]-3H-1,2,4-triazol-3-one (from Step B) was reacted with propionyl bromide in the presence of DMAP. The crude product was reconcentrated from toluene and flash chromatographed on silica gel (gradient elution with 1–2% MeOH in $CH_2Cl_2$) to give a 65% yield of the title compound as a stiff foam, mp 113°–116° C.; homogeneous by TLC in 9:1 $CH_2Cl_2$; mass spectrum (FAB) m/e 764 (M+1)$^+$.

400 MHz $^1$H NMR ($CDCl_3$) δ0.85 (t, J=7.3 Hz, 3H), 1.18 (t, J=7.5 Hz, 3H), 1.31 (m, 2H), 1.57 (m, 2H), 2.3–2.4 (m, 4H), 4.79 (s, 2H), 6.74 (d, J=8.1 Hz, 1H), 6.98–7.65 (m, 17H), 7.77 (br s 1H), 8.06 (dd, J=8.0, 1.8 Hz, 1H), 8.41 (dd, J=7.8, 1.6 Hz, 1H), 9.63 (s, 1H).

EXAMPLE 72

5-n-Butyl-2-[2-chloro-5-(propionylamino)phenyl]-4-[[2'-[N-(3,4-dichloro-2-furoyl)sulfamoyl]biphenyl-4-yl]methyl]-2,4-dihydro-3H-1,2,4-triazol-3-one The title compound was prepared according to the methods of Example 71, except that 3,4-dichloro-2-furoic acid was substituted for 2-phenoxybenzoic acid in Step A. The material was obtained as a solid, mp 223°–226° C.; homogeneous by TLC in 9:1 $CH_2Cl_2$; mass spectrum (FAB) m/e 769 (M+K)$^+$.

400 MHz $^1$H NMR ($CD_3OD$) δ0.89 (t, J=7.4 Hz, 3H), 1.18 (t, J=7.6 Hz, 3H), 1.38 (m, 2H), 1.61 (m, 2H), 2.38 (q, J=7.6 Hz, 2H), 2.58 (t, J=7.5 Hz, 2H), 4.95 (s, 2H), 7.19 (d, J=8.3 Hz, 2H), 7.24 (dd, J=7.5, 1.3 Hz, 1H), 7.41–7.62 (m, 6H), 7.69 (s, 1H), 7.95 (d, J=2.5 Hz, 1H), 8.22 (dd, J=8.0, 1.3 Hz, 1H).

EXAMPLE 73

5-n-Butyl-4-[[2'-[N-(2-chlorobenzoyl)sulfamoyl]-5'-ethylbiphenyl-4-yl]methyl]-2-[2-chloro-5-(propionylamino)phenyl]-2,4-dihydro-3H-1,2,4-triazol-3-one Step A: 5-n-Butyl-4-[[2'-(N-t-butylsulfamoyl)-5'-ethylbiphenyl-4-yl]methyl]-2-[2-chloro-5-nitrophenyl]-2,4-dihydro-3H-1,2,4-triazol-3-one By the procedure of Example 68, Step D, 5-n-butyl-2,4-dihydro-2-[2-(trifluormethyl)phenyl]-3H-1,2,4-triazol-3-one (from Example 59, Step A) was reacted with [2'-(N-t-butylsulfamoyl)-5'-ethylbiphenyl-4-yl]methanol (prepared from 4-ethylbenzenesulfonyl chloride by the methods of Example 68, Steps A–C) in the presence of triphenylphosphine and diisopropyl azodicarboxylate. The crude product was purified by flash chromatography on silica gel (gradient elution with 5:1 to 3:1 hexane-EtOAc) to give a 61% yield of the title compound as a cream-colored solid.

400 MHz NMR ($CDCl_3$) δ0.92 (t, J=7.3 Hz, 3H), 0.98 (s, 9H), 1.25 (t, J=7.6 Hz, 3H), 1.40 (m, 2H), 1.68 (m, 2H), 2.52 (t, J=7.7 Hz, 2H), 2.70 (q, J=7.6 Hz, 2H), 3.48 (s, 1H), 4.95 (s, 2H), 7.09 (m, 1H), 7.26–7.54 (m, 6H), 7.69 (d, J=8.9 Hz, 1H), 8.04 (dd, J=8.2, 2.0 Hz, 1H), 8.21 (dd, J=8.9, 2.7 Hz, 1H), 8.39 (d, J=2.7 Hz, 1H).

Step B: 5-n-Butyl-2-[2-chloro-5-nitrophenyl]-2,4-dihydro-4-[(2'-sulfamoyl-5'-ethylbiphenyl-4-yl)methyl]-3H-1,2,4-triazol-3-one Deprotection of 5-n-butyl-4-[[2'-(N-t-butylsulfamoyl)-5'-ethylbiphenyl-4-yl]methyl]-2-[2-chloro-5-nitrophenyl]-2,4-dihydro-3H-1,2,4-triazol-3-one (from Step A) with trifluoroacetic acid according to the procedure of Example 13, Step B, afforded a 76% yield of the title compound as a cream-colored solid; homogeneous by TLC in 95:5 $CH_2Cl_2$—MeOH; mass spectrum (FAB) m/e 570 (M+1)$^+$.

400 MHz NMR ($CDCl_3$) δ0.91 (t, J=7.3 Hz, 3H), 1.25 (t, J=7.5 Hz, 3H), 1.40 (m, 2H), 1.67 (m, 2H), 2.53 (t, J=7.7 Hz, 2H), 2.71 (q, J=7.5 Hz, 2H), 4.18 (s, 2H), 4.96 (s, 2H), 7.12 (d, J=1.8 Hz, 1H), 7.32 (dd, J=8.5, 1.7 Hz, 1H), 7.38 (d, J=8.1 Hz, 2H), 7.50 (d, J=8.1 Hz, 2H), 7.69 (d, J=8.9 Hz, 1H), 8.05 (d, J=8.2 Hz, 1H), 8.20 (dd, J=8.7, 2.5 Hz, 1H), 8.40 (d, J=2.8 Hz, 1H).

Step C: 5-n-Butyl-4-[[2'-[N-(2-chlorobenzoyl)sulfamoyl]-5'-ethylbiphenyl-4-yl]methyl]-2-(2-chloro-5-nitrophenyl)-2,4-dihydro-3H-1,2,4-triazol-3-one The reaction of 5-n-butyl-2-[2-chloro-5-nitrophenyl]-2,4-dihydro-4-[(2'-sulfamoyl-5'-ethylbiphenyl-4-yl)methyl]-3H-1,2,4-triazol-3-one (from Step B) with 2-chlorobenzoic acid (3 equivalents), CDI (3 equiv), and DBU (3 equiv) was carried out according to the procedure of Example 51 to give an 80% yield of the title compound as a yellow solid; minor impurity by TLC in 95:5 $CH_2Cl_2$—MeOH but suitable for use without further purification; mass spectrum (FAB) m/e 708 $(M+1)^+$.

400 MHz NMR ($CDCl_3$) δ0.91 (t, J=7.3 Hz, 3H), 1.26 (t, J=7.6 Hz, 3H), 1.40 (m, 2H), 1.67 (m, 2H), 2.49 (t, J=7.7 Hz, 2H), 2.73 (q, J=7.6 Hz, 2H), 4.89 (s, 2H), 7.09-7.52 (m, 9H), 7.69 (m, 2H), 8.21 (dd, J=8.9, 2.6 Hz, 1H), 8.26 (d, J=8.3 Hz, 1H), 8.38 (d, J=2.6 Hz, 1H), 8.54 (s, 1H).

Step D: 2-(5-Amino-2-chlorophenyl)-5-n-butyl-4-[[2'-[N-(2-chlorobenzoyl)sulfamoyl]-5'-ethylbiphenyl-4-yl]methyl]-2,4-dihydro-3H-1,2,4-triazol-3-one A mixture of 135 mg (0.191 mmole) of 5-n-butyl-4-[[2'-[N-(2-chlorobenzoyl)sulfamoyl]-5'-ethylbiphenyl-4-yl]methyl]-2-(2-chloro-5-nitrophenyl)-2,4-dihydro-3H-1,2,4-triazol-3-one (from Step C), 10 mg of platinum oxide, and 2 mL of ethyl acetate was stirred under an atmosphere of hydrogen (balloon) for 1 day and then then filtered through Celite. The crude product was chromatographed on a column of silica gel (gradient elution with 0.5-4% MeOH in $CH_2Cl_2$) to give 81 mg (63%) of the title compound; homogeneous by TLC in 9:1$CH_2Cl_2$—MeOH; m/e 678 $(M+1)^+$.

400 MHz NMR ($CD_3OD$) δ0.89 (t, J=7.4 Hz, 3H), 1.28 (t, J=7.6 Hz, 3H), 1.37 (m, 2H), 1.61 (m, 2H), 2.55 (t, J=7.6 Hz, 2H), 2.77 (q, J=7.6 Hz, 2H), 5.01 (s, 2H), 6.77 (m, 2H), 7.1-7.5 (m, 11H), 8.20 (d, J=8.3 Hz, 1H).

Step E: 5-n-Butyl-4-[[2'-[N-(2-chlorobenzoyl)sulfamoyl]-5'-ethylbiphenyl-4-yl]methyl]-2-[2-chloro-5-(propionylamino)phenyl]-2,4-dihydro-3H-1,2,4-triazol-3-one By the procedure of Example 69, 2-(5-amino-2-chlorophenyl)-5-n-butyl-4-[[2'-[N-(2-chlorobenzoyl)sulfamoyl]-5'-ethylbiphenyl-4-yl]methyl]-2,4-dihydro-3H-1,2,4-triazol-3-one (from Step D) was reacted with propionyl bromide in the presence of DMAP. Purification of the crude product by flash chromatography on silica gel (gradient elution with 1-4% MeOH in $CH_2Cl_2$) afforded a 65% yield of the title compound as a cream-colored solid, mp 144°-146° C.; homogeneous by TLC in 9:1 $CH_2Cl_2$—MeOH; m/e 734 $(M+1)^+$.

Analysis: ($C_{37}H_{37}Cl_2N_5O_5S.0.25CH_2Cl_2$) Calcd: C, 59.19; H, 5.00; N, 9.27. Found: C, 58.99; H, 4.84; N, 9.15.

400 MHz NMR ($CD_3OD$) δ0.89 (t, J=7.4 Hz, 3H), 1.18 (t, J=7.6 Hz, 3H), 1.27 (t, J=7.6 Hz, 3H), 1.37 (m, 2H), 1.61 (m, 2H), 2.39 (q, J=7.6 Hz, 2H), 2.56 (t, J=7.5 Hz, 2H), 2.75 (q, J=7.6 Hz, 2H), 5.01 (s, 2H), 7.10-7.16 (m, 2H), 7.26 (m, 1H), 7.3-7.4 (m, 5H), 7.43 (dd, J=8.3, 1.8 Hz, 1H), 7.52 (d, J=8.7 Hz, 2H), 7.63 (dd, J=8.8, 2.5 Hz, 1H), 7.92 (d, J=2.5 Hz, 1H), 8.19 (d, J=8.3 Hz, 1H).

EXAMPLE 74

5-n-Butyl-4-[[2'-[N-(2-chlorobenzoyl)sulfamoyl]-5'-ethylbiphenyl-4-yl]methyl]-2-[2-chloro-5-(valerylamino)phenyl]-2,4-dihydro-3H-1,2,4-triazol-3-one The title compound was prepared as in Example 73, Step E, except that valeryl chloride was substituted for propionyl bromide, giving a 53% yield of glassy white solid, mp 127°-130° C.; homogeneous by TLC in 9:1 $CH_2Cl_2$—MeOH; m/e 762 $(M+1)^+$.

Analysis: ($C_{39}H_{41}Cl_2N_5O_5S.0.25CH_2Cl_2$) Calcd: C, 60.13; H, 5.34; N, 8.93. Found: C, 60.47; H, 5.45; N, 8.71.

400 MHz NMR ($CD_3OD$) δ0.90 (t, J=7.4 Hz, 3H), 0.95 (t, J=7.4 Hz, 3H), 1.28 (t, J=7.6 Hz, 3H), 1.39 (m, 4H), 1.57-1.70 (m, 4H), 2.38 (t, J=7.5 Hz, 2H), 2.56 (t, J=7.6 Hz, 2H), 2.76 (q, J=7.6 Hz, 2H), 5.01 (s, 2H), 7.10-7.17 (m, 2H), 7.25-7.53 (m, 9H), 7.63 (dd, J=8.9, 2.5 Hz, 1H), 7.93 (d, J=2.5 Hz, 1H), 8.19 (d, J=8.3 Hz, 1H).

EXAMPLE 75

5-n-Butyl-4-[[2'-[N-(2-chlorobenzoyl)sulfamoyl]biphenyl-4-yl]methyl]-2,4-dihydro-2-[5-(propionylamino)-2-(trifluoromethyl)phenyl]-3H-1,2,4-triazol-3-one Step A: 2-(2-Bromo-5-nitrophenyl)-5-n-butyl-2,4-dihydro-3H-1,2,4-triazol-3-one By the procedure of Example 4, Step C, the title compound was prepared from 2-bromo-5-nitrophenylhydrazine [generated from the hydrochloride, which was prepared from 2-bromo-5-nitroaniline according to H. Stroh and G. Westphal, Chem. Ber., 96, 184 (1963), by partitioning between ether and 1N sodium carbonate] and ethyl N-carbethoxy-valerimidate (from Example 4, Step B) in 58% yield as a brown solid, mp 125°-127° C.; homogeneous by TLC in 98:2 $CH_2Cl_2$—MeOH; mass spectrum (FAB) m/e 341, 343 $(M+1)^+$.

200 MHz $^1$H NMR ($CDCl_3$) δ0.90 (t, J=7.3 Hz, 3H), 1.37 (m, 2H), 1.66 (m, 2H), 2.57 (t, J=7.6 Hz, 2H), 7.89 (d, J=8.8 Hz, 1H), 8.14 (dd, J=8.8, 2.6 Hz, 1H), 8.34 (d, J=2.6 Hz, 1H), 11.93 (br s, 1H).

Step B: 2-(2-Bromo-5-nitrophenyl)-4-[[2'-(N-t-butylsulfamoyl)biphenyl-4-yl]methyl]-5-n-butyl-2,4-dihydro-3H-1,2,4-triazol-3-one The alkylation of 2-(2-bromo-5-nitrophenyl)-5-n-butyl-2,4-dihydro-3H-1,2,4-triazol-3-one (from Step A) with [2'-(N-t-butylsulfamoyl)-biphenyl-4-yl]methyl bromide (from Example 12, Step D) was carried out according to the procedure of Example 13, Step A, to give a 92% yield of the title compound as a yellow solid, mp 126°-128° C.; homogeneous by TLC in 98:2 $CH_2Cl_2$—MeOH; mass spectrum (FAB) m/e 642, 644 $(M+1)^+$.

400 MHz $^1$H NMR ($CDCl_3$) δ0.91 (t, J=7.3 Hz, 3H), 0.98 (s, 9H), 1.40 (m, 2H), 1.68 (m, 2H), 2.52 (t, J=7.7 Hz, 2H), 3.47 (s, 1H), 4.96 (s, 2H), 7.2-7.6 (m, 7H), 7.89 (d, J=8.8 Hz, 1H), 8.11-8.17 (m, 2H), 8.35 (d, J=2.6 Hz, 1H).

Step C: 5-n-Butyl-4-[[2'-(N-t-butylsulfamoyl)biphenyl-4-yl]methyl]-2,4-dihydro-2-[5-nitro-2-(trifluoromethyl)-phenyl]-3H-1,2,4-triazol-3-one To a solution of 600 mg (0.935 mmol) of 2-(2-bromo-5-nitrophenyl)-4-[[2'-(N-t-butylsulfamoyl)biphenyl-4-yl]methyl]-5-n-butyl-2,4-dihydro-3H-1,2,4-triazol-3-one (from Step B) in 1.87 mL of DMF were added 65 mg (1.12 mmol) of potassium fluoride, 179 mg (0.935 mmol) of cuprous iodide, and 197 μL (270 mg, 1.87 mmol) of methyl chlorodifluoroacetate. The mixture was stirred in a sealed tube at 120° C. for 12 hours. The cooled mixture was diluted with $H_2O$ and extracted 3× with ethyl acetate. The combined organic extracts were washed with $H_2O$, then brine, and dried over $Na_2SO_4$. The residue obtained upon evaporation of the filtered solution was flash chromatographed on silica gel (gradient elution with 8.5:1 to 5:1 hexane-EtOAc) to give 216 mg (37%) of the title compound as a solid, mp 135°–137° C. [Subsequently eluted was 187 mg (32%) of the corresponding 2-chloro-5-nitrophenyl analog, obtained as a byproduct.] The desired product was homogeneous by TLC (98:2 CH$_2$Cl$_2$—MeOH); mass spectrum (FAB) m/e 638 (M+Li)$^+$.

400 MHz $^1$H NMR (CDCl$_3$) δ0.90 (t, J=7.3 Hz, 3H), 0.98 (s, 9H), 1.39 (m, 2H), 1.66 (m, 2H), 2.51 (t, J=7.6 Hz, 2H), 4.96 (s, 2H), 7.25–7.6 (m, 7H), 7.99 (d, J=8.7 Hz, 1H), 8.16 (dd, J=7.8, 1.3 Hz, 1H), 8.36 (dd, J=8.6, 1.5 Hz, 1H), 8.47 (d, J=2.2 Hz, 1H).

Step D: 2-[5-Amino-2-(trifluoromethyl)phenyl]-5-n-butyl-4-[[2'-(N-t-butylsulfamoyl)biphenyl-4-yl]methyl]-2,4-dihydro-3H-1,2,4-triazol-3-one A mixture of 200 mg (0.317 mmole) of 5-n-butyl-4-[[2'-(N-t-butylsulfamoyl)biphenyl-4-yl]methyl]-2,4-dihydro-2-[5-nitro-2-(trifluoromethyl)phenyl] -3H-1,2,4-triazol-3-one (from Step C), 15 mg of platinum oxide, 10 mL of ethyl acetate, and 2 mL of ethanol was shaken with hydrogen at approximately 4 atm for a few hours until complete and then centrifuged. The supernatant was decanted off, and the catalyst pellet was extracted 3× with ethanol in the same manner. The combined supernatant fractions were concentrated to give 190 mg (100%) of the title compound as a brown foam, which was suitable for use without further purification; TLC in 95:5 CH$_2$Cl$_2$—MeOH; mass spectrum (FAB) m/e 608 (M+Li)$^+$.

400 MHz $^1$H NMR (CD$_3$OD) δ0.89 (t, J=7.4 Hz, 3H), 0.99 (s, 9H), 1.37 (m, 2H), 1.59 (m, 2H), 2.58 (t, J=7.5 Hz, 2H), 5.02 (s, 2H), 6.71 (d, J=2.3 Hz, 1H), 6.79 (dd, J=8.6, 1.9 Hz, 1H), 7.29–7.62 (m, 8H), 8.11 (d, J=7.9 Hz, 1H).

Step E: 5-n-Butyl-4-[[2'-(N-t-butylsulfamoyl)biphenyl-4-yl]methyl]-2,4-dihydro-2-[5-(propionylamino)-2-(trifluoromethyl)phenyl]-3H-1,2,4-triazol-3-one Reaction of 2-[5-amino-2-(trifluoromethyl)phenyl]-5-n-butyl-4-[[2'-(N-t-butylsulfamoyl)biphenyl-4-yl]methyl]-2,4-dihydro-3H-1,2,4-triazol-3-one (from Step D) with propionyl bromide (2 equivalents) in the presence of DMAP (1 equiv) according to the procedure of Example 69 gave a 67% yield of the title compound; homogeneous by TLC in 95:5 CH$_2$Cl$_2$—MeOH.

400 MHz $^1$H NMR (CDCl$_3$) δ0.87 (t, J=7.3 Hz, 3H), 0.98 (s, 9H), 1.16 (t, J=7.4 Hz, 3H), 1.35 (m, 2H), 1.6 (m, 2H, partially obscured by H$_2$O peak), 2.32 (q, J=7.4 Hz, 2H), 2.47 (t, J=7.5 Hz, 2H), 3.57 (s, 1H), 4.95 (s, 2H), 7.26 (dd, J=7.5, 1.3 Hz, 1H), 7.33 (d, J=8.1 Hz, 2H), 7.45–7.57 (m, 6H), 7.80 (br, 1H), 8.15 (dd, J=7.9, 1.3 Hz, 1H), 8.33 (br s, 1H).

Step F: 5-n-Butyl-2,4-dihydro-2-[5-(propionylamino)-2-(trifluoromethyl)phenyl]-4-[(2'-sulfamoylbiphenyl]-4-yl)methyl]-3H-1,2,4-triazol-3-one By the procedure of Example 13, Step B, 5-n-butyl-4-[[2'-(N-t-butylsulfamoyl)biphenyl-4-yl]methyl]-2,4-dihydro-2-[5-(propionylamino)-2-(trifluoromethyl)phenyl]-3H-1,2,4-triazol-3-one (from Step E) was deprotected with trifluoroacetic acid. Flash chromatography of the crude product on silica gel gave a 96% yield of the title compound as an off-white foam, homogeneous by TLC in 95:5 CH$_2$Cl$_2$—MeOH; mass spectrum (FAB) m/e 608 (M+Li)$^+$.

400 MHz $^1$H NMR (CDCl$_3$) δ0.87 (t, J=7.3 Hz, 3H), 1.15 (t, J=7.5 Hz, 3H), 1.36 (m, 2H), 1.6 (m, 2H, partially obscured by H$_2$O peak), 2.32 (q, J=7.5 Hz, 2H), 2.50 (t, J=7.6 Hz, 2H), 4.33 (s, 2H), 4.95 (s, 2H), 7.29–7.59 (m, 9H), 7.80 (s, 1H), 8.14 (dd, J=7.9, 1.3 Hz, 1H), 8.34 (s, 1H).

Step G: 5-n-Butyl-4-[[2'-[N-(2-chlorobenzoyl)sulfamoyl]biphenyl-4-yl]methyl]-2,4-dihydro-2-[5-(propionylamino)-2-(trifluoromethyl)phenyl]-3H-1,2,4-triazol-3-one Following the procedure of Example 51, 5-n-butyl-2,4-dihydro-2-[5-(propionylamino)-2-(trifluoromethyl)phenyl]-4-[(2'-sulfamoylbiphenyl-4-yl)methyl]-3H-1,2,4-triazol-3-one (from Step F) was reacted with 2-chlorobenzoic acid (3 equivalents), CDI (3 equiv), and DBU (3 equiv). Flash chromatography of the crude product on silica gel (gradient elution with 0.5–2% MeOH in CH$_2$Cl$_2$) afforded a 50% yield of the title compound as a solid, mp 102°–105° C.; homogeneous by TLC in 9:1 CH$_2$Cl$_2$—MeOH; mass spectrum (FAB) m/e 740 (M+1)$^+$.

400 MHz $^1$H NMR (CDCl$_3$) δ0.85 (t, J=7.3 Hz, 3H), 1.17 (t, J=7.5 Hz, 3H), 1.32 (m, 2H), 1.57 (m, 2H), 2.33–2.43 (m, 4H), 4.79 (s, 2H), 7.17 (d, J=8.1 Hz, 2H), 7.25–7.67 (m, 10H), 7.78 (d, J=8.7 Hz, 1H), 7.95 (d, J=8.5 Hz, 1H), 8.39 (dd, J=7.9, 1.4 Hz, 1H), 9.58 (br s, 1H).

EXAMPLE 76

5-n-Butyl-2-[5-(N-n-butylcarbamoyl)-2-chlorophenyl]4-[[2'-[N-(2-chloro-benzoyl)sulfamoyl]-3-fluorobiphenyl-4-yl]methyl]-2,4-dihydro-3H-1,2,4-triazol-3-one Step A: Methyl 3-Amino-4-chlorobenzoate To a solution of 2 mL of concentrated sulfuric acid in 50 mL of methanol was added 7.0 g (41 mmole) of 2-amino-3-chlorobenzoic acid, and the mixture was stirred under gentle reflux for 24 hours. The cooled solution was partially evaporated to remove most of the methanol, and the residue was partitioned between ethyl acetate and water. The organic layer was washed successively with 5% NaHCO$_3$ (aqueous), water, and brine. The ethyl acetate phase was then dried over Na$_2$SO$_4$, filtered, and concentrated to yield 7 g (92%) of the title compound as a solid, mp 83°–84° C.; homogeneous by TLC in 98:2 CH$_2$Cl$_2$—MeOH.

200 MHz $^1$H NMR (CDCl$_3$) δ3.89 (s, 3H, superimposed on v br mound, 2H), 7.2–7.5 (m, 3H).

Step B: Methyl 4-Chloro-3-hydrazinobenzoate

A solution of 11.9 g (63.9 mmole) of methyl 3-amino-4-chlorobenzoate (prepared as in Step A) was maintained at −5° to +5° C. and subjected to vigorous mechanical stirring as a solution of 4.41 g (63.9 mmole) of sodium nitrite in 19.3 mL of H$_2$O was added slowly via a dropping funnel. Stirring was continued at this temperature for 1 hour, and the mixture was filtered while cold. The filtrate was immediately added to a rapidly stirred solution of 28.8 g (128 mmole) of stannous chloride dihydrate in 37.3 mL of concentrated HCl, which was also maintained at >0° C. Precipitation of a cream-colored solid began at once. After being stirred at 0° C. for 0.5 hour, the mixture was refrigerated overnight. The solid was collected on a filter and triturated with ether to give, after air-drying, approximately 22 g of cream-colored solid (mp 218°–220° C.), which was stored in the freezer. As needed, a portion of this hydrochloride salt was partitioned between 5% NaHCO$_3$ (aqueous) and a mixture of CH$_2$Cl$_2$ and ethyl acetate to liberate the title compound as the free base, which was isolated by concentration of the organic phase to give a cream-colored solid, homogeneous by TLC (95:5 CH$_2$Cl$_2$—MeOH); mass spectrum (EI) m/e 200 (M$^+$). This material was used immediately in the next reaction.

200 MHz $^1$H NMR (CDCl$_3$ doped with CD$_3$OD) δ3.85 (s, 3H), 7.2–7.6 (m, 3H).

Step C: 5-n-Butyl-2-[2-chloro-5-(methoxycarbonyl)-phenyl]-2,4-dihydro-3H-1,2,4-triazol-3-one By the procedure of Example 4, Step C, the title compound was prepared from methyl 4-chloro-3-hydrazinobenzoate (from Step B) and ethyl N-carbethoxyvalerimidate (from Example 4, Step B) in 37% yield as an orange gum (TLC in 95:5 CH$_2$Cl$_2$—MeOH), mass spectrum (FAB) m/e 310 (M+1)$^+$.

400 MHz $^1$H NMR (CDCl$_3$) δ0.87 (t, J=7.3 Hz, 3H), 1.34 (m, 2H), 1.61 (m, 2H), 2.53 (t, J=7.7 Hz, 2H), 3.90 (s, 3H), 7.58 (d, J=8.4 Hz, 1H), 8.01 (dd, J=8.4, 2 Hz, 1H), 8.13 (d, J=2 Hz, 1H), 11.96 (s, 1H).

Step D: 4-(4-Bromo-2-fluorobenzyl)-5-n-butyl-2-[2-chloro-5-(methoxycarbonyl)phenyl]-2,4-dihydro-3H-1,2,4-triazol-3-one A mixture of 789 mg (2.55 mmole) of 5-n-butyl-2-[2-chloro-5-(methoxycarbonyl)phenyl]-2,4-dihydro-3H-1,2,4-triazol-3-one (from Step C), 122.4 mg (3.06 mmole) of sodium hydride (60% in oil), and 2 mL of dry DMF was stirred at 50° C. for 2.5 hours, during which time hydrogen was evolved. A solution of 820 mg (3.06 mmole) of 4-bromo-2-fluorobenzyl bromide in DMF was added, and the mixture was stirred at 50° C. overnight. The cooled reaction mixture was diluted with H$_2$O and extracted twice with ethyl acetate. The combined organic phase was washed with H$_2$O and brine and then dried over Na$_2$SO$_4$. The filtered solution was concentrated, and the residue was flash chromatographed on 250 cc of silica gel packed in hexane (gradient elution with 6:1 to 5:1 hexane-EtOAc; some unreacted starting material was recovered by further elution with 95:5 CH$_2$Cl$_2$—MeOH), yielding 503 mg (40%) of the title compound as an orange gum (TLC in 4:1 hexane-EtOAc), mass spectrum (FAB) m/e 496, 498 (M+1)$^+$.

400 MHz $^1$H NMR (CDCl$_3$) δ0.87 (t, J=7.4 Hz, 3H), 1.36 (m, 2H), 1.62 (m, 2H), 2.48 (t, J=7.7 Hz, 2H), 3.88 (s, 3H), 4.87 (s, 2H), 7.2–7.3 (m, 3H), 7.55 (d, J=8.4 Hz, 1H), 7.98 (dd, J=8.4, 1.0 Hz, 1H), 8.11 (d, J=1.0 Hz, 1H).

Step E: 4-(4-Bromo-2-fluorobenzyl)-5-n-butyl-2-[5-(N-n-butylcarbamoyl)-2-chloro-phenyl]-2,4-dihydro-3H-1,2,4-triazol-3-one A solution of 50 mg (0.10 mmole) of 4-(4-bromo-2-fluorobenzyl)-5-n-butyl-2-[2-chloro-5-(methoxycarbonyl)phenyl]-2,4-dihydro-3H-1,2,4-triazol-3-one (from Step D) in 1 mL of n-butylamine was stirred overnight at 65° C. and then evaporated in vacuo. The residue was flash chromatographed on 15 cc of silica gel (gradient elution with 1–5% MeOH in CH$_2$Cl$_2$) to yield 41 mg (76%) of colorless, glassy solid, mp 114°–116° C.; homogeneous by TLC (95:5 CH$_2$Cl$_2$—MeOH); mass spectrum (FAB) m/e 537, 539 (M+1)$^+$.

400 MHz $^1$H NMR (CDCl$_3$) δ0.88 (t, J=7.4 Hz, 3H), 0.94 (t, J=7.3 Hz, 3H), 1.38 (m, 4H), 1.58 (m, 4H), 2.58 (t, J=7.5 Hz, 2H), 3.35 (t, J=7.2 Hz, 2H), 4.98 (s, 2H), 7.25 (dd, J=8, 8 Hz, 1H), 7.35–7.45 (m, 2H), 7.67 (d, J=8.4 Hz, 1H), 7.89 (dd, J=8.4, 2.2 Hz, 1H), 7.96 (d, J=2.2 Hz, 1H).

Step F: 5-n-Butyl-2-[5-(N-n-butylcarbamoyl)-2-chlorophenyl]-4-[[2'-(N-t-butylsulfamoyl)-3-fluorobiphenyl-4-yl]methyl]-2,4-dihydro-3H-1,2,4-triazol-3-one A solution of 41 mg (0.076 mmole) of 4-(4-bromo-2-fluorobenzyl)-5-n-butyl-2-[5-(N-n-butylcarbamoyl)-2-chlorophenyl]-2,4-dihydro-3H-1,2,4-triazol-3-one (from Step E) in 1 mL of toluene was treated with 39.2 mg (0.153 mmole) of 2-(N-t-butylsulfamoyl)phenylboronic acid (prepared from benzenesulfonyl chloride according to the procedures of Example 68, Steps A and B) in 157 μL of ethanol, followed by an additional 0.5 mL of ethanol, 0.24 mL (0.305 mmole) of 1.25 N sodium hydroxide (aqueous), and 4.4 mg 0.0038 mmole) of tetrakis(triphenylphosphine)-palladium(0). The mixture was stirred at 90° C. for 6 hours and then concentrated. The residue was taken up in ethyl acetate and washed with H$_2$O and then brine. The organic phase was dried over Na$_2$SO$_4$, filtered, and concentrated. The crude product was purified by flash chromatography on 15 cc of silica gel (gradient elution with 0.5–2% MeOH in CH$_2$Cl$_2$), yielding 36 mg (71%) of white solid, mp 84°–86° C.; TLC in 95:5 CH$_2$Cl$_2$—MeOH; mass spectrum (FAB) m/e 676 (M+Li)$^+$.

400 MHz $^1$H NMR (CD$_3$OD) δ0.9–1.0 (m, 6H), 1.04 (s, 9H), 1.35–1.46 (m, 4H), 1.59 (m, 2H), 1.61 (m, 2H), 2.66 (t, J=7.6 Hz, 2H), 3.37 (t, J=7.2 Hz, 2H), 5.10 (s, 2H), 7.25–7.66 (m, 6H), 7.67 (d, J=8.4 Hz, 1H), 7.92 (dd, J=8.4, 2.2 Hz, 1H), 7.98 (d, J=2.2 Hz, 1H), 8.11 (d, J=8 Hz, 1H).

Step G: 5-n-Butyl-2-[5-(N-n-butylcarbamoyl)-2-chlorophenyl]-4-[(3-fluoro-2'-sulfamoylbiphenyl-4-yl)methyl]-2,4-dihydro-3H-1,2,4-triazol-3-one A solution of 32 mg (0.048 mmole) of 5-n-butyl-2-[5-(N-n-butylcarbamoyl)-2-chlorophenyl]-4-[[2'-(N-t-butylsulfamoyl)-3-fluorobiphenyl-4-yl]methyl]-2,4-dihydro-3H-1,2,4-triazol-3-one (from Step F) in 0.5 mL of trifluoroacetic acid (TFA) containing 2 drops of anisole was stirred overnight at room temperature. The excess TFA was removed by evaporation under a gentle stream of N$_2$. The residue was reconcentrated from toluene twice in vacuo and flash chromatographed over 15 cc of silica gel (gradient elution with 0.5–2% MeOH in CH$_2$Cl$_2$) to give 20 mg (69%) of the title compound as a white solid, mp 108°–110° C.; homogeneous by TLC (95:5 CH$_2$Cl$_2$—MeOH); mass spectrum (FAB) m/e 614 (M+1)$^+$.

400 MHz $^1$H NMR (CD$_3$OD) δ0.92, 0.96 (overlapping t, J=7.4 Hz, 6H total), 1.41 (m, 4H), 1.59, 1.65 (overlapping m, 4H total), 2.65 (t, J=7.6 Hz, 2H), 3.37 (t, J=7.1 Hz, 2H), 5.10 (s, 2H), 7.23–7.36 (m, 4H), 7.53–7.64 (m, 2H), 7.71 (d, J=8.4 Hz, 1H), 7.92 (dd, J=8.4, 2.2 Hz, 1H), 7.98 (d, J=2.2 Hz, 1H), 8.11 (d, J=8 Hz, 1H).

Step H: 5-n-Butyl-2-[5-(N-n-butylcarbamoyl)-2-chlorophenyl]-4-[[2'-[N-(2-chlorobenzoyl)sulfamoyl]-3-fluorobiphenyl-4-yl]methyl]-2,4-dihydro-3H-1,2,4-triazol-3-one By the procedure of Example 51, 5-n-butyl-2-[5-(N-n-butylcarbamoyl)-2-chlorophenyl]-4-[(3-fluoro-2'-sulfamoylbiphenyl-4-yl)methyl]-2,4-dihydro-3H-1,2,4-triazol-3-one (from Step G) was reacted with 2-chlorobenzoic acid (2 equivalents), CDI (2 equiv), and DBU (2 equiv). Flash chromatography of the crude product on silica gel (gradient elution with 0.5–5% MeOH in CH$_2$Cl$_2$) followed by trituration with ether afforded a 42% yield of the title compound as a white solid, mp 218°–220° C.; homogeneous by TLC (95:5 CH$_2$Cl$_2$—MeOH); mass spectrum (FAB) m/e 753 (M+1)$^+$.

400 MHz $^1$H NMR (CD$_3$OD doped with CDCl$_3$) d 0.92, 0.96 (overlapping t, J≈7.4 Hz, 6H total), 1.40 (m, 4H), 1.59, 1.65 (overlapping m, 4H total), 2.61 (t, J=7.6 Hz, 2H), 3.37 (m, 2H), 5.06 (s, 2H), 7.19–7.48 (m, 7H), 7.62–7.80 (m, 4H), 7.92 (dd, J=8.4, 2.1 Hz, 1H), 7.96 (d, J=2.1 Hz, 1H), 8.29 (d, J=8 Hz, 1H), 8.63 (br t, J=5.4 Hz).

EXAMPLE 77

5-n-Butyl-4-[[2'-[N-(2-chlorobenzoyl)sulfamoyl]-3-fluorobiphenyl-4-yl]methyl]-2,4-dihydro-2-[2-(trifluoromethyl)phenyl]-3H-1,2,4-triazol-3-one The title compound was prepared from 5-n-butyl-2,4-dihydro-2-[2-(trifluoromethyl)phenyl]-3H-1,2,4-triazol-3-one (from Example 16, Step A) by a sequence analogous to Example 76, Steps D–H. The material was obtained in 43% yield as a white, stiff foam, mp 88°–90° C.; homogeneous by TLC in 95:5 $CH_2Cl_2$—MeOH; mass spectrum (FAB) m/e 687 $(M+1)^+$.

400 MHz $^1H$ NMR (CDCl$_3$) δ0.90 (t, J=7.3 Hz, 3H), 1.38 (m, 2H), 1.65 (m, 2H), 2.51 (t, J=7.6 Hz, 2H), 4.92 (s, 2H), 7.11–7.69 (m, 13H), 7.77 (d, J=7.7 Hz, 1H), 8.38 (dd, J=7.8, 1.4 Hz, 1H), 8.9 (br mound, 1H).

EXAMPLE 78

5-n-Butyl-4-[[2'-[N-(2-chlorobenzoyl)sulfamoyl]-3-fluoro-5'-n-propylbiphenyl-4-yl]methyl]-2,4-dihydro-2-[2-(trifluoromethyl)phenyl]-3H-1,2,4-triazol-3-one The title compound was prepared analogously to Example 77, except that 2-(N-t-butylsulfamoyl)-5-n-propylphenylboronic acid (from Example 68, Step B) was substituted for 2-(N-t-butylsulfamoyl)phenylboronic acid in the palladium-catalyzed biaryl coupling step. The material was obtained in 47% yield as a solid, mp 79°–82° C.; TLC in 95:5 $CH_2Cl_2$—MeOH; mass spectrum (FAB) m/e 729 $(M+1)^+$.

400 MHz $^1H$ NMR (CDCl$_3$) δ0.90 (t, J=7.3 Hz, 3H), 0.94 (t, J=7.3 Hz, 3H), 1.38 (m, 2H), 1.66 (m, 4H), 2.51 (t, J=7.6 Hz, 2H), 2.66 (t, J=7.7 Hz, 2H), 4.92 (s, 2H), 7.07 (d, J=1.8 Hz, 1H), 7.11–7.68 (m, 11H), 7.77 (d, J=7.2 Hz, 1H), 8.27 (d, J=8.3 Hz, 1H), 8.86 (br s, 1H).

EXAMPLE 79

5-n-Butyl-4-[[2'-[N-(2-chlorobenzoyl)sulfamoyl]-3-fluorobiphenyl-4-yl]methyl]-2-[2-chloro-5-(propionylamino)phenyl]-2,4-dihydro-3H-1,2,4-triazol-3-one Step A: 4-(4-Bromo-2-fluorobenzyl)-5-n-butyl-2-(2-chloro-5-nitrophenyl)-2,4-dihydro-3H-1,2,4-triazol-3-one By the procedure of Example 76, Step D, 5-n-butyl-2-(2-chloro-5-nitrophenyl)-2,4-dihydro-3H-1,2,4-triazol-3-one (from Example 59, Step A) was alkylated with 4-bromo-2-fluorobenzyl bromide to give a 79% yield of the title compound as an off-white foam, homogeneous by TLC in 4:1 hexane-EtOAc; mass spectrum (FAB) m/e 483, 485 $(M+1)^+$.

400 MHz $^1H$ NMR (CDCl$_3$) δ0.91 (t, J=7.3 Hz, 3H), 1.40 (m, 2H), 1.65 (m, 2H), 2.52 (t, J=7.7 Hz, 2H), 4.89 (s, 2H), 7.24–7.32 (m, 3H), 7.68 (d, J=8.8 Hz, 1H), 8.19 (dd, J=8.8, 2.6 Hz, 1H), 8.36 (d, J=2.6 Hz, 1H).

Step B: 5-n-Butyl-4-[[2'-(N-t-butylsulfamoyl)-3-fluorobiphenyl-4-yl]methyl]-2-(2-chloro-5-nitrophenyl)-2,4-dihydro-3H-1,2,4-triazol-3-one The palladium(0)-catalyzed coupling of 4-(4-bromo-2-fluorobenzyl)-5-n-butyl-2-(2-chloro-5-nitrophenyl)-2,4-dihydro-3H-1,2,4-triazol-3-one (from Step A) with 2-(N-t-butylsulfamoyl)phenylboronic acid was carried out according to the procedure of Example 76, Step F. Purification of the crude product by flash chromatography on silica gel (gradient elution with 6:1 to 4:1 hexane-EtOAc) provided a 52% yield of the title compound as a pale yellow, stiff foam, mp 124°–126° C.; homogeneous by TLC in 4:1 hexane-EtOAc); mass spectrum (FAB) m/e 616 $(M+1)^+$.

400 MHz $^1H$ NMR (CDCl$_3$) δ0.93 (t, J=7.3 Hz, 3H), 1.03 (s, 9H), 1.43 (m, 2H), 1.70 (m, 2H), 2.59 (t, J=7.7 Hz, 2H), 3.62 (s, 1H), 5.00 (s, 2H), 7.2–7.6 (m, 6H), 7.69 (d, J=8.8 Hz, 1H), 8.15 (dd, J=7.8, 1.3 Hz, 1H), 8.20 (dd, J=8.8, 2.6 Hz, 1H), 8.38 (d, J=2.6 Hz, 1H).

Step C: 2-(5-Amino-2-chlorophenyl)-5-n-butyl-4-[[2'-(N-t-butylsulfamoyl)-3-fluorobiphenyl-4-yl]methyl]-2,4-dihydro-3H-1,2,4-triazol-3-one By the method of Example 73, Step D, 5-n-butyl-4-[[2'-(N-t-butylsulfamoyl)-3-fluorobiphenyl-4-yl]methyl]-2-(2-chloro-5-nitrophenyl)-2,4-dihydro-3H-1,2,4-triazol-3-one (from Step B) was hydrogenated to give a 78% yield of the title compound as an off-white, stiff foam, mp 167°–170° C.; homogeneous by TLC in 1:1 hexane-EtOAc; mass spectrum (FAB) m/e 586 $(M+1)^+$.

400 MHz $^1H$ NMR ((CDCl$_3$) δ0.90 (t, J=7.3 Hz, 3H), 1.00 (s, 9H), 1.39 (m, 2H), 1.66 (m, 2H), 2.53 (t, J=7.7 Hz, 2H), 3.74 (s, 1H), 4.98 (s, 2H), 6.68 (br m, 1H), 6.85 (br m, 1H), 7.19–7.30 (m, 4H), 7.38–7.56 (m, 3H), 8.14 (dd, J=7.9, 1.4 Hz, 1H).

Step D: 5-n-Butyl-4-[[2'-(N-t-butylsulfamoyl)-3-fluorobiphenyl-4-yl]methyl]-2-[2-chloro-5-(propionylamino)phenyl]-2,4-dihydro-3H-1,2,4-triazol-3-one Propionyl bromide was reacted with 2(5-amino-2-chlorophenyl)-5-n-butyl-4-[[2'-(N-t-butylsulfamoyl)-3-fluorobiphenyl-4-yl]methyl]-2,4-dihydro-3H-1,2,4-triazol-3-one (from Step C) in the presence of DMAP according to the procedure of Example 69. Flash chromatography of the crude product on silica gel (gradient elution with 3:1 to 1:1 hexane-EtOAc) gave an 84% yield of the title compound as a white solid, mp 103°–105° C.; homogeneous by TLC (1:1 hexane-EtOAc); mass spectrum (FAB) m/e 648 $(M+Li)^+$.

400 MHz $^1H$ NMR (CDCl$_3$) δ0.91 (t, J=7.3 Hz, 3H), 1.02 (s, 9H), 1.19 (t, J=7.5 Hz, 3H), 1.40 (m, 2H), 1.65 (m, 2H), 2.35 (q, J=7.5 Hz, 2H), 2.55 (t, J=7.7 Hz, 2H), 3.67 (s, 1H), 5.00 (s, 2H), 7.23–7.58 (m, 8H), 7.71 (d, J=2.5 Hz, 1H), 8.15 (dd, J=7.9, 1.3 Hz, 1H).

Step E: 5-n-Butyl-2-[2-chloro-5-(propionylamino)phenyl]-2,4-dihydro-4-[(3-fluoro-2'-sulfamoylbiphenyl--4-yl)methyl]-3H-1,2,4-triazol-3-one The title compound was prepared in 90% yield by deprotection of 5-n-butyl-4-[[2'-(N-t-butylsulfamoyl)-3-fluorobiphenyl-4-yl]methyl]-2-[2-chloro-5-(propionylamino)phenyl]-2,4-dihydro-3H-1,2,4-triazol-3-one (from Step D) with trifluoroacetic acid in the presence of anisole according to the procedure of Example 76, Step G. The material was obtained as a white solid, mp 135°–137° C.; satisfactory purity by TLC (95:5 $CH_2Cl_2$—MeOH); mass spectrum (FAB) m/e 586 $(M+1)^+$.

400 MHz $^1H$ NMR (CDCl$_3$) δ0.91 (t, J=7.4 Hz, 3H), 1.17 (t, J=7.5 Hz, 3H), 1.40 (m, 2H), 1.67 (m, 2H), 2.33 (q, J=7.5 Hz, 2H), 2.57 (t, J=7.7 Hz, 2H), 4.48.(br s, 2H), 4.99 (s, 2H), 7.2–7.6 (m, 8H), 7.71 (d, J=2.3 Hz, 1H), 7.75 (br s, 1H), 8.14 (dd, J=7.9, 1.3 Hz, 1H).

Step F: 5-n-Butyl-4-[[2'-[N-(2-chlorobenzoyl)sulfamoyl]-3-fluorobiphenyl-4-yl]methyl]-2-[2-chloro-5-(propionylamino)-phenyl]-2,4-dihydro-3H-1,2,4-triazol-3-one Following the procedure of Example 51, 5-n-butyl-2-[2-chloro-5-(propionylamino)phenyl]-2,4-dihydro-4-[(3-fluoro-2'-sulfamoylbiphenyl-4-yl)methyl]-3H-1,2,4-triazol-3-one (from Step E) was reacted with 2-chlorobenzoic acid (2 equivalents), CDI (2 equiv), and DBU (2 equiv). Purification of the crude product by flash chromatography on silica gel (gradient elution with 1–5% MeOH in CH$_2$Cl$_2$) gave a 65% yield of the title compound as a white solid, mp >152° C. (gradual); homogeneous by TLC in 95:5 CH$_2$Cl$_2$—MeOH; mass spectrum (FAB) m/e 762 (M+K)$^+$.

400 MHz $^1$H NMR (CD$_3$OD) δ0.91 (t, J=7.4 Hz, 3H), 1.18 (t, J=7.6 Hz, 3H), 1.40 (m, 2H), 1.64 (m, 2H), 2.39 (q, J=7.6 Hz, 2H), 2.59 (t, J=7.5 Hz, 2H), 5.05 (s, 2H), 7.18–7.70 (m, 12H), 7.90 (d, J=2.5 Hz, 1H), 8.29 (d, J=7.9 Hz, 1H).

EXAMPLE 80

5-n-Butyl-2-[2-chloro-5-(propionylamino)phenyl]-4-[[2'-[N-(2,5-dichlorobenzoyl)sulfamoyl]-3-fluorobiphenyl-4-yl]methyl]-2,4-dihydro-3H-1,2,4-triazol-3-one The title compound was prepared according to the methods of Example 79, except that 2,5-dichlorobenzoic acid was substituted for 2-chlorobenzoic acid in the final step. The material was obtained in 60% yield as a white solid, mp 169°–172° C.; homogeneous by TLC in 9:1 CH$_2$Cl$_2$—MeOH; mass spectrum (FAB) m/e 797 (M+K)$^+$.

400 MHz $^1$H NMR (CD$_3$OD) δ0.91 (t, J=7.4 Hz, 3H), 1.18 (t, J=7.6 Hz, 3H), 1.39 (m, 2H), 1.63 (m, 2H), 2.39 (q, J=7.6 Hz, 2H), 2.59 (t, J=7.6 Hz, 2H), 5.07 (s, 2H), 7.19 (s, 1H), 7.30–7.69 (m, 9H), 7.74 (s, 1H), 7.90 (d, J=2.5 Hz, 1H), 8.28 (d, J=7.9 Hz, 1H).

EXAMPLE 81

5-n-Butyl-4-[[2'-[N-(2-chloro-6-fluorobenzoyl)sulfamoyl]-3-fluorobiphenyl-4-yl]methyl]-2-[2-chloro-5(propionylamino)phenyl]-2,4-dihydro-3H-1,2,4-triazol-3-one The title compound was prepared according to the methods of Example 79, except that 2-chloro-6-fluorobenzoic acid (with the addition of 3 equivalents of DMAP) was substituted for 2-chlorobenzoic acid in the final step. The material was obtained in 80% yield as a white solid, mp 200°–203° C.; homogeneous by TLC in 9:1 CH$_2$Cl$_2$—MeOH; mass spectrum (FAB) m/e 780 (M+K)$^+$.

400 MHz $^1$H NMR (CD$_3$OD) δ0.91 (t, J=7.3 Hz, 3H), 1.18 (t, J=7.6 Hz, 3H), 1.40 (m, 2H), 1.63 (m, 2H), 2.39 (q, J=7.6 Hz, 2H), 2.59 (t, J=7.5 Hz, 2H), 5.04 (s, 2H), 7.06 (dd, J=8.7, 8.7 Hz, 1H), 7.19 (d, J=8.0 Hz, 1H), 7.24–7.38 (m, 5H), 7.48–7.67 (m, 4H), 7.87 (d, J=2.5 Hz, 1H), 8.29 (d, J=7.1 Hz, 1H).

EXAMPLE 82

2-[5-(Acetylamino)-2-chlorophenyl]-5-n-butyl-4-[[2'-[N-(2-chlorobenzoyl)-sulfamoyl]-3-fluoro-5'-n-propylbiphenyl-4-yl]methyl]-2,4-dihydro-3H-1,2,4-triazol-3-one Step A: 4-(4-Bromo-2-fluorobenzyl)-5-n-butyl-2-(2-chloro-5-nitrophenyl)-2,4-dihydro-3H-1,2,4-triazol-3-one By the procedure of Example 76, Step D, 5-n-butyl-2-(2-chloro-5-nitrophenyl)-2,4-dihydro-3H-1,2,4-triazol-3-one (from Example 59, Step A) was alkylated with 4-bromo-2-fluorobenzyl bromide to give a 79% yield of the title compound as an off-white foam, homogeneous by TLC in 4:1 hexane-EtOAc; mass spectrum (FAB) m/e 483, 485 (M+1)$^+$.

400 MHz $^1$H NMR (CDCl$_3$) δ0.91 (t, J=7.3 Hz, 3H), 1.40 (m, 2H), 1.65 (m, 2H), 2.52 (t, J=7.7 Hz, 2H), 4.89 (s, 2H), 7.24–7.32 (m, 3H), 7.68 (d, J=8.8 Hz, 1H), 8.19 (dd, J=8.8, 2.6 Hz, 1H), 8.36 (d, J=2.6 Hz, 1H).

Step B: 5-n-Butyl-4-[[2'-(N-t-butylsulfamoyl)-3-fluoro-5'-n-propylbiphenyl-4-yl]methyl]-2-(2-chloro-5-nitrophenyl)-2,4-dihydro-3H-1,2,4-triazol-3-one Using the method of Example 76, Step F, 4-(4-bromo-2-fluorobenzyl)-5-n-butyl-2-(2-chloro-5-nitrophenyl)-2,4-dihydro-3H-1,2,4-triazol-3-one (from Step A) was coupled with 2-(N-t-butylsulfamoyl)-5-n-propylphenylboronic acid (from Example 68, Step B). Flash chromatography of the crude product on silica gel (gradient elution with 6:1 to 2:1 hexane-EtOAc) gave a 43% yield of the title compound as a cream-colored solid, mp 84°–86° C.; homogeneous by TLC (4:1 hexane-EtOAc).

400 MHz $^1$H NMR (CDCl$_3$) δ0.91 (m, 6H), 1.01 (s, 9H), 1.41 (m, 2H), 1.58–1.72 (m, 4H), 2.54–2.64 (m, 4H), 3.62 (s, 1H), 4.98 (s, 2H), 7.04 (d, J=1.7 Hz, 1H), 7.23–7.31 (m, 3H), 7.42 (dd, J=7.8, 7.8 Hz, 1H), 7.67 (d, J=8.9 Hz, 1H), 8.01 (d, J=8.2 Hz, 1H), 8.17 (dd, J=8.9, 2.7 Hz, 1H), 8.37 (d, J=2.7 Hz, 1H).

Step C: 2-(5-Amino-2-chlorophenyl)-5-n-butyl-4-[[2'-(N-t-butylsulfamoyl)-3-fluoro-5'-n-propylbiphenyl-4-yl]methyl]-2,4-dihydro-3H-1,2,4-triazol-3-one By the procedure of Example 73, Step D, 5-n-butyl-4-[[2'-(N-t-butylsulfamoyl)-3-fluoro-5'-n-propylbiphenyl-4-yl]methyl]-2-(2-chloro-5-nitrophenyl)-2,4-dihydro-3H-1,2,4-triazol-3-one (from Step B) was hydrogenated to give the title compound as a cream-colored solid, mp 85°–87° C.; satisfactory purity by TLC in 95:5 CH$_2$Cl$_2$—MeOH.

400 MHz $^1$H NMR (CD$_3$OD) δ0.92, 0.95 (overlapping t, 6H total), 1.02 (s, 9H), 1.41 (m, 2H), 1.61–1.72 (m, 4H), 2.61–2.70 (m, 4H), 5.08 (s, 2H), 6.73–6.78 (m, 2H), 7.13 (d, J=1.8 Hz, 1H), 7.20–7.38 (m, 5H), 8.37 (dd, J=8.3, 2.5 Hz, 1H).

Step D: 2-[5-(Acetylamino)-2-chlorophenyl]-5-n-butyl-4-[[2'-(N-t-butylsulfamoyl)-3-fluoro-5'-n-propylbiphenyl-4-yl]methyl]-2,4-dihydro-3H-1,2,4-triazol-3-one The reaction of 2-(5-amino-2-chlorophenyl)-5-n-butyl-4-[[2'-(N-t-butylsulfamoyl)-3-fluoro-5'-n-propylbiphenyl-4-yl]methyl]-2,4-dihydro-3H-1,2,4-triazol-3-one (from Step C) with acetyl chloride was carried out according to the procedure of Example 69, affording an 88% yield of the title compound as a cream-colored solid, mp 125°–128° C.; satisfactory purity by TLC in 95:5 CH$_2$Cl$_2$—MeOH; mass spectrum (FAB) m/e 676 (M+Li)$^+$.

400 MHz $^1$H NMR (CD$_3$OD) δ0.93, 0.95 (overlapping t, 6H total), 1.03 (s, 9H), 1.43 (m, 2H), 1.67 (m, 4H), 2.13 (s, 3H), 2.63–2.70 (m, 4H), 5.09 (s, 2H), 7.14 (d, J=1.8 Hz, 1H), 7.24–7.38 (m, 4H), 7.51 (d, J=8.8 Hz, 1H), 7.61 (dd, J=8.8, 2.6 Hz, 1H), 7.90 (d, J=2.5 Hz, 1H), 8.01 (d, J=8.2 Hz, 1H).

Step E: 2-[5-(Acetylamino)-2-chlorophenyl]-5-n-butyl-2,4-dihydro-4-[(3-fluoro-5'-n-propyl-2'-sulfamoylbiphenyl-4-yl)methyl]-3H-1,2,4-triazol-3-one Deprotection of 2-[5-(acetylamino)-2-chlorophenyl]-5-n-butyl-4-[[2'-(N-t-butylsulfamoyl)-3-fluoro-5'-n-propylbiphenyl-4-yl]methyl]-2,4-dihydro-3H-1,2,4-triazol-3-one (from Step D) with trifluoroacetic acid according to the procedure of Example 76, Step G, gave an 88% yield of the title compound as a white powder, mp 149°–152° C.; homogeneous by TLC (95:5

CH$_2$Cl$_2$—MeOH); mass spectrum (FAB) m/e 614 (M+1)$^+$.

400 MHz $^1$H NMR (CD$_3$OD) δ0.92, 0.95 (overlapping t, J=7.3 Hz, 3H each), 1.41 (m, 2H), 1.6–1.7 (m, 4H), 2.13 (s, 3H), 2.64, 2.68 (overlapping t, J=7.6 Hz, 2H each), 5.09 (s, 2H), 7.14 (d, J=1.8 Hz, 1H), 7.22–7.39 (m, 4H), 7.51 (d, J=8.8 Hz, 1H), 7.63 (dd, J=8.8, 2.5 Hz, 1H), 7.88 (d, J=2.5 Hz, 1H), 8.00 (d, J=8.2 Hz, 1H).

Step F: 2-[5-(Acetylamino)-2-chlorophenyl]-5-n-butyl-4-[[2′-[N-(2-chlorobenzoyl)-sulfamoyl]-3-fluoro-5′-n-propylbiphenyl-4-yl]methyl]-2,4-dihydro-3H-1,2,4-triazol-3-one Reaction of 2-[5-(acetylamino)-2-chlorophenyl]-5-n-butyl-2,4-dihydro-4-[(3-fluoro-5′-n-propyl-2′-sulfamoylbiphenyl-4-yl)methyl]-3H-1,2,4-triazol-3-one (from Step E) with 2-chlorobenzoic acid (2 equivalents), CDI (2 equiv), and DBU (2 equiv) according to the procedure of Example 69 gave a 56% yield of the title compound as a white, glassy solid, mp 144°–146° C.; homogeneous by TLC (95:5 CH$_2$Cl$_2$—MeOH); mass spectrum (FAB) m/e 752 (M+1)$^+$.

400 MHz $^1$H NMR (CD$_3$OD) δ0.92 (t, J=7.4 Hz, 3H), 0.96 (t, J=7.4 Hz, 3H), 1.40 (m, 2H), 1.59–1.74 (m, 4H), 2.12 (s, 3H), 2.59 (t, J=7.6 Hz, 2H), 2.69 (t, J=7.7 Hz, 2H), 5.05 (s, 2H), 7.13 (d, J=1.6 Hz, 1H), 7.16–7.42 (m, 8H), 7.51 (d, J=8.9 Hz, 1H), 7.63 (m, 1H), 7.86 (d, J=2.5 Hz, 1H), 8.18 (d, J=8.2 Hz, 1H).

EXAMPLE 83

2-[5-(Acetylamino)-2-chlorophenyl]-5-n-butyl-2,4-dihydro-4-[[3-fluoro-2′-[N-(2-fluorobenzoyl)sulfamoyl]-5′-n-propylbiphenyl-4-yl]methyl]-3H-1,2,4-triazol-3-one The title compound was prepared as in Example 82 except that 2-fluorobenzoic acid was substituted for 2-chlorobenzoic acid in the final step. The material was obtained in 56% yield as a white, glassy solid, mp 148°–150° C.; homogeneous by TLC (95:5 CH$_2$Cl$_2$—MeOH); mass spectrum (FAB) m/e 736 (M+1)$^+$.

400 MHz $^1$H NMR (CD$_3$OD) δ0.92 (t, J=7.4 Hz, 3H), 0.96 (t, J=7.4 Hz, 3H), 1.41 (m, 2H), 1.60–1.71 (m, 4H), 2.12 (s, 3H), 2.59 (t, J=7.5 Hz, 2H), 2.68 (t, J=7.6 Hz, 2H), 5.03 (s, 2H), 7.04–7.45 (m, 8H), 7.52 (d, J=8.8 Hz, 1H), 7.61 (dd, J=8.9, 2.5 Hz, 1H), 7.86 (m, 1H), 7.90 (d, J=2.5 Hz, 1H), 8.16 (d, J=8.2 Hz, 1H).

EXAMPLE 84

5-n-Butyl-4-[[2′-[N-(2-chlorobenzoyl)sulfamoyl]-3-fluorobiphenyl-4-yl]methyl]-2,4-dihydro-2-[5-(propionylamino)-2-(trifluoromethyl)phenyl]-3H-1,2,4-triazol-3-one Step A: 3-Fluoro-4-methyl-2′-(N-t-butylsulfamoyl)-biphenyl The palladium(0)-catalyzed coupling of 4-bromo-2-fluorotoluene with 2-(N-t-butylsulfamoyl)phenylboronic acid was carried out according to the procedure of Example 76, Step F. Purification of the crude product by flash chromatography (elution with hexane-EtOAc) gave a 92% yield of the title compound as an off-white foam (TLC in 4:1 hexane-EtOAc); mass spectrum (FAB) m/e 322 (M+1)$^+$.

400 MHz $^1$H NMR (CDCl$_3$) δ1.01 (s, 9H), 2.32 (s, 3H), 3.59 (br s, 1H), 7.13–7.28 (m, 4H), 7.44–7.56 (m, 2H), 8.14 (dd, J=7.8, 1.4 Hz, 1H).

Step B: [3-Fluoro-2′-(N-t-butylsulfamoyl)biphenyl-4-yl]methyl Bromide

A solution of 1.08 g (3.36 mmol) of 3-fluoro-4-methyl-2′-(N-t-butylsulfamoyl)biphenyl (from Step A) in 20 mL of CCl$_4$ was stirred at reflux under irradiation from a 100-watt tungsten lamp as a solution of 3.5 mmol of bromine in approximately 13 mL of CCl$_4$ was added dropwise over 1.5 hour. After being stirred at reflux overnight, the solution was cooled and concentrated. The residue was crystallized from EtOAc-hexane to give 1.10 g of the title compound as an off-white solid, mp 138°–140° C. (estimated purity 87%; contained minor unbrominated and dibrominated contaminants by TLC); mass spectrum (FAB) m/e 400, 402 (M+1)$^+$.

400 MHz $^1$H NMR (CDCl$_3$) δ1.01 (s, 9H), 3.56 (br s, 1H), 4.54 (s, 2H), 72–7.6 (m, 6H), 8.15 (dd, J=8, 1.3 Hz, 1H).

Step C: 2-(2-Bromo-5-nitrophenyl)-4-[[2′-(N-t-butylsulfamoyl)-3-fluorobiphenyl-4-yl]methyl]-5-n-butyl-2,4-dihydro-3H-1,2,4-triazol-3-one The alkylation of 2-(2-bromo-5-nitrophenyl)-5-n-butyl-2,4-dihydro-3H-1,2,4-triazol-3-one (from Example 75, Step A) with [3-fluoro-2′-(N-t-butylsulfamoyl)-biphenyl-4-yl]methyl bromide (from Step B) was carried out according to the procedure of Example 13, Step A, to give a 93% yield of the title compound as a brownish, stiff foam, mp 137°–139° C., homogeneous by TLC in 98:2 CH$_2$Cl$_2$—MeOH; mass spectrum (FAB) m/e 666, 668 (M+Li)$^+$.

400 MHz $^1$H NMR (CDCl$_3$) δ0.93 (t, J=7.4 Hz, 3H), 1.03 (s, 9H), 1.43 (m, 2H), 1.70 (m, 2H), 2.58 (t, J=7.7 Hz, 2H), 3.62 (s, 1H), 5.00 (s, 2H), 7.23–7.33 (m, 3H), 7.42–7.58 (m, 3H), 7.88 (d, J=8.8 Hz, 1H), 8.10–8.16 (m, 2H), 8.33 (d, J=2.6 Hz, 1H).

Step D: 5-n-Butyl-4-[[2′-(N-t-butylsulfamoyl)-3-fluorobiphenyl-4-yl]methyl]-2,4-dihydro-2-[5-nitro-2-(trifluoromethyl)phenyl]-3H-1,2,4-triazol-3-one A mixture of 400 mg (0.606 mmol) of 2-(2-bromo-5-nitrophenyl)-4-[[2′-(N-t-butylsulfamoyl)-3-fluorobiphenyl-4-yl]methyl]-5-n-butyl-2,4-dihydro-3H-1,2,4-triazol-3-one (from Step C), 128 µL (175 mg (1.21 mmol) of methyl chlorodifluoroacetate. 42 mg (0.73 mmol) of potassium fluoride, 116 mg (0.606 mmol) of cuprous iodide, 72 mg (0.606 mmol) of potassium bromide, and 1.2 mL of DMF was stirred under N$_2$ at 120° C. in a sealed tube for 15 hours. The cooled mixture was diluted with water and extracted 3× with ethyl acetate. The combined organic fractions were washed with brine, dried (Na$_2$SO$_4$), and filtered. The filtrate was concentrated, and the residue was flash chromatographed on silica gel (elution with 6:1 hexane-EtOAc) to give 243 mg (62%) of the title compound as a pale yellow foam. [Subsequently eluted was 28 mg of the 2-chloro-5-nitrophenyl analog.] The desired product was homogeneous by TLC in 5:1 hexane-EtOAc; mass spectrum (FAB) m/e 656 (M+Li)$^+$.

400 MHz $^1$H NMR (CDCl$_3$) δ0.92 (t, J=7.3 Hz, 3H), 1.02 (s, 9H), 1.41 (m, 2H), 1.68 (m, 2H), 2.57 (t, J=7.6 Hz, 2H), 3.60 (s, 1H), 5.00 (s, 2H), 7.2–7.6 (m, 6H), 7.99 (d, J=8.8 Hz, 1H), 8.15 (dd, J=8, 1.3 Hz, 1H), 8.35 (dd, J=9, 2 Hz, 1H), 8.45 (d, J=2.2 Hz, 1H).

Step E: 5-n-Butyl-2,4-dihydro-4-[(3-fluoro-2′-sulfamoylbiphenyl-4-yl)methyl]-2-[5-nitro-2-(trifluoromethyl)phenyl]-3H-1,2,4-triazol-3-one Reaction of 5-n-butyl-4-[[2′-(N-t-butylsulfamoyl)-3-fluorobiphenyl-4-yl]methyl]-2,4-dihydro-2-[5-nitro-2-(trifluoromethyl)phenyl]-3H-1,2,4-triazol-3-one (from Step D) with trifluoroacetic acid in the presence of anisole according to the procedure of Example 76, Step G, gave a 94% yield of the title compound as a pale yellow foam, homogeneous by TLC (95:5 CH₂Cl₂—MeOH); mass spectrum (FAB) m/e 594 (M+1)⁺.

400 MHz ¹H NMR (CDCl₃) δ0.91 (t, J=7.3 Hz, 3H), 1.41 (m, 2H), 1.68 (m, 2H), 2.58 (t, J=7.6 Hz, 2H), 4.38 (s, 1H), 5.00 (s, 2H), 7.25–7.62 (m, 6H), 7.99 (d, J=8.8 Hz, 1H), 8.14 (dd, J=8.0, 1.4 Hz, 1H), 8.35 (dd, J=8.7, 1.5 Hz, 1H), 8.46 (d, J=2.1 Hz, 1H).

Step F: 5-n-Butyl-4-[[2'-[N-(2-chlorobenzoyl)sulfamoyl]-3-fluorobiphenyl-4-yl]methyl]-2,4-dihydro-2-[5-nitro-2-(trifluoromethyl)phenyl]-3H-1,2,4-triazol-3-one By the procedure of Example 51, 5-n-butyl-2,4-dihydro-4-[(3-fluoro-2'-sulfamoylbiphenyl-4-yl)methyl]-2-[5-nitro-2-(trifluoromethyl)-phenyl]-3H-1,2,4-triazol-3-one (from Step E) was reacted with 2-chlorobenzoic acid (3 equivalents), CDI (3 equiv), and DBU (3 equiv). Flash chromatography of the crude product on silica gel afforded an 86% yield of the title compound as a foam; homogeneous by TLC (95:5 CH₂Cl₂—MeOH); mass spectrum (FAB) m/e 732 (M+1)⁺.

400 MHz ¹H NMR (CDCl₃) δ0.91 (t, J=7.3 Hz, 3H), 1.40 (m, 2H), 1.67 (m, 2H), 2.54 (t, J=7.6 Hz, 2H), 4.94 (s, 2H), 7.13–7.73 (m, 10H), 7.99 (d, J=8.8 Hz, 1H), 8.37 (m, 2H), 8.44 (d, J=2.4 Hz, 1H), 8.68 (s, 1H).

Step G: 2-[5-Amino-2-(trifluoromethyl)phenyl]-5-n-butyl-4-[[2'-[N-(2-chlorobenzoyl)sulfamoyl]-3-fluorobiphenyl-4-yl]methyl]-2,4-dihydro-3H-1,2,4-triazol-3-one The title compound was prepared by hydrogenation of 5-n-butyl-4-[[2' -[N-(2-chlorobenzoyl)sulfamoyl]-3-fluorobiphenyl-4-yl]methyl]-2,4-dihydro-2-[5-nitro-2-(trifluoromethyl)phenyl]-3H-1,2,4-triazol-3-one (from Step F) according to the procedure of Example 75, Step D. The title compound was obtained in quantitative yield as a yellow-brown foam, suitable for use without further purification; homogeneous by TLC in 95:5 CH₂Cl₂—MeOH; mass spectrum (FAB) m/e 702 (M+1)⁺.

400 MHz ¹H NMR (CD₃OD) δ0.90 (t, J=7.4 Hz, 3H), 1.38 (m, 2H), 1.60 (m, 2H), 2.56 (t, J=7.5 Hz, 2H), 5.04 (s, 2H), 6.67 (d, J=2.2 Hz, 1H), 6.79 (d, J=8.7 Hz, 1H), 7.19–7.74 (m, 11H), 8.30 (d, J=8.1 Hz, 1H).

Step H: 5-n-butyl-4-[[2'-[N-(2-chlorobenzoyl)sulfamoyl]-3-fluorobiphenyl-4-yl]methyl]-2,4-dihydro-2-[5-(propionylamino)-2-(trifluoromethyl)phenyl]-3H-1,2,4-triazol-3-one The title compound was synthesized by reaction of 2-[5-amino-2-(trifluoromethyl)phenyl]-5-n-butyl-4-[[2'-[N-(2-chlorobenzoyl)sulfamoyl]-3-fluorobiphenyl-4-yl]methyl]-2,4-dihydro-3H-1,2,4-triazol-3-one (from Step G) with propionyl bromide (3 equivalents) and DBU (1.1 equiv) according to the method of Example 69. The material was obtained in 60% yield as a pale yellow solid, mp 181°–183° C.; homogeneous by TLC in 9:1 CH₂Cl₂-MeOH; mass spectrum (FAB) m/e 796 (M+K)⁺.

400 MHz ¹H NMR (CD₃OD) δ0.90 (t, J=7.4 Hz, 3H), 1.18 (t, J=7.6 Hz, 3H), 1.38 (m, 2H), 1.61 (m, 2H), 2.41 (q, J=7.6 Hz, 2H), 2.57 (t, J=7.5 Hz, 2H), 5.04 (s, 2H), 7.2–7.4 (m, 8H), 7.54–7.63 (m, 2H), 7.78 (d, J=8.8 Hz, 1H), 7.84 (d, J=8.7 Hz, 1H), 7.89 (s, 1H), 8.28 (d, J=7.9 Hz, 1H).

EXAMPLE 85

5-n-Butyl-4-[[2'-[N-(2-chlorobenzoyl)sulfamoyl]-3-fluorobiphenyl-4-yl]methyl]-2,4-dihydro-2-[2-(trifluoromethyl)-5-(valerylamino)phenyl]-3H-1,2,4-triazol-3-one The title compound was made as in Example 84, except that valeryl chloride was substituted for propionyl bromide in the final step. The material was obtained in 55% yield as a pale yellow solid, mp 145°–147° C.; homogeneous by TLC in 9:1 CH₂Cl₂—MeOH; mass spectrum (FAB) m/e 824 (M+K)⁺.

400 MHz ¹H NMR (CD₃OD) δ0.90 (t, J=7.4 Hz, 3H), 0.94 (t, J=7.4 Hz, 3H), 1.38 (m, 4H), 1.57–1.68 (m, 4H), 2.39 (t, J=7.5 Hz, 2H), 2.57 (t, J=7.5 Hz, 2H), 5.04 (s, 2H), 7.2–7.85 (m, 12H), 7.91 (s, 1H), 8.29 (d, J=7.9 Hz, 1H).

EXAMPLE 86

2-[5-(Benzoylamino)-2-(trifluoromethyl)phenyl]-5-n-butyl-4-[[2'-[N-(2-chlorobenzoyl)sulfamoyl]-3-fluorobiphenyl-4-yl]methyl]-2,4-dihydro-3H-1,2,4-triazol-3-one The title compound was prepared as in Example 84, except that benzoyl chloride was substituted for propionyl bromide in the final step. The material was obtained in 29% yield as a solid, mp 210°–212° C.; homogeneous by TLC in 9:1 CH₂Cl₂—MeOH; mass spectrum (FAB) m/e 806 (M+1)⁺.

400 MHz ¹H NMR (CD₃OD) δ0.90 (t, J=7.4 Hz, 3H), 1.39 (m, 2H), 1.63 (m, 2H), 2.59 (t, J=7.5 Hz, 2H), 5.05 (s, 2H), 7.19–7.63 (m, 9H), 7.85 (d, J=9 Hz, 1H), 7.93 (d, J=9 Hz, 2H), 8.06 (s, 1H), 8.28 (d, J=6.6 Hz, 1H), 8.52 (d, J≈4.5 Hz, 1H).

EXAMPLE 87

5-n-Butyl-2,4-dihydro-4-[[3-fluoro-2'-[N-(2-fluorobenzoyl)sulfamoyl]-biphenyl-4-yl]methyl]-2-[5-(propionylamino)-2-(trifluoromethyl)phenyl]-3H-1,2,4-triazol-3-one Step A: 2-[5-Amino-2-(trifluoromethyl)phenyl]-5-n-butyl-4-[[2'-(N-t-butylsulfamoyl)-3-fluorobiphenyl-4-yl]methyl]-2,4-dihydro-3H-1,2,4-triazol-3-one Hydrogenation of 5-n-butyl-4-[[2'-(N-t-butylsulfamoyl)-3-fluoro-biphenyl-4-yl]methyl]-2,4-dihydro-2-[5-nitro-2-(trifluoromethyl)phenyl]-3H-1,2,4-triazol-3-one (from Example 84, Step D) was carried out according to the procedure of Example 75, Step D, except that a 4:1 ratio of ethanol and ethyl acetate was used as solvent. The title compound was obtained in 91% yield oas an off-white foam, suitable for use without further purification; nearly homogeneous by TLC in 95:5 CH₂Cl₂—MeOH; mass spectrum (FAB) m/e 626 (M+Li)⁺.

400 MHz ¹H NMR (CD₃OD) δ0.91 (t, J=7.4 Hz, 3H), 1.03 (s, 9H), 1.40 (m, 2H), 1.63 (m, 2H), 2.62 (t, J=7.5 Hz, 2H), 5.07 (s, 2H), 6.69 (d, J=1.3 Hz, 1H), 6.79 (dd, J=8.3, 1.8 Hz, 1H), 7.24–7.35 (m, 4H), 7.47 (d, J=8.7 Hz, 1H), 7.55 (m, 1H), 7.63 (m, 2H), 8.11 (dd, J=7.9, 1.4 Hz, 1H).

Step B: 5-n-Butyl-4-[[2'-(N-t-butylsulfamoyl)-3-fluorobiphenyl-4-yl]methyl]-2,4-dihydro-2-[5-(propionylamino)-2-(trifluoromethyl)phenyl]-3H-1,2,4-triazol-3-one The title compound was prepared by reaction of 2-[5-amino-2-(trifluoromethyl)phenyl]-5-n-butyl-4-[[2'-(N-t-butylsulfamoyl)-3-fluorobiphenyl-4-yl]methyl]-

2,4-dihydro-3H-1,2,4-triazol-3-one (from Step A) with propionyl bromide (3 equivalents) in the presence of DMAP (1.1 equiv) following the method of Example 69. Chromatographic purification of the crude product on silica gel (elution with 0.8% MeOH in CH$_2$Cl$_2$) afforded a nearly quantitative yield of off-white, stiff foam; homogeneous by TLC in 95:5 CH$_2$Cl$_2$—MeOH; mass spectrum (FAB) m/e 682 (M+Li)$^+$.

400 MHz $^1$H NMR (CDCl$_3$) δ0.88 (t, J=7.3 Hz, 3H), 1.02 (s, 9H), 1.12 (br t, J=7.5 Hz, 3H), 1.36 (m, 2H), 1.61 (m, 2H), 2.29 (br m, 2H), 2.51 (t, J=7.6 Hz, 2H), 3.81 (br s, 1H), 5.00 (s, 2H), 7.22–7.56 (m, 8H), 7.82 (br s, 1H), 8.14 (d, J=7.8 Hz, 1H), 8.6 (br s, 1H).

Step C: 5-n-Butyl-2,4-dihydro-4-[(3-fluoro-2'-sulfamoylbiphenyl-4-yl)methyl]-2-[5-(propionylamino)-2-(trifluoromethyl)phenyl]-3H-1,2,4-triazol-3-one Deprotection of 5-n-butyl-4-[[2'-(N-t-butylsulfamoyl)-3-fluorobiphenyl-4-yl]methyl]-2,4-dihydro-2-[5-(propionylamino)-2-(trifluoromethyl)phenyl]-3H-1,2,4-triazol-3-one (from Step B) with trifluoroacetic acid according to the procedure of Example 76, Step G, furnished an 86% yield of the title compound as a white, stiff foam; homogeneous by TLC in 95:5 CH$_2$Cl$_2$—MeOH; mass spectrum (FAB) m/e 620 (M+1)$^+$.

400 MHz $^1$H NMR (CDCl$_3$) δ0.89 (t, J=7.3 Hz, 3H), 1.15 (t, J=7.6 Hz, 3H), 1.39 (m, 2H), 1.65 (m, 2H), 2.32 (q, J=7.6 Hz, 2H), 2.56 (t, J=7.5 Hz, 2H), 4.50 (br s, 1H), 4.98 (s, 2H), 7.2–7.35 (m, 4H), 7.5–7.6 (m, 4H), 7.74 (s, 1H), 8.13 (dd, J=7.9, 1.3 Hz, 1H), 8.22 (s, 1H).

Step D: 5-n-Butyl-2,4-dihydro-4-[[3-fluoro-2'-[N-(2-fluorobenzoyl)sulfamoyl]biphenyl-4-yl]methyl]-2-[5-(propionylamino)-2-(trifluoromethyl)phenyl]-3H-1,2,4,-triazol-3-one Reaction of 5-n-butyl-2,4-dihydro-4-[(3-fluoro-2'-sulfamoyl-biphenyl-4-yl)methyl]-2-[5-(propionylamino)-2-(trifluoromethyl)phenyl]-3H-1,2,4-triazol-3-one (from Step C) with 2-fluorobenzoic acid (3 equivalents), CDI (3 equiv), DBU (3 equiv), and DMAP (3 equiv) according to the method of Example 51 (as modified in Example 81) gave a a 93% yield of the title compound as a white, stiff foam, mp 119°–122° C.; homogeneous by TLC in 9:1 CH$_2$Cl$_2$—MeOH; mass spectrum (FAB) m/e 742 (M+1)$^+$.

400 MHz $^1$H NMR (CD$_3$OD) δ0.91 (t, J=7.3 Hz, 3H), 1.18 (t, J=7.6 Hz, 3H), 1.40 (m, 2H), 1.63 (m, 2H), 2.42 (q, J=7.6 Hz, 2H), 2.59 (t, J=7.5 Hz, 2H), 5.04 (s, 2H), 7.1–7.95 (m, 13H), 8.28 (d, J=8 Hz, 1H).

The following representative compounds of formula (I) can be prepared using the procedures of the foregoing Examples and Reaction Schemes:

(1) 5-n-butyl-2,4,-dihydro-2-isopropyl-N$^3$-phenyl-4-[[2'-(5-tetrazolyl)biphenyl-4-yl]methyl]-3H-1,2,4-triazol-3-imine;

(2) 4-[[2'-(N-benzoylsulfamoyl)biphenyl-4-yl]methyl]-5-n-butyl-2,4-dihydro-N$^3$-methyl-2-[2-(trifluoromethyl)phenyl]-3H-1,2,4-triazol-3-imine;

(3) 4-[[2'-(N-benzoylsulfamoyl)biphenyl-4-yl]methyl]-5-n-butyl-2,4-dihydro-2-[2-(trifluoromethyl)phenyl]-3H-1,2,4-triazole-3-thione;

(4) 4-[[2'-(N-benzoylsulfamoyl)biphenyl-4-yl]methyl]-5-n-butyl-2-(3-chloro-2-pyridyl)-2,4-dihydro-3H-1,2,4-triazol-3-one;

(5) 5-n-butyl-4-[[2'-[N-(2,2-dichlorocyclopropanecarbonyl)sulfamoyl]biphenyl-4-yl]methyl]-2,4-dihydro-2-[2-(trifluoromethyl)phenyl]-3H-1,2,4-triazol-3-one;

(6) 5-n-butyl-4-[[2'-[N-(3-chloro-2-furoyl)sulfamoyl]biphenyl-4-yl]methyl]-2,4-dihydro-2-[2-(trifluoromethyl)phenyl]-3H-1,2,4-triazol-3-one;

(7) 5-n-butyl-4-[[2'-(N-benzoylsulfamoyl)-3-fluorobiphenyl-4-yl]methyl]-2,4-dihydro-2-[2-(trifluoromethyl)phenyl]-3H-1,2,4-triazol-3-one;

(8) 5-n-butyl-2,4-dihydro-4-[[3-fluoro-2'-[N-(2-fluorobenzoyl)sulfamoyl]biphenyl-4-yl]methyl]-2-[2-(trifluoromethyl)phenyl]-3H-1,2,4-triazol-3-one;

(9) 5-n-butyl-4-[[2'-[N-(2,5-difluorobenzoyl)sulfamoyl]-3-fluorobiphenyl-4-yl]methyl]-2,4-dihydro-2-[5-(propionylamino)-2-[2-(trifluoromethyl)phenyl]-3H-1,2,4-triazol-3-one;

(10) 5-n-butyl-4-[[2'-[N-(2,5-dichlorobenzoyl)sulfamoyl]-3-fluorobiphenyl-4-yl]methyl]-2,4-dihydro-2-[5-(propionylamino)-2-[2-(trifluoromethyl)phenyl]-3H-1,2,4-triazol-3-one;

(11) 2-[2-bromo-5-[(2-ethoxyacetyl)amino]phenyl]-5-n-butyl-2,4-dihydro-4-[[2'-[3-fluoro-N-(2-fluorobenzoyl)sulfamoyl]biphenyl-4-yl]methyl]-3H-1,2,4-triazol-3-one;

(12) 5-n-butyl-2,4-dihydro-2-[5-[(2-ethoxyacetyl)amino]-2-(trifluoromethyl)phenyl]-4-[[3-fluoro-2'-[N-(2-fluorobenzoyl)sulfamoyl]-biphenyl-4-yl]methyl]-3H-1,2,4-triazol-3-one;

(13) 5-n-butyl-4-[[2'-[N-(2-chlorobenzoyl)sulfamoyl]-3-fluorobiphenyl-4-yl]methyl]-2,4-dihydro-2-[5-[(2-ethoxyacetyl)amino]-2-(trifluoromethyl)phenyl]-3H-1,2,4-triazol-3-one;

(14) 5-n-butyl-4-[[2'-[N-(2,5-difluorobenzoyl)sulfamoyl]-3-fluorobiphenyl-4-yl]methyl]-2,4-dihydro-2-[5-[(2-ethoxyacetyl)amino]-2-(trifluoromethyl)phenyl]-3H-1,2,4-triazol-3-one;

(15) 5-n-butyl-2,4-dihydro-4-[[3-fluoro-2'-[N-(2-fluorobenzoyl)sulfamoyl]biphenyl-4-yl]methyl]-2-[5-[(2-methoxyacetyl)amino]-2-(trifluoromethyl)phenyl]-3H-1,2,4-triazol-3-one;

(16) 5-n-butyl-4-[[2'-[N-(2-chlorobenzoyl)sulfamoyl]-3-fluorobiphenyl-4-yl]methyl]-2,4-dihydro-2-[5-[(2-methoxyacetyl)amino]-2-(trifluoromethyl)phenyl]-3H-1,2,4-triazol-3-one;

(17) 5-n-butyl-4-[[2'-[N-(2,5-difluorobenzoyl)sulfamoyl]-3-fluorobiphenyl-4-yl]methyl]-2,4-dihydro-2-[5-[(2-methoxyacetyl)amino]-2-(trifluoromethyl)phenyl]-3H-1,2,4-triazol-3-one;

(18) 5-n-butyl-2,4-dihydro-2-[5-[(3-ethoxypropionyl)amino]-2-(trifluoromethyl)phenyl]-4-[[3-fluoro-2'-[N-(2-fluorobenzoyl)sulfamoyl]-biphenyl-4-yl]methyl]-3H-1,2,4-triazol-3-one;

(19) 5-n-butyl-4-[[2'-[N-(2,5-difluorobenzoyl)sulfamoyl]-3-fluorobiphenyl-4-yl]methyl]-2,4-dihydro-2-[5-[(3-ethoxypropionyl)amino]-2-(trifluoromethyl)phenyl]-3H-1,2,4-triazol-3-one;

(20) 5-n-butyl-2,4-dihydro-4-[[3-fluoro-2'-[N-(2-fluorobenzoyl)sulfamoyl]biphenyl-4-yl]methyl]-2-[5-[(3'-methoxypropionyl)amino]-2-(trifluoromethyl)phenyl]-3H-1,2,4-triazol-3-one;

(21) 5-n-butyl-4-[[2'-[N-(2,5-difluorobenzoyl)sulfamoyl]-3-fluorobiphenyl-4-yl]methyl]-2,4-dihydro-2-[5-[(3-methoxypropionyl)amino]-2-(trifluoromethyl)phenyl]-3H-1,2,4-triazol-3-one;

(22) 5-n-butyl-2,4-dihydro-4-[[3-fluoro-2'-[N-(2-fluorobenzoyl)sulfamoyl]biphenyl-4-yl]methyl]-2-[5-[[2-(methylthio)acetyl]amino]-2-(trifluoromethyl)phenyl]-3H-1,2,4-triazol-3-one;

(23) 5-n-butyl-2,4-dihydro-4-[[3-fluoro-2'-[N-(2-fluorobenzoyl)sulfamoyl]biphenyl-4-yl]methyl]-2-[5-

(nicotinoylamino)-2-(trifluoromethyl)phenyl]-3H-1,2,4-triazol-3-one;
(24) 5-n-butyl-4-[[2'-[N-(2,5-difluorobenzoyl)sulfamoyl]-3-fluorobiphenyl-4-yl]methyl]-2,4-dihydro-2-[5-(nicotinoylamino)-2-(trifluoromethyl)phenyl]-3H-1,2,4-triazol-3-one;
(25) 5-n-butyl-2,4-dihydro-4-[[3-fluoro-2'-[N-(2-fluorobenzoyl)sulfamoyl]biphenyl-4-yl]methyl]-2-[5-(isonicotinoylamino)-2-(trifluoromethyl)phenyl]-3H-1,2,4-triazol-3-one;
(26) 5-n-butyl-4-[[2'-[N-(2,5-difluorobenzoyl)sulfamoyl]-3-fluorobiphenyl-4-yl]methyl]-2,4-dihydro-2-[5-(isonicotinoylamino)-2-(trifluoromethyl)phenyl]-3H-1,2,4-triazol-3-one;
(27) 2-[2-bromo-5-(N-n-butylcarbamoyl)phenyl]-5-n-butyl-2,4-dihydro-4-[[3-fluoro-2'-[N-(2-fluorobenzoyl)sulfamoyl]biphenyl-4-yl]methyl]-3H-1,2,4-triazol-3-one;
(28) 5-n-butyl-2-[5-(N-n-butylcarbamoyl)-2-(trifluoromethyl)phenyl]-2,4-dihydro-4-[[3-fluoro-2'-[N-(2-fluorobenzoyl)sulfamoyl]biphenyl-4-yl]methyl]-3H-1,2,4-triazol-3-one;
(29) 5-n-butyl-2-[5-(N-n-butylcarbamoyl)-2-(trifluoromethyl)phenyl]-4-[[2'-[N-(2-chlorobenzoyl)sulfamoyl]-3-fluorobiphenyl-4-yl]methyl]-2,4-dihydro-3H-1,2,4-triazol-3-one;
(30) 5-n-butyl-2-[5-(N-n-butylcarbamoyl)-2-(trifluoromethyl)phenyl]-4-[[2'-[N-(2,5-difluorobenzoyl)sulfamoyl]-3-fluorobiphenyl-4-yl]methyl]-2,4-dihydro-3H-1,2,4-triazol-3-one;
(31) 5-n-butyl-2,4-dihydro-4-[[3-fluoro-2'-[N-(2-fluorobenzoyl)sulfamoyl]biphenyl-4-yl]methyl]-2-[5-(N-n-propylcarbamoyl)-2-(trifluoromethyl)phenyl]-3H-1,2,4-triazol-3-one;
(32) 5-n-butyl-4-[[2'-[N-(2,5-difluorobenzoyl)sulfamoyl]-3-fluorobiphenyl-4-yl]methyl]-2,4-dihydro-2-[5-(N-n-propylcarbamoyl)-2-trifluoromethyl)phenyl]-3H-1,2,4-triazol-3-one;
(33) 5-n-butyl-2,4-dihydro-2-[5-(N-ethylcarbamoyl)-2-(trifluoromethyl)phenyl]-4-[[3-fluoro-2'-[N-(2-fluorobenzoyl)sulfamoyl]biphenyl-4-yl]methyl]-3H-1,2,4-triazol-3-one;
(34) 5-n-butyl-4-[[2'-[N-(2,5-difluorobenzoyl)sulfamoyl]-3-fluorobiphenyl-4-yl]methyl]-2,4-dihydro-2-[5-(N-ethylcarbamoyl)-2-trifluoromethyl)phenyl]-3H-1,2,4-triazol-3-one;
(35) 5-n-butyl-2-[2-chloro-5-[N-(2-methoxyethyl)carbamoyl]phenyl]-2,4-dihydro-4-[[3-fluoro-2'-[N-(2-fluorobenzoyl)sulfamoyl]biphenyl-4-yl]methyl]-3H-1,2,4-triazol-3-one;
(36) 2-[2-bromo-5-[N-(2-methoxyethyl)carbamoyl]phenyl]-5-n-butyl-2,4-dihydro-4-[[3-fluoro-2'-[N-(2-fluorobenzoyl)sulfamoyl]biphenyl-4-yl]methyl]-3H-1,2,4-triazol-3-one;
(37) 5-n-butyl-2,4-dihydro-4-[[3-fluoro-2'-[N-(2-fluorobenzoyl)sulfamoyl]biphenyl-4-yl]methyl]-2-[5-[N-(2-methoxyethyl)carbamoyl]-2-(trifluoromethyl)phenyl]-3H-1,2,4-triazol-3-one;
(38) 5-n-butyl-4-[[2'-[N-(2,5-difluorobenzoyl)sulfamoyl]-3-fluorobiphenyl-4-yl]methyl]-2,4-dihydro-2-[5-[N-(2-methoxyethyl)carbamoyl]-2-(trifluoromethyl)phenyl]-3H-1,2,4-triazol-3-one;
(39) 5-n-butyl-2,4-dihydro-4-[[3-fluoro-2'-[N-(2-fluorobenzoyl)sulfamoyl]biphenyl-4-yl]methyl]-2-[5-[N-(2-methoxyethyl)carbamoyl]-2-(trifluoromethyl)phenyl]-3H-1,2,4-triazol-3-one;
(40) 5-n-butyl-4-[[3,3'-difluoro-2'-[N-(2-fluorobenzoyl)sulfamoyl]biphenyl-4-yl]methyl]-2,4-dihydro-2-[5-(propionylamino)-2-(trifluoromethyl)phenyl]-3H-1,2,4-triazol-3-one;
(41) 5-n-butyl-4-[[3,3'-difluoro-2'-[N-(2,5-difluorobenzoyl)sulfamoyl]biphenyl-4-yl]methyl]-2,4-dihydro-2-[5-(propionylamino)-2-(trifluoromethyl)phenyl]-3H-1,2,4-triazol-3-one;
(42) 5-n-butyl-2,4-dihydro-4-[[2'-[N-(2-fluorobenzoyl)sulfamoyl]-3,3',6'-trifluorobiphenyl-4-yl]methyl]-2-[5-(propionylamino)-2-(trifluoromethyl)phenyl]-3H-1,2,4-triazol-3-one;
(43) 2,4-dihydro-4-[[3-fluoro-2'-[N-(2-fluorobenzoyl)sulfamoyl]biphenyl-4-yl]methyl]-2-[5-(propionylamino)-2-(trifluoromethyl)phenyl]-5-n-propyl-3H-1,2,4-triazol-3-one;
(44) 5-n-butyl-2-(2-chloro-5-valerylphenyl)-2,4-dihydro-4-[[3-fluoro-2'-[N-(2-fluorobenzoyl)sulfamoyl]biphenyl-4-yl]methyl]-3H-1,2,4-triazol-3one;
(45) 2-(2-bromo-5-valerylphenyl)-5-n-butyl-2,4-dihydro-4-[[3-fluoro-2'-[N-(2-fluorobenzoyl)sulfamoyl]biphenyl-4-yl]methyl]-3H-1,2,4-triazol-3-one;
(46) 5-n-butyl-2,4-dihydro-4-[[3-fluoro-2'-[N-(2-fluorobenzoyl)sulfamoyl]biphenyl-4-yl]methyl]-2-[2-(trifluoromethyl)-5-valerylphenyl]-3H-1,2,4-triazol-3-one;
(47) 5-n-butyl-2,4-dihydro-4-[[2'-[N-(2,5-difluorobenzoyl)sulfamoyl]-3-fluorobiphenyl-4-yl]methyl]-2-[2-(trifluoromethyl)-5-valerylphenyl]-3H-1,2,4-triazol-3-one;
(48) 5-n-butyl-2-[5-butyryl-2-(trifluoromethyl)phenyl]-2,4-dihydro-4-[[3-fluoro-2'-[N-(2-fluorobenzoyl)sulfamoyl]biphenyl-4-yl]methyl]-3H-1,2,4-triazol-3-one;
(49) 5-n-butyl-2-[5-butyryl-2-(trifluoromethyl)phenyl]-2,4-dihydro-4-[[2'-[N-(2,5-difluorobenzoyl)sulfamoyl]-3-fluorobiphenyl-4-yl]methyl]-3H-1,2,4-triazol-3-one;
(50) 2-[5-(acetylamino)-2-chlorophenyl]-5-n-butyl-2,4-dihydro-4-[[3-fluoro-2'-[N-(2-fluorobenzoyl)sulfamoyl]biphenyl-4-yl]methyl]-3H-1,2,4-triazol-3-one;
(51) 5-n-butyl-2-[2-chloro-5-[(cyclopropanecarbonyl)amino]phenyl]-2,4-dihydro-4-[[3-fluoro-2'-[N-(2-fluorobenzoyl)sulfamoyl]-5'-n-propylbiphenyl-4-yl]methyl]-3H-1,2,4-triazol-3-one;
(52) 5-n-butyl-2-[3-(N-n-butylcarbamoyl)-2-chlorophenyl]-2,4-dihydro-4-[[3-fluoro-2'-[N-(2-fluorobenzoyl)sulfamoyl]biphenyl-4-yl]methyl]-3H-1,2,4-triazol-3-one;
(53) 5-n-butyl-2,4-dihydro-4-[[3-fluoro-2'-[N-(2-fluorobenzoyl)sulfamoyl]biphenyl-4-yl]methyl]-2-[5-(picolinoylamino)-2-(trifluoromethyl)phenyl]-3H-1,2,4-triazol-3-one;
(54) 5-n-butyl-2,4-dihydro-4-[[3-fluoro-2'-[N-(2-fluorobenzoyl)sulfamoyl]biphenyl-4-yl]methyl]-2-[5-(2-furoylamino)-2-(trifluoromethyl)phenyl]-3H-1,2,4-triazol-3-one;
(55) 5-n-butyl-2,4-dihydro-4-[[3-fluoro-2'-[N-(2-fluorobenzoyl)sulfamoyl]biphenyl-4-yl]methyl]-2-[5-[(1-propanesulfonyl)amino]-2-(trifluoromethyl)phenyl]-3H-1,2,4-triazol-3-one;
(56) 5-n-butyl-2-[5-(N-n-butylsulfamoyl)-2-chlorophenyl]-2,4-dihydro-4-[[3-fluoro-2'-[N-(2-fluorobenzoyl)sulfamoyl]biphenyl-4-yl]methyl]-3H-1,2,4-triazol-3-one;
(57) 2,4-Dihydro-4-[[3-fluoro-2'-[N-(2-fluorobenzoyl)sulfamoyl]biphenyl-4-yl]methyl]-2-[5-[(2-methoxyacetyl)amino]-2-(trifluoromethyl)phenyl]-3H-1,2,4-triazol-3-one.

EXAMPLE 88

Typical Pharmaceutical Compositions Containing a Compound of the Invention

A: Dry Filled Capsules Containing 50 mg of Active Ingredient Per Capsule

| Ingredient | Amount Per capsule (mg) |
|---|---|
| 4-[[2'-(N-Benzoylsulfamoyl)biphenyl-4-yl]methyl]-5-n-butyl-2,4-dihydro-2-[2-(trifluoromethyl)phenyl]-3H-1,2,4-triazole-3-one, | 50 |
| Lactose | 149 |
| Magnesium stearate | 1 |
| Capsule (size No. 1) | 200 |

The active compound, 4-[[2'-(N-benzoylsulfamoyl)-biphenyl-4-yl]methyl]-5-n-butyl-2,4-dihydro-2-[2-(trifluoromethyl)phenyl]-3H-1,2,4-triazole-3-one, can be reduced to a No. 60 powder and the lactose and magnesium stearate can then be passed through a No. 60 blotting cloth onto the powder. The combined ingredients can then be mixed for about 10 minutes and filled into a No. 1 dry gelatin capsule.

B: Tablet

A typical tablet contains the active compound (25 mg), pregelatinized starch USP (82 mg), microcrystalline cellulose (82 mg) and magnesium stearate (1 mg).

C: Combination Tablet

A typical combination tablet contains, for example, a diuretic such as hydrochlorothiazide and consist of the active compound of this invention (7.5 mg), hydrochlorothiazide (50 mg) pregelatinized starch USP (82 mg), microcrystalline cellulose (82 mg) and magnesium stearate (1 mg).

D: Suppository

Typical suppository formulations for rectal administration contains the active compound (1–25 mg), butylated hydroxyanisole (0.08–1.0 mg), disodium calcium edetate (0.25–0.5 mg), and polyethylene glycol (775–1600 mg). Other suppository formulations can be made by substituting, for example, butylated hydroxytoluene (0.04–0.08 mg) for the disodium calcium edetate and a hydrogenated vegetable oil (675–1400 mg) such as Suppocire L, Wecobee FS, Wecobee M, Witepsols, and the like, for the polyethylene glycol. Further, these suppository formulations can also include another active ingredient such as another antihypertensive and/or a diuretic and/or an angiotensin converting enzyme and/or a calcium channel blocker in pharmaceutically effective amounts as described, for example, in C above.

E: Injection

A typical injectible formulation contains the active compound (5.42 mg), sodium phosphate dibasic anhydrous (11.4 mg) benzyl alcohol (0.01 ml) and water for injection (1.0 ml). Such an injectible formulation can also include a pharmaceutically effective amount of another active ingredient such as another antihypertensive and/or a diuretic and/or an angiotensin converting enzyme inhibitor and/or a calcium channel blocker.

What is claimed is:

1. A compound having the formula (I):

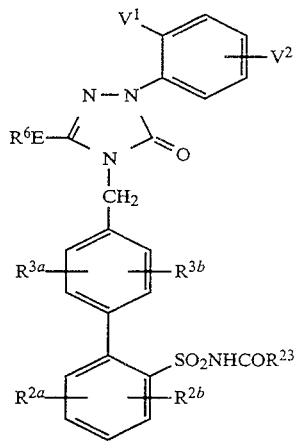

or a pharmaceutically acceptable salt thereof, wherein:

$R^{2a}$ is:
(a) hydrogen, or
(b) —Cl, —Br, —I, or —F;

$R^{2b}$ is:
(a) hydrogen,
(b) —Cl, —Br, —I, or —F, or
(c) $C_1$–$C_4$-alkyl;

$R^{3a}$ is
(a) —H, or
(b) —Cl, —Br, —I, or —F;

$R^{3b}$ is —H, —Cl, —Br, —I, —F, or $C_1$–$C_4$-alkyl;

E is a single bond;

$R^6$ is $C_1$–$C_6$-alkyl is unsubstituted or substituted with one or more substituents selected from the group consisting of: $C_3$–$C_7$-cycloalkyl and $CF_3$;

$R^9$ is H, $C_1$–$C_5$-alkyl, aryl or —$CH_2$-aryl;

aryl is phenyl, biphenyl, or naphthyl, unsubstituted or substituted with one, two or three substituents selected from the group consisting of —Cl, —Br, —I, —F, $C_1$–$C_6$-alkyl, $C_1$–$C_6$-alkoxy, $NO_2$, $CF_3$, $C_1$–$C_6$-alkyl-S(O)$_p$—, —$CF_3SO_2$—, —OH, —$NR^9R^{10}$, $CO_2H$, —$CO_2$-$C_1$–$C_4$-alkyl, —$CONR^9R^{10}$, —CN, —$NHCOR^9$, $OCF_3$, phenyl-$C_1$–$C_2$-alkyl, phenyl-S(O)$_p$, and phenyl-$C_1$–$C_2$-alkyl-S(O)$_p$;

$R^{10}$ is H, or $C_1$–$C_4$-alkyl;

$R^{21}$ is H or $R^{22}$;

$R^{22}$ is
(a) $C_1$–$C_6$-alkyl, $C_2$–$C_6$-alkenyl or $C_2$–$C_6$-alkynyl each of which is unsubstituted or substituted with one or more substituents selected from the group consisting of: aryl, wherein aryl is as defined under $R^9$ above, $C_3$–$C_7$-cycloalkyl, Cl, Br, I, F, —OH, —O—$C_1$–$C_4$-alkyl,
(b) $C_3$–$C_7$-cycloalkyl unsubstituted or substituted with one or more substituents selected from the group consisting of: $C_1$–$C_4$-alkyl, phenyl, Cl, Br, F, and I, or
(c) aryl, wherein aryl is as defined under $R^9$ above;

$R^{23}$ is
(a) phenyl, unsubstituted or substituted with one or two substituents selected from the group consisting of: Cl, Br, F, I, $CH_3$ and $CF_3$, at least one of which occupies an ortho position;
(b) branched $C_3$–$C_7$-alkyl;
(c) $C_3$–$C_7$-cycloalkyl, unsubstituted or substituted at the 1- or 2-position with one to three substituents selected from the group consisting of: $C_1$-$C_4$-alkyl, Cl, Br, F, or I;
  (j) norbonan-2-yl, adamantan-1-yl or noradamantan-3-yl;
$V_1$ is H, $CH_3$, $CF_3$ or halogen, with the proviso that $V_1$ is $CF_3$, when $V_2$ is H; and
$V_2$ is:
  (a) H,
  (b) —$NO_2$,
  (c) —$NR^{10}R^{21}$;
  (d) —$CONR^{21}R^{22}$,
  (e) —$COR^{22}$,
  (f) —$NR^{21}COR^{22}$,
  (g) —$NR^{21}CO_2R^{22}$,
  (h) —$NR^{21}CONR^{23}R^{22}$, or
  (i) —$S(O)_pR^{22}$, wherein p is 0 to 2.

2. A pharmaceutical composition useful in the treatment of hypertension which comprises a pharmaceutically acceptable carrier and a pharmaceutically effective amount of a compound of claim 1.

3. A method of treating hypertension which comprises administering to a patient in need of such treatment a pharmaceutically effective amount of a compound of claim 1.

4. An ophthalmological formulation for the treatment of ocular hypertension comprising an ophthalmologically acceptable carrier and an effective ocular antihypertensive amount of a compound of claim 1.

5. A method of treating ocular hypertension comprising administering to a patient in need of such treatment an effective ocular antihypertensive amount of a compound of claim 1.

6. The compound of claim 1 wherein:
$R^{2a}$ is H or F;
$R^{2b}$ is H, F, Cl, $CF_3$ or $C_1$-$C_4$-alkyl;
$R^{3a}$ is H, F or —$C_1$-$C_3$-alkyl;
$R^{3b}$ is H, F, Cl;
$V_1$ is H, $CH_3$, $CF_3$ or halogen, with the proviso that $V_1$ is $CF_3$, when $V_2$ is H; and
$V_2$ is:
  (a) —$NO_2$,
  (b) —$NR^{10}R^{21}$;
  (c) —$CONR^{21}R^{22}$,
  (d) —$COR^{22}$,
  (e) —$NR^{21}COR^{22}$,
  (f) —$NR^{21}CO_2R^{22}$,
  (g) —$NR^{21}CONR^{23}R^{22}$, or
  (h) —$S(O)_pR^{22}$, wherein p is 0 to 2.

7. The compound of claim 6 wherein:
$R^{2a}$ is H or F;
$R^{2b}$ is H, F, Cl, $CF_3$ or $C_1$-$C_4$-alkyl;
$R^{3a}$ is H, F or —$C_1$-$C_3$-alkyl;
$R^{3b}$ is H, F, Cl;
$R^6$ is n-butyl or n-propyl;
$V_1$ is $CF_3$ or halogen; and
$V_2$ is:
  (a) —$NO_2$,
  (b) —$NR^{10}R^{21}$;
  (c) —$CONR^{21}R^{22}$,
  (d) —$COR^{22}$,
  (e) —$NR^{21}COR^{22}$,
  (f) —$NR^{21}CO_2R^{22}$,
  (g) —$NR^{21}CONR^{23}R^{22}$, or
  (h) —$S(O)_pR^{22}$, wherein p is 0 to 2.

8. The compound of claim 7 wherein:
$R^{2a}$ and $R^{2b}$ are H;
$R^{3a}$ is H;
$R^{3b}$ is H or F;
$V_1$ is $CF_3$; and
$V_2$ is H.

9. The compound of claim 1 selected from the group consisting of:
  (1) 4-[[2'-(N-benzoylsulfamoyl)biphenyl-4-yl]methyl]-5-n-butyl-2,4-dihydro-2-[2-(trifluoromethyl)phenyl]-3H-1,2,4-triazol-3-one;
  (2) 5-n-butyl-2,4-dihydro-4-[[2'-[N-[(S)-2,2-dimethylcyclopropanecarbonyl]sulfamoyl]biphenyl-4-yl]methyl]-2-[2-(trifluoromethyl)phenyl]-3H-1,2,4-triazol-3-one;
  (3) 5-n-butyl-2,4-dihydro-4-[[2'-[N-(2-fluorobenzoyl)sulfamoyl]biphenyl-4-yl]methyl]-2-[2-(trifluoromethyl)phenyl]-3H-1,2,4-triazol-3-one;
  (4) 2-[5-(acetylamino)-2-chlorophenyl]-5-n-butyl-2,4-dihydro-4-[[3-fluoro-2'-[N-(2-fluorobenzoyl)sulfamoyl]-5'-n-propylbiphenyl-4-yl]methyl]-3H-1,2,4-triazol-3-one;
  (5) 5-n-butyl-4-[[2'-[N-(2-fluorobenzoyl)sulfamoyl]-3-fluorobiphenyl-4-yl]methyl]-2,4-dihydro-2-[5-(propionylamino)-2-(trifluoromethyl)phenyl]-3H-1,2,4-triazol-3-one;
  (6) 5-n-butyl-4-[[2'-[N-(2-fluorobenzoyl)sulfamoyl]-3-fluorobiphenyl-4-yl]methyl]-2,4-dihydro-2-[5-[(2-ethoxyacetyl)amino]-2-(trifluoromethyl)phenyl]-3H-1,2,4-triazol-3-one;
  (7) 5-n-butyl-4-[[2'-[N-(2-fluorobenzoyl)sulfamoyl]-3-fluorobiphenyl-4-yl]methyl]-2,4-dihydro-2-[5-[(2-methoxyacetyl)amino]-2-(trifluoromethyl)phenyl]-3H-1,2,4-triazol-3-one;
  (8) 5-n-butyl-2-[5-(N-n-butylcarbamoyl)-2-(trifluoromethyl)phenyl]-4-[[2'-[N-(2-fluorobenzoyl)sulfamoyl]-3-fluorobiphenyl-4-yl]methyl]-2,4-dihydro-3H-1,2,4-triazol-3-one;
  (9) 5-n-butyl-4-[[2'-[N-(2-fluorobenzoyl)sulfamoyl]-3-fluorobiphenyl-4-yl]methyl]-2,4-dihydro-2-[5-[N-(2-methoxyethyl)carbamoyl]-2-(trifluoromethyl)phenyl]-3H-1,2,4-triazol-3-one;
  (10) 5-n-butyl-2,4-dihydro-4-[[2'-[N-(2-fluorobenzoyl)sulfamoyl]-3-fluorobiphenyl-4-yl]methyl]-2-[2-(trifluoromethyl)-5-valerylphenyl]-3H-1,2,4-triazol-3-one.

* * * * *